US008178092B2

(12) United States Patent
Valdes et al.

(10) Patent No.: US 8,178,092 B2
(45) Date of Patent: May 15, 2012

(54) METHODS OF TREATING PSORIASIS BY ADMINISTRATION OF ANTIBODIES TO THE P40 SUBUNIT OF IL-12 AND/OR IL-23

(75) Inventors: Joaquin Mario Valdes, Mundelein, IL (US); Susan K. Paulson, Downers Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 232 days.

(21) Appl. No.: 12/402,342

(22) Filed: Mar. 11, 2009

(65) Prior Publication Data

US 2010/0028363 A1 Feb. 4, 2010

Related U.S. Application Data

(60) Provisional application No. 61/069,840, filed on Mar. 18, 2008, provisional application No. 61/095,275, filed on Sep. 8, 2008, provisional application No. 61/207,904, filed on Feb. 18, 2009.

(51) Int. Cl.
*A61K 39/395* (2006.01)

(52) U.S. Cl. ............... 424/130.1; 424/141.1; 424/142.1; 514/885; 514/886

(58) Field of Classification Search ........................ None
See application file for complete search history.

(56) References Cited

U.S. PATENT DOCUMENTS

| | | | |
|---|---|---|---|
| 4,816,397 | A | 3/1989 | Boss et al. |
| 5,530,101 | A | 6/1996 | Queen et al. |
| 5,643,768 | A | 7/1997 | Kawasaki |
| 5,650,492 | A | 7/1997 | Gately et al. |
| 5,652,138 | A | 7/1997 | Burton et al. |
| 5,658,754 | A | 8/1997 | Kawasaki |
| 5,780,597 | A | 7/1998 | Gately et al. |
| 5,792,838 | A | 8/1998 | Smith et al. |
| 5,811,523 | A | 9/1998 | Trinchieri et al. |
| 5,853,697 | A | 12/1998 | Strober et al. |
| 5,910,486 | A | 6/1999 | Curiel et al. |
| 6,090,382 | A | 7/2000 | Salfeld et al. |
| 6,342,634 | B2 | 1/2002 | Nicholson et al. |
| 6,713,610 | B1 | 3/2004 | Kucherlapati et al. |
| 6,902,734 | B2 | 6/2005 | Giles-Komar et al. |
| 6,914,128 | B1 | 7/2005 | Salfeld |
| 7,060,268 | B2 | 6/2006 | Andya et al. |
| 7,063,964 | B2 | 6/2006 | Giles-Komar et al. |
| 7,166,285 | B2 | 1/2007 | Giles-Komar et al. |
| 7,279,157 | B2 | 10/2007 | Giles-Komar et al. |
| 7,504,485 | B2 | 3/2009 | Salfeld |
| 7,560,247 | B2 | 7/2009 | Giles-Komar et al. |
| 7,776,331 | B1 | 8/2010 | Chartash |
| 7,883,704 | B2 | 2/2011 | Salfeld |
| 2002/0161199 | A1 | 10/2002 | Ashkenzai |
| 2002/0194631 | A1 | 12/2002 | Ehrhardt et al. |
| 2003/0070185 | A1 | 4/2003 | Jakobovits et al. |
| 2004/0156835 | A1 | 8/2004 | Imoto et al. |
| 2004/0191265 | A1 | 9/2004 | Schenerman et al. |
| 2005/0159364 | A1 | 7/2005 | Cooper |
| 2005/0276823 | A1 | 12/2005 | Cini |
| 2007/0009526 | A1 | 1/2007 | Benson et al. |
| 2007/0020255 | A1 | 1/2007 | Ueno et al. |
| 2007/0172475 | A1 | 7/2007 | Matheus et al. |
| 2008/0071063 | A1 | 3/2008 | Allan |
| 2008/0292642 | A1 | 11/2008 | Borhani |
| 2008/0305114 | A1 | 12/2008 | Salfeld |
| 2009/0175857 | A1 | 7/2009 | Salfeld |
| 2009/0269302 | A1 | 10/2009 | Salfeld |
| 2010/0028363 | A1 | 2/2010 | Valdes |
| 2010/0172862 | A1 | 7/2010 | Correia |
| 2010/0297143 | A1 | 11/2010 | Chartash |
| 2011/0123544 | A1 | 5/2011 | Salfeld |
| 2011/0206680 | A1 | 8/2011 | Valdes |

FOREIGN PATENT DOCUMENTS

| | | | |
|---|---|---|---|
| EP | 0638644 | | 2/1995 |
| EP | 0659766 | A1 | 6/1995 |
| EP | 953639 | | 11/1999 |
| WO | WO 92/01047 | A1 | 1/1992 |
| WO | WO 92/09690 | A2 | 6/1992 |
| WO | WO 92/20791 | A1 | 11/1992 |
| WO | WO 94/04679 | A1 | 3/1994 |
| WO | WO 95/24918 | A1 | 9/1995 |
| WO | WO96/33735 | | 10/1996 |
| WO | WO 97/15327 | A1 | 5/1997 |
| WO | WO 98/16248 | | 4/1998 |
| WO | WO 98/22137 | | 5/1998 |
| WO | WO 98/41232 | | 9/1998 |
| WO | WO 98/42378 | | 10/1998 |
| WO | WO 99/09055 | | 2/1999 |
| WO | WO 99/22766 | | 5/1999 |
| WO | WO 99/37682 | | 7/1999 |
| WO | WO 95/14780 | | 11/1999 |
| WO | WO 00/56772 | A1 | 9/2000 |
| WO | WO 02/12500 | A2 | 2/2002 |

(Continued)

OTHER PUBLICATIONS

Balashov, K.E., et al. "Increased interleukin 12 production in progressive multiple sclerosis induction by activated CD4+ T cells via CD40 ligand." Proc Natl Acad Sci USA. Jan. 21, 1997;94(2) :599-603.

Baldock, P. et al. "A Comparison of Microbatch and Vapor Diffusion for Initial Screening of Crystallization Conditions." 1996 J. Crystal Growth 168 (1-4); pp. 170-174 (abstract only).

Barbas, III, C.F., et al. "Assembly of combinatorial antibody libraries on phage surfaces: the gene III site." Proc Natl Acad Sci USA. Sep. 15, 1991; 88:7978-82.

Barrie et al. "The interleukin-12 family of cytokines: Therapeutic targets for inflammatory disease mediation." 2005 Clinical and Applied Immun. Rev. 5(4): 225-240.

Berrebi, D., et al. "Interleukin-12 expression is focally enhanced in the gastric mucosa of pediatric patients with Crohn's disease." Am J Pathol. Mar. 1998; 152(3):667-72.

(Continued)

*Primary Examiner* — Prema Mertz

(74) *Attorney, Agent, or Firm* — McCarter & English, LLP; Maria Laccotripe Zacharakis; Jill A. Mello

(57) ABSTRACT

The invention provides a method of treating psoriasis in a subject by administering to a subject an antibody capable of binding to the p40 subunit of IL-12 and/or IL-23.

8 Claims, 35 Drawing Sheets

FOREIGN PATENT DOCUMENTS

| | | |
|---|---|---|
| WO | WO 02/072636 | 9/2002 |
| WO | WO 2005/121177 | 12/2005 |
| WO | WO 2006/012500 | 6/2006 |
| WO | WO 2006/069036 | 6/2006 |
| WO | WO2008/088823 | 7/2008 |
| WO | WO 99/57151 | 10/2010 |

OTHER PUBLICATIONS

Bird, R.E., et al. "Single-chain antigen-binding proteins." Science. Oct. 21, 1988; 242(4877):423-426.

Brown, Jr., P.S., et al. "Anti-Tac-H, a humanized antibody to the interleukin 2 receptor prolongs primate cardiac allograft survival." Proc Natl Acad Sci USA. Apr. 1, 1991; 88(7):2663-7.

Bucht, A, et al. "Expression of interferon-gamma (IFN-gamma), IL-10, IL-12 and transforming growth factor-beta (TGF-beta) mRNA in synovial fluid cells from patients in the early and late phases of rheumatoid arthritis (RA)." Clin Exp Immunol. Mar. 1996 103 (3) :357-67.

Cambridge Antibody Technology Group pic, "Applying technology to target disease," Annual Report (1998).

Cambridge Antibody Technology, "Clinical Trials From CAT," PR Newswire(1999).

Carter, R.W., et al. Production and characterization of monoclonal antibodies to human interleukin-12. Hybridoma. 1997. 16(4):363-9.

Casset et al. "A peptide mimetic of an anti-CD4 monoclonal antibody by rational design." 2003 Biochem and Biophys Res Comm 307:198-205.

Chizzonite, R. et al., "IL-12: Monoclonal antibodies specific to the 40-kDa subunit block receptor binding and biological activity on activated human lymphoblasts," J. Immunol., 1991, vol. 147:1548-1556.

Clackson, T., et al. "Making antibody fragments using phage display libraries." Nature. Aug. 15, 1991; 352(6336):624-28.

Clark, Steven C., "Interleukin 12: Molecular, Biological and Clinical Perspectives," Molecular Biology of Haematopoeiesis, vol. 3:3-14 (1993).

Cordoba et al. "Non-enzymatic hinge region fragmentation of antibodies in solution" 2005 J Chromatogr B Analyt Technol Biomed Life Sci 818:115-121.

Dall'AcQua, W., et al. "Antibody engineering." Curr Opin Struct Biol. 1998; 8(4):443-50.

D'Andrea, A. et al., "Production of Natural Killer Cell Stimulatory Factor (Interleukin 12) by Peripheral Blood Mononuclear cells," J. Exp. Med., 1992, vol. 176:1387-1398.

Daugherty et al. "Antibody affinity maturation using bacterial surface display." 1998 Protein Eng. 11(9):825-832.

Ding, et al. "ABT-874, a fully human monoclonal anti-IL-12/IL-23 antibody for the potential treatment of autoimmune diseases." 2008 Current Opinion in Investigational Drugs 9(5):515-522.

Duchmann, R., et al. "Tolerance towards resident intestinal flora in mice is abrogated in experimental colitis and restored by treatment with interleukin-10 or antibodies to interleukin 12." Eur. J. Immunol. 1996, 26:934-8.

Fais, S., et al. "Interferon expression in Crohn's disease patients: increased interferon-gamma and -alpha mRNA in the intestinal lamina propria mononuclear cells." J Interferon Res. 1994; Oct. 14(5):235-8.

Fauchet et al. "Characterization of Monoclonal Antibodies against Human Interleukin-12 and Their Use in an Elisa for the Measurement of This Cytokine." 1996 Annals of the New York Academy of Sciences, vol. 795, pp. 334-336.

Fehr et al. "Nucleotide and Predicted Peptide Sequence of Feline Interleukin-12 (IL-12)." 1997 DNA sequence 8:77-82.

Fuchs, P., et al. "Targeting recombinant antibodies to the surface of *Escherichia coli*: fusion to a peptidoglycan associated lipoprotein." Biotechnology (NY). Dec. 1991; 9(12):1369-72.

Fuss, I.J., et al. "Disparate CD4+ lamina propria (LP) lymphokine secretion profiles in inflammatory bowel disease, Crohn's disease LP cells manifest increased secretion of IFN gamma whereas ulcerative colitis LP cells manifest increased secretion of IL-5." J Immunol. Aug. 1, 1996; 157(3):1261-1270.

Garrard, L.J., et al. "Fab assembly and enrichment in a monovalent phage display system," Biotechnolooy (NY), Dec. 1991; vol. 12:1373-7.

Gately, M.K., et al. "The interleukin-12/interleukin-12-receptor system: role in normal and pathologic immune responses." Annu Rev Immunol. 1995; 16:495-521.

Gram, H., et al. "In vitro selection and affinity maturation of antibodies from a naïve combinatorial immunoglobulin library." Proc Natl Acad Sci USA. Apr. 15, 1992; 89(8):3576-80.

Griffiths, A.D., et al. "Human anti-self antibodies with high specificity from phage display libraries." EMBOJ. Feb. 1993; 12(2):725-34.

Hamid, Q., et al. "In vivo expression of IL-12 and IL-13 in atopic dermatitis." J Allergy Clin Immunol. Jul. 1996; 98(1 ):225-31.

Hanes, J., et al. "In vitro selection and evolution of functional proteins by using ribosome display." Proc Natl Acad Sci USA. May 13, 1997; 94(10):4937-42.

Hawkins, R.E., et al. "Selection of phage antibodies by binding affinity. Mimicking affinity maturation." J Mol Bioi. Aug. 5, 1992; 226(3):889-96.

Hay, B.N., et al. "Bacteriophage cloning and *Escherichia coli* expression of a human IgM Fab." Hum Antibodies Hybridomas. Apr. 1992; 3(2) :81-5.

He, M., et al. "Antibody-ribosome-mRNA (ARM) complexes as efficient selection particles for in vitro display and evolution of antibody combining sites." Nucleic Acids Res. Dec. 15, 1997; 25(24):5132-4.

Heinzel et al. "Interleukin 12 is Produced in Vivo during Endotoxemia and Stimulates Synthesis of Gamma Interferon." 1994 Infection and Immunity 62(10):4244-4249.

Hoogenboom, H.R., et al. "Multi-subunit proteins on the surface of filamentous phage:methodologies for displaying antibody (Fab) heavy and light chains." Nucleic Acids Res. Aug. 11, 1991; 19(15):4133-7.

Hoogenboom, Hennie R. et al., "Antibody phage display technology and its applications," Immunotechnology, 1998, 4:1-20.

Hoogenboom, Hennie R., "Designing and optimizing library selection strategies for generating high-affinity antibodies," Trends Biotechnol. 1997, 15(2):62-70.

http://www.bdbiosciences.com "Purified mouse anti-human IL-12, p40/p70 monoclonal antibody, clone C8.6." 2005 BD Pharmingen Technical Data Sheet for product #554659.

http://www.biolegend.com "LEAF Purified anti-human IL-12/IL-23, p40 (monomer, dimer, heterodimer), clone 11.5." May 1, 2007 Technical Data Sheet for product #501812.

http://www.clinicaltrials.gov "A Safety and Efficacy Study of CNTO 1275 in Patients with Multiple Sclerosis" 2009 ClinicalTrials.gov Identifier: NCT00207727; (Jul. 14, 2009).

http://www.clinicaltrials.gov "A Study of the Safety and Efficacy of CNTO 1275 in Patients with Active Psoriatic Arthritis." 2009 ClinicalTrials.gov Identifier: NCT00267956; (Jul. 14, 2009).

http://www.clinicaltrials.gov "A Study of the Safety and Efficacy of CNTO 1275 in Patients with Severe Plaque-Type Psoriasis" 2009 ClinicalTrials.gov Identifier: NCT00267969; (Jul. 14, 2009).

http://www.clinicaltrials.gov "A Study of the Safety and Efficacy of CNTO 1275 in Subjects with Severe Plaque-Type Psoriasis." 2009 ClinicalTrials.gov Identifier: NCT00320216; (Jul. 14, 2009).

http://www.clinicaltrials.gov "Efficacy and Safety of ABT-874 in Subjects With Moderate to Severe Chronic Plaque Psoriasis." 2009 ClinicalTrials.gov Identifier: NCT00292396; (Jul. 14, 2009).

http://www.clinicaltrials.gov "Monoclonal Antibody Treatment of Crohn's Disease" 2009 ClinicalTrials.gov Identifier: NCT00007163; (Jul. 14, 2009).

http://www.clinicaltrials.gov "Safety and Effectiveness of Two Doses of ABT-874 as Compared to Placebo in Subjects with Multiple Sclerosis." (MS) 2009 ClinicalTrials.gov Identifier: NCT00086671; (Jul. 14, 2009).

Huse, W.D., et al. "Generation of a large combinatorial library of the immunoglobulin repertoire in phage lambda." Science. Dec. 8, 1989; 246(4935):1275-81.

Huston, J.S., et al. "Protein engineering of antibody binding sites: recovery of specific activity in an anti-digoxin single-chain Fv analogue produced in *Escherichia coli*." Proc Natl Acad Sci USA. Aug. 1988; 85(16):5879-83.

International Search Report for Application No. PCT/US08/00564, dated Aug. 8, 2008.
International Search Report for Application No. PCT/US09/65714, dated Mar. 25, 2010.
Irving, R.A., et al. "Affinity maturation of recombinant antibodies using *E. coli* mutator cells." Immunotechnology. Jun. 1996; 2(2):127-43.
Jackson Jr, et al. In vitro antibody maturation. Improvement of a high affinity, neutralizing antibody against IL-1 beta. J Immunol. 1995; 154(7):3310-9.
Junghans, R.P., et al. "Anti-Tac-H, a humanized antibody to the interleukin 2 receptor with new features for immunotherapy in malignant and immune disorders." Cancer Res. Mar. 1, 1990; 50(5):1495-502.
Kabat, E.A., et al. "Attempts to locate complementarity-determining residues in the variable positions of light and heavy chains." Ann NY Acad Sci. Dec. 31, 1971; 190:382-93.
Kabat, E.A., et al. Accession No. PS91-192898, Sequences of Proteins of Immunological Interest, Fifth Edition, U.S. Department of Health and Human Services, NIH Publication No. 91-3242,1991.
Kasper et al., "A phase I trial of an interleukin-12/23 monoclonal antibody in relapsing multiple sclerosis" 2006 Current Medical Research and Opinion, 22(9):1671-1678.
Kauffman, et al. "A Phase I Study Evaluating the Safety, Pharmacokinetics, and Clinical Response of a Human IL-12 p40 Antibody in Subjects with Plaque Psoriasis" 2004 J. Invest. Dermatology, vol. 123:1037-1044.
Kettleborough, C.A., et al. "Humanization of a mouse monoclonal antibody by CDR-grafting: the importance of framework residues on loop conformation." Protein Eng. 1991, 4:773-83.
Kimball, et al "Safety and Efficacy of ABT-874, a Fully Human Interleukin 12/23 Monoclonal Antibody, in the Treatment of Moderate to Severe Chronic Plaque Psoriasis" 2008 ARCH Dermatol, 144(2):200-207.
Kobayashi, M., et al. "Identification and purification of natural killer cell stimulatory factor (NKSF), a cytokine with multiple biologic effects on human lymphocytes." J Exp Med. Sep. 1, 1989;170(3):827-45.
Leonard et al. "Prevention of Experimental Autoimmune Encephalomyelitis by Antibodies Against Interleukin 12" 1995 J. Exp. Med.181:381-386.
Ling, P., et ai. "Human IL-12 p40 homodimer binds to the IL-12 receptor but does not mediate biologic activity." J Immunol. Jan. 1, 1995; 154(1):116-27.
Liu et al. "Analysis of the Interrelationship between IL-12, TNF-alpha, and IFN-gamma Production during Murine Listeriosis" 1995 Cellular Immunology 163(2):260-267.
Mannon et al., "Anti-Interleukin-12 Antibody for Active Crohn's Disease" 2004 New England J. Med. 351:2069-2079.
McCafferty, J., et al. "Phage antibodies: filamentous phage displaying antibody variable domains." Nature. Dec. 6, 1990; 348 (6301):552-4.
McPherson "A comparison of salts for the crystallization of macromolecules" 2001 Protein Science, vol. 10:418-422.
Meager et al. "Spontaneous Neutralising Antibodies to Interferon-alpha and Interleukin-12 in Thymoma-Associated Autoimmune Disease" Lancet 1997; 9091:596-1597.
Medical News Today, Press release. Abbott's ABT 874 Shows Positive Results for Maintenance of Response in Phase II Psoriasis Study. (created Oct. 2, 2007) Retrieved from internet Dec. 17, 2009 http://www.medicalnewstoday.com/printerfriendlynews.php?news.php?newsid=84202.
Monteleone, G., et al. "Interleukin 12 is expressed and actively released by Crohn's disease intestinal lamina propria mononuclear cells." Gastroenterology. Apr. 1997; 112(4):1169-78.
Morita,Y., et al. "Expression of interleukin-12 in synovial tissue from patients with rheumatoid arthritis." Arthritis Rheum. Feb. 1998; 41(2):306-14.
Neri et al. Targeting by affinity-matured recombinant antibody fragments of an angiogenesis associated fibronectin isoform. 1997 Nature Biotechnology 15(12) 1271-1275.
Neurath, M.F., et al. "Antibodies to interleukin 12 abrogate established experimental colitis in mice." J Exp Med. Nov. 1, 1995; 182(5):1281-90.
Oppmann, B. et al., "Novel p19 Protein Engages IL-12p40 to form a cytokine, IL-23, with biological activities similar as well as distinct from IL-12," Immunity, 2000, vol. 13:715-725.
Oswald et al. Interleukin-12 Synthesis is a Required Step in Terhalose Dimycolate-Induced Activation of Mouse Peritoneal Macrophages 1997 Infection and Immunity 65(4):1364-1369.
Panaccione et al. Briakinumab (Anti-interleukin 12/23p40, ABT874) for Treatment of Crohn's Disease (CD) 2010 abstract of submission to American College of Gastroenterology Annual Scientific Meeting.
Paper 128 of Patent Interference 105,592 McK, Technology Center 1600, *Centocor, Inc.*, vs. *Abbott GmbH & Co.*, KG entered Jul. 1, 2008.
Paper 20 of Patent Interference 105,592 McK, Technology Center 1600, *Centocor, Inc.*, vs. *Abbott GmbH & Co.* KG entered Feb. 5, 2008.
Parronchi, P., et al. "Type 1 T-helper cell predominance and interleukin-12 expression in the gut of patients with Crohn's disease." Am J Pathol. Mar. 1997; 150(3):823-32.
Paul 1993 Fundamental Immunology 3rd Ed., 1993 292-29.
Pini, A., et al. "Design and use of a phage display library. Human antibodies with subnanomolar affinity against a marker of angiogenesis eluted from a two-dimensional gel." J Biol Chem. Aug. 21, 1998; 273(34):21769-76.
Pini, A., et al. "Hierarchical affinity maturation of a phage library derived antibody for the selective removal of cytomegalovirus from plasma." J Immunol Methods. Aug. 7, 1997; 206(1-2):171-82.
Podlaski, F.J., et al. "Molecular characterization of interleukin 12." Arch Biochem Biophys. Apr. 1992; 294(1):230-7.
Riechmann, Lutz et al., "Phage Display and Selection of a Site-Directed Randomized Single-Chain Antibody Fv Fragment for Its Affinity Improvement," Biochemistry, vol. 32:8848-8855.
Schwaller et al. Interleukin-12 Expression in Human Lymphomas and Nonneoplastic Lympohoid Disorders 1995 Blood 85(8): 2182-2188.
Seder, A.A., et al. "Interleukin 12 acts directly on CD4+ T cells to enhance priming for interferon gamma production and diminishes interleukin 4 inhibition of such priming." Proc Natl Acad Sci USA. Nov. 1, 1993; 90(21 ):10188-92.
Sharon, J. "Structural correlates of high antibody affinity: three engineered amino acid substitutions can increase the affinity of an anti-p-azophenylarsonate antibody 200-fold." Proc Natl Acad Sci USA. Jun. 1990; 87(12):4814-7.
Short et al. Contribution of Antibody Heavy Chain CDR1 to Digoxin Binding Analyzed by Random Mutagenesis of Phage-displayed Fab 26-10, 1995, J. Biol. Chem. 270(48):28541-28550.
Smith et al. Specific cleavage of immunoglobulin G by copper ions 1996 Int J Peptide Protein Res 48:48-55.
Supplemental European Search Report for European Application No. EP08742311, Feb. 26, 2010.
Tao, W. et al., "P19ARF Stabilizes p53 by Blocking Nucleo-cytoplasmic shuttling of Mdm2," Proc. Natl. Acad. Sci. USA., 1999, vol. 96:6937-6941.
Taylor, L.D., et al. "A transgenic mouse that expresses a diversity of human sequence heavy and light chain immunoglobulins." Nucleic Acids Res. Dec. 11, 1992; 20(23):6287-95.
Toichi et al., An anti-IL-12p40 antibody down-regulates type 1 cytokines, chemokines, and 1L-12/1L-23 in psoriasis. 2006. J Immunol. 177:4917-4926.
Tomlinson, Ian M. et al., "The Imprint of Somatic Hypermutation on the Repertoire of Human Germline V Genes," J. Mol. Biol., vol. 256:813-817 (1996).
Trinchieri, Giorgio, "Interleukin-12 and its role in the generation of TH1 cells," Immunology Today, vol. 14(7):335-338 (1993).
Turka, L.A., et al. "Interleukin 12: a potential link between nerve cells and the immune response in inflammatory disorders." Mol Med. Sep. 1995; 1(6):690-9.
United States Patent and Trademark Office, "Patent Interference No. 105,592," Centocor Motion 1 (2007) United States Patent and Trademark Office, "Patent Interference No. 105,592," Declaration.

Valiante, Nicholas M. et al., "Role of the Production of Natural Killer Cell Stimulatory Factor (NKSF/IL-12) in the Ability of B Cell Lines to Stimulate T and NK Cell Proliferation," Cellular Immunology, vol. 145:187-198 (1992).
Vaughan et al., Human Antibodies with Sub-nanomolar Affinities Isolated from a Large Non-immunized Phage Display Library 1996 Nature Biotec hnology, 14:309-314.
Vollmer et al. A Phase 2, 24-Week, Randomized, Placebo-Controlled, Double-Blind Study Examining the Efficacy and Safety of an Anti-Interleukin-12 and -23 Monoclonal Antibody in Patients With Relapsing-Remitting or Secondary-Progressive Multiple Sclerosis. 2010, manuscript submission to Multiple Sclerosis; Mult Scler. Dec. 6, 2010. [Epub ahead of print].
Wilkinson et al. Characterization of anti-mouse IL-12 monoclonal antibodies and measurement of mouse IL-12 by ELISA 1996. J. Immun. Methods 189(1): 15-24.
Williamson et al. Neutralizing IL-12 During Induction of Murine Acute Graft-Versus-Host Disease Polarizes the Cytokine Profile Toward a Th2-Type Alloimmune Response and Confers Long Term Protection From Disease 1997 J. Immun.159:1208-1215.
Windhagen, A., et al. "Expression of costimulatory molecules B7-1 (COSO), B7-2 (CD86), and interleukin 12 cvtokine in multiple sclerosis lesions." J Exp Med. Dec. 1, 1995; 182(6):1985-96.
Winter, G., et al. "Making antibodies by phage display technology." Annu Rev Immunol. 1994; 12:433•55.
Wolf, S.F. et al., "Cloning of eDNA for Natural Killer Cell Stimulatory Factor, A Heterodimeric Cytokine with Multiple Biologic Effects on T and Natural Killer Cells," J. Immunol. 1991, 146:3074-3081.
Wu et al., Simultaneous targeting of multiple disease mediators by a dual-variable-domain immunoqlobulin 2007 Nature Biotechnoloav, 25(11): 1290-1297.
Yang et al. Crystalline monoclonal antibodies for subcutaneous delivery 2003 PNAs vol. 100(12):6934-6939.
Yawalkar et al. Expression of Interleukin-12 is Increased in Psoriatic Skin 1998 Journal of Investigative Dermatology, vol. 111, pp. 1053-1057.
Bendig, Humanization of rodent monoclonal antibodies by CDR grafting, Methods: A Comparison to Methods in Immunology, 8:83-93, 1995.
Chames et al., Improving the affinity and the fine specificity of an anti-cortisol antibody by parsimonious mutagenesis and phage display, J. Immunol., 161:5421-5429, 1998.
Chen et al., Interleukin-23 receptor gene polymorphism is associated with dilated cardiomyopathy in Chinese Han population, Tissue Antigens, 73(4):330-334, 2009.
Deng et al., Basis for selection of improved carbohydrate-binding single-chain antibodies from synthetic gene libraries, Proc. Nat'l. Acad. Sci., 92(11):4992-4996, 1995.
Fishwild et al., High-avidity human IgG kappa monoclonal antibodies from novel strain of minilocus transgenic mice, Nat. Biotech., 14:845-851, 1996.
http://www.clinicaltrials.gov, A Study of the Safety and Efficacy of CNTO 1275 in patients with severe plaque-type psoriasis, ClinicalTrials.gov Identifier: NCT00307437 (Jul. 14, 2009).
Kimball et al., Retreatment efficacy and long-term safety of the fully human, interleukin-12/-23 monoclonal antibody ABT-874 in the treatment of moderate to severe psoriasis: 48-week results from a phase II trial, J. American Acad. Dermatol., 2009.
Kimball, Efficacy and safety of ABT-874, a monoclonal anti-interleukin 12/23 antibody, for the treatment of chronic plaque psoriasis: 36-week observation/retreatment and 60-week open-label extension phases of a randomized phase II trial, J. American Acad. Dermatol., 64(2):263-274, 2011.
Kosako et al., Isolation and characterization of neutralizing single-chain antibodies against Xenopus mitogen-activated protein kinase kinase from phage display libraries, Biochemistry, 35(40):13212-13221, 1996.
Krueger, A human interleukin-12/23 monoclonal antibody for the treatment of psoriasis, New England J. Med., 356(6):580-592, 2007.
Leonardi, Efalizumab: an overview, J. Am. Acad. Dermatol., 49:S98-104, 2003.
Leonardi, Efficacy and safety of ustekinumab, a human interleukin-12/23 monoclonal antibody, in patients with psoriasis: 76-week results from randomized, double-blind, placebo-controlled trial (PHOENIX 1), The Lancet, 371(9625):1665-1674, 2008.
Longbrake et al., Why did IL-12/IL-23 antibody therapy fail in multiple sclerosis, Expert Rev. Neurother., 9(3):319-321, 2009.
MacCallum, Antibody-antigen interactions: Contact analysis and binding site topography, J. Mol., Biol., 256:813-817, 1998.
Mendez et al., Functional transplant of megabase human immunoglobulin loci recapitulates human antibody response in mice, Nat. Genet., 15:146-156, 1997.
Mérienne, K. et al., The Functional Architecture of an Acetylcholine Receptor-mimicking Antibody, J. Biol. Chem., 272(38):23775-23783, 1997.
Papp et al., Efficacy and safety of ustekinumab, human interleukin-12/23 monoclonal antibody, in patients with psoriasis: a 52-week results from a randomized, double-blind, placebo-controlled trial (PHOENIX 2), The Lancet, 371(9625):1675-1684, 2008.
Parhami-Seren, B. and Margolies, MN, Contribution of Heavy Chain junctional Amino Acid Diversity to Antibody Affinity Among p-Azophenylarsonate-Specific Antibodies, J. Immunol., 157:2066-2072, 1996.
Ryan et al., The use of ustekinumab in autoimmune disease, Expert Opinion Biol. Ther., 10(4):587-604, 2010.
Scherl et al., Review of the safety and efficacy of ustekinumab, Ther. Adv. Gastroenterol., 3(5):321-328, 2010.
Schwaller et al., Interleukin-12 expression in human lymphomas and nonneoplastic lymphoid disorders, Blood, 85(8):2182-2188, 1995.
Segal et al., Repeated subcutaneous injections of IL23/23 p40 neutralising antibody, ustekinumab, in patients with relapsing-remitting multiple sclerosis: a phase II, double-blind, placebo-controlled, randomised, dose-ranging study, Lancet Neurol., 7:796-804, 2008.
Yago et al., IL-23 induced human osteoclastogenesis via IL-17 in vitro, and anti-IL-23 antibody attenuates collagen-induced arthritis in rats, Arthritis Res. Ther., 2007.

NRI.
*p<0.001 for all active treatment arms vs. placebo.

Patient numbers per group are denoted in parentheses above bars

FIG. 8A

Heavy Chain Variable Region Sequences

| SEQ ID NO.: | Kabat number | 1 2 3 4 5 6 7 8 9 10 11 12 13 14 15 16 17 18 19 20 21 22 23 24 25 26 27 28 29 30 | CDR H1<br>31 32 33 34 35 | 36 37 38 39 40 41 42 43 44 45 46 47 48 49 | CDR H2<br>50 51 52 52A 54 54 55 56 |
|---|---|---|---|---|---|
| 33 | JOE9wt VH | QVQLVQSGGGVVQPGRSLRLSCAASGFTFS | SYGMH | WVRQAPGKGLEWVA | FIRYDGSN |
| 35 | Cos-3/JH3 VH | .....E.........G.............. | ..... | .............. | ........ |
| 37 | 70-1 VH | .............................. | ..... | .............. | ........ |
| 39 | 78-34 VH | .............................. | ..... | .............. | ........ |
| 41 | 79-1 VH | .............................. | ..... | .............. | ........ |
| 43 | 101-11 VH | .............................. | ..... | .............. | ........ |
| 45 | 26-1 VH | .............................. | ..... | .............. | ........ |
| 47 | 136-15 VH | .............................. | ..... | .............. | ........ |
| 49 | 136-15 VH germline | .....E........................ | ..... | .............. | ........ |
| 51 | 149-5 VH | .............................. | ..... | .............. | ........ |
| 53 | 149-6 VH | .............................. | ..... | .............. | ........ |
| 55 | 103-4 VH | .............................. | ..... | .............. | ........ |
| 57 | 103-8 VH | .............................. | ..... | .............. | ........ |
| 59 | 103-14 VH | .............................. | ..... | .............. | ........ |
| 61 | G6 VH | .............................. | ..... | .............. | ........ |
| 63 | Y139 VH | .............................. | ..... | .............. | ........ |
| 65 | AO3 VH | .............................. | ..... | .............. | ........ |
| 67 | AO3 VH germline | .....E........................ | ..... | .............. | ........ |
| 23 | Y61 VH | .............................. | ..... | .............. | ........ |
| 69 | Y61 VH germline | .....E........................ | ..... | .............. | ........ |
| 71 | Y61-H31E VH | .............................. | E.... | .............. | ........ |
| 73 | Y61 L50Y VH | .............................. | ..... | .............. | ........ |
| 75 | Y61-L94Y VH | .............................. | ..... | .............. | ........ |
| 31 | J695 | .....E........................ | ..... | .............. | ........ |

FIG. 8B

Heavy Chain Variable Region Sequences

| SEQ ID NO.: | Kabat number | CDR H2<br>57 58 59 60 61 62 63 64 65 | 66 67 68 69 70 71 72 73 74 75 76 77 78 79 80 81 82 82A 82B 82C 83 84 85 86 87 88 89 90 91 92 93 94 | CDR H3<br>95 96 97 98 101 102 | 103 104 105 106 107 108 109 110 111 112 113 |
|---|---|---|---|---|---|
| 33 | JOE9wt VH | KYYADSVKG | RFTISRDNSKNTLYLQMKSLRAEDTAVYYCTT | SGSYDY | WGQGTMVTVSS |
| 35 | Cos-3/JH3 VH | ......... | .................N............AK | | ........... |
| 37 | 70-1 VH | ......... | ................................ | H..H.N | ........... |
| 39 | 78-34 VH | ......... | ................................ | ...... | ........... |
| 41 | 79-1 VH | ......... | ................................ | ...... | ........... |
| 43 | 101-11 VH | ......... | ................................ | H..H.N | ........... |
| 45 | 26-1 VH | ......... | ................................ | H..H.N | ........... |
| 47 | 136-15 VH | ......... | ..............................K. | H..H.N | ........... |
| 49 | 136-15 VH germline | ......... | .................N............K. | H..H.N | ........... |
| 51 | 149-5 VH | ......... | ................................ | H..H.N | ........... |
| 53 | 149-6 VH | ......... | ................................ | H..H.N | ........... |
| 55 | 103-4 VH | ......... | ................................ | H..H.N | ........... |
| 57 | 103-8 VH | ......... | ..............................K. | H..H.N | ........... |
| 59 | 103-14 VH | ......... | ..............................K. | H..H.N | ........... |
| 61 | G6 VH | ......... | ..............................K. | H..H.N | ........... |
| 63 | Y139 VH | ......... | ..............................K. | H..H.N | ........... |
| 65 | AO3 VH | ......... | ..............................K. | H..H.N | ........... |
| 67 | AO3 VH germline | ......... | .................N............K. | H..H.N | ........... |
| 23 | Y61 VH | ......... | ..............................K. | H..H.N | ........... |
| 69 | Y61 VH germline | ......... | .................N............K. | H..H.N | ........... |
| 71 | Y61-H31E VH | ......... | ..............................K. | H..H.N | ........... |
| 73 | Y61 L50Y VH | ......... | ..............................K. | H..H.N | ........... |
| 75 | Y61-L94Y VH | ......... | ..............................K. | H..H.N | ........... |
| 31 | J695 | ......... | .................N............K. | H..H.N | ........... |

FIG. 8C

Light Chain Variable Region Sequences

| SEQ ID NO.: | Kabat number | 1-23 | CDR L1 24-34 (incl. 27A, 27B) | 35-49 | CDR L2 50-56 |
|---|---|---|---|---|---|
| 34 | JOE9 VL wt | SYVLTQPPSVSGTPGQRVTISC | SGGRSNIGSNTVK | WYQQLPGTAPKLLIY | GNDQRPS |
| 36 | Dp18 Lv1042/Jλ1 | QS..........A.......... | T.SS....AGYD.H | ............... | ..SN... |
| 38 | 70-1 VL | ....................... | ............. | ............... | ....... |
| 40 | 78-34 VL | ....................... | ............. | ............... | ....... |
| 42 | 79-1 VL | ....................... | ............. | ............... | ....... |
| 44 | 101-11 VL | ....................... | ............. | ............... | ....... |
| 46 | 26-1 VL | ....................... | ............. | ............... | ....... |
| 48 | 136-15 VL | ....................... | ..S.......... | ............... | ....... |
| 50 | 136-15 VL germline | QS..........A.......... | ..S.......... | ............... | ....... |
| 52 | 149-5 VL | ....................... | ............. | ............... | ....... |
| 54 | 149-6 VL | ....................... | .......V..... | ............... | ....... |
| 56 | 103-4 VL | ....................... | .......V..... | ............... | ....... |
| 58 | 103-8 VL | ....................... | ............. | ............... | ....... |
| 60 | 103-14 VL | ....................... | ............. | ............... | ....... |
| 62 | G6 VL | ....................... | ............. | ............... | ....... |
| 64 | Y139 VL | ....................... | ............. | ............... | ....... |
| 66 | AO3 VL | ....................... | ............. | ............... | ....... |
| 68 | AO3 VL germline | QS..........A.......... | ..S.......... | ............... | ....... |
| 24 | Y61 VL | ....................... | ............. | ............... | ....... |
| 70 | Y61 VL germline | QS..........A.......... | ..S.......... | ............... | ....... |
| 72 | Y61-H31E VL | QS..........A.......... | ..S.......... | ............... | ....... |
| 74 | Y61 L50Y VL | QS..........A.......... | ..S.......... | ............... | Y...... |
| 76 | Y61-L94Y VL | QS..........A.......... | ..S.......... | ............... | ....... |
| 32 | J695 VL | QS..........A.......... | ..S.......... | ............... | Y...... |

FIG. 8D

Light Chain Variable Region Sequences

| SEQ ID NO.: | Kabat number | 57–88 | CDR L3 89 90 91 92 93 94 95 95A 95B 95C 96 97 | 98 99 100 101 102 103 104 105 106 106A 107 |
|---|---|---|---|---|
| 34 | JOE9 VL wt | GVPDRFSGSKSGTSASLAITGVQAEDEADYYC | QSYDSSLRGSRV | FGTGTKVTVLG |
| 36 | Dp18 Lv1042/Jλ1 | .....................L.......... | .......S.... | ........... |
| 38 | 70-1 VL | ................................ | ............ | ........... |
| 40 | 78-34 VL | ................................ | ....RGFT.... | ........... |
| 42 | 79-1 VL | ................................ | .......W.... | ........... |
| 44 | 101-11 VL | ................................ | ....RGFT.... | ........... |
| 46 | 26-1 VL | ................................ | .......W.... | ........... |
| 48 | 136-15 VL | ................................ | .T..KGFT..S. | ........... |
| 50 | 136-15 VL germline | .....................L.......... | .T..KGFT..S. | ........... |
| 52 | 149-5 VL | ................................ | .......W.T.. | ........... |
| 54 | 149-6 VL | ................................ | ....RGFT.... | ........... |
| 56 | 103-4 VL | ................................ | ....RGFT.A.. | ........... |
| 58 | 103-8 VL | ................................ | .T..KGFT..S. | ........... |
| 60 | 103-14 VL | ................................ | ...EKGFT..M. | ........... |
| 62 | G6 VL | ................................ | ....RGTHPLTI | ........... |
| 64 | Y139 VL | ................................ | ....RGSHPALT | ........... |
| 66 | AO3 VL | ................................ | ....RGTHPLTM | ........... |
| 68 | AO3 VL germline | .....................L.......... | ....RGTHPLTM | ........... |
| 24 | Y61 VL | ................................ | ....RGTHPALL | ........... |
| 70 | Y61 VL germline | .....................L.......... | ....RGTHPALL | ........... |
| 72 | Y61-H31E VL | .....................L.......... | ....RGTHPALL | ........... |
| 74 | Y61 L50Y VL | .....................L.......... | ....RGTHPALL | ........... |
| 76 | Y61-L94Y VL | .....................L.......... | ....RYTHPALL | ........... |
| 32 | J695 VL | .....................L.......... | ....RYTHPALL | ........... |

Fig. 9A

Y61 Heavy Chain CDR H1 Mutagenesis

| | | CDR H1 | | | | | | | | | |
|---|---|---|---|---|---|---|---|---|---|---|---|
| SEQ ID NO: | | 27 | 28 | 29 | 30 | 31 | 32 | 33 | 34 | 35 | $k_{off}$ ($x 10^5$) |
| 21 | Y61 | F | T | F | S | S | Y | G | M | H | |
| 288 | | . | . | . | E | . | . | . | . | . | 22.8 |
| 289 | | . | . | . | S | . | . | . | . | . | 16.8 |
| 290 | | . | . | . | Y | . | . | . | . | . | 31.9 |
| 291 | | . | . | . | H | . | . | . | . | . | 29.6 |
| 292 | | . | . | . | K | . | . | . | . | . | 22.5 |
| 293 | | . | . | . | R | . | . | . | . | . | 24.5 |
| 294 | | . | . | . | N | . | . | . | . | . | 30.1 |
| 295 | | . | . | . | T | . | . | . | . | . | 32.0 |
| 296 | | . | . | . | G | . | . | . | . | . | 23.3 |
| 297 | | . | . | . | V | . | . | . | . | . | 39.9 |
| 298 | | . | . | . | I | . | . | . | . | . | 20.7 |
| 299 | | . | . | . | W | . | . | . | . | . | 21.6 |
| 300 | | . | . | . | . | E | . | . | . | . | 21.9 |
| 301 | | . | . | . | . | C | . | . | . | . | 12.0 |
| 302 | | . | . | . | . | S | . | . | . | . | 24.9 |
| 303 | | . | . | . | . | Y | . | . | . | . | 39.8 |
| 304 | | . | . | . | . | H | . | . | . | . | 30.9 |
| 305 | | . | . | . | . | R | . | . | . | . | 66.4 |
| 306 | | . | . | . | . | N | . | . | . | . | 19.1 |
| 307 | | . | . | . | . | Q | . | . | . | . | 15.2 |
| 308 | | . | . | . | . | T | . | . | . | . | 71.6 |
| 309 | | . | . | . | . | A | . | . | . | . | 20.5 |
| 310 | | . | . | . | . | I | . | . | . | . | 33.4 |
| 311 | | . | . | . | . | . | E | . | . | . | 229.0 |
| 312 | | . | . | . | . | . | C | . | . | . | 383.0 |
| 313 | | . | . | . | . | . | S | . | . | . | 157.5 |
| 314 | | . | . | . | . | . | Y | . | . | . | 33.7 |
| 315 | | . | . | . | . | . | H | . | . | . | 46.1 |
| 316 | | . | . | . | . | . | R | . | . | . | 448.5 |
| 317 | | . | . | . | . | . | N | . | . | . | 297.0 |
| 318 | | . | . | . | . | . | T | . | . | . | 148.0 |
| 319 | | . | . | . | . | . | A | . | . | . | 165.5 |
| 320 | | . | . | . | . | . | V | . | . | . | 133.5 |
| 321 | | . | . | . | . | . | L | . | . | . | 226.0 |
| 322 | | . | . | . | . | . | I | . | . | . | 160.5 |
| 323 | | . | . | . | . | . | . | D | . | . | 152.0 |
| 324 | | . | . | . | . | . | . | E | . | . | 189.0 |
| 325 | | . | . | . | . | . | . | C | . | . | 286.5 |
| 326 | | . | . | . | . | . | . | S | . | . | 39.9 |
| 327 | | . | . | . | . | . | . | Y | . | . | 250.5 |
| 328 | | . | . | . | . | . | . | N | . | . | 30.8 |
| 329 | | . | . | . | . | . | . | G | . | . | 17.8 |
| 330 | | . | . | . | . | . | . | A | . | . | 27.3 |
| 331 | | . | . | . | . | . | . | V | . | . | 191.0 |
| 332 | | . | . | . | . | . | . | M | . | . | 21.5 |
| 333 | | . | . | . | . | . | . | I | . | . | 250.0 |
| 334 | | . | . | . | . | . | . | P | . | . | 159.5 |

Fig. 9B

Y61 Heavy Chain CDR H2 Mutagenesis

| SEQ ID NO: | | CDR H2 | | | | | | | | | | | | | | | | | $k_{off}$ (x $10^5$) |
|---|---|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 | |
| 19 | Y61 | F | I | R | Y | D | G | S | N | K | Y | Y | A | D | S | V | K | G | |
| 335 | | E | . | . | . | . | . | . | . | . | . | . | . | . | . | . | . | . | 34.7 |
| 336 | | C | . | . | . | . | . | . | . | . | . | . | . | . | . | . | . | . | 28.5 |
| 337 | | Y | . | . | . | . | . | . | . | . | . | . | . | . | . | . | . | . | 23.0 |
| 338 | | H | . | . | . | . | . | . | . | . | . | . | . | . | . | . | . | . | 30.9 |
| 339 | | K | . | . | . | . | . | . | . | . | . | . | . | . | . | . | . | . | 61.2 |
| 340 | | N | . | . | . | . | . | . | . | . | . | . | . | . | . | . | . | . | 34.4 |
| 341 | | Q | . | . | . | . | . | . | . | . | . | . | . | . | . | . | . | . | 42.0 |
| 342 | | T | . | . | . | . | . | . | . | . | . | . | . | . | . | . | . | . | 20.5 |
| 343 | | L | . | . | . | . | . | . | . | . | . | . | . | . | . | . | . | . | 44.0 |
| 344 | | F | . | . | . | . | . | . | . | . | . | . | . | . | . | . | . | . | 20.4 |
| 345 | | . | . | E | . | . | . | . | . | . | . | . | . | . | . | . | . | . | 31.8 |
| 346 | | . | . | S | . | . | . | . | . | . | . | . | . | . | . | . | . | . | 29.2 |
| 347 | | . | . | Y | . | . | . | . | . | . | . | . | . | . | . | . | . | . | 29.8 |
| 348 | | . | . | H | . | . | . | . | . | . | . | . | . | . | . | . | . | . | 40.7 |
| 349 | | . | . | K | . | . | . | . | . | . | . | . | . | . | . | . | . | . | 26.2 |
| 350 | | . | . | R | . | . | . | . | . | . | . | . | . | . | . | . | . | . | 20.6 |
| 351 | | . | . | Q | . | . | . | . | . | . | . | . | . | . | . | . | . | . | 28.5 |
| 352 | | . | . | T | . | . | . | . | . | . | . | . | . | . | . | . | . | . | 37.4 |
| 353 | | . | . | G | . | . | . | . | . | . | . | . | . | . | . | . | . | . | 32.1 |
| 354 | | . | . | A | . | . | . | . | . | . | . | . | . | . | . | . | . | . | 17.1 |
| 355 | | . | . | V | . | . | . | . | . | . | . | . | . | . | . | . | . | . | 31.7 |
| 356 | | . | . | L | . | . | . | . | . | . | . | . | . | . | . | . | . | . | 34.7 |
| 357 | | . | . | W | . | . | . | . | . | . | . | . | . | . | . | . | . | . | 35.1 |
| 358 | | . | . | . | . | D | . | . | . | . | . | . | . | . | . | . | . | . | 15.1 |
| 359 | | . | . | . | . | E | . | . | . | . | . | . | . | . | . | . | . | . | 39.9 |
| 360 | | . | . | . | . | S | . | . | . | . | . | . | . | . | . | . | . | . | 36.8 |
| 361 | | . | . | . | . | Y | . | . | . | . | . | . | . | . | . | . | . | . | 61.1 |
| 362 | | . | . | . | . | K | . | . | . | . | . | . | . | . | . | . | . | . | 158.0 |
| 363 | | . | . | . | . | R | . | . | . | . | . | . | . | . | . | . | . | . | 166.5 |
| 364 | | . | . | . | . | N | . | . | . | . | . | . | . | . | . | . | . | . | 72.7 |
| 365 | | . | . | . | . | Q | . | . | . | . | . | . | . | . | . | . | . | . | 79.2 |
| 366 | | . | . | . | . | T | . | . | . | . | . | . | . | . | . | . | . | . | 50.0 |
| 367 | | . | . | . | . | A | . | . | . | . | . | . | . | . | . | . | . | . | 40.4 |
| 368 | | . | . | . | . | V | . | . | . | . | . | . | . | . | . | . | . | . | 44.0 |
| 369 | | . | . | . | . | L | . | . | . | . | . | . | . | . | . | . | . | . | 109.5 |
| 370 | | . | . | . | . | I | . | . | . | . | . | . | . | . | . | . | . | . | 94.4 |
| 371 | | . | . | . | . | F | . | . | . | . | . | . | . | . | . | . | . | . | 168.5 |
| 372 | | . | . | . | . | . | D | . | . | . | . | . | . | . | . | . | . | . | 45.5 |
| 373 | | . | . | . | . | . | E | . | . | . | . | . | . | . | . | . | . | . | 35.1 |
| 374 | | . | . | . | . | . | S | . | . | . | . | . | . | . | . | . | . | . | 37.3 |
| 375 | | . | . | . | . | . | Y | . | . | . | . | . | . | . | . | . | . | . | 64.6 |
| 376 | | . | . | . | . | . | K | . | . | . | . | . | . | . | . | . | . | . | 40.7 |
| 377 | | . | . | . | . | . | R | . | . | . | . | . | . | . | . | . | . | . | 2.5 |
| 378 | | . | . | . | . | . | N | . | . | . | . | . | . | . | . | . | . | . | 44.7 |
| 379 | | . | . | . | . | . | Q | . | . | . | . | . | . | . | . | . | . | . | 31.6 |
| 380 | | . | . | . | . | . | T | . | . | . | . | . | . | . | . | . | . | . | 64.4 |
| 381 | | . | . | . | . | . | G | . | . | . | . | . | . | . | . | . | . | . | 17.8 |
| 382 | | . | . | . | . | . | V | . | . | . | . | . | . | . | . | . | . | . | 43.5 |

Fig. 9C

Y61 Heavy Chain CDR H2 Mutagenesis

| | | CDR H2 | | | | | | | | | | | | | | | | | |
|---|---|---|---|---|---|---|---|---|---|---|---|---|---|---|---|---|---|---|---|
| SEQ ID NO: | | 50 | 51 | 52 | 52A | 53 | 54 | 55 | 56 | 57 | 58 | 59 | 60 | 61 | 62 | 63 | 64 | 65 | $k_{off}$ ($x 10^5$) |
| 19 | Y61 | F | I | R | Y | D | G | S | N | K | Y | Y | A | D | S | V | K | G | |
| 383 | | . | . | . | . | . | F | . | . | . | . | . | . | . | . | . | . | . | 66.3 |
| 384 | | | . | . | . | . | . | . | S | . | . | . | . | . | . | . | . | . | 62.4 |
| 385 | | | . | . | . | . | . | . | Y | . | . | . | . | . | . | . | . | . | 39.0 |
| 386 | | | . | . | . | . | . | . | H | . | . | . | . | . | . | . | . | . | 42.0 |
| 387 | | | . | . | . | . | . | . | N | . | . | . | . | . | . | . | . | . | 38.5 |
| 388 | | | . | . | . | . | . | . | T | . | . | . | . | . | . | . | . | . | 23.5 |
| 389 | | | . | . | . | . | . | . | G | . | . | . | . | . | . | . | . | . | 27.2 |
| 390 | | | . | . | . | . | . | . | M | . | . | . | . | . | . | . | . | . | 38.3 |
| 391 | | | . | . | . | . | . | . | L | . | . | . | . | . | . | . | . | . | 26.4 |
| 392 | | | . | . | . | . | . | . | I | . | . | . | . | . | . | . | . | . | 16.9 |
| 393 | | . | . | . | . | . | . | . | P | . | . | . | . | . | . | . | . | . | 29.9 |
| 394 | | . | . | . | . | . | . | . | F | . | . | . | . | . | . | . | . | . | 34.5 |
| 395 | | . | . | . | . | . | . | . | . | . | E | . | . | . | . | . | . | . | 41.5 |
| 396 | | . | . | . | . | . | . | . | . | . | S | . | . | . | . | . | . | . | 94.1 |
| 397 | | . | . | . | . | . | . | . | . | . | Y | . | . | . | . | . | . | . | 31.0 |
| 398 | | . | . | . | . | . | . | . | . | . | N | . | . | . | . | . | . | . | 83.1 |
| 399 | | . | . | . | . | . | . | . | . | . | V | . | . | . | . | . | . | . | 52.4 |
| 400 | | . | . | . | . | . | . | . | . | . | L | . | . | . | . | . | . | . | 73.0 |
| 401 | | . | . | . | . | . | . | . | . | . | I | . | . | . | . | . | . | . | 65.7 |
| 402 | | . | . | . | . | . | . | . | . | . | P | . | . | . | . | . | . | . | 62.8 |
| 403 | | . | . | . | . | . | . | . | . | . | F | . | . | . | . | . | . | . | 79.4 |

Fig. 9D

Y61 Heavy Chain CDR H3 Mutagenesis

| | | CDR H3 | | | | | | |
|---|---|---|---|---|---|---|---|---|
| SEQ ID NO: | | 95 | 96 | 97 | 98 | 101 | 102 | $k_{off}$ ($x 10^5$) |
| 17 | Y61 | H | G | S | H | D | N | |
| 404 | | E | . | . | . | . | . | 231.5 |
| 405 | | S | . | . | . | . | . | 193.0 |
| 406 | | H | . | . | . | . | . | 28.7 |
| 407 | | K | . | . | . | . | . | 227.5 |
| 408 | | Q | . | . | . | . | . | 85.9 |
| 409 | | T | . | . | . | . | . | 202.0 |
| 410 | | A | . | . | . | . | . | 150.0 |
| 411 | | L | . | . | . | . | . | 147.5 |
| 412 | | P | . | . | . | . | . | 471.0 |
| 413 | | F | . | . | . | . | . | 514.0 |
| 414 | | . | D | . | . | . | . | 223.5 |
| 415 | | . | C | . | . | . | . | 24.2 |
| 416 | | . | H | . | . | . | . | 23.7 |
| 417 | | . | R | . | . | . | . | 96.2 |
| 418 | | . | T | . | . | . | . | 186.0 |
| 419 | | . | G | . | . | . | . | 39.7 |
| 420 | | . | V | . | . | . | . | 38.2 |
| 421 | | . | M | . | . | . | . | 204.5 |
| 422 | | . | L | . | . | . | . | 261.0 |
| 423 | | . | I | . | . | . | . | 207.5 |
| 424 | | . | P | . | . | . | . | 129.0 |
| 425 | | . | W | . | . | . | . | 197.0 |
| 426 | | . | . | D | . | . | . | 202.0 |
| 427 | | . | . | S | . | . | . | 37.5 |
| 428 | | . | . | Y | . | . | . | 273.0 |
| 429 | | . | . | H | . | . | . | 190.5 |
| 430 | | . | . | R | . | . | . | 224.0 |
| 431 | | . | . | N | . | . | . | 221.5 |
| 432 | | . | . | T | . | . | . | 58.8 |
| 433 | | . | . | G | . | . | . | 229.0 |
| 434 | | . | . | A | . | . | . | 143.0 |
| 435 | | . | . | I | . | . | . | 208.0 |
| 436 | | . | . | P | . | . | . | 300.0 |
| 437 | | . | . | W | . | . | . | 239.0 |
| 438 | | . | . | F | . | . | . | 180.5 |
| 439 | | . | . | . | H | . | . | 25.5 |
| 440 | | . | . | . | R | . | . | 34.0 |
| 441 | | . | . | . | T | . | . | 22.7 |
| 442 | | . | . | . | A | . | . | 67.3 |
| 443 | | . | . | . | V | . | . | 29.3 |
| 444 | | . | . | . | L | . | . | 59.8 |
| 445 | | . | . | . | I | . | . | 34.3 |
| 446 | | . | . | . | F | . | . | 68.8 |
| 447 | | . | . | . | . | D | . | 14.4 |
| 448 | | . | . | . | . | S | . | 44.9 |
| 449 | | . | . | . | . | Y | . | 465.0 |
| 450 | | . | . | . | . | H | . | 327.0 |
| 451 | | . | . | . | . | R | . | 110.0 |

Fig. 9E

Y61 Heavy Chain CDR H3 Mutagenesis

| | | CDR H3 | | | | | | |
|---|---|---|---|---|---|---|---|---|
| SEQ ID NO: | | 95 | 96 | 97 | 98 | 101 | 102 | $K_{off}$ (x $10^5$) |
| 17 | Y61 | H | G | S | H | D | N | |
| 452 | | | . | . | . | N | . | 223.0 |
| 453 | | | . | . | . | G | . | 375.0 |
| 454 | | | . | . | . | A | . | 106.5 |
| 455 | | | . | . | . | V | . | 163.0 |
| 456 | | | . | . | . | I | . | 162.5 |
| 457 | | | . | . | . | . | S | 32.5 |
| 458 | | | . | . | . | . | H | 18.0 |
| 459 | | | . | . | . | . | K | 40.5 |
| 460 | | | . | . | . | . | R | 57.5 |
| 461 | | | . | . | . | . | N | 40.3 |
| 462 | | | . | . | . | . | T | 33.3 |
| 463 | | | . | . | . | . | G | 69.2 |
| 464 | | | . | . | . | . | A | 38.2 |
| 465 | | | . | . | . | . | L | 95.6 |
| 466 | | | . | . | . | . | I | 99.6 |
| 467 | | | . | . | . | . | P | 181.5 |
| 468 | | | . | . | . | . | W | 23.5 |
| 469 | | | . | . | . | . | F | 31.8 |

Fig. 9F

Y61 Light Chain CDR L1 Mutagenesis

| | | CDR L1 | | | | | | | | | | | | | |
|---|---|---|---|---|---|---|---|---|---|---|---|---|---|---|---|
| SEQ ID NO: | | 24 | 25 | 26 | 27 | 27A | 27B | 28 | 29 | 30 | 31 | 32 | 33 | 34 | $-k_{off}$ (x $10^5$) |
| 22 | Y61 | S | G | G | R | S | N | I | G | S | N | T | V | K | |
| 470 | | . | . | . | . | . | . | . | . | D | . | . | . | . | 22.0 |
| 471 | | . | . | . | . | . | . | . | . | C | . | . | . | . | 18.6 |
| 472 | | . | . | . | . | . | . | . | . | S | . | . | . | . | 21.1 |
| 473 | | . | . | . | . | . | . | . | . | Y | . | . | . | . | 48.3 |
| 474 | | . | . | . | . | . | . | . | . | K | . | . | . | . | 34.6 |
| 475 | | . | . | . | . | . | . | . | . | R | . | . | . | . | 18.2 |
| 476 | | . | . | . | . | . | . | . | . | N | . | . | . | . | 16.6 |
| 477 | | . | . | . | . | . | . | . | . | T | . | . | . | . | 22.6 |
| 478 | | . | . | . | . | . | . | . | . | P | . | . | . | . | 25.0 |
| 479 | | . | . | . | . | . | . | . | . | . | D | . | . | . | 58.0 |
| 480 | | . | . | . | . | . | . | . | . | . | E | . | . | . | 38.4 |
| 481 | | . | . | . | . | . | . | . | . | . | S | . | . | . | 39.2 |
| 482 | | . | . | . | . | . | . | . | . | . | Y | . | . | . | 35.7 |
| 483 | | . | . | . | . | . | . | . | . | . | H | . | . | . | 31.5 |
| 484 | | . | . | . | . | . | . | . | . | . | K | . | . | . | 33.1 |
| 485 | | . | . | . | . | . | . | . | . | . | N | . | . | . | 22.9 |
| 486 | | . | . | . | . | . | . | . | . | . | Q | . | . | . | 29.2 |
| 487 | | . | . | . | . | . | . | . | . | . | T | . | . | . | 30.9 |
| 488 | | . | . | . | . | . | . | . | . | . | G | . | . | . | 36.6 |
| 489 | | . | . | . | . | . | . | . | . | . | M | . | . | . | 17.4 |
| 490 | | . | . | . | . | . | . | . | . | . | I | | . | . | 9.7 |
| 491 | | . | . | . | . | . | . | . | . | . | . | D | . | . | 25.2 |
| 492 | | . | . | . | . | . | . | . | . | . | . | C | . | . | 381.5 |
| 493 | | . | . | . | . | . | . | . | . | . | . | S | . | . | 191.0 |
| 494 | | . | . | . | . | . | . | . | . | . | . | Y | . | . | 21.3 |
| 495 | | . | . | . | . | . | . | . | . | . | . | H | . | . | 26.0 |
| 496 | | . | . | . | . | . | . | . | . | . | . | K | . | . | 31.8 |
| 497 | | . | . | . | . | . | . | . | . | . | . | R | . | . | 690.0 |
| 498 | | . | . | . | . | . | . | . | . | . | . | N | . | . | 196.5 |
| 499 | | . | . | . | . | . | . | . | . | . | . | Q | . | . | 247.0 |
| 500 | | . | . | . | . | . | . | . | . | . | . | T | . | . | 24.1 |
| 501 | | . | . | . | . | . | . | . | . | . | . | A | . | . | 190.5 |
| 502 | | . | . | . | . | . | . | . | . | . | . | V | . | . | 164.5 |
| 503 | | . | . | . | . | . | . | . | . | . | . | L | . | . | 215.5 |
| 504 | | . | . | . | . | . | . | . | . | . | . | I | . | . | 154.0 |
| 505 | | . | . | . | . | . | . | . | . | . | . | P | . | . | 42.4 |

Y61 Mutagenesis: L30

Y61 Mutagenesis: L31

Y61 Mutagenesis: L32

Fig. 9G

Y 61 Light Chain CDR L2 Mutagenesis

| | | CDR L2 | | | | | | | |
|---|---|---|---|---|---|---|---|---|---|
| SEQ ID NO: | | 50 | 51 | 52 | 53 | 54 | 55 | 56 | k off (x $10^5$) |
| 20 | Y61 | G | N | D | Q | R | P | S | |
| 506 | | D | . | . | . | . | . | . | 34.8 |
| 507 | | E | . | . | . | . | . | . | 61.7 |
| 508 | | C | . | . | . | . | . | . | 46.7 |
| 509 | | S | . | . | . | . | . | . | 28.6 |
| 510 | | Y | . | . | . | . | . | . | 17.4 |
| 511 | | H | . | . | . | . | . | . | 76.1 |
| 512 | | K | . | . | . | . | . | . | 242.5 |
| 513 | | R | . | . | . | . | . | . | 44.4 |
| 514 | | N | . | . | . | . | . | . | 30.5 |
| 515 | | Q | . | . | . | . | . | . | 34.8 |
| 516 | | T | . | . | . | . | . | . | 27.2 |
| 517 | | G | . | . | . | . | . | . | 21.5 |
| 518 | | A | . | . | . | . | . | . | 37.2 |
| 519 | | V | . | . | . | . | . | . | 38.5 |
| 520 | | M | . | . | . | . | . | . | 95.3 |
| 521 | | L | . | . | . | . | . | . | 61.6 |
| 522 | | I | . | . | . | . | . | . | 120.5 |
| 523 | | P | . | . | . | . | . | . | 41.0 |
| 524 | | W | . | . | . | . | . | . | 38.2 |
| 525 | | F | . | . | . | . | . | . | 3,476.7 |
| 526 | | . | . | . | S | . | . | . | 86.6 |
| 527 | | . | . | . | Y | . | . | . | 73.3 |
| 528 | | . | . | . | R | . | . | . | 61.4 |
| 529 | | . | . | . | Q | . | . | . | 29.7 |
| 530 | | . | . | . | T | . | . | . | 83.4 |
| 531 | | . | . | . | A | . | . | . | 55.4 |
| 532 | | . | . | . | I | . | . | . | 85.5 |
| 533 | | . | . | . | P | . | . | . | 97.4 |

Fig. 9H

Y61 Light Chain CDR L3 Mutagenesis

| | | CDR L3 | | | | | | | | | | | | |
|---|---|---|---|---|---|---|---|---|---|---|---|---|---|---|
| SEQ ID NO: | | 89 | 90 | 91 | 92 | 93 | 94 | 95 | 95A | 95B | 95C | 96 | 97 | $k_{off}$ (x $10^5$) |
| 18 | Y61 | Q | S | Y | D | R | G | T | H | P | A | L | L | |
| 534 | | . | . | . | D | . | . | . | . | . | . | . | . | 25.9 |
| 535 | | . | . | . | C | . | . | . | . | . | . | . | . | 45.3 |
| 536 | | . | . | . | S | . | . | . | . | . | . | . | . | 30.7 |
| 537 | | . | . | . | Y | . | . | . | . | . | . | . | . | 51.1 |
| 538 | | . | . | . | N | . | . | . | . | . | . | . | . | 34.7 |
| 539 | | . | . | . | Q | . | . | . | . | . | . | . | . | 42.7 |
| 540 | | . | . | . | T | . | . | . | . | . | . | . | . | 40.8 |
| 541 | | . | . | . | G | . | . | . | . | . | . | . | . | 34.9 |
| 542 | | . | . | . | A | . | . | . | . | . | . | . | . | 35.7 |
| 543 | | . | . | . | L | . | . | . | . | . | . | . | . | 72.8 |
| 544 | | . | . | . | I | . | . | . | . | . | . | . | . | 61.8 |
| 545 | | . | . | . | W | . | . | . | . | . | . | . | . | 72.0 |
| 546 | | . | . | . | F | . | . | . | . | . | . | . | . | 44.9 |
| 547 | | . | . | . | . | D | . | . | . | . | . | . | . | 34.3 |
| 548 | | . | . | . | . | C | . | . | . | . | . | . | . | 32.0 |
| 549 | | . | . | . | . | S | . | . | . | . | . | . | . | 34.1 |
| 550 | | . | . | . | . | Y | . | . | . | . | . | . | . | 33.5 |
| 551 | | . | . | . | . | R | . | . | . | . | . | . | . | 19.9 |
| 552 | | . | . | . | . | N | . | . | . | . | . | . | . | 31.6 |
| 553 | | . | . | . | . | Q | . | . | . | . | . | . | . | 30.0 |
| 554 | | . | . | . | . | T | . | . | . | . | . | . | . | 31.6 |
| 555 | | . | . | . | . | G | . | . | . | . | . | . | . | 39.2 |
| 556 | | . | . | . | . | A | . | . | . | . | . | . | . | 31.0 |
| 557 | | . | . | . | . | V | . | . | . | . | . | . | . | 26.9 |
| 558 | | . | . | . | . | M | . | . | . | . | . | . | . | 27.5 |
| 559 | | . | . | . | . | L | . | . | . | . | . | . | . | 30.0 |
| 560 | | . | . | . | . | I | . | . | . | . | . | . | . | 29.5 |
| 561 | | . | . | . | . | P | . | . | . | . | . | . | . | 34.9 |
| 562 | | . | . | . | . | W | | . | . | . | . | . | . | 34.9 |
| 563 | | . | . | . | . | . | D | . | . | . | . | . | . | 25.3 |
| 564 | | . | . | . | . | . | C | . | . | . | . | . | . | 52.0 |
| 565 | | . | . | . | . | . | S | . | . | . | . | . | . | 28.7 |
| 566 | | . | . | . | . | . | Y | . | . | . | . | . | . | 13.1 |
| 567 | | . | . | . | . | . | H | . | . | . | . | . | . | 18.7 |
| 568 | | . | . | . | . | . | R | . | . | . | . | . | . | 23.1 |
| 569 | | . | . | . | . | . | N | . | . | . | . | . | . | 13.7 |
| 570 | | . | . | . | . | . | Q | . | . | . | . | . | . | 25.0 |
| 571 | | . | . | . | . | . | T | . | . | . | . | . | . | 30.5 |
| 572 | | . | . | . | . | . | G | . | . | . | . | . | . | 25.6 |
| 573 | | . | . | . | . | . | A | . | . | . | . | . | . | 52.6 |
| 574 | | . | . | . | . | . | V | . | . | . | . | . | . | 35.1 |
| 575 | | . | . | . | . | . | L | . | . | . | . | . | . | 24.4 |
| 576 | | . | . | . | . | . | I | . | . | . | . | . | . | 27.6 |
| 577 | | . | . | . | . | . | P | . | . | . | . | . | . | 33.2 |
| 578 | | . | . | . | . | . | W | . | . | . | . | . | . | 29.3 |
| 579 | | . | . | . | . | . | F | . | . | . | . | . | . | 23.6 |

METHODS OF TREATING PSORIASIS BY ADMINISTRATION OF ANTIBODIES TO THE P40 SUBUNIT OF IL-12 AND/OR IL-23

RELATED APPLICATIONS

This application claims the benefit of U.S. Provisional Application No. 61/069,840, filed on Mar. 18, 2008; U.S. Provisional Application No. 61/095,275, filed on Sep. 8, 2008; and U.S. Provisional Application No. 61/207,904, filed on Feb. 18, 2009, the entire contents of each of which are incorporated herein by reference.

SUBMISSION ON COMPACT DISC

This application incorporates by reference the ASCII text file identified by the name 2009-09-02 117813-32903 ST25.txt, containing 223 KB of data, created on Sep. 28, 2009 and filed in computer-readable format (CRF).

BACKGROUND OF THE INVENTION

Psoriasis is a T cell-mediated inflammatory disease that is considered to be one of the most common autoimmune diseases, affecting approximately 2% to 3% of adults, though the global prevalence varies widely (Stem R. S., et al., *J Investig Dermatol Symp Proc* 2004, 9: 136-39; Davidson A and Diamond B. *N Engl J Med* 2001, 345: 340-50; Langley R. G. B., et al., *Ann Rheum Dis* 2005, 64(Suppl II): ii18-23). Psoriasis has a major impact on quality of life (de Korte J, et al., *J Investig Dermatol Symp Proc* 2004, 9: 140-7; Krueger G, et al., *Arch Dermatol* 2001, 137: 280-4; Finlay A Y and Coles E C, *Br J Dermatol* 1995, 132: 236-44) and is associated with a number of psychological and psychosocial problems (Kimball A B, et al., *Am J Clin Dermatol* 2005, 6: 383-92; Russo P A, et al., *Australas J Dermatol* 2004, 45: 155-9). Many traditional psoriasis therapies have toxic adverse effects; therefore, their long-term use is limited (Lebwohl M. and Ali S., *J Am Acad Dermatol* 2001, 45: 487-98; Lebwohl M. and Ali S., *J Am Acad Dermatol* 2001, 45: 649-61). In addition, many patients with psoriasis are dissatisfied with traditional therapies (Stem R S, et al., *J Investig Dermatol Symp Proc* 2004, 9: 136-39; Finlay A Y and Ortonne J P, *J Cutan Med Surg* 2004, 8: 310-20); thus, there is a clear need for therapies that are safer and easier to use and that can be prescribed on a long-term basis.

Interleukin-12 (IL-12) and the related cytokine IL-23 are members of the IL-12 superfamily of cytokines that share a common p40 subunit (Anderson E J R, et al., *Springer Semin Immunopathol* 2006, 27: 425-42). Both cytokines contribute to the development of the type 1T helper cell (Th1) immune response in psoriasis, but each has a unique role (Rosmarin D and Strober B E, *J Drugs Dermatol* 2005, 4: 318-25; Hong K, et al., *J Immunol* 1999, 162: 7480-91; Yawalkar N, et al., *J Invest Dermatol* 1998, 111: 1053-57). IL-12 primarily stimulates differentiation of Th1 cells and subsequent secretion of interferon-gamma, whereas IL-23 preferentially stimulates differentiation of naïve T cells into effector T helper cells (Th17) that secrete IL-17, a proinflammatory mediator Rosmarin D and Strober B E, *J Drugs Dermatol* 2005, 4: 318-25; Harrington Le, et al., *Nature Immunol* 2005, 6: 1123-32; Park H, et al. *Nature Immunol* 2005, 6: 1132-41). The overexpression of IL-12 p40 and IL-23 p40 messenger RNA in psoriatic skin lesions suggests that the inhibition of IL-12 and IL-23 with a neutralizing antibody to the IL-12/23 p40 subunit protein may offer an effective therapeutic approach for the treatment of psoriasis (Yawalkar N, et al., *J Invest Dermatol* 1998, 111: 1053-57; Lee E, et al., *J Exp Med* 2004, 199: 125-30; Shaker O G, et al., *Clin Biochem* 2006, 39: 119-25; Piskin G, et al., *J Immunol* 2006, 176: 1908-15). Such therapeutic approaches for the treatment of psoriasis are clearly needed in the art.

SUMMARY OF THE INVENTION

The present invention provides methods and compositions for treating psoriasis, e.g., chronic psoriasis, using an antibody, or antigen-binding portion thereof, that binds human IL-12 and/or human IL-23.

In one aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject maintains at least a PASI 75 response for a first extended period following initial administration of the antibody, or antigen-binding portion thereof, wherein the subject exhibits a loss of response following discontinuation of administration of the antibody, or antigen-binding portion thereof, and wherein the subject maintains at least a PASI 75 response for a second extended period following re-administration of the antibody, or antigen-binding portion thereof, thereby treating psoriasis in the subject.

In one embodiment, the first extended period is at least about 4, 5, 6, 7, 8, 9, 10, 11, 12, 13 or 14 weeks, and preferably 12 weeks.

In one embodiment, administration of the antibody is discontinued for at least about 4, 5, 6, 7, 8, 9, 10, 11, 12, 13 or 14 weeks, and preferably 12 weeks.

In one embodiment, the second extended period is at least about 4, 5, 6, 7, 8, 9, 10, 11, 12, 13 or 14 weeks, and preferably 12 weeks.

In one embodiment the antibody, or antigen-binding portion thereof, is administered biweekly. In one embodiment, the antibody, or antigen-binding portion thereof, is administered weekly. In one embodiment, the antibody, or antigen-binding portion thereof, is administered in a single dose.

In one embodiment, the antibody, or antigen-binding portion thereof, is administered in a dose of about 100 mg, 110 mg, 120 mg, 130 mg, 140 mg, 150 mg, 160 mg, 170 mg, 180 mg, 190 mg, 200 mg, 210 or 220 mg.

In one embodiment, the psoriasis is chronic psoriasis. In one embodiment, the psoriasis is plaque psoriasis, e.g., chronic plaque psoriasis. In another embodiment, the psoriasis is chronic psoriasis, e.g., chronic plaque psoriasis. In yet another embodiment, the psoriasis is moderate to severe psoriasis, e.g., moderate to severe plaque psoriasis, moderate to severe chronic psoriasis or moderate to severe chronic plaque psoriasis. In one embodiment, the subject has had a clinical diagnosis of psoriasis for at least 6 months. In another embodiment, the subject has had stable plaque psoriasis for at least 2 months.

In another aspect, the invention provides a method of treating psoriasis in a subject comprising administering to the subject a single dose of an antibody, or antigen-binding portion thereof, which is capable of binding to an epitope of the p40 subunit of IL-12 and/or IL-23, wherein at least one pharmacokinetic characteristic selected from the group consisting of a half-life of at least about 3 days, a $T_{max}$ of less than or equal to about 4 days, and a bioavailability of at least about 40% is achieved following administration of the antibody, or antigen-binding portion thereof.

In various embodiments, a half life of at least about 2 days, 3 days, 4 days, 5 days, 6 days, 7 days, 8 days, 9 days or 10 days is achieved.

In various embodiments, a $T_{max}$ of less than or equal to about 1 day, 2 days, 3 days, 4 days, 5 days, 6 days or more is achieved.

In various embodiments, a bioavailability of at least about 0.1%, 1%, 5%, 10%, 20%, 30%, 40%, 50%, 60%, 70%, 80% or more is achieved.

In one embodiment, the antibody is administered via intravenous injection.

In one embodiment, the antibody is administered via subcutaneous injection.

In one embodiment, the single dose is between about 0.1 and about 5.0 mg/kg (e.g., about 0.1 to about 1.0 mg/kg, about 0.1 to about 2.0 mg/kg, about 0.1 to about 3.0 mg/kg, about 0.1 to about 4.0 mg/kg, about 1.0 to about 2.0 mg/kg, about 1.0 to about 3.0 mg/kg. about 1.0 to about 4.0 mg/kg or about 1.0 to about 5.0 mg/kg) of the antibody, or antigen-binding portion thereof.

In another aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject maintains at least a PASI 75 response for a first extended period following initial administration of the antibody, or antigen-binding portion thereof, wherein the subject exhibits a loss of response following discontinuation of administration of the antibody, or antigen-binding portion thereof, and wherein the subject maintains at least a PASI 50 response for a second extended period following re-administration of the antibody, or antigen-binding portion thereof, thereby treating psoriasis in the subject.

In one embodiment, the first extended period is at least about 4, 5, 6, 7, 8, 9, 10, 11, 12, 13 or 14 weeks, and preferably 12 weeks.

In one embodiment, administration of the antibody is discontinued for at least about 4, 5, 6, 7, 8, 9, 10, 11, 12, 13 or 14 weeks, and preferably 12 weeks.

In one embodiment, the second extended period is at least about 4, 5, 6, 7, 8, 9, 10, 11, 12, 13 or 14 weeks, and preferably 12 weeks.

In one embodiment, the antibody, or antigen-binding portion thereof, is administered biweekly. In one embodiment, the antibody, or antigen-binding portion thereof, is administered weekly.

In one embodiment, the antibody, or antigen-binding portion thereof, is administered in a single dose. In one embodiment, the antibody, or antigen-binding portion thereof, is administered in a dose of about 100 mg, 110 mg, 120 mg, 130 mg, 140 mg, 150 mg, 160 mg, 170 mg, 180 mg, 190 mg or 200 mg.

In one embodiment, the psoriasis is chronic psoriasis.

In another aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject maintains at least a PASI 75 response for a first extended period following initial administration of the antibody, or antigen-binding portion thereof, wherein the subject exhibits a loss of response following discontinuation of administration of the antibody, or antigen-binding portion thereof, and wherein the subject maintains a clear or minimal PGA score for a second extended period following re-administration of the antibody, or antigen-binding portion thereof, thereby treating psoriasis in the subject.

In one embodiment, the first extended period is at least about 4, 5, 6, 7, 8, 9, 10, 11, 12, 13 or 14 weeks, and preferably 12 weeks.

In one embodiment, administration of the antibody is discontinued for at least about 4, 5, 6, 7, 8, 9, 10, 11, 12, 13 or 14 weeks, and preferably 12 weeks.

In one embodiment, the second extended period is at least about 4, 5, 6, 7, 8, 9, 10, 11, 12, 13 or 14 weeks, and preferably 12 weeks.

In one embodiment, the antibody, or antigen-binding portion thereof, is administered biweekly. In one embodiment, the antibody, or antigen-binding portion thereof, is administered weekly.

In one embodiment, the antibody, or antigen-binding portion thereof, is administered in a single dose. In one embodiment, the antibody, or antigen-binding portion thereof, is administered in a dose of about 100 mg, 110 mg, 120 mg, 130 mg, 140 mg, 150 mg, 160 mg, 170 mg, 180 mg, 190 mg or 200 mg.

In one embodiment, the psoriasis is chronic psoriasis.

In yet another aspect, the invention provides a method of treating psoriasis in a subject comprising administering to the subject a single dose of an antibody, or antigen-binding portion thereof, which is capable of binding to an epitope of the p40 subunit of IL-12 and/or IL-23, wherein at least one pharmacokinetic characteristic selected from the group consisting of a maximum serum concentration ($C_{max}$) of between about 0.15 and about 150 μg/mL (e.g., between about 0.2 and about 140 μg/mL, between about 0.5 and about 125 μg/mL, between about 1.0 and about 100 μg/mL, between about 10 and about 90 μg/mL, between about 25 and about 75 μg/mL, between about 35 and about 60 μg/mL and between about 40 and about 50 μg/mL) and an area under the serum concentration-time curve (AUC) of between about 80 and about 13,000 μg×hr/mL (e.g., between about 100 and about 12,000 μg×hr/mL, between about 150 and about 10,000 μg×hr/mL, between about 200 and about 8,000 μg×hr/mL, between about 400 and about 6,000 μg×hr/mL, between about 800 and about 4,000 μg×hr/mL, between about 1000 and about 2,000 μg×hr/mL, between about 145 and about 13,000 μg×hr/mL, and between about 80 and about 5,000 μg×hr/mL) is achieved following administration of the antibody, or antigen-binding portion thereof.

In one embodiment, the antibody is administered via intravenous injection.

In a preferred embodiment, the $C_{max}$ is between about 1 and about 150 μg/mL (e.g., between about 2 and about 125 μg×hr/mL, about 5 and about 100 μg×hr/mL, about 10 and about 80 μg×hr/mL, about 20 and about 60 μg×hr/mL, about 30 and about 50 μg×hr/mL, about 1 and about 20 μg×hr/mL, about 20 and about 300 μg×hr/mL, and about 140 and about 150 μg×hr/mL).

In a preferred embodiment, the AUC is between about 145 and about 13,000 μg×hr/mL (e.g., between about 200 and about 11,000 μg×hr/mL, about 500 and about 10,000 μg×hr/mL, about 1000 and about 5,000 μg×hr/mL, about 2000 and about 4000 μg×hr/mL, about 145 and about 165 μg×hr/mL, about 500 and about 600 μg×hr/mL, about 2000 and about 3000 μg×hr/mL and about 12000 and about 13000 μg×hr/mL).

In one embodiment, the antibody is administered via subcutaneous injection.

In a preferred embodiment, the $C_{max}$ is between about 0.15 and about 20 μg/mL (e.g., between about 0.25 and about 15 μg/mL, about 0.5 and about 13 μg/mL, about 1 and about 10 μg/mL, about 2 and about 8 μg/mL, about 0.15 and about 0.3

μg/mL, about 0.5 and about 2 μg/mL, about 2 and about 4 μg/mL, and about 10 and about 15 μg/mL).

In a preferred embodiment, the AUC is between about 80 and about 5000 μg×hr/mL (e.g., between about 200 and 3000 μg×hr/mL, between about 400 and 2000 μg×hr/mL, between about 500 and 1500 μg×hr/mL, between about 4000 and 5000 μg×hr/mL, between about 80 and 90 μg×hr/mL, and between about 200 and 300 μg×hr/mL).

In one embodiment, the single dose is between about 0.1 and about 5.0 mg/kg (e.g., about 0.1 to about 1.0 mg/kg, about 0.1 to about 2.0 mg/kg, about 0.1 to about 3.0 mg/kg, about 0.1 to about 4.0 mg/kg, about 1.0 to about 2.0 mg/kg, about 1.0 to about 3.0 mg/kg. about 1.0 to about 4.0 mg/kg or about 1.0 to about 5.0 mg/kg) of the antibody, or antigen-binding portion thereof.

In another aspect, the invention provides a method of treating psoriasis in a subject comprising administering to the subject a single dose of an antibody, or antigen-binding portion thereof, which is capable of binding to an epitope of the p40 subunit of IL-12 and/or IL-23, wherein at least one pharmacokinetic characteristic selected from the group consisting of a clearance (CL) of between about 30 and about 600 mL/hr (e.g., between about 50 and about 500 mL/hr, between about 75 and about 400 mL/hr, between about 100 and about 300 mL/hr, between about 150 and about 250 mL/hr, between about 30 and about 40 mL/hr, between about 40 and about 60 mL/hr and between about 500 and about 600 mL/hr), and a volume of distribution (Vz) of between about 8 and about 11 L (e.g., between about 8 and about 10 L, between about 8 and about 9 L, between about 9 and about 10 L, between about 10 and about 11 L and between about 8.5 and 9.5 L) is achieved following intravenous administration of the antibody, or antigen-binding portion thereof.

In a related aspect, the invention provides a method of treating psoriasis in a subject comprising administering to the subject a single dose of an antibody, or antigen-binding portion thereof, which is capable of binding to an epitope of the p40 subunit of IL-12 and/or IL-23, wherein at least one pharmacokinetic characteristic selected from the group consisting of an apparent clearance (CL/F) of between about 90 and about 250 mL/hr (e.g., between about 100 and about 225 mL/hr, between about 125 and about 200 mL/hr, between about 140 and about 180 mL/hr, between about 90 and about 100 mL/hr, between about 150 and about 200 mL/hr, and between about 200 and about 250 mL/hr) and an apparent volume of distribution (V/F) of between about 23 and about 67 L (e.g., between about 25 and about 60 L, between about 30 and about 55 L, between about 35 and about 50 L, between about 40 and about 45 L, between about 23 and about 35 L and between about 60 and about 70 L) is achieved following subcutaneous administration of the antibody, or antigen-binding portion thereof.

In one embodiment, the single dose is between about 0.1 and about 5.0 mg/kg (e.g., about 0.1 to about 1.0 mg/kg, about 0.1 to about 2.0 mg/kg, about 0.1 to about 3.0 mg/kg, about 0.1 to about 4.0 mg/kg, about 1.0 to about 2.0 mg/kg, about 1.0 to about 3.0 mg/kg. about 1.0 to about 4.0 mg/kg or about 1.0 to about 5.0 mg/kg) of the antibody, or antigen-binding portion thereof.

In another aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject exhibits a PASI 75 response following initial administration of the antibody, or antigen-binding portion thereof, wherein the subject exhibits a loss of response following discontinuation of administration of the antibody, or antigen-binding portion thereof, and wherein the subject exhibits at least a PASI 75 response by about 25 days following re-administration of the antibody, or antigen-binding portion thereof, thereby treating psoriasis in the subject.

In one embodiment, the subject exhibits at least a PASI 75 response by about 50 days following re-administration of the antibody, or antigen-binding portion thereof. In one embodiment, the subject exhibits at least a PASI 75 response by about 60 days following re-administration of the antibody, or antigen-binding portion thereof. In one embodiment, the subject exhibits at least a PASI 75 response by about 30, 35, 40, 45, 50, 60, 65, 70, 75, 80, 85, 90 or more days following re-administration of the antibody, or antigen-binding portion thereof.

In one embodiment, initial administration of the antibody is for at least about 12 weeks.

In one embodiment, administration of the antibody is discontinued for at least about 4, 5, 6, 7, 8, 9, 10, 11 or 12 weeks.

In one embodiment the antibody, or antigen-binding portion thereof, is administered biweekly. In one embodiment, the antibody, or antigen-binding portion thereof, is administered weekly. In one embodiment, the antibody, or antigen-binding portion thereof, is administered in a single dose.

In one embodiment, the antibody, or antigen-binding portion thereof, is administered in a dose of about 100 mg, 110 mg, 120 mg, 130 mg, 140 mg, 150 mg, 160 mg, 170 mg, 180 mg, 190 mg or 200 mg.

In one embodiment, the psoriasis is chronic psoriasis.

In yet another aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject exhibits a PASI 75 response following initial administration of the antibody, or antigen-binding portion thereof, wherein the subject exhibits a loss of response by about 60 days following discontinuation of administration of the antibody, or antigen-binding portion thereof, and wherein the subject achieves a PASI 75 response following re-administration of the antibody, or antigen-binding portion thereof, thereby treating psoriasis in the subject.

In one embodiment, the subject exhibits a loss of response by about 120 days following discontinuation of administration of the antibody, or antigen-binding portion thereof. In one embodiment, the subject exhibits a loss of response by about 180 days following discontinuation of administration of the antibody, or antigen-binding portion thereof. In one embodiment, the subject exhibits a loss of response by about 50, 55, 60, 65, 70, 75, 80, 85, 90, 95, 100, 110, 120, 130, 140, 150, 160, 170, 180, 190, 200 or more days following discontinuation of administration of the antibody, or antigen-binding portion thereof.

In one embodiment, initial administration of the antibody is for at least about 12 weeks.

In one embodiment the antibody, or antigen-binding portion thereof, is administered biweekly. In one embodiment, the antibody, or antigen-binding portion thereof, is administered weekly. In one embodiment, the antibody, or antigen-binding portion thereof, is administered in a single dose.

In one embodiment, the antibody, or antigen-binding portion thereof, is administered in a dose of about 100 mg, 110 mg, 120 mg, 130 mg, 140 mg, 150 mg, 160 mg, 170 mg, 180 mg, 190 mg or 200 mg.

In one embodiment, the psoriasis is chronic psoriasis.

In another aspect, the invention provides a method of treating psoriasis in a subject comprising administering to a subject a biweekly weekly or single dose of an antibody, or antigen-binding portion thereof, directed against human an IL-12 and/or human IL-23. In a related aspect, the invention provides a method of treating psoriasis in a subject comprising the steps of: (i) selecting a subject who is suffering from chronic psoriasis; and (ii) administering to the subject an antibody, or antigen-binding portion thereof, which is capable of binding to an epitope of the p40 subunit of IL-12 and/or IL-23; thereby treating chronic psoriasis in the subject.

In another related aspect, the invention provides a method of treating psoriasis in a subject comprising administering to the subject an antibody, or antigen-binding portion thereof, which is capable of binding to an epitope of the p40 subunit of IL-12 and/or IL-23, wherein the subject maintains at least a PASI 50 response, at least a PASI 75 response or at least a PASI 90 response for an extended period following discontinuation of administration of the antibody, or antigen-binding portion thereof, thereby treating psoriasis in the subject.

In yet another aspect, the invention provides a method of treating psoriasis in a subject comprising administering to the subject an antibody, or antigen-binding portion thereof, which is capable of binding to an epitope of the p40 subunit of IL-12 and/or IL-23 to the subject, wherein the subject maintains a clear or minimal PGA rating for an extended period following initial administration of the antibody, or antigen-binding portion thereof, thereby treating psoriasis in the subject.

In a still further aspect, the invention provides a method of treating psoriasis in a subject comprising administering to the subject an antibody, or antigen-binding portion thereof, which is capable of binding to an epitope of the p40 subunit of IL-12 and/or IL-23 to the subject, wherein the subject exhibits an improved PASI score by about 8 weeks following initial administration of the antibody, or antigen-binding portion thereof, thereby treating psoriasis in the subject. In one embodiment, the subject exhibits an improved PASI score by about 7 weeks, about 6 weeks, about 5 weeks, about 4 weeks, about 3 weeks, about 2 weeks or about 1 week following initial administration of the antibody, or antigen binding portion thereof.

In one embodiment, the extended period following discontinuation of administration of the antibody is at least about 12 weeks. In one embodiment, the extended period is at least about 12, 13, 14, 15, 16, 17, 18, 19, 20, 21, 22, 23 or 24 weeks. In one embodiment, the antibody is administered for at least about 12 weeks.

In one embodiment, the antibody, or antigen-binding portion thereof, used in the methods of the invention is capable of binding to an epitope of the p40 subunit of IL-12.

In another embodiment, the antibody, or antigen-binding portion thereof, is capable of binding to the epitope of the p40 subunit when the p40 subunit is bound to the p35 subunit of IL-12. In yet another embodiment, the antibody, or antigen-binding portion thereof, is capable of binding to the epitope of the p40 subunit when the p40 subunit is bound to a p19 subunit. In one embodiment, the antibody, or antigen-binding portion thereof, is capable of binding to the epitope of the p40 subunit when the p40 subunit is bound to the p35 subunit of IL-12 and when the p40 subunit is bound to a p19 subunit.

In one embodiment, the antibody, or antigen binding portion thereof, binds to an epitope of the p40 subunit of IL-12 to which an antibody selected from the group consisting of Y61 and J695 binds.

In another embodiment, the antibody is further capable of binding to a first heterodimer and is also capable of binding to a second heterodimer, wherein the first heterodimer comprises the p40 subunit of Il-12 and the p35 subunit of Il-12, and wherein the second heterodimer comprises the p40 subunit of IL-12 and a p19 subunit.

In a further embodiment, the antibody neutralizes the activity of the first heterodimer. In another embodiment, the antibody neutralizes the activity of the second heterodimer. In yet another embodiment, the antibody neutralizes the activity of the first heterodimer and the second heterodimer.

In a further embodiment, the antibody, or antigen binding portion thereof, used in the methods of the invention inhibits phytohemagglutinin blast proliferation in an in vitro PHA assay with an $IC_{50}$ of $1\times10^{-9}$ M or less, or which inhibits human IFNγ production with an $IC_{50}$ of $1\times10^{-10}$ M or less.

In one embodiment, the antibody, or antigen binding portion thereof, used in the methods of the invention dissociates from the p40 subunit of IL-12 with a $K_d$ of $1\times10^{-10}$ M or less or a $k_{off}$ rate constant of $1\times10^{-3}$ $s^{-1}$ or less, as determined by surface plasmon resonance.

In one embodiment, the isolated antibody, or antigen binding portion thereof, used in the methods of the invention is a chimeric antibody, a humanized antibody or a human antibody.

In another embodiment, the antibody, or antigen binding portion thereof, used in the methods of the invention has a heavy chain CDR3 comprising the amino acid sequence of SEQ ID NO: 25 and a light chain CDR3 comprising the amino acid sequence of SEQ ID NO: 26;

In a further embodiment, the antibody, or antigen binding portion thereof, used in the methods of the invention has a heavy chain CDR2 comprising the amino acid sequence of SEQ ID NO: 27 and a light chain CDR2 comprising the amino acid sequence of SEQ ID NO: 28.

In one embodiment, the antibody, or antigen binding portion thereof, used in the methods of the invention has a heavy chain CDR1 comprising the amino acid sequence of SEQ ID NO: 29 and a light chain CDR1 comprising the amino acid sequence of SEQ ID NO: 30.

In another embodiment, the antibody, or antigen-binding portion thereof, used in the methods of the invention is capable of binding to an interleukin comprising a p40 subunit. In one embodiment, the interleukin comprises a p40 subunit and a p35 subunit, e.g., the interleukin is IL-12. In another embodiment, the interleukin comprises a p40 subunit and a p19 subunit. In yet another embodiment, the antibody, or antigen binding portion thereof, neutralizes the activity of the interleukin.

In one embodiment, the antibody, or antigen binding portion thereof, binds to an epitope of the p40 subunit.

In one embodiment, the antibody, or antigen-binding portion thereof, is administered to a subject in a pharmaceutical composition comprising the antibody, or antigen binding portion thereof, and a pharmaceutically acceptable carrier. The pharmaceutical composition may also comprise an additional agent, such as a therapeutic agent, e.g., budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

In another embodiment, the therapeutic agent in the pharmaceutical composition administered to the subject may be selected from the group consisting of anti-TNF antibodies and antibody fragments thereof, TNFR-Ig constructs, TACE inhibitors, PDE4 inhibitors, cortico steroids, budeno side, dexamethasone, sulfasalazine, 5-aminosalicylic acid, olsalazine, IL-1β converting enzyme inhibitors, IL-1ra, tyrosine kinase inhibitors, 6-mercaptopurines and IL-11.

In another embodiment, the therapeutic agent may be selected from the group consisting of corticosteroids, prednisolone, methylprednisolone, azathioprine, cyclophosphamide, cyclosporine, methotrexate, 4-aminopyridine, tizanidine, interferon-β1a, interferon-β1b, Copolymer 1, hyperbaric oxygen, intravenous immunoglobulin, clabribine, antibodies or agonists of TNF, LT, IL-1, IL-2, IL-6, IL-7, IL-8, IL-15, IL-16, IL-18, EMAP-II, GM-CSF, FGF, PDGF, antibodies to CD2, CD3, CD4, CD8, CD25, CD28, CD30, CD40, CD45, CD69, CD80, CD86, CD90 or their ligands, methotrexate, cyclosporine, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38 or MAP kinase inhibitors, IL-1β converting enzyme inhibitors, TACE inhibitors, T-cell signalling inhibitors, kinase inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, sIL-13R, anti-P7s, p-selectin glycoprotein ligand (PSGL), antiinflammatory cytokines, IL-4, IL-10, IL-13 and TGFβ.

In one embodiment, the antibody, or antigen-binding portion thereof, used in the methods of the invention binds to human IL-12 and/or human IL-23 and dissociates from human IL-12 and/or human IL-23, respectively, with a $K_d$ of $1\times10^{-10}$ M or less and a $k_{off}$ rate constant of $1\times10^{-3}$ $s^{-1}$ or less, as determined by surface plasmon resonance. In one embodiment, the antibody, or antigen-binding portion thereof, dissociates from human IL-12 and/or human IL-23 with a $k_{off}$ rate constant of $1\times10^{-4}$ $s^{-1}$ or less. In another embodiment, the antibody, or antigen-binding portion thereof, dissociates from human IL-12 and/or human IL-23 with a $k_{off}$ rate constant of $1\times10^{-5}s^{-1}$ or less.

In another embodiment, the antibody, or antigen-binding portion thereof, binds to human IL-12 and/or human IL-23 and dissociates from human IL-12 and/or human Il-23, respectively, with a $k_{off}$ rate constant of $1\times10^{-2}$ $s^{-1}$ or less, as determined by surface plasmon resonance. In yet another embodiment, the antibody, or antigen-binding portion thereof, dissociates from human IL-12 and/or human IL-23 with a $k_{off}$ rate constant of $1\times10^{-3}$ $s^{-1}$ or less. In a still further another embodiment, the antibody, or antigen-binding portion thereof, dissociates from human IL-12 and/or human IL-23 with a $k_{off}$ rate constant of $1\times10^{-4}$ $s^{-1}$ or less. In another embodiment, the antibody, or antigen-binding portion thereof, dissociates from human IL-12 and/or human IL-23 with a $k_{off}$ rate constant of $1\times10^{-5}$ $s^{-1}$ or less.

In still another embodiment, the antibody, or antigen-binding portion thereof, binds to human IL-12 and/or human IL-23 and dissociates from human IL-12 and/or human IL-23, respectively, with a $K_d$ of $1.34\times10^{-10}$ M or less. In yet another embodiment, the antibody, or antigen-binding portion thereof, binds to human IL-12 and/or human IL-23 and dissociates from human IL-12 and/or human IL-23, respectively, with a $K_d$ of $9.74\times10^{-11}$ M or less. In one embodiment, the antibody, or antigen-binding portion thereof, is a recombinant antibody, or antigen-binding portion thereof.

In one embodiment, the antibody, or antigen-binding portion thereof, used in the methods of the invention is a neutralizing antibody, e.g., neutralizes the activity of human IL-12 and/or human IL-23. In one embodiment, the neutralizing antibody, or antigen-binding portion thereof, inhibits phytohemagglutinin blast proliferation in an in vitro PHA assay with an $IC_{50}$ of $1\times10^{-9}$ M or less. In another embodiment, the neutralizing antibody, or antigen-binding portion thereof, inhibits phytohemagglutinin blast proliferation in an in vitro PHA assay with an $IC_{50}$ of $1\times10^{-10-}$M or less. In still another embodiment, the neutralizing antibody of, or antigen-binding portion thereof, inhibits phytohemagglutinin blast proliferation in an in vitro PHA assay with an $IC_{50}$ of $1\times10^{-11-}$M or less. In yet another embodiment, the neutralizing antibody, or antigen-binding portion thereof, inhibits phytohemagglutinin blast proliferation in an in vitro phytohemagglutinin blast proliferation assay (PHA assay) with an $IC_{50}$ of $1\times10^{-7}$ M or less. In still another embodiment, the neutralizing antibody, or antigen-binding portion thereof, inhibits phytohemagglutinin blast proliferation in an in vitro PHA assay with an $IC_{50}$ of $1\times10^{-8}$ M or less. In one embodiment, the neutralizing antibody, or antigen-binding portion thereof, inhibits human IFNγ production with an $IC_{50}$ of $1\times10^{-10}$ M or less. In still another embodiment, the neutralizing antibody, or antigen-binding portion thereof, inhibits human IFNγ production with an $IC_{50}$ of $1\times10^{-11}$ M or less. In yet a further embodiment, the neutralizing antibody, or antigen-binding portion thereof, inhibits human IFNγ production with an $IC_{50}$ of $5\times10^{-12}$ M or less.

In one embodiment, the antibody, or an antigen-binding portion thereof, used in the methods of the invention a) inhibits phytohemagglutinin blast proliferation in an in vitro PHA assay with an $IC_{50}$ of $1\times10^{-9}$M or less;

b) has a heavy chain CDR3 comprising the amino acid sequence of SEQ ID NO: 25; and c) has a light chain CDR3 comprising the amino acid sequence of SEQ ID NO: 26. In one embodiment, the antibody further has a heavy chain CDR2 comprising the amino acid sequence of SEQ ID NO: 27; and a light chain CDR2 comprising the amino acid sequence of SEQ ID NO: 28. In still another embodiment, the antibody, or antigen-binding portion thereof, further has a heavy chain CDR1 comprising the amino acid sequence of SEQ ID NO: 29; and a light chain CDR1 comprising the amino acid sequence of SEQ ID NO: 30. In still another embodiment, the antibody, or antigen-binding portion thereof, further inhibits phytohemagglutinin blast proliferation in an in vitro PHA assay with an $IC_{50}$ of $1\times10^{-10}$ M or less. In still another embodiment, the antibody, or antigen-binding portion thereof, further inhibits phytohemagglutinin blast proliferation in an in vitro PHA assay with an $IC_{50}$ of $1\times10^{-11}$ M or less.

In one embodiment, the antibody, or antigen-binding portion thereof, used in the methods of the invention has a heavy chain variable region comprising the amino acid sequence of SEQ ID NO: 31, and a light chain variable region comprising the amino acid sequence of SEQ ID NO: 32.

In one embodiment, the antibody, or antigen-binding portion thereof, used in the methods of the invention comprises a heavy chain constant region selected from the group consisting of IgG1, IgG2, IgG3, IgG4, IgM, IgA and IgE constant regions. In one embodiment, the antibody heavy chain constant region is IgG1. In another embodiment, the antibody is a Fab fragment, $F(ab')_2$ fragment, or a a single chain Fv fragment.

In one embodiment, the antibody, or antigen-binding portion thereof, used in the methods of the invention dissociates from human IL-12 and/or human IL-23 with a $K_d$ of $1\times10^{-10}$ M or less and binds to an epitope on the p40 subunit of human IL-12 and/or human IL-23.

In one embodiment, the antibody, or antigen-binding portion thereof, used in the methods of the invention is a human antibody, or antigen-binding portion thereof, which a) dissociates from human IL-12 with a $k_{off}$ rate constant of $1\times10^{-3}$ $s^{-1}$ or less, as determined by surface plasmon resonance;

b) has a heavy chain CDR3 comprising the amino acid sequence of SEQ ID NO: 25; and c) has a light chain CDR3 comprising the amino acid sequence of SEQ ID NO: 26.

In another embodiment, the antibody, or antigen-binding portion thereof, used in the methods of the invention dissociates from human IL-12 with a $k_{off}$ rate constant of $1\times10^{-4}$ $s^{-1}$ or less. In a further embodiment, the human antibody, or antigen-binding portion thereof, dissociates from human IL-12 with a $k_{off}$ rate constant of $1\times10^{-5}$ $s^{-1}$ or less.

In one embodiment, the antibody, or antigen-binding portion thereof, used in the methods of the invention is a human antibody, or antigen-binding portion thereof, that binds to human IL-12 and comprises:

a light chain CDR3 domain comprising the amino acid sequence of SEQ ID NO: 26; and a heavy chain CDR3 domain comprising the amino acid sequence of SEQ ID NO: 25.

In one embodiment, the antibody, or antigen-binding portion thereof, has a light chain variable region (LCVR) having a CDR3 domain comprising the amino acid sequence of SEQ ID NO: 26, and has a heavy chain variable region (HCVR) having a CDR3 domain comprising the amino acid sequence of SEQ ID NO: 25. In another embodiment, the antibody, or antigen-binding portion thereof, comprises an LCVR further having a CDR2 domain comprising the amino acid sequence of SEQ ID NO: 28 and an HCVR further comprising a CDR2 domain comprising the amino acid sequence of SEQ ID NO: 27. In yet another embodiment, the LCVR further has CDR1 domain comprising the amino acid sequence of SEQ ID NO: 30 and the HCVR has a CDR1 domain comprising the amino acid sequence of SEQ ID NO: 29.

In one embodiment, the antibody, or antigen-binding portion thereof, binds human IL-12 and/or human IL-23 and is the antibody J695 (also referred to as ABT-874), or an antigen binding portion thereof.

In one embodiment, the antibody, or antigen-binding portion thereof, binds to human IL-12 and/or human IL-23 and dissociates from human IL-12 with a $K_d$ of $1.34\times10^{-10}$ M or less, and neutralizes human IL-12 and/or human IL-23. In one embodiment, the antibody, or antigen-binding portion thereof, dissociates from human IL-12 and/or human IL-23 with a $K_d$ of $9.74\times10^{-11}$ M or less. In one embodiment, the antibody, or antigen-binding portion thereof, inhibits phytohemagglutinin blast proliferation in an in vitro PHA assay with an $IC_{50}$ of $1\times10^{-7}$ M or less. In one embodiment, the antibody, or antigen-binding portion thereof, inhibits phytohemagglutinin blast proliferation in an in vitro PHA assay with an $IC_{50}$ of $1\times10^{-8}$ M or less. In one embodiment, the antibody, or antigen-binding portion thereof, inhibits phytohemagglutinin blast proliferation in an in vitro PHA assay with an $IC_{50}$ of $1\times10^{-9}$ M or less. In one embodiment, the antibody, or antigen-binding portion thereof, inhibits phytohemagglutinin blast proliferation in an in vitro PHA assay with an $IC_{50}$ of $1\times10^{-10}$–M or less. In one embodiment, the antibody, or antigen-binding portion thereof, inhibits phytohemagglutinin blast proliferation in an in vitro PHA assay with an $IC_{50}$ of $1\times10^{-11}$–M or less. In one embodiment, the antibody, or antigen-binding portion thereof, inhibits human IFNγ production with an $IC_{50}$ of $1\times10^{-10}$ M or less. In one embodiment, the antibody, or antigen-binding portion thereof, inhibits human IFNγ production with an $IC_{50}$ of $1\times10^{-11}$ M or less. In one embodiment, the antibody, or antigen-binding portion thereof, inhibits human IFNγ production with an $IC_{50}$ of $5\times10^{-12}$ M or less.

In one embodiment, the antibody, or antigen-binding portion thereof, used in the methods of the invention inhibits IL-12 and/or IL-23 binding to its receptor in an IL-12 or IL-23 receptor binding assay (RBA), respectively, with an $IC_{50}$ of $1\times10^{-9}$ M or less.

In one embodiment, the antibody, or antigen-binding portion thereof, inhibits IL-12 and/or IL-23 binding to its receptor in an IL-12 or IL-23 receptor binding assay (RBA), respectively, with an $IC_{50}$ of $1\times10^{-10}$ M or less. In one embodiment, the antibody, or antigen-binding portion thereof, inhibits IL-12 and/or IL-23 binding to its receptor in an IL-12 or IL-23 receptor binding assay (RBA), respectively, with an $IC_{50}$ of $1\times10^{-11}$ M or less.

BRIEF DESCRIPTION OF THE DRAWINGS

FIGS. 8A-8B show the heavy chain variable region amino acid sequence alignments of a series of human antibodies that bind human IL-12 compared to germline sequences Cos-3/JH3 and Dpl18 Lv1042. Kabat numbering is used to identify amino acid positions. For the Joe 9 wild type, the full sequence is shown. For the other antibodies, only those amino acids positions that differ from Joe 9 wild type are shown.

FIGS. 8C-8D show the light chain variable region amino acid sequence alignments of a series of human antibodies that bind human IL-12. Kabat numbering is used to identify amino acid positions. For the Joe 9 wild type, the full sequence is shown. For the other antibodies, only those amino acids positions that differ from Joe 9 wild type are shown.

DETAILED DESCRIPTION OF THE INVENTION

Figure 1:
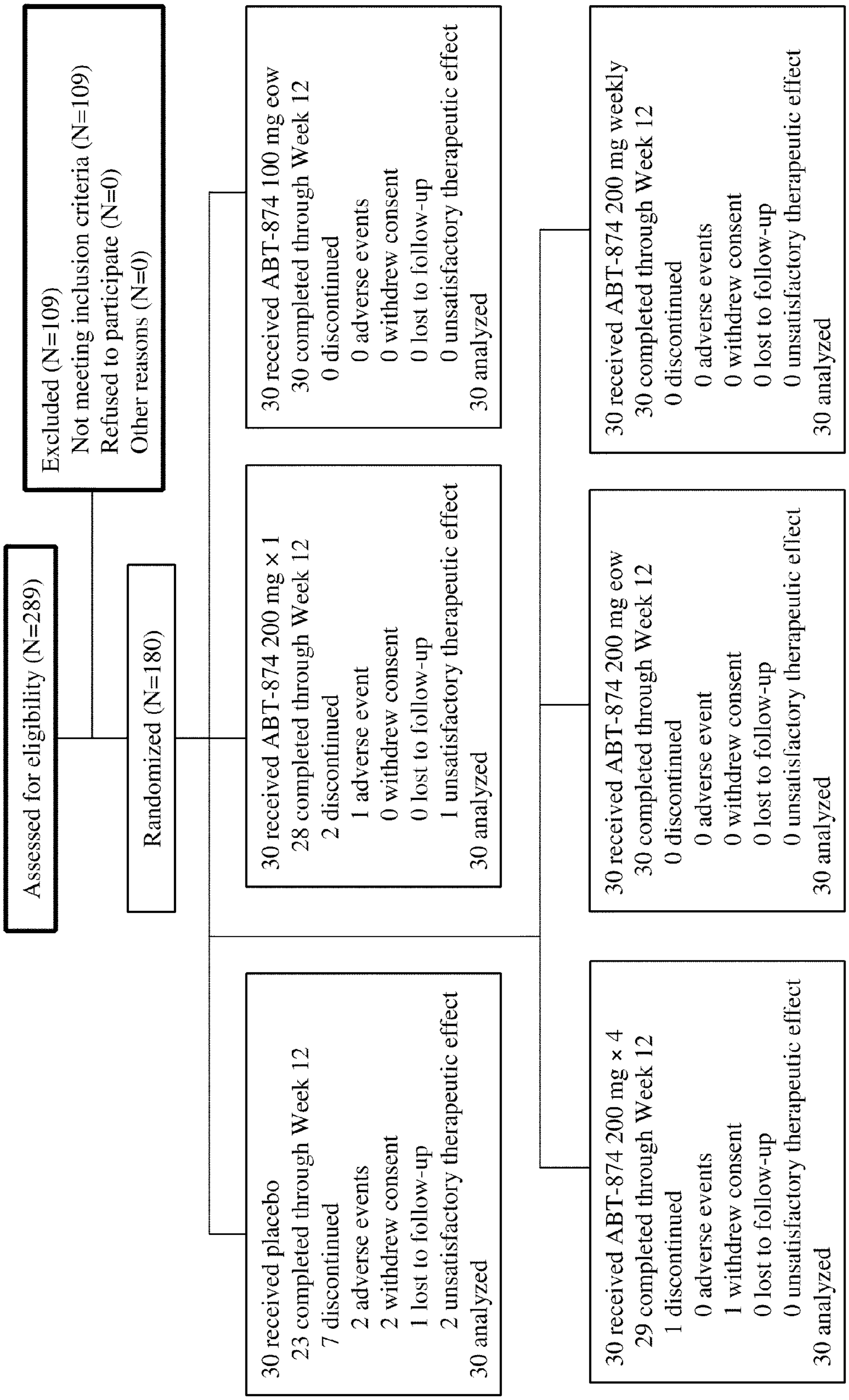
FIG. 1 shows the patient disposition of the trial. (The term "eow" refers to every other week dosing.)

In order that the present invention may be more readily understood, certain terms are first defined.

The term "activity enhancing amino acid residue" includes an amino acid residue which improves the activity of the antibody. It should be understood that the activity enhancing amino acid residue may replace an amino acid residue at a contact, hypermutation or preferred selective mutagenesis position and, further, more than one activity enhancing amino acid residue can be present within one or more CDRs. An activity enchancing amino acid residue include, an amino acid residue that improves the binding specificity/affinity of an antibody, for example anti-human IL-12 antibody binding to human IL-12. The activity enhancing amino acid residue is also intended to include an amino acid residue that improves the neutralization potency of an antibody, for example, the human IL-12 antibody which inhibits human IL-12.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In one embodiment, the antibody used in the compositions and methods of the invention is the antibody described in U.S. Pat. No. 6,914,128, incorporated by reference herein. In another embodiment, the antibody used in the compositions and methods of the invention is the antibody ABT-874 (also referred to as J695; Abbott Laboratories).

The term "antigen-binding portion" of an antibody (or "antibody portion") includes fragments of an antibody that retain the ability to specifically bind to an antigen (e.g., hIL-12). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Still further, an antibody or antigen-binding portion thereof may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

The term "backmutation" refers to a process in which some or all of the somatically mutated amino acids of a human antibody are replaced with the corresponding germline residues from a homologous germline antibody sequence. The heavy and light chain sequences of the human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmuation may occur at any stage of antibody optimization; preferably, backmutation occurs directly before or after the selective mutagenesis approach. More preferably, backmutation occurs directly before the selective mutagenesis approach.

The phrase "human interleukin 12" (abbreviated herein as hIL-12, or IL-12), as used herein, includes a human cytokine that is secreted primarily by macrophages and dendritic cells. The term includes a heterodimeric protein comprising a 35 kD subunit (p35) and a 40 kD subunit (p40) which are both linked together with a disulfide bridge. The heterodimeric protein is referred to as a "p70 subunit". The structure of human IL-12 is described further in, for example, Kobayashi, et al. (1989) *J. Exp Med.* 170:827-845; Seder, et al. (1993) *Proc. Nat. Acad. Sci.* 90:10188-10192; Ling, et al. (1995) *J. Exp Med.* 154:116-127; Podlaski, et al. (1992) *Arch. Biochem. Biophys.* 294:230-237. The term human IL-12 is intended to include recombinant human IL-12 (rh IL-12), which can be prepared by standard recombinant expression methods.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The Kabat numbering is used herein to indicate the positions of amino acid modifications made in antibodies of the invention. For example, the Y61 anti-IL-12 antibody can be mutated from serine (S) to glutamic acid (E) at position 31 of the heavy chain CDR1 (H31S→E), or glycine (G) can be mutated to tyrosine (Y) at position 94 of the light chain CDR3 (L94G→Y).

The term "human antibody" includes antibodies having variable and constant regions corresponding to human germline immunoglobulin sequences as described by Kabat et al. (See Kabat, et al. (1991) *Sequences of Proteins of Immunological Interest, Fifth Edition*, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The mutations preferably are introduced using the "selective mutagenesis approach" described herein. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described further in Section III, below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat, E. A., et al. (1991) *Sequences of Proteins of Immunological Interest, Fifth Edition*, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or backmutation or both.

An "isolated antibody" includes an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may bind IL-12 molecules from other species (discussed in further detail below). Moreover, an isolated antibody may be substantially free of other cellular material and/or chemicals.

A "neutralizing antibody" (or an "antibody that neutralized hIL-12 activity") includes an antibody whose binding to hIL-12 results in inhibition of the biological activity of hIL-12. This inhibition of the biological activity of hIL-12 can be assessed by measuring one or more indicators of hIL-12 biological activity, such as inhibition of human phytohemagglutinin blast proliferation in a phytohemagglutinin blast proliferation assay (PHA), or inhibition of receptor binding in a human IL-12 receptor binding assay (see Example 3-Interferon-gamma Induction Assay of U.S. Pat. No. 6,914,128). These indicators of hIL-12 biological activity can be assessed by one or more of several standard in vitro or in vivo assays known in the art (see Example 3 of U.S. Pat. No. 6,914,128).

The term "activity" includes activities such as the binding specificity/affinity of an antibody for an antigen, for example, an anti-hIL-12 antibody that binds to an IL-12 antigen and/or the neutralizing potency of an antibody, for example, an anti-hIL-12 antibody whose binding to hIL-12 inhibits the biological activity of hIL-12, e.g. inhibition of PHA blast proliferation or inhibition of receptor binding in a human IL-12 receptor binding assay (see Example 3 of U.S. Pat. No. 6,914,128).

The phrase "surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 of U.S. Pat. No. 6,914,128 and Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but preferably is double-stranded DNA.

The phrase "isolated nucleic acid molecule", as used herein in reference to nucleic acids encoding antibodies or antibody portions (e.g., VH, VL, CDR3) that bind hIL-12 including "isolated antibodies"), includes a nucleic acid molecule in which the nucleotide sequences encoding the antibody or antibody portion are free of other nucleotide sequences encoding antibodies or antibody portions that bind antigens other than hIL-12, which other sequences may naturally flank the nucleic acid in human genomic DNA. Thus, for example, an isolated nucleic acid of the invention encoding a VH region of an anti-IL-12 antibody contains no other sequences encoding other VH regions that bind antigens other than IL-12. The phrase "isolated nucleic acid molecule" is also intended to include sequences encoding bivalent, bispecific antibodies, such as diabodies in which VH and VL regions contain no other sequences other than the sequences of the diabody.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The phrase "contact position" includes an amino acid position of in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the 26 known solved structures of antibody-antigen complexes contacts the antigen, then that amino acid can be considered to occupy a contact position. Contact positions have a higher probability of being occupied by an amino acid which contact antigen than non-contact positions. Preferably a contact position is a CDR position which contains an amino acid that contacts antigen in greater than 3 of the 26 structures (>11.5%). Most preferably a contact position is a CDR position which contains an amino acid that contacts antigen in greater than 8 of the 25 structures (>32%).

The term "hypermutation position" includes an amino acid residue that occupies position in the CDR1, CDR2 or CDR3 region of the heavy chain variable region or the light chain variable region of an antibody that is considered to have a high frequency or probability for somatic hypermutation during in vivo affinity maturation of the antibody. "High frequency or probability for somatic hypermutation" includes frequencies or probabilities of a 5 to about 40% chance that the residue will undergo somatic hypermutation during in vivo affinity maturation of the antibody. It should be understood that all ranges within this stated range are also intended to be part of this invention, e.g., 5 to about 30%, e.g., 5 to about 15%, e.g., 15 to about 30%.

The term "preferred selective mutagenesis position" includes an amino acid residue that occupies a position in the CDR1, CDR2 or CDR3 region of the heavy chain variable region or the light chain variable region which can be considered to be both a contact and a hypermutation position.

The phrase "selective mutagenesis approach" includes a method of improving the activity of an antibody by selecting and individually mutating CDR amino acids at least one preferred selective mutagenesis position, hypermutation, and/or contact position. A "selectively mutated" human antibody is an antibody which contains a mutation at a position selected using a selective mutagenesis approach. In another embodiment, the selective mutagenesis approach is intended to provide a method of preferentially mutating selected individual amino acid residues in the CDR1, CDR2 or CDR3 of the heavy chain variable region (hereinafter H1, H2, and H3, respectively), or the CDR1, CDR2 or CDR3 of the light chain variable region (hereinafter referred to as L1, L2, and L3, respectively) of an antibody. Amino acid residues may be selected from preferred selective mutagenesis positions, contact positions., or hypermutation positions. Individual amino acids are selected based on their position in the light or heavy chain variable region. It should be understood that a hypermutation position can also be a contact position. In an embodiment, the selective mutagenesis approach is a "targeted approach". The language "targeted approach" is intended to include a method of preferentially mutating selected individual amino acid residues in the CDR1, CDR2 or CDR3 of the heavy chain variable region or the CDR1, CDR2 or CDR3 of the light chain variable region of an antibody in a targeted manner, e.g., a "Group-wise targeted approach" or "CDR-wise targeted approach". In the "Group-wise targeted approach", individual amino acid residues in particular groups are targeted for selective mutations including groups I (including L3 and H3), II (including H2 and L1) and III (including L2 and H1), the groups being listed in order of preference for targeting. In the "CDR-wise targeted approach", individual amino acid residues in particular CDRs are targeted for selective mutations with the order of preference for targeting as follows: H3, L3, H2, L1, H1 and L2. The selected amino acid residue is mutated, e.g., to at least two other amino acid residues, and the effect of the mutation on the activity of the antibody is determined. Activity is measured as a change in the binding specificity/affinity of the antibody, and/or neutralization potency of the antibody. It should be understood that the selective mutagenesis approach can be used for the optimization of any antibody derived from any source including phage display, transgenic animals with human IgG germline genes, human antibodies isolated from human B-cells. Preferably, the selective mutagenesis approach is used on antibodies which can not be optimized further using phage display technology. It should be understood that antibodies from any source including phage display, transgenic animals with human IgG germline genes, human antibodies isolated from human B-cells can be subject to backmutation prior to or after the selective mutagenesis approach.

The term "activity enhancing amino acid residue" includes an amino acid residue which improves the activity of the antibody. It should be understood that the activity enhancing amino acid residue may replace an amino acid residue at a preferred selective mutagenesis position, contact position, or a hypermutation position and, further, more than one activity enhancing amino acid residue can be present within one or more CDRs. An activity enchancing amino acid residue include, an amino acid residue that improves the binding specificity/affinity of an antibody, for example anti-human IL-12 antibody binding to human IL-12. The activity enhancing amino acid residue is also intended to include an amino acid residue that improves the neutralization potency of an antibody, for example, the human IL-12 antibody which inhibits human IL-12.

The term "$C_{max}$" refers to the maximum or peak serum or plasma concentration of an agent observed in a subject after its administration.

The term "$T_{max}$" refers to the time at which $C_{max}$ occurred.

The term "bioavailability" or "F %" refers to a fraction or percent of a dose which is absorbed and enters the systemic circulation after administration of a given dosage form. The dose of the agent may be administered through any route, and, preferably, via intravenous or subcutaneous injection.

The term "dosing", as used herein, refers to the administration of a substance (e.g., an anti-IL-12, anti-IL-23 antibody) to achieve a therapeutic objective (e.g., the treatment of rheumatoid arthritis).

The terms "biweekly dosing regimen", "biweekly dosing", and "biweekly administration", as used herein, refer to the time course of administering a substance (e.g., an anti-IL-12, anti-IL-23 antibody) to a subject to achieve a therapeutic objective, wherein the time course is every other week (eow). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an an anti-IL-12, anti-IL-23 antibody and another drug. The other drug(s) may be administered concomitant with, prior to, or following the administration of an an anti-IL-12, anti-IL-23 antibody.

The term "kit" as used herein refers to a packaged product comprising components with which to administer the anti-IL-12, anti-IL-23 antibody of the invention for treatment of a IL-12 related disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering an anti-IL-12, anti-IL-23 antibody.

Various aspects of the invention are described in further detail in the following subsections.

I. Human Antibodies that Bind Human IL-12

This invention provides methods and compositions for using human antibodies, or antigen-binding portions thereof, that bind to human IL-12 for the treatment of psoriasis. The invention also includes methods and compositions for using an antibody which binds both IL-12 and IL-23. Preferably, the human antibodies used in the invention are recombinant, neutralizing human anti-hIL-12 antibodies.

In one embodiment, the antibody used in the invention is the antibody ABT-874 (see U.S. Pat. No. 6,914,128). ABT-874 is a fully human antibody against interleukin 12 (IL-12) and IL-23. It binds with great affinity to the p40 subunit common to both IL-12 and IL-23, validated targets in the treatment of psoriasis (Ps).

Antibodies that bind to human IL-12 can be selected, for example, by screening one or more human $V_L$ and $V_H$ cDNA libraries with hIL-12, such as by phage display techniques as described in Example 1 of U.S. Pat. No. 6,914,128. Screening of human $V_L$ and $V_H$ cDNA libraries initially identified a series of anti-IL-12 antibodies of which one antibody, referred to herein as "Joe 9" (or "Joe 9 wild type"), was selected for further development. Joe 9 is a relatively low affinity human IL-12 antibody (e.g., a $K_{off}$ of about 0.1 $sec^{-1}$), yet is useful for specifically binding and detecting hIL-12. The affinity of the Joe 9 antibody was improved by conducting mutagenesis of the heavy and light chain CDRs, producing a panel of light and heavy chain variable regions that were "mixed and matched" and further mutated, leading to numerous additional anti-hIL-12 antibodies with increased affinity for hIL-12 (see Example 1, table 2 of U.S. Pat. No. 6,914,128 (see table 2 of Appendix A attached hereto)) and the sequence alignments of FIGS. 1A-D of U.S. Pat. No. 6,914,128 (see FIG. 8A-D herein).

Of these antibodies, the human anti-hIL-12 antibody referred to herein as Y61 demonstrated a significant improvement in binding affinity (e.g., a $K_{off}$ of about $2\times10^{-4}$ $sec^{-1}$). The Y61 anti-hIL-12 antibody was selected for further affinity maturation by individually mutating specific amino acids residues within the heavy and light chain CDRs. Amino acids residues of Y61 were selected for site-specific mutation (selective mutagenesis approach) based on the amino acid residue occupying a preferred selective mutagenesis position, contact and/or a hypermutation position. A summary of the substitutions at selected positions in the heavy and light chain CDRs is shown in FIGS. 2A-2H of U.S. Pat. No. 6,914,128 (FIGS. 9A-H herein). A preferred recombinant neutralizing antibody of the invention, referred to herein as J695 (also referred to as ABT-874 (Abbott Laboratories), resulted from a Gly to Tyr substitution at position 50 of the light chain CDR2 of Y61, and a Gly to Tyr substitution at position 94 of the light chain CDR3 of Y61.

Amino acid sequence alignments of the heavy and light chain variable regions of a panel of anti-IL-12 antibodies used in the invention, on the lineage from Joe 9 wild type to J695, are shown in FIGS. 1A-1D of U.S. Pat. No. 6,914,128 (FIGS. 8A-D herein). These sequence alignments allowed for the identification of consensus sequences for preferred heavy and light chain variable regions of antibodies of the invention that bind hIL-12, as well as consensus sequences for the CDR3, CDR2, and CDR1, on the lineage from Joe 9 to J695. Moreover, the Y61 mutagenesis analysis summarized in FIGS. 2A-2H of U.S. Pat. No. 6,914,128 (FIGS. 9A-H herein) allowed for the identification of consensus sequences for heavy and light chain variable regions that bind hIL-12, as well as consensus sequences for the CDR3, CDR2, and CDR1 that bind hIL-12 on the lineage from Y61 to J695 that encompasses sequences with modifications from Y61 yet that retain good hIL-12 binding characteristics. Preferred CDR, VH and VL sequences of the invention (including consensus sequences) as identified by sequence identifiers in the attached Sequence Listing, are summarized below.

| SEQ ID NO: | ANTIBODY CHAIN | REGION | SEQUENCE |
|---|---|---|---|
| 1 | Consensus Joe 9 to J695 | CDR H3 | (H/S)-G-S-(H/Y)-D-(N/T/Y) |
| 2 | Consensus Joe 9 to J695 | CDR L3 | Q-(S/T)-Y-(D/E)-(S/R/K)-(S/G/Y)-(L/F/T/S)-(R/S/T/W/H)-(G/P)-(S/T/A/L) (R/S/M/T/L)-(V/I/T/M/L) |
| 3 | Consensus Joe 9 to J695 | CDR H2 | F-I-R-Y-D-G-S-N-K-Y-Y-A-D-S-V-K-G |
| 4 | Consensus Joe 9 to J695 | CDR L2 | (G/Y)-N-(D/S)-(Q/N)-R-P-S |
| 5 | Consensus Joe 9 to J695 | CDR H1 | F-T-F-S-(S/E)-Y-G-M-H |
| 6 | Consensus Joe 9 to J695 | CDR L1 | (S/T)-G-(G/S)-(R/S)-S-N-I (G/V)-(S/A)-(N/G/Y)-(T/D)-V-(K/H) |
| 7 | Consensus Joe 9 to J695 | VH | (full VH sequence; see sequence listing) |
| 8 | Consensus Joe 9 to J695 | VL | (full VL sequence; see sequence listing) |
| 9 | Consensus Y61 to J695 | CDR H3 | H-(G/V/C/H)-(S/T) (H/T/V/R/I)-(D/S)-(N/K/A/T/S/F/W/H) |
| 10 | Consensus Y61 to J695 | CDR L3 | Q-S-Y-(D/S)-(Xaa)-(G/D/Q/L/F/R/H/N/Y)-T-H-P-A-L-L |
| 11 | Consensus Y61 to J695 | CDR H2 | (F/T/Y)-I-(R/A)-Y-(D/S/E/A)-(G/R)-S-(Xaa)-K-(Y/E)-Y-A-DS-V-K-G |
| 12 | Consensus Y61 to J695 | CDR L2 | (G/Y/S/T/N/Q)-N-D-Q-R-P-S |
| 13 | Consensus Y61 to J695 | CDR H1 | F-T-F-(Xaa)-(Xaa)-(Y/H)-(G/M/A/N/S)-M-H |
| 14 | Consensus Y61 to J695 | CDR L1 | S-G-G-R-S-N-I-G (S/C/R/N/D/T)-(N/M/I)-(T/Y/D/H/K/P)-V-K |
| 15 | Consensus Y61 to J695 | VH | (full VH sequence; see sequence listing) |
| 16 | Consensus Y61 to J695 | VL | (full VL sequence; see sequence listing) |
| 17 | Y61 | CDR H3 | H-G-S-H-D-N |
| 18 | Y61 | CDR L3 | Q-S-Y-D-R-G-T-H-P-A-L-L |
| 19 | Y61 | CDR H2 | F-I-R-Y-D-G-S-N-K-Y-Y-A-D-S V-K-G |
| 20 | Y61 | CDR L2 | G-N-D-Q-R-P-S |
| 21 | Y61 | CDR H1 | F-T-F-S-S-Y-G-M-H |
| 22 | Y61 | CDR L1 | S-G-G-R-S-N-I-G-S-N-T-V-K |
| 23 | Y61 | VH | (full VH sequence; see sequence listing) |
| 24 | Y61 | VL | (full VL sequence; see sequence listing) |

-continued

| SEQ ID NO: | ANTIBODY CHAIN | REGION | SEQUENCE |
|---|---|---|---|
| 25 | J695 | CDR H3 | H-G-S-H-D-N |
| 26 | J695 | CDR L3 | Q-S-Y-D-R-Y-T-H-P-A-L-L |
| 27 | J695 | CDR H2 | F-I-R-Y-D-S-S-N-K-Y-Y-A-D-S V-K-S |
| 28 | J695 | CDR L2 | Y-N-D-Q-R-P-S |
| 29 | J695 | CDR H1 | F-T-F-S-S-Y-S-M-H |
| 30 | J695 | CDR L1 | S-G-S-R-S-N-I-G-S-N-T-V-K |
| 31 | J695 | VH | (full VH sequence; see sequence listing) |
| 32 | J695 | VL | (full VL sequence; see sequence listing) |

Antibodies produced from affinity maturation of Joe 9 wild type were functionally characterized by surface plasmon resonance analysis to determine the $K_d$ and $K_{off}$ rate. A series of antibodies were produced having a $K_{off}$ rate within the range of about 0.1 $s^{-1}$ to about $1\times10^{-5}$ $s^{-1}$, and more preferably a $K_{off}$ of about $1\times10^{-4}$ $S^{-1}$ to $1\times10^{-5}$ $s^{-1}$ or less. Antibodies were also characterized in vitro for their ability to inhibit phytohemagglutinin (PHA) blast proliferation, as described in Example 3 of U.S. Pat. No. 6,914,128. A series of antibodies were produced having an $IC_{50}$ value in the range of about $1\times10^{-6}$ M to about $1\times10^{-11}$ M, more preferably about $1\times10^{-10}$ M to $1\times10^{-11}$ M or less.

Accordingly, in one aspect, the invention provides methods and compositions for using an isolated human antibody, or antigen-binding portion thereof, that binds to human IL-12 and dissociates from human IL-12 with a $K_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less. In preferred embodiments, the isolated human IL-12 antibody, or an antigen-binding portion thereof, dissociates from human IL-12 with a $K_{off}$ rate constant of $1\times10^{-2}$ $s^{-1}$ or less, or inhibits phytohemagglutinin blast proliferation in an in vitro PHA assay with an $IC_{50}$ of $1\times10^{-7}$ M or less. In more preferred embodiments, the isolated human IL-12 antibody, or an antigen-binding portion thereof, dissociates from human IL-12 with a $K_{off}$ rate constant of $1\times10^{-3}$ $s^{-1}$ or less, or inhibits phytohemagglutinin blast proliferation in an in vitro PHA assay with an $IC_{50}$ of $1\times10^{-8}$ M or less. In more preferred embodiments, the isolated human IL-12 antibody, or an antigen-binding portion thereof, dissociates from human IL-12 with a $K_{off}$ rate constant of $1\times10^{-4}$ $s^{-1}$ or less, or inhibits phytohemagglutinin blast proliferation in an in vitro PHA assay with an $IC_{50}$ of $1\times10^{-9}$ M or less. In more preferred embodiments, the isolated human IL-12 antibody, or an antigen-binding portion thereof, dissociates from human IL-12 with a $K_{off}$ rate constant of $1\times10^{-5}$ $s^{-1}$ or less, or inhibits phytohemagglutinin blast proliferation in an in vitro PHA assay with an $IC_{50}$ of $1\times10^{-10}$ M or less. In even more preferred embodiments, the isolated human IL-12 antibody, or an antigen-binding portion thereof, dissociates from human IL-12 with a $K_{off}$ rate constant of $1\times10^{-5}$ $s^{-1}$ or less, or inhibits phytohemagglutinin blast proliferation in an in vitro PHA assay with an $IC_{50}$ of $1\times10^{-11}$ M or less.

The dissociation rate constant ($K_{off}$) of an IL-12 antibody can be determined by surface plasmon resonance (see Example 5 of U.S. Pat. No. 6,914,128). Generally, surface plasmon resonance analysis measures real-time binding interactions between ligand (recombinant human IL-12 immobilized on a biosensor matrix) and analyte (antibodies in solution) by surface plasmon resonance (SPR) using the BIAcore system (Pharmacia Biosensor, Piscataway, N.J.). Surface plasmon analysis can also be performed by immobilizing the analyte (antibodies on a biosensor matrix) and presenting the ligand (recombinant IL-12 in solution). Neutralization activity of IL-12 antibodies, or antigen binding portions thereof, can be assessed using one or more of several suitable in vitro assays (see Example 3 of U.S. Pat. No. 6,914,128).

It is well known in the art that antibody heavy and light chain CDRs play an important role in the binding specificity/affinity of an antibody for an antigen. Accordingly, the invention encompasses human antibodies having light and heavy chain CDRs of Joe 9, as well as other antibodies having CDRs that have been modified to improve the binding specificity/affinity of the antibody. As demonstrated in Example 1 of U.S. Pat. No. 6,914,128, a series of modifications to the light and heavy chain CDRs results in affinity maturation of human anti-hIL-12 antibodies. The heavy and light chain variable region amino acid sequence alignments of a series of human antibodies ranging from Joe 9 wild type to J695 that bind human IL-12 is shown in FIGS. 1A-1D of U.S. Pat. No. 6,914,128 (FIGS. 8A-D herein). Consensus sequence motifs for the CDRs of antibodies can be determined from the sequence alignment. For example, a consensus motif for the VH CDR3 of the lineage from Joe 9 to J695 comprises the amino acid sequence: (H/S)-G-S-(H/Y)-D-(N/T/Y) (SEQ ID NO: 1), which encompasses amino acids from position 95 to 102 of the consensus HCVR shown in SEQ ID NO: 7. A consensus motif for the VL CDR3 comprises the amino acid sequence: Q-(S/T)-Y-(D/E)-(S/R/K)-(S/G/Y)-(L/F/T/S)-(R/S/T/W/H)-(G/P)-(S/T/A/L)-(R/S/M/T/L-V/I/T/M/L) (SEQ ID NO: 2), which encompasses amino acids from position 89 to 97 of the consensus LCVR shown in SEQ ID NO: 8.

Accordingly, in another aspect, the invention provides methods and compositions comprising an isolated human antibody, or an antigen-binding portion thereof, which has the following characteristics:

a) inhibits phytohemagglutinin blast proliferation in an in vitro PHA assay with an $IC_{50}$ of $1\times10^{-6}$ M or less;

b) has a heavy chain CDR3 comprising the amino acid sequence of SEQ ID NO: 1; and c) has a light chain CDR3 comprising the amino acid sequence of SEQ ID NO: 2.

In a preferred embodiment, the antibody further comprises a VH CDR2 comprising the amino acid sequence: F-I-R-Y-D-G-S-N-K-Y-Y-A-D-S-V-K-G (SEQ ID NO: 3) (which encompasses amino acids from position 50 to 65 of the consensus HCVR comprising the amino acid sequence SEQ ID NO: 7) and further comprises a VL CDR2 comprising the amino acid sequence: (G/Y)-N-(D/S)-(Q/N)-R-P-S (SEQ ID NO: 4) (which encompasses amino acids from position 50 to 56 of the consensus LCVR comprising the amino acid sequence SEQ ID NO: 8).

In another preferred embodiment, the antibody further comprises a VH CDR1 comprising the amino acid sequence: F-T-F-S-(S/E)-Y-G-M-H (SEQ ID NO: 5) (which encompasses amino acids from position 27 to 35 of the consensus HCVR comprising the amino acid sequence SEQ ID NO: 7) and further comprises a VL CDR1 comprising the amino acid sequence: (S/T)-G-(G/S)-(R/S)-S-N-I-(G/V)-(S/A)-(N/G/

Y)-(T/D)-V-(K/H) (SEQ ID NO: 6) (which encompasses amino acids from position 24 to 34 of the consensus LCVR comprising the amino acid sequence SEQ ID NO: 8).

In yet another preferred embodiment, the antibody used in the invention comprises a HCVR comprising the amino acid sequence of SEQ ID NO: 7 and a LCVR comprising the amino acid sequence of SEQ ID NO: 8.

Additional consensus motifs can be determined based on the mutational analysis performed on Y61 that led to the J695 antibody (summarized in FIGS. 2A-2H of U.S. Pat. No. 6,914,128; FIGS. 9A-H herein). As demonstrated by the graphs shown in FIGS. 2A-2H of U.S. Pat. No. 6,914,128 (FIGS. 9A-H herein), certain residues of the heavy and light chain CDRs of Y61 were amenable to substitution without significantly impairing the hIL-12 binding properties of the antibody. For example, individual substitutions at position 30 in CDR H1 with twelve different amino acid residues did not significantly reduce the $K_{off}$ rate of the antibody, indicating that is position is amenable to substitution with a variety of different amino acid residues. Thus, based on the mutational analysis (i.e., positions within Y61 that were amenable to substitution by other amino acid residues) consensus motifs were determined. The consensus motifs for the heavy and light chain CDR3s are shown in SEQ ID NOs: 9 and 10, respectively, consensus motifs for the heavy and light chain CDR2s are shown in SEQ ID NOs: 11 and 12, respectively, and consensus motifs for the heavy and light chain CDR1s are shown in SEQ ID NOs: 13 and 14, respectively. Consensus motifs for the VH and VL regions are shown in SEQ ID NOs: 15 and 16, respectively.

Accordingly, in one aspect, the invention includes an isolated human antibody, or an antigen-binding portion thereof, which has the following characteristics:

a) inhibits phytohemagglutinin blast proliferation in an in vitro PHA assay with an $IC_{50}$ of $1\times10^{-9}$ M or less;

b) has a heavy chain CDR3 comprising the amino acid sequence of SEQ ID NO: 9; and c) has a light chain CDR3 comprising the amino acid sequence of SEQ ID NO: 10.

In a preferred embodiment, the antibody further comprises a VH CDR2 comprising the amino acid sequence of SEQ ID NO: 11 and further comprises a VL CDR2 comprising the amino acid sequence of SEQ ID NO: 12.

In another preferred embodiment, the antibody further comprises a VH CDR1 comprising the amino acid sequence of SEQ ID NO: 13 and further comprises a VL CDR1 comprising the amino acid sequence of SEQ ID NO: 14.

In yet another preferred embodiment, the antibody used in the invention comprises a HCVR comprising the amino acid sequence of SEQ ID NO: 15 and a LCVR comprising the amino acid sequence of SEQ ID NO: 16.

A preferred antibody used in the invention, the human anti-hIL-12 antibody Y61, can be produced by affinity maturation of Joe 9 wild type by PCR mutagenesis of the CDR3 (as described in Example 1 of U.S. Pat. No. 6,914,128). Y61 had an improved specificity/binding affinity determined by surface plasmon resonance and by in vitro neutralization assays. The heavy and light chain CDR3s of Y61 are shown in SEQ ID NOs: 17 and 18, respectively, the heavy and light chain CDR2s of Y61 are shown in SEQ ID NOs: 19 and 20, respectively, and the heavy and light chain CDR1s of Y61 are shown in SEQ ID NOs: 21 and 22, respectively. The VH of Y61 has the amino acid sequence of SEQ ID NO: 23 and the VL of Y61 has the amino acid sequence of SEQ ID NO: 24 (these sequences are also shown in FIGS. 1A-1D of U.S. Pat. No. 6,914,128 (FIGS. 8A-D herein) aligned with Joe9).

Accordingly, in another aspect, the invention features use of an isolated human antibody, or an antigen-binding portion thereof, which a) inhibits phytohemagglutinin blast proliferation in an in vitro PHA assay with an $IC_{50}$ of $1\times10^{-9}$ M or less;

b) has a heavy chain CDR3 comprising the amino acid sequence of SEQ ID NO: 17; and c) has a light chain CDR3 comprising the amino acid sequence of SEQ ID NO: 18.

In a preferred embodiment, the isolated human antibody, or an antigen-binding portion thereof, used in the methods and compositions of the invention has a heavy chain CDR2 comprising the amino acid sequence of SEQ ID NO: 19 and a light chain CDR2 comprising the amino acid sequence of SEQ ID NO: 20.

In another preferred embodiment, the isolated human antibody, or an antigen-binding portion thereof, used in the methods and compositions of the invention, has a heavy chain CDR1 comprising the amino acid sequence of SEQ ID NO: 21 and a light chain CDR1 comprising the amino acid sequence of SEQ ID NO: 22.

In yet another preferred embodiment, the isolated human antibody, or an antigen-binding portion thereof, used in the methods and compositions of the invention comprising a the heavy chain variable region comprising the amino acid sequence of SEQ ID NO: 23, and a light chain variable region comprising the amino acid sequence of SEQ ID NO: 24.

In certain embodiments, the full length antibody comprises a heavy chain constant region, such as IgG1, IgG2, IgG3, IgG4, IgM, IgA and IgE constant regions, and any allotypic variant therein as described in Kabat (Kabat, E. A., et al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be an Fab fragment, an $F(ab'_2)$ fragment or a single chain Fv fragment.

Modifications of individual residues of Y61 led to the production of a panel of antibodies shown in FIGS. 2A-2H of U.S. Pat. No. 6,914,128 (FIGS. 9A-H herein). The specificity/binding affinity of each antibody was determined by surface plasmon resonance and/or by in vitro neutralization assays.

Accordingly, in another aspect, the invention features an isolated human antibody, or an antigen-binding portion thereof, which a) inhibits phytohemagglutinin blast proliferation in an in vitro PHA assay with an $IC_{50}$ of $1\times10^{-9}$ M or less;

b) has a heavy chain CDR3 comprising the amino acid sequence selected from the group consisting of SEQ ID NO: 404-SEQ ID NO: 469; and c) has a light chain CDR3 comprising the amino acid sequence selected from the group consisting of SEQ ID NO: 534-SEQ ID NO: 579.

In preferred embodiment, the isolated human antibody, or an antigen-binding portion thereof, used in the methods and compositions of the invention has a heavy chain CDR2 comprising the amino acid sequence selected from the group consisting of SEQ ID NO:335-SEQ ID NO: 403; and a light chain CDR2 comprising the amino acid sequence selected from the group consisting of SEQ ID NO: 506-SEQ ID NO: 533.

In another preferred embodiment, the isolated human antibody, or an antigen-binding portion thereof, has a heavy chain CDR1 comprising the amino acid sequence selected from the group consisting of SEQ ID NO: 288-SEQ ID NO: 334; and a light chain CDR1 comprising the amino acid sequence selected from the group consisting of SEQ ID NO: 470-SEQ ID NO: 505.

In yet another preferred embodiment, the isolated human antibody, or an antigen-binding portion thereof, comprising a the heavy chain variable region comprising the amino acid sequence of SEQ ID NO: 23, and a light chain variable region comprising the amino acid sequence of SEQ ID NO: 24.

In certain embodiments, the full length antibody comprising a heavy chain constant region such as IgG1, IgG2, IgG3, IgG4, IgM, IgA and IgE constant regions and any allotypic variant therein as described in Kabat (, Kabat, E. A., et al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be a Fab fragment, an F(ab'$_2$) fragment or a single chain Fv fragment.

A particularly preferred recombinant, neutralizing antibody, J695, which may be used in the invention was produced by site-directed mutagenesis of contact and hypermutation amino acids residues of antibody Y61 (see Example 2 of U.S. Pat. No. 6,914,128 and section III below). J695 differs from Y61 by a Gly to Tyr substitution in Y61 at position 50 of the light chain CDR2 and by a Gly to Tyr substitution at position 94 of the light chain CDR3. The heavy and light chain CDR3s of J695 are shown in SEQ ID NOs: 25 and 26, respectively, the heavy and light chain CDR2s of J695 are shown in SEQ ID NOs: 27 and 28, respectively, and the heavy and light chain CDR1s of J695 are shown in SEQ ID NOs: 29 and 30, respectively. The VH of J695 has the amino acid sequence of SEQ ID NO: 31 and the VL of J695 has the amino acid sequence of SEQ ID NO: 32 (these sequences are also shown in FIGS. 1A-1D of U.S. Pat. No. 6,914,128 (FIGS. 8A-D herein), aligned with Joe9).

Accordingly, in another aspect, the invention features an isolated human antibody, or an antigen-binding portion thereof, which a) inhibits phytohemagglutinin blast proliferation in an in vitro PHA assay with an $IC_{50}$ of $1\times10^{-9}$ M or less; b) has a heavy chain CDR3 comprising the amino acid sequence of SEQ ID NO: 25; and c) has a light chain CDR3 comprising the amino acid sequence of SEQ ID NO: 26.

In preferred embodiment, the isolated human antibody, or an antigen-binding portion thereof, used in the invention has a heavy chain CDR2 comprising the amino acid sequence of SEQ ID NO: 27, and a light chain CDR2 comprising the amino acid sequence of SEQ ID NO: 28.

In another preferred embodiment, the isolated human antibody, or an antigen-binding portion thereof, used in the invention has a heavy chain CDR1 comprising the amino acid sequence of SEQ ID NO: 29, and a light chain CDR1 comprising the amino acid sequence of SEQ ID NO: 30.

In yet another preferred embodiment, the isolated human antibody, or an antigen-binding portion thereof, used in the invention has a heavy chain variable region comprising the amino acid sequence of SEQ ID NO: 31, and a light chain variable region comprising the amino acid sequence of SEQ ID NO: 32.

In certain embodiments, the full length antibody comprises a heavy chain constant region, such as IgG1, IgG2, IgG3, IgG4, IgM, IgA and IgE constant regions and any allotypic variant therein as described in Kabat (, Kabat, E. A., et al. (1991) *Sequences of Proteins of Immunological Interest, Fifth Edition*, U.S. Department of Health and Human Services, NIH Publication No. 91-3242). Preferably, the antibody heavy chain constant region is an IgG1 heavy chain constant region. Alternatively, the antibody portion can be an Fab fragment, an F(ab'$_2$) fragment or a single chain Fv fragment.

Additional mutations in the preferred consensus sequences for CDR3, CDR2, and CDR1 of antibodies on the lineage from Joe 9 to J695, or from the lineage Y61 to J695, can be made to provide additional anti-IL-12 antibodies of the invention. Such methods of modification can be performed using standard molecular biology techniques, such as by PCR mutagenesis, targeting individual contact or hypermutation amino acid residues in the light chain and/or heavy chain CDRs-, followed by kinetic and functional analysis of the modified antibodies as described herein (e.g., neutralization assays described in Example 3 of U.S. Pat. No. 6,914,128, and by BIAcore analysis, as described in Example 5 of U.S. Pat. No. 6,914,128).

Accordingly, in another aspect the invention features use of an isolated human antibody, or an antigen-binding portion thereof, which a) inhibits phytohemagglutinin blast proliferation in an in vitro PHA assay with an $IC_{50}$ of $1\times10^{-6}$ M or less;

b) comprises a heavy chain CDR3 comprising the amino acid sequence of SEQ ID NO: 1, a heavy chain CDR2 comprising the amino acid sequence of SEQ ID NO: 3 and a heavy chain CDR1 comprising the amino acid sequence of SEQ ID NO: 5, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 1, a heavy chain CDR2 comprising the amino acid sequence of SEQ ID NO: 3, and a heavy chain CDR1 comprising the amino acid sequence of SEQ ID NO: 5; and c) comprises a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 2, a light chain CDR2 comprising the amino acid sequence of SEQ ID NO: 4, and a light chain CDR1 comprising the amino acid sequence of SEQ ID NO: 6.

In another aspect the invention features use of an isolated human antibody, or an antigen-binding portion thereof, which a) inhibits phytohemagglutinin blast proliferation in an in vitro PHA assay with an $IC_{50}$ of $1\times10^{-9}$ M or less;

b) comprises a heavy chain CDR3 comprising the amino acid sequence of SEQ ID NO: 9, a heavy chain CDR2 comprising the amino acid sequence of SEQ ID NO: 11 and a heavy chain CDR1 comprising the amino acid sequence of SEQ ID NO: 13, or a mutant thereof having one or more amino acid substitutions at a preferred selective mutagenesis position, contact position or a hypermutation position, wherein said mutant has a $k_{off}$ rate no more than 10-fold higher than the antibody comprising a heavy chain CDR3 comprising the amino acid sequence of SEQ ID NO: 9, a heavy chain CDR2 comprising the amino acid sequence of SEQ ID NO: 11, and a heavy chain CDR1 comprising the amino acid sequence of SEQ ID NO: 13; and c) comprises a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14, or a mutant thereof having one or more amino acid substitutions at a preferred selective mutagenesis position, contact position or a hypermutation position, wherein said mutant has a $k_{off}$ rate no more than 10-fold higher than the antibody comprising a light chain CDR3 comprising the amino acid sequence of SEQ ID NO: 10, a light chain CDR2 comprising the amino acid sequence of SEQ ID NO: 12, and a light chain CDR1 comprising the amino acid sequence of SEQ ID NO: 14.

An ordinarily skilled artisan will also appreciate that additional mutations to the CDR regions of an antibody, for example in Y61 or in J695, can be made to provide additional anti-IL-12 antibodies of the invention. Such methods of modification can be performed using standard molecular biology techniques, as described above. The functional and kinetic analysis of the modified antibodies can be performed as described in Example 3 of U.S. Pat. No. 6,914,128 and Example 5 of U.S. Pat. No. 6,914,128, respectively. Modifications of individual residues of Y61 that led to the identification of J695 are shown in FIGS. 2A-2H of U.S. Pat. No. 6,914,128 (FIGS. 9A-H herein) and are described in Example 2 of U.S. Pat. No. 6,914,128.

Accordingly, in another aspect the invention features use of an isolated human antibody, or an antigen-binding portion thereof, which a) inhibits phytohemagglutinin blast proliferation in an in vitro PHA assay with an $IC_{50}$ of $1\times10^{-9}$ M or less;

b) comprises a heavy chain CDR3 comprising the amino acid sequence of SEQ ID NO: 17, a heavy chain CDR2 comprising the amino acid sequence of SEQ ID NO: 19 and a heavy chain CDR1 comprising the amino acid sequence of SEQ ID NO: 21, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 17, a heavy chain CDR2 comprising the amino acid sequence of SEQ ID NO: 19, and a heavy chain CDR1 comprising the amino acid sequence of SEQ ID NO: 21; and c) comprises a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 18, a light chain CDR2 comprising the amino acid sequence of SEQ ID NO: 20, and a light chain CDR1 comprising the amino acid sequence of SEQ ID NO: 22.

In another aspect the invention features use of an isolated human antibody, or an antigen-binding portion thereof, which a) inhibits phytohemagglutinin blast proliferation in an in vitro PHA assay with an $IC_{50}$ of $1\times10^{-9}$ M or less;

b) comprises a heavy chain CDR3 comprising the amino acid sequence of SEQ ID NO: 25, a heavy chain CDR2 comprising the amino acid sequence of SEQ ID NO: 27 and a heavy chain CDR1 comprising the amino acid sequence of SEQ ID NO: 29, or a mutant thereof having one or more amino acid substitutions at a preferred selective mutagenesis position or a hypermutation position, wherein said mutant has a $k_{off}$ rate no more than 10-fold higher than the antibody comprising a heavy chain CDR3 comprising the amino acid sequence of SEQ ID NO: 25, a heavy chain CDR2 comprising the amino acid sequence of SEQ ID NO: 27, and a heavy chain CDR1 comprising the amino acid sequence of SEQ ID NO: 29; and c) comprises a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30, or a mutant thereof having one or more amino acid substitutions at a preferred selective mutagenesis position or a hypermutation position, wherein said mutant has a $k_{off}$ rate no more than 10-fold higher than the antibody comprising a light chain CDR3 comprising the amino acid sequence of SEQ ID NO: 26, a light chain CDR2 comprising the amino acid sequence of SEQ ID NO: 28, and a light chain CDR1 comprising the amino acid sequence of SEQ ID NO: 30.

In yet another embodiment, the invention provides use of an isolated human antibodies, or antigen-binding portions thereof, that neutralize the activity of human IL-12, and at least one additional primate IL-12 selected from the group consisting of baboon IL-12, marmoset IL-12, chimpanzee IL-12, cynomolgus IL-12 and rhesus IL-12, but which do not neutralize the activity of the mouse IL-12.

II Selection of Recombinant Human Antibodies

Recombinant human antibodies which may be used in the invention can be isolated by screening of a recombinant combinatorial antibody library, preferably a scFv phage display library, prepared using human VL and VH cDNAs prepared from mRNA derived from human lymphocytes. Methods for identifying antibodies which may be used in the methods and compositions of the invention are described in U.S. Pat. No. 6,914,128, incorporated by reference herein. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Kang et al. PCT Publication No. WO 92/18619; Winter et al. PCT Publication No. WO 92/20791; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 2:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 2:1373-1377; Hoogenboom et al (1991) *Nuc Acid Res* 19:4133-4137; and Barbas et al. (1991) *PNAS* 88:7978-7982.

The antibody libraries used in this method are preferably scFv libraries prepared from human VL and VH cDNAs. The scFv antibody libraries are preferably screened using recombinant human IL-12 as the antigen to select human heavy and light chain sequences having a binding activity toward IL-12. To select for antibodies specific for the p35 subunit of IL-12 or the p70 heterodimer, screening assays were performed in the presence of excess free p40 subunit. Subunit preferences can be determined, for example by, micro-Friguet titration, as described in Example 1 of U.S. Pat. No. 6,914,128.

Once initial human VL and VH segments are selected, "mix and match" experiments, in which different pairs of the selected VL and VH segments are screened for IL-12 binding, are performed to select preferred VL/VH pair combinations (see Example 1 of U.S. Pat. No. 6,914,128). Additionally, to further improve the affinity and/or lower the off rate constant for hIL-12 binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be reselected and rescreened for binding to hIL-12 and sequences that exhibit high affinity and a low off rate for IL-12 binding can be selected. Table 2 of Appendix A of U.S. Pat. No. 6,914,128 (see table 2 of Appendix A attached hereto) shows antibodies that displayed altered binding specificity/affinity produced as a result of in vitro affinity maturation.

Following selection, isolation and screening of an anti-hIL-12 antibody of the invention from a recombinant immunoglobulin display library, nucleic acid encoding the selected antibody can be recovered from the phage particle(s) (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV below.

Methods for selecting human IL-12 binding antibodies by phage display technology, and affinity maturation of selected antibodies by random or site-directed mutagenesis of CDR regions are described in further detail in Example 1 of U.S. Pat. No. 6,914,128.

As described in Example 1 of U.S. Pat. No. 6,914,128, screening of human VL and VH cDNA libraries identified a series of anti-IL-12 antibodies, of which the Joe 9 antibody was selected for further development. A comparison of the heavy chain variable region of Joe 9 with the heavy chain germline sequences selected from the VBASE database, revealed that Joe 9 was similar to the COS-3 germline sequence. COS-3 belongs to the $V_H3$ family of germline sequences.

The $V_H3$ family is part of the human VH germline repertoire which is grouped into seven families, $V_H1$-$V_H7$, based on nucleotide sequence homology (Tomlinson et al. (1992) *J. Mol. Biol.,* 227, 776-798 and Cook et al. (1995) *Immunology Today,* 16, 237-242). The $V_H3$ family contains the highest number of members and makes the largest contribution to the germline repertoire. For any given human $V_H3$-germline antibody sequence, the amino acid sequence identity within the entire $V_H3$ family is high (See e.g., Tomlinson et al. (1992) *J. Mol. Biol.,* 227, 776-798 and Cook et al. (1995) *Immunology Today,* 16, 237-242). The range of amino acid sequence identity between any two germline VH sequences of the $V_H3$ family varies from 69-98 residues out of approximately 100 VH residues, (i.e., 69-98% amino acid sequence homology between any two germline VH sequences). For most pairs of germline sequences there is at least 80 or more identical amino acid residues, (i.e., at least 80% amino acid sequence homology). The high degree of amino acid sequence homology between the $V_H3$ family members results in certain amino acid residues being present at key sites in the CDR and framework regions of the VH chain. These amino acid residues confer structural features upon the CDRs.

Studies of antibody structures have shown that CDR conformations can be grouped into families of canonical CDR structures based on the key amino acid residues that occupy certain positions in the CDR and framework regions. Consequently, there are similar local CDR conformations in different antibodies that have canonical structures with identical key amino acid residues (Chothia et al. (1987) *J. Mol. Biol.,* 196, 901-917 and Chothia et al. (1989) *Nature,* 342, 877-883). Within the $V_H3$ family there is a conservation of amino acid residue identity at the key sites for the CDR1 and CDR2 canonical structures (Chothia et al. (1992) *J. Mol. Biol.,* 227, 799-817).

The COS-3 germline VH gene, is a member of the $V_H3$ family and is a variant of the 3-30 (DP-49) germline VH allele. COS-3, differs from Joe9 VH amino acid sequences at only 5 positions. The high degree of amino acid sequence homology between Joe9 VH and COS-3, and between Joe9 VH and the other $V_H3$ family members also confers a high degree of CDR structural homology (Chothia et al. (1992) *J. Mol. Biol.,* 227, 799-817; Chothia et al. (1987) *J. Mol. Biol.,* 196, 901-917 and Chothia et al. (1989) *Nature,* 342, 877-883).

The skilled artisan will appreciate that based on the high amino acid sequence and canonical structural similarity to Joe 9, other $V_H3$ family members could also be used to generate antibodies that bind to human IL-12. This can be performed, for example, by selecting an appropriate VL by chain-shuffling techniques (Winter et al. (1994) *Annual Rev. Immunol.,* 12, 433-55), or by the grafting of CDRs from a rodent or other human antibody including CDRs from antibodies of this invention onto a $V_H3$ family framework.

The human V lambda germline repertoire is grouped into 10 families based on nucleotide sequence homology (Williams et al. (1996) *J. Mol. Biol.,* 264, 220-232). A comparison of the light chain variable region of Joe 9 with the light chain germline sequences selected from the VBASE database, revealed that Joe 9 was similar to the DPL8 lambda germline. The Joe9 VL differs from DPL8 sequence at only four framework positions, and is highly homologous to the framework sequences of the other $V_\lambda1$ family members. Based on the high amino acid sequence homology and canonical structural similarity to Joe 9, other $V_\lambda1$ family members may also be used to generate antibodies that bind to human IL-12. This can be performed, for example, by selecting an appropriate VH by chain-shuffling techniques (Winter et al. Supra, or by the grafting of CDRs from a rodent or other human antibody including CDRs from antibodies of this invention onto a $V_\lambda1$ family framework.

The methods of the invention are intended to include recombinant antibodies that bind to hIL-12, comprising a heavy chain variable region derived from a member of the $V_H3$ family of germline sequences, and a light chain variable region derived from a member of the $V_\lambda1$ family of germline sequences. Moreover, the skilled artisan will appreciate that any member of the $V_H3$ family heavy chain sequence can be combined with any member of the $V_\lambda1$ family light chain sequence.

Those skilled in the art will also appreciate that DNA sequence polymorphisms that lead to changes in the amino acid sequences of the germline may exist within a population (e.g., the human population). Such genetic polymorphism in the germline sequences may exist among individuals within a population due to natural allelic variation. Such natural allelic variations can typically result in 1-5% variance in the nucleotide sequence of the a gene. Any and all such nucleotide variations and resulting amino acid polymorphisms in germline sequences that are the result of natural allelic variation are intended to be within the scope of the invention.

Accordingly, in one aspect, the invention features an isolated human antibody, or an antigen-binding portion thereof, which has the following characteristics:

a) that binds to human IL-12 and dissociates from human IL-12 with a $k_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.

b) has a heavy chain variable region comprising an amino acid sequence selected from a member of the $V_H3$ germline family, wherein the heavy chain variable region has a mutation at a contact or hypermutation position with an activity enhancing amino acid residue.

c) has a light chain variable region comprising an amino acid sequence selected from a member of the $V_\lambda 1$ germline family, wherein the light chain variable region has a mutation at a preferred selective mutagenesis position, contact or hypermutation position with an activity enhancing amino acid residue.

In a preferred embodiment, the isolated human antibody, or antigen binding has mutation in the heavy chain CDR3. In another preferred embodiment, the isolated human antibody, or antigen binding has mutation in the light chain CDR3. In another preferred embodiment, the isolated human antibody, or antigen binding has mutation in the heavy chain CDR2. In another preferred embodiment, the isolated human antibody, or antigen binding has mutation in the light chain CDR2. In another preferred embodiment, the isolated human antibody, or antigen binding has mutation in the heavy chain CDR1. In another preferred embodiment, the isolated human antibody, or antigen binding has mutation in the light chain CDR1.

An ordinarily skilled artisan will appreciate that based on the high amino acid sequence similarity between members of the $V_H3$ germline family, or between members of the light chain $V_\lambda 1$ germline family, that mutations to the germlines sequences can provide additional antibodies that bind to human IL-12. Table 1 of U.S. Pat. No. 6,914,128 (see Table 1 of Appendix A attached hereto) shows the germline sequences of the $V_H3$ family members and demonstrates the significant sequence homology within the family members. Also shown in table 1 of U.S. Pat. No. 6,914,128 (see table 1 of Appendix A, attached hereto) are the germline sequences for $V_\lambda 1$ family members. The heavy and light chain sequences of Joe 9 are provided as a comparison. Mutations to the germline sequences of $V_H3$ or $V_\lambda 1$ family members may be made, for example, at the same amino acid positions as those made in the antibodies of the invention (e.g. mutations in Joe 9). The modifications can be performed using standard molecular biology techniques, such as by PCR mutagenesis, targeting individual amino acid residues in the germline sequences, followed by kinetic and functional analysis of the modified antibodies as described herein (e.g., neutralization assays described in Example 3 of U.S. Pat. No. 6,914,128, and by BIAcore analysis, as described in Example 5 of U.S. Pat. No. 6,914,128).

Accordingly, in one aspect, the invention features use of an isolated human antibody, or an antigen-binding portion thereof, which has the following characteristics:

a) has a heavy chain variable region comprising an amino acid sequence selected from the group consisting of SEQ ID NOs: 595-667, wherein the heavy chain variable region has a mutation at a preferred selective mutagenesis position, contact or hypermutation position with an activity enhancing amino acid residue.

b) has a light chain variable region comprising an amino acid sequence selected from the group consisting of SEQ ID NOs: 669-675, wherein the light chain variable region has a mutation at a preferred selective mutagenesis position, contact or hypermutation position with an activity enhancing amino acid residue.

An ordinarily skilled artisan will appreciate that based on the high amino acid sequence similarity between Joe 9 and COS-3 heavy chain germline sequence, and between Joe 9 and DPL8 lambda germline sequence, that other mutations to the CDR regions of these germlines sequences can provide additional antibodies that bind to human IL-12. Such methods of modification can be performed using standard molecular biology techniques as described above.

Accordingly, in one aspect, the invention features use of an isolated human antibody, or an antigen-binding portion thereof, which has the following characteristics:

a) that binds to human IL-12 and dissociates from human IL-12 with a $k_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.

b) has a heavy chain variable region comprising the COS-3 germline amino acid sequence, wherein the heavy chain variable region has a mutation at a preferred selective mutagenesis position, contact or hypermutation position with an activity enhancing amino acid residue.

c) has a light chain variable region comprising the DPL8 germline amino acid sequence, wherein the light chain variable region has a mutation at a preferred selective mutagenesis position, contact or hypermutation position with an activity enhancing amino acid residue.

Due to certain amino acid residues occupying key sites in the CDR and framework regions in the light and heavy chain variable region, structural features are conferred at these regions. In particular, the CDR2 and CDR1 regions are subject to canonical structural classifications. Since there is a high degree of amino acids sequence homology between family members, these canonical features are present between family members. The skilled artisan will appreciate that modifications at the amino acid residues that confer these canonical structures would produce additional antibodies that bind to IL-12. The modifications can be performed using standard molecular biology techniques as described above.

Accordingly, in another aspect, the invention features use of an isolated human antibody, or an antigen-binding portion thereof, which has the following characteristics:

a) that binds to human IL-12 and dissociates from human IL-12 with a $k_{off}$ rate constant of 0.1 $s^{-1}$ or less, as determined by surface plasmon resonance, or which inhibits phytohemagglutinin blast proliferation in an in vitro phytohemagglutinin blast proliferation assay (PHA assay) with an $IC_{50}$ of $1\times10^{-6}$ M or less.

b) has a heavy chain variable region comprising an amino acid sequence selected from a member of the $V_H3$ germline family, wherein the heavy chain variable region comprises a CDR2 that is structurally similar to CDR2s from other $V_H3$ germline family members, and a CDR1 that is structurally similar to CDR1s from other $V_H3$ germline family members, and wherein the heavy chain variable region has a mutation at a preferred selective mutagenesis position, contact or hypermutation position with an activity enhancing amino acid residue;

c) has a light chain variable region comprising an amino acid sequence selected from a member of the $V_{\lambda}1$ germline family, wherein the light chain variable region comprises a CDR2 that is structurally similar to CDR2s from other $V_{\lambda}1$ germline family members, and a CDR1 that is structurally similar to CDR1s from other $V_{\lambda}1$ germline family members, and wherein the light chain variable region has a mutation at a preferred selective mutagenesis position, contact or hypermutation position with an activity enhancing amino acid residue.

Recombinant human antibodies used in the invention have variable and constant regions which are homologous to human germline immunoglobulin sequences selected from the VBASE database. Mutations to the recombinant human antibodies (e.g., by random mutagenesis or PCR mutagenesis) result in amino acids that are not encoded by human germline immunoglobulin sequences. Also, libraries of recombinant antibodies which were derived from human donors will contain antibody sequences that differ from their corresponding germline sequences due to the normal process of somatic mutation that occurs during B-cell development. It should be noted that if the "germline" sequences obtained by PCR amplification encode amino acid differences in the framework regions from the true germline configuration (i.e., differences in the amplified sequence as compared to the true germline sequence), it may be desirable to change these amino acid differences back to the true germline sequences (i.e., "backmutation" of framework residues to the germline configuration). Thus, the present invention can optionally include a backmutation step. To do this, the amino acid sequences of heavy and light chain encoded by the germline (as found as example in VBASE database) are first compared to the mutated immunoglobulin heavy and light chain framework amino acid sequences to identify amino acid residues in the mutated immunoglobulin framework sequence that differ from the closest germline sequences. Then, the appropriate nucleotides of the mutated immunoglobulin sequence are mutated back to correspond to the germline sequence, using the genetic code to determine which nucleotide changes should be made. Mutagenesis of the mutated immunoglobulin framework sequence is carried out by standard methods, such as PCR-mediated mutagenesis (in which the mutated nucleotides are incorporated into the PCR primers such that the PCR product contains the mutations) or site-directed mutagenesis. The role of each amino acid identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. Assays to determine the characteristics of the antibody resulting from mutagenesis can include ELISA, competitive ELISA, in vitro and in vivo neutralization assays and/or (see e.g. Example 3 of U.S. Pat. No. 6,914,128) immunohistochemistry with tissue sections from various sources (including human, primate and/or other species).

To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. This would assure that any peptide epitope presented to the immune system by professional antigen presenting cells in a subject treated with the human antibody of the invention would not be foreign but identical to a self-antigen, i.e. the immunoglobulin encoded by that second germline sequence. Backmutation may occur at any stage of antibody optimization; preferably, backmutation occurs directly before or after the selective mutagenesis approach. More preferably, backmutation occurs directly before the selective mutagenesis approach.

III. Modifications to Preferred Selective Mutagenesis Positions, Contact and/or Hypermutation Positions Typically, selection of antibodies with improved affinities can be carried out using phage display methods, as described in section II above and in U.S. Pat. No. 6,914,128, incorporated by reference herein. This can be accomplished by randomly mutating combinations of CDR residues and generating large libraries containing antibodies of different sequences. However, for these selection methods to work, the antibody-antigen reaction must tend to equilibrium to allow, over time, preferential binding of higher affinity antibodies to the antigen. Selection conditions that would allow equilibrium to be established could not be determined (presumably due to additional non-specific interactions between the antigen and phage particle) when phage display methods were used to improve the affinity of selected anti-IL-12 antibodies, upon attaining a certain level of affinity achieved (i.e., that of antibody Y61). Accordingly, antibodies with even higher affinities could not be selected by phage display methods. Thus, for at least certain antibodies or antigens, phage display methods are limiting in their ability to select antibodies with a highly improved binding specificity/affinity. Accordingly, a method termed Selective Mutagenesis Approach which does not require phage display affinity maturation of antibodies, was established to overcome this limitation and is provided by the invention. Although this Selective Mutagenesis Approach was developed to overcome limitations using the phage display system, it should be noted that this method can also be used with the phage display system. Moreover, the selective mutagenesis approach can be used to improve the activity of any antibody.

To improve the activity (e.g., affinity or neutralizing activity) of an antibody, ideally one would like to mutate every CDR position in both the heavy and light chains to every other possible amino acid residue. However, since there are, on average, 70 CDR positions within an antibody, such an approach would be very time consuming and labor intensive. Accordingly, the method of the invention allows one to improve the activity of the antibody by mutating only certain selected residues within the heavy and/or light chain CDRs. Furthermore, the method of the invention allows improvement in activity of the antibody without affecting other desirable properties of the antibody.

Determining which amino acid residues of an antibody variable region are in contact with an antigen cannot be accurately predicted based on primary sequence or their positions within the variable region. Nevertheless, alignments of sequences from antibodies with different specificities conducted by Kabat et al. have identified the CDRs as local regions within the variable regions which differ significantly among antibodies (Kabat et al. (1971) *Ann. NY Acad, Sci.* 190:382-393, Kabat, E. A., et al (1991) *Sequences of Proteins of Immunological Interest, Fifth Edition*, U.S. Department of Health and Human Services, NIH Publication No. 91-3242). Structural studies have shown that the antigen binding surface is formed by amino acid residues present in the CDRs. Other amino acid residues outside the CDR are also known to play structural roles or be directly involved in antigen binding.

Therefore, for each antigen-antibody pair, amino acid residues within and outside of the CDRs may be important.

The sequence alignment studies by Tomlison et al identified a number of positions in the heavy and light chain CDR1 and CDR2, and in a portion of the kappa chain CDR3 which are frequent sites of somatic mutation. (Tomlison et al (1996) *J. Mol. Biol.* 256: 813-817). In particular, positions H31, H31B, H33, H33B, H52B, H56, H58, L30, L31, L31A, L50, L53, L91, L92, L93 and L94 were identified as frequent sites for somatic mutation. However, this analysis excludes the important heavy chain CDR3 regions, and sections of the light chain CDR3 which are known to lie in the center of an antibody binding site, and potentially provide important interactions with an antigen. Furthermore, Tomlison et al. propose that somatic diversity alone does not necessarily predict a role of a specific amino acid in antigen binding, and suggest conserved amino acid residues that contact the antigen, and diverse amino acid residues which do not contact the antigen. This conclusion is further supported by mutational studies on the role of somatic mutations to antibody affinity (Sharon, (1990), *PNAS,* 87:4814-7). Nineteen somatic mutations in a high-affinity anti-p-azophenylarsonate (Ars) antibody were simultaneously replaced with their corresponding germline residues, generating a germline version of the anti-Ars antibody which had a two-hundred fold loss in activity. The full affinity of the anti-Ars antibody could be recovered by restoring only three of the nineteen somatic mutations, demonstrating that many somatic mutations may be permitted that do not contribute to antigen binding activity.

The result can be explained in part by the nature of antibody diversity itself. Immature B-cells may produce initially low affinity antibodies that recognize a number of self or non-self antigens. Moreover, antibodies may undergo in the course of affinity maturation sequence variations that may cause self-reactivity. Hypermutation of such low affinity antibodies may serve to abolish self-reactivity ("negative selection") and increase affinity for the foreign antigen. Therefore, the analysis of primary and structural data of a large number of antibodies does not provide a method of predicting either (1) the role of somatic hyper-mutation sites in the affinity maturation process versus the process of decreasing affinity towards unwanted antigens, or (2) how a given amino acid contributes to the properties of a specific antigen-antibody pair.

Other attempts to address the role of specific amino acid residues in antigen recognition were made by analyzing a number of crystal structures of antigen-antibody complexes (MacCallum et al. (1996) *J. Mol. Biol.* 262: 732-745). The potential role of positions located within and outside the CDRs was indicated. Positions in CDRs involved in antigen binding in more than 10 of 26 analyzed structures included H31, H33, H50, H52, H53, H54, H56, H58, H95, H96, H97, H98 and H100 in the heavy chain and L30A, L32, L91, L92, L93, L94, L96 in the light chain. However, the authors noted that prediction of antigen contacts using these and other structural data may over and under predict contact positions, leading to the speculation that a different strategy may have to be applied to different antigens.

Pini et al. describe randomizing multiple residues in antibody CDR sequences in a large phage display library to rapidly increase antibody affinity (Pini et al. (1998) *J. Biol Chem.* 273: 21769-21776). However, the high affinity antibodies discussed by Pini et al. had mutations in a total of eight positions, and a reductionary analysis of which changes are absolutely required to improve affinity of the antibody becomes impractical because of the large number of possible combinations to be tested for the smallest number of amino acids required.

Furthermore, randomizing multiple residues may not necessarily preserve other desired properties of the antibody. Desirable properties or characteristics of an antibody are art-recognized and include for example, preservation of non-cross reactivity, e.g., with other proteins or human tissues and preservation of antibody sequences that are close to human germline immunoglobulin sequences improvement of neutralization potency. Other desirable properties or characteristics include ability to preserve species cross reactivity, ability to preserve epitope specificity and ability to preserve high expression levels of protein in mammalian cells. The desirable properties or characteristics can be observed or measured using art-recognized techniques including but not limited to ELISA, competitive ELISA, in vitro and in vivo neutralization assays (see e.g. Example 3 of U.S. Pat. No. 6,914,128), immunohistochemistry with tissue sections from different sources including human, primate or other sources as the need may be, and studies to expression in mammalian cells using transient expression or stable expression.

In addition, the method of Pini et al may introduce more changes than the minimal number actually required to improve affinity and may lead to the antibodies triggering anti-human-antibody (HAMA) formation in human subjects. Further, as discussed elsewhere, the phage display as demonstrated here, or other related method including ribosome display may not work appropriately upon reaching certain affinities between antibody and antigen and the conditions required to reach equilibrium may not be established in a reasonable time frame because of additional interactions including interactions with other phage or ribosome components and the antigen.

The ordinarily skilled artisan may glean interesting scientific information on the origin of antibody diversity from the teachings of the references discussed above. The present invention, however, provides a method for increasing antibody affinity of a specific antigen-antibody pair while preserving other relevant features or desirable characteristics of the antibody. This is especially important when considering the desirability of imparting a multitude of different characteristics on a specific antibody including antigen binding.

If the starting antibody has desirable properties or characteristics which need to be retained, a selective mutagenesis approach can be the best strategy for preserving these desirable properties while improving the activity of the antibody. For example, in the mutagenesis of Y61, the aim was to increase affinity for hIL-12, and to improve the neutralization potency of the antibody while preserving desired properties. Desired properties of Y61 included (1) preservation of non-cross reactivity with other proteins or human tissues, (2) preservation of fine epitope specificity, i.e. recognizing a p40 epitope preferably in the context of the p70 (p40/p35) heterodimer, thereby preventing binding interference from free soluble p40; and (3) generation of an antibody with heavy and light chain amino acid sequences that were as close as possible to their respective germline immunoglobulin sequences.

In one embodiment, the method of the invention provides a selective mutagenesis approach as a strategy for preserving the desirable properties or characteristics of the antibody while improving the affinity and/or neutralization potency. The term "selective mutagenesis approach" is as defined above and includes a method of individually mutating selected amino acid residues. The amino acid residues to be mutated may first be selected from preferred selective mutagenesis positions, then from contact positions, and then from hypermutation positions. The individual selected position can be mutated to at least two other amino acid residue and the effect of the mutation both on the desired properties of the antibody, and improvement in antibody activity is determined.

The Selective Mutagenesis approach comprises the steps of:

selecting candidate positions in the order 1) preferred selective mutagenesis positions; 2) contact positions; 3) hypermutation positions and ranking the positions based on the location of the position within the heavy and light chain variable regions of an antibody (CDR3 preferred over CDR2 preferred over CDR1);

individually mutating candidate preferred selective mutagenesis positions, hypermutation and/or contact positions in the order of ranking, to all possible other amino acid residues and analyzing the effect of the individual mutations on the activity of the antibody in order to determine activity enhancing amino acid residues;

if necessary, making stepwise combinations of the individual activity enhancing amino acid residues and analyzing the effect of the various combinations on the activity of the antibodies; selecting mutant antibodies with activity enhancing amino acid residues and ranking the mutant antibodies based on the location and identity of the amino acid substitutions with regard to their immunogenic potential. Highest ranking is given to mutant antibodies that comprise an amino acid sequence which nearly identical to a variable region sequence that is described in a germline database, or has an amino acid sequence that is comparable to other human antibodies. Lower ranking is given to mutant antibodies containing an amino acid substitution that is rarely encountered in either germline sequences or the sequences of other human antibodies. The lowest ranking is given to mutant antibodies with an amino acid substitution that has not been encountered in a germline sequence or the sequence of another human antibody. As set forth above, mutant antibodies comprising at least one activity enhancing amino acid residue located in CDR3 is preferred over CDR2 which is preferred over CDR1. The CDRs of the heavy chain variable regions are preferred over those of the light chain variable region.

The mutant antibodies can also be studied for improvement in activity, e.g. when compared to their corresponding parental antibody. The improvement in activity of the mutant antibody can be determined for example, by neutralization assays, or binding specificity/affinity by surface plasmon resonance analysis (see Example 3 of U.S. Pat. No. 6,914,128). Preferably, the improvement in activity can be at least 2-20 fold higher than the parental antibody. The improvement in activity can be at least "$x_1$" to "$x_2$" fold higher than the parental antibody wherein "$x_1$" and "$x_2$" are integers between and including 2 to 20, including ranges within the state range, e.g. 2-15, e.g. 5-10.

The mutant antibodies with the activity enhancing amino acid residue also can be studied to determine whether at least one other desirable property has been retained after mutation. For example, with anti-hIL-12 antibodies testing for, (1) preservation of non-cross reactivity with other proteins or human tissues, (2) preservation of epitope recognition, i.e. recognizing a p40 epitope preferably in the context of the p70 (p40/p35) heterodimer, thereby preventing binding interference from free soluble p40; and (3) generation of antibodies with heavy and light chain amino acid sequences that were as close as possible to their respective germline immunoglobulin sequences, and determining which would be least likely to elicit a human immune response based on the number of differences from the germline sequence. The same observations can be made on an antibody having more than one activity enhancing amino acid residues, e.g. at least two or at least three activity enhancing amino acid residues, to determine whether retention of the desirable property or characteristic has occurred.

An example of the use of a "selective mutagenesis approach", in the mutagenesis of Y61 is described below. The individual mutations H31S→E, L50→Y, or L94G→Y each improved neutralization activity of the antibody. However, when combination clones were tested, the activity of the combined clone H31S→E+L50→Y+L94G→Y was no better than L50→Y+L94G→Y (J695). Therefore, changing the germline amino acid residue Ser to Glu at position 31 of CDR1 was unnecessary for the improved activity of J695 over Y61. The selective mutagenesis approach therefore, identified the minimal number of changes that contributed to the final activity, thereby reducing the immunogenic potential of the final antibody and preserving other desired properties of the antibody.

Isolated DNA encoding the VH and VL produced by the selected mutagenesis approach can be converted into full length antibody chain genes, to Fab fragment genes as to a scFV gene, as described in section IV. For expression of VH and VL regions produced by the selected mutagenesis approach, expression vectors encoding the heavy and light chain can be transfected into variety host cells as described in detail in section IV. Preferred host cells include either prokaryotic host cells, for example, *E coli*, or eukaryotic host cells, for example, yeast cells, e.g., *S. cerevisae*. Most preferred eukaryotic host cells are mammalian host cells, described in detail in section IV.

The selective mutagenesis approach provides a method of producing antibodies with improved activities without prior affinity maturation of the antibody by other means. The selective mutagenesis approach provides a method of producing antibodies with improved affinities which have been subject to back mutations. The selective mutagenesis approach also provides a method of improving the activity of affinity matured antibodies.

The skilled artisan will recognize that the selective mutagenesis approach can be used in standard antibody manipulation techniques known in the art. Examples include, but are not limited to, CDR grafted antibodies, chimeric antibodies, scFV fragments, Fab fragments of a full length antibodies and human antibodies from other sources, e.g., transgenic mice.

Rapid large scale mutational analysis of antibodies include in vitro transcription and translation using ribosome display technology (see e.g., Hanes et al., (1997) *Proc. Natl. Acad. Sci.* 94: 4937-4942; Dall Acqua et al., (1998) *Curr. Opin. Struc. Biol.* 8: 443-450; He et al, (1997) *Nucleic Acid Res.* 25:5132-5134), and U.S. Pat. Nos. 5,643,768 and 5,658,754 issued to Kawasaki. The selective mutagenesis approach also provides a method of producing antibodies with improved activities that can be selected using ribosomal display techniques.

In the methods of the invention, antibodies or antigen binding portions thereof are further modified by altering individual positions in the CDRs of the HCVR and/or LCVR. Although these modifications can be made in phage-displayed antibodies, the method is advantageous in that it can be performed with antibodies that are expressed in other types of host systems, such as bacterial, yeast or mammalian cell expression systems. The individual positions within the CDRs selected for modification are based on the positions being a contact and/or hypermutation position.

Preferred contact positions and hypermutation positions as defined herein are shown in Table 3 of U.S. Pat. No. 6,914,128 (see Appendix A of U.S. Pat. No. 6,914,128 and Table 3 of Appendix A attached herto) and their modification in accordance with the method of the invention is described in detail in Example 2 of U.S. Pat. No. 6,914,128. Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred amino acid residues (referred to as “preferred selective mutagenesis positions”) are both contact and hypermutation positions and are selected from the group consisting of H30, H31, H31B, H32, H33, H52, H56, H58, L30, L31, L32, L50, L91, L92, L93, L94. Particularly preferred contact positions are selected from the group consisting of L50 and L94. Preferred activity enhancing amino acid residues replace amino acid residues located at positions selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94, and L96. More preferred activity enhancing amino acid residues replace amino acid residues located at positions H30, H31, H31B, H32, H33, H52, H56, H58, L30, L31, L32, L50, L91, L92, L93, L94. Particularly, preferred activity enhancing amino acid residues replace amino acid residues located at positions selected from the group consisting of L50 and L94.

In general, the method of the invention involves selecting a particular preferred selective mutagenesis position, contact and/or hypermutation position within a CDR of the heavy or light chain of a parent antibody of interest, or antigen binding portion thereof, randomly mutagenizing that individual position (e.g., by genetic means using a mutagenic oligonucleotide to generate a “mini-library” of modified antibodies), or mutating a position to specific desired amino acids, to identify activity enhancing amino acid residues expressing, and purifying the modified antibodies (e.g., in a non-phage display host system), measuring the activity of the modified antibodies for antigen (e.g., by measuring $k_{off}$ rates by BIAcore analysis), repeating these steps for other CDR positions, as necessary, and combining individual mutations shown to have improved activity and testing whether the combination(s) generate an antibody with even greater activity (e.g., affinity or neutralizing potency) than the parent antibody, or antigen-binding portion thereof.

Accordingly, in one embodiment, the invention provides a method for improving the activity of an antibody, or antigen-binding portion thereof, comprising:

a) providing a parent antibody or antigen-binding portion thereof;

b) selecting in order a 1) preferred selective mutagenesis position, 2) contact position, or 3) hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof;

e) optionally, repeating steps a) through d) for at least one other preferred selective mutagenesis position, contact or hypermutation position;

f) combining, in the parent antibody, or antigen-binding portion thereof, individual mutations shown to have improved activity, to form combination antibodies, or antigen-binding portions thereof; and g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained. Preferably, the selected antibody or antibodies have an improved activity without loss or with retention of at least one desirable characteristic or property of the parental antibody as described above. The desirable characteristic or property can be measured or observed by the ordinarily skilled artisan using art-recognized techniques.

Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

In another embodiment, the invention provides a method for improving the activity of an antibody, or antigen-binding portion thereof, comprising:

a) providing a parent antibody or antigen-binding portion thereof;

b) selecting a preferred selective mutagenesis position, contact or hypermutation position within a complementarity determining region (CDR) for mutation;

c) individually mutating said selected preferred selective mutagenesis position, contact or hypermutation position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) optionally, repeating steps a) through d) for at least one other preferred selective mutagenesis position, contact or hypermutation position;

f) combining, in the parent antibody, or antigen-binding portion thereof, two individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof;

until an antibody, or antigen-binding portion thereof, with an improved activity, relative to the parent antibody, or antigen-binding portion thereof, is obtained.

Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

In another embodiment, the invention provides a method for improving the activity of an antibody, or antigen-binding portion thereof, comprising:

a) providing a parent antibody or antigen-binding portion thereof;

b) selecting a preferred selective mutagenesis position, contact or hypermutation position within a complementarity determining region (CDR) for mutation;

c) individually mutating said selected preferred selective mutagenesis position, contact or hypermutation position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) optionally, repeating steps a) through d) for at least one other preferred selective mutagenesis position, contact or hypermutation position;

f) combining, in the parent antibody, or antigen-binding portion thereof, three individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof;

until an antibody, or antigen-binding portion thereof, with an improved activity, relative to the parent antibody, or antigen-binding portion thereof, is obtained.

Preferably, the activity enhancing amino acid residue replaces amino acid residues located at positions selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96.

Following mutagenesis of individual selected positions, mutated clones can be sequenced to identify which amino acid residues have been introduced into the selected position in each clone. A small number of clones (e.g., about 24) can be selected for sequencing, which statistically should yield 10-15 unique antibodies, whereas larger numbers of clones (e.g., greater than 60) can be sequenced to ensure that antibodies with every possible substitution at the selected position are identified.

In one embodiment, contact and/or hypermutation positions within the CDR3 regions of the heavy and/or light chains are first selected for mutagenesis. However, for antibodies that have already been affinity matured in vitro by random mutagenesis of the CDR3 regions via phage display selection, it may be preferably to first select contact and/or hypermutation positions within CDR1 or CDR2 of the heavy and/or light chain.

In a more preferred embodiment, preferred selective mutagenesis positions within the CDR3 regions of the heavy and/or light chains are first selected for mutagenesis. However, for antibodies that have already been affinity matured in vitro by random mutagenesis of the CDR3 regions via phage display selection, it may be preferably to first select preferred selective mutagenesis positions within CDR1 or CDR2 of the heavy and/or light chain.

In another preferred embodiment, the optimization of a selected antibody by the selective mutagenesis approach is done sequentially as follows: preferred selective mutagenesis positions selected from the group consisting of H30, H31, H31B, H32, H33, H52, H56, H58, L30, L31, L32, L50, L91, L92, L93, L94 are mutated first to at least 2 other amino acids each (preferably 5-14 other amino acids) and the resulting antibodies are characterized for increased affinity, neutralization potency (and possibly also for at least one other retained characteristic or property discussed elsewhere). If a mutation of a single preferred selective mutagenesis position does not increase the affinity or neutralization potency at all or sufficiently and if even the combination of multiple activity enhancing amino acids replacing amino acids in preferred selective mutagenesis positions does not result in an combination antibody which meets the target activity (including affinity and/or neutralization potency), additional amino acid residues will be selected for selective mutagenesis from the group consisting of H35, H50, H53, H54, H95, H96, H97, H98, L30A and L96 are mutated to at least 2 other amino acids each (preferably 5-14 other amino acids) and the resulting antibodies are characterized for increased affinity, neutralization potency (and possibly also for at least one other retained characteristic or property discussed elsewhere).

If a mutation of a single amino acid residue selected from the group consisting of H35, H50, H53, H54, H95, H96, H97, H98, L30A and L96 does not increase the activity (including affinity and/or neutralization potency) at all or not sufficiently and if even the combination of multiple activity enhancing amino acids replacing amino acids in those positions does not result in an combination antibody which meets the targeted activity (including affinity and/or target neutralization potency), additional amino acid residues will be selected for selective mutagenesis from the group consisting of H33B, H52B, L31A and are mutated to at least 2 other amino acids each (preferably 5-14 other amino acids) and the resulting antibodies are characterized for increased affinity, neutralization potency (and possibly also for at least one other retained characteristic or property discussed elsewhere).

It should be understood that the sequential selective mutagenesis approach may end at any of the steps outline above as soon as an antibody with the desired activity (including affinity and neutralization potency) has been identified. If mutagenesis of the preselected positions has identified activity enhancing amino acids residues but the combination antibody still do not meet the targets set for activity (including affinity and neutralization potency) and/or if the identified activity enhancing amino acids also affect other desired characteristics and are therefore not acceptable, the remaining CDR residues may be subjected to mutagenesis (see section IV).

The method of the invention can be used to improve activity of an antibody, or antigen binding portion thereof, to reach a predetermined target activity (e.g. a predetermined affinity and/or neutralization potency, and/or a desired property or characteristic).

Accordingly, the invention provides a method of improving the activity of an antibody, or antigen-binding portion thereof, to attain a predetermined target activity, comprising:

a) providing a parent antibody a antigen-binding portion thereof;

b) selecting a preferred selective mutagenesis position selected from group consisting of H30, H31, H31B, H32, H33, H52, H56, H58, L30, L31, L32, L50, L91, L92, L93, L94.

c) individually mutating the selected preferred selective mutagenesis position to at least two other amino acid residues to hereby create a first panel of mutated antibodies, or antigen binding portions thereof;

d) evaluating the activity of the first panel of mutated antibodies, or antigen binding portions thereof to determined if mutation of a single selective mutagenesis position produces an antibody or antigen binding portion thereof with the predetermined target activity or a partial target activity;

e) combining in a stepwise fashion, in the parent antibody, or antigen binding portion thereof, individual mutations shown to have an improved activity, to form combination antibodies, or antigen binding portions thereof.

f) evaluating the activity of the combination antibodies, or antigen binding portions thereof to determined if the combination antibodies, or antigen binding portions thereof have the predetermined target activity or a partial target activity.

g) if steps d) or f) do not result in an antibody or antigen binding portion thereof having the predetermined target activity, or result an antibody with only a partial activity, additional amino acid residues selected from the group consisting of H35, H50, H53, H54, H95, H96, H97, H98, L30A and L96 are mutated to at least two other amino acid residues to thereby create a second panel of mutated antibodies or antigen-binding portions thereof;

h) evaluating the activity of the second panel of mutated antibodies or antigen binding portions thereof, to determined if mutation of a single amino acid residue selected from the group consisting of H35, H50, H53, H54, H95, H96, H97, H98, L30A and L96 results an antibody or antigen binding portion thereof, having the predetermined target activity or a partial activity;

i) combining in stepwise fashion in the parent antibody, or antigen-binding portion thereof, individual mutations of step g) shown to have an improved activity, to form combination antibodies, or antigen binding portions thereof;

j) evaluating the activity of the combination antibodies or antigen binding portions thereof, to determined if the combination antibodies, or antigen binding portions thereof have the predetermined target activity or a partial target activity;

k) if steps h) or j) do not result in an antibody or antigen binding portion thereof having the predetermined target activity, or result in an antibody with only a partial activity, additional amino acid residues selected from the group consisting of H33B, H52B and L31A are mutated to at least two other amino acid residues to thereby create a third panel of mutated antibodies or antigen binding portions thereof;

l) evaluating the activity of the third panel of mutated antibodies or antigen binding portions thereof, to determine if a mutation of a single amino acid residue selected from the group consisting of H33B, H52B and L31A resulted in an antibody or antigen binding portion thereof, having the predetermined target activity or a partial activity;

m) combining in a stepwise fashion in the parent antibody, or antigen binding portion thereof, individual mutation of step k) shown to have an improved activity, to form combination antibodies, or antigen binding portions, thereof;

n) evaluating the activity of the combination antibodies or antigen-binding portions thereof, to determine if the combination antibodies, or antigen binding portions thereof have the predetermined target activity to thereby produce an antibody or antigen binding portion thereof with a predetermined target activity.

A number of mutagenesis methods can be used, including PCR assembly, Kunkel (dut-ung-) and thiophosphate (Amersham Sculptor kit) oligonucleotide-directed mutagenesis.

A wide variety of host expression systems can be used to express the mutated antibodies, including bacterial, yeast, baculoviral and mammalian expression systems (as well as phage display expression systems). An example of a suitable bacterial expression vector is pUC119(Sfi). Other antibody expression systems are known in the art and/or are described below in section IV.

The modified antibodies, or antigen binding portions thereof, produced by the method of the invention can be identified without the reliance on phage display methods for selection. Accordingly, the method of the invention is particularly advantageous for improving the activity of a recombinant parent antibody or antigen-binding portion thereof, that was obtained by selection in a phage-display system but whose activity cannot be further improved by mutagenesis in the phage-display system.

Accordingly, in another embodiment, the invention provides a method for improving the affinity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof;

e) optionally repeating steps b) through d) for at least one other preferred selective mutagenesis position, contact or hypermutation position;

f) combining, in the parent antibody, or antigen-binding portion thereof, individual mutations shown to have improved activity, to form combination antibodies, or antigen-binding portions thereof; and g) evaluating the activity of the combination antibodies, or antigen-binding portions thereof, relative to the parent antibody or antigen-binding portion thereof; until an antibody, or antigen-binding portion thereof, with an improved activity, relative to the parent antibody, or antigen-binding portion thereof, is obtained.

Preferred contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96. Preferred hypermutation positions are selected from the group consisting of H30, H31, H31B, H32, H52, H56, H58, L30, L31, L32, L53 and L93. More preferred preferred selective mutagenesis positions are selected from the group consisting of H30, H31, H31B, H32, H33, H52, H56, H58, L30, L31, L32, L50, L91, L92, L93 and L94. Particularly preferred contact positions are selected from the group consisting of L50 and L94.

With available methods it is not possible or it is extremely laborious to derive an antibody with increased binding affinity and neutralization potency while retaining other properties or characteristics of the antibodies as discussed above. The method of this invention, however, can readily identify such antibodies. The antibodies subjected to the method of this invention can come from any source.

Therefore, in another embodiment, the invention provides a method for improving the activity of an antibody, or antigen-binding portion thereof, comprising:

a) providing a recombinant parent antibody or antigen-binding portion thereof;

b) selecting a preferred selective mutagenesis position, contact or hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof and expressing said panel in an appropriate expression system;

d) evaluating the activity of the panel of mutated antibodies, or antigen-binding portions thereof, relative to the parent antibody or antigen-binding portion thereof, thereby identifying an activity enhancing amino acid residue;

e) evaluating the panel of mutated antibodies, or antigen-binding portions thereof, relative to the parent antibody or antigen-binding portion thereof for at least one other property or characteristics, wherein the property or characteristic is one that needs to be retained in the antibody;

until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

If therefore, the affinity of an antibody for a specific antigen should be improved, but where the phage display (or related system including ribosome display) method is no longer applicable, and other desirable properties or characteristics should be retained, the method of the invention can be used. Accordingly, in another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected preferred selective mutagenesis position, contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.

f) optionally, repeating steps a) through e) for at least one other preferred selective mutagenesis position, contact or hypermutation position;

g) combining, in the parent antibody, or antigen-binding portion thereof, at least two individual activity enhancing amino acid residues shown to have improved activity and at least one retained property or characteristic, to form combination antibodies, or antigen-binding portions thereof; and h) evaluating the activity of the combination antibodies, or antigen-binding portions thereof, relative to the parent antibody or antigen-binding portion thereof; until an antibody, or antigen-binding portion thereof, with an improved activity and at least one retained other property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected contact or hypermutation position;

c) individually mutating said selected preferred selective mutagenesis position, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a preferred selective mutagenesis position, contact or hypermutation position within a complementarity determining region (CDR) for mutation, thereby identifying a selected contact or hypermutation position;

c) individually mutating said selected preferred selective mutagenesis positions, contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof for at least one other property or characteristic, wherein the property or characteristic is one that needs to be retained, until an antibody, or antigen-binding portion thereof, with an improved activity and at least one retained characteristic, relative to the parent antibody, or antigen-binding portion thereof, is obtained.

f) optionally, repeating steps a) through e) for at least one other preferred selective mutagenesis position, contact or hypermutation position;

g) combining, in the parent antibody, or antigen-binding portion thereof, at least two individual activity enhancing amino acid residues shown to have improved activity and at least on retained other characteristic, to form combination antibodies, or antigen-binding portions thereof; and h) evaluating the activity of the combination antibodies, or antigen-binding portions thereof, relative to the parent antibody or antigen-binding portion thereof; until an antibody, or antigen-binding portion thereof, with an improved activity and at least one retained property or characteristic, relative to the parent antibody, or antigen-binding portion thereof, is obtained.

In a preferred embodiment, the contact positions are selected from the group consisting of H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In another preferred embodiment, the hypermutation positions are selected from the group consisting of H30, H31, H31B, H32, H52, H56, H58, L30, L31, L32, L53 and L93 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment the residues for selective mutagenesis are selected from the preferred selective mutagenesis positions from the group consisting of H30, H31, H31B, H32, H33, H52, H56, H58, L30, L31, L32, L50, L91, L92, L93, L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

In a more preferred embodiment, the contact positions are selected from the group consisting of L50 and L94 and the other characteristic is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

IV. Modifications of Other CDR Residues

Ultimately, all CDR residues in a given antibody-antigen pair identified by any means to be required as activity enhancing amino acid residues and/or required directly or indirectly for binding to the antigen and/or for retaining other desirable properties or characteristics of the antibody. Such CDR residues are referred to as “preferred selective mutagenesis positions”. It should be noted that in specific circumstances that preferred selective mutagenesis residues can be identified also by other means including co-crystallization of antibody and antigen and molecular modeling.

If the preferred attempts to identify activity enhancing amino acids focussing on the preferred selective mutagenesis positions, contact or hypermutation positions described above are exhausted, or if additional improvements are required, the remaining CDR residues may be modified as described below. It should be understood that the antibody could already be modified in any one or more contact or hypermutation positions according to the embodiments discussed above but may require further improvements. Therefore, in another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position e.g., to at least two other amino acid residues to thereby create a mutated antibody or a panel of mutated antibodies, or antigen-binding portions thereof;

d) evaluating the activity of the mutated antibody or the panel of mutated antibodies, or antigen-binding portions thereof, relative to the parent antibody or antigen-binding portion thereof thereby identifying an activity enhancing amino acid residue;

e) evaluating the mutated antibody or the panel of mutated antibodies, or antigen-binding portions thereof, relative to the parent antibody or antigen-binding portion thereof, for changes in at least one other property or characteristic until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e) repeating steps b) through d) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity, to form combination antibodies, or antigen-binding portions thereof; and g) evaluating the activity of the combination antibodies, or antigen-binding portions thereof with two activity enhancing amino acid residues, relative to the parent antibody or antigen-binding portion thereof until an antibody, or antigen-binding portion thereof, with an improved activity, relative to the parent antibody, or antigen-binding portion thereof, is obtained.

If the preferred attempts to identify activity enhancing amino acids focussing on the contact or hypermutation positions described above are exhausted, or if additional improvements are required, and the antibody in question can not further be optimized by mutagenesis and phage display (or related ribosome display) methods the remaining CDR residues may be modified as described below. It should be understood that the antibody could already be modified in any one or more preferred selective mutagenesis position, contact or hypermutation positions according to the embodiments discussed above but may require further improvements.

Therefore, in another embodiment, the invention provides a method for improving the activity of an antibody, or antigen-binding portion thereof, comprising:

a) providing a recombinant parent antibody or antigen-binding portion thereof; that was obtained by selection in a phage-display system but whose activity cannot be further improved by mutagenesis in said phage-display system;

b) selecting a selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and;

c) individually mutating said selected contact or hypermutation position to at least two other amino acid residues to thereby create a panel of mutated antibodies, or antigen-binding portions thereof, and expressing said panel in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof, for changes in at least one other property or characteristic, until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence.

If a single mutagenesis is not sufficient to increase the affinity of the antibody other residues may be included in the mutagenesis. Therefore, in another embodiment, the invention provides a method for improving the activity of an antibody, or antigen-binding portion thereof, comprising:

a) providing a parent antibody or antigen-binding portion thereof that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof and expression in a non-phage display system;

d) evaluating the activity of the panel of mutated antibodies, or antigen-binding portions thereof, relative to the parent antibody or antigen-binding portion thereof thereby identifying an activity enhancing amino acid residue;

e) repeating steps b) through d) for at least one other position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94;

g) combining, in the parent antibody, or antigen-binding portion thereof, at least two individual activity enhancing amino acid residues shown to have improved activity, to form combination antibodies, or antigen-binding portions thereof; and h) evaluating the activity and other property or characteristic of the combination antibodies, or antigen-binding portions thereof with two activity enhancing amino acid residues, relative to the parent antibody or antigen-binding portion thereof; until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence The preferred attempts to identify activity enhancing amino acids focussing on the preferred selective mutagenesis positions, contact or hypermutation positions described may be exhausted, or additional improvements may be required, and it is important to retain other properties or characteristics of the antibody.

Therefore, in another embodiment, the invention provides a method for improving the activity of an antibody, or antigen-binding portion thereof, without affecting other characteristics, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity and retained other property or characteristic, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:

a) providing a parent antibody or antigen-binding portion thereof;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof;

d) evaluating the activity of the panel of mutated antibodies, or antigen-binding portions thereof, relative to the parent antibody or antigen-binding portion thereof, thereby identifying an activity enhancing amino acid residue;

e.) evaluating the panel of mutated antibodies or antigen-binding portions thereof, relative to the parent antibody or antigen-portion thereof, for changes in at least one other characteristic or property;

e) repeating steps b) through e) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity and not affecting at least one other property or characteristic, to form combination antibodies, or antigen-binding portions thereof; and g) evaluating the activity and the retention of at least one other property or characteristic of the combination antibodies, or antigen-binding portions thereof with two activity enhancing amino acid residues, relative to the parent antibody or antigen-binding portion thereof until an antibody, or antigen-binding portion thereof, with an improved activity and at least one retained other property or characteristic, relative to the parent antibody, or antigen-binding portion thereof, is obtained.

Mutagenesis of the preferred selective mutagenesis position, contact and hypermutation residues may not have increased the affinity of the antibody sufficiently, and mutagenesis and the phage display method (or related ribosome display method) may no longer be useful and at least one other characteristic or property of the antibody should be retained.

Therefore, in another embodiment the invention provides a method to improve the affinity of an antibody or antigen-binding portion thereof, comprising:

a) providing a parent antibody or antigen-binding portion thereof that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof and expression in a non-phage display system;

d) evaluating the activity of the panel of mutated antibodies, or antigen-binding portions thereof, relative to the parent antibody or antigen-binding portion thereof thereby identifying an activity enhancing amino acid residue;

e) evaluating the panel of mutated antibodies, or antigen-binding portions thereof, relative to the parent antibody or antigen-binding portion thereof, for changes in at least one other property or characteristic until an antibody, or antigen-binding portion thereof, with an improved activity, relative to the parent antibody, or antigen-binding portion thereof, is obtained.

Preferably, the other characteristic or property is selected from 1) preservation of non-crossreactivity with other proteins or human tissues, 2) preservation of epitope recognition, i.e. recognizing p40 epitope preferably in the context of the p70 p40/p35 heterodimer preventing binding interference from free, soluble p40 and/or 3) to produce an antibody with a close to germline immunoglobulin sequence If mutagenesis of a single residue is not sufficient other residues can be included; therefore, in another embodiment, the invention provides a method for improving the activity of an antibody, or antigen-binding portion thereof, comprising:

a) providing a parent antibody or antigen-binding portion thereof that was obtained by selection in a phage-display system but whose activity cannot be further improved by mutagenesis in said phage-display system;

b) selecting an amino acid residue within a complementarity determining region (CDR) for mutation other than H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

c) individually mutating said selected position to at least two other amino acid residues to thereby create a panel of mutated antibodies, or antigen-binding portions thereof and expression in a non-phage display system;

d) evaluating the activity and retention of at least one other property or characteristic of the panel of mutated antibodies, or antigen-binding portions thereof, relative to the parent antibody or antigen-binding portion thereof, thereby identifying an activity enhancing amino acid residue;

e) repeating steps b) through d) for at least one other CDR position which is neither the position selected under b) nor a position at H30, H31, H31B, H32, H33, H35, H50, H52, H52A, H53, H54, H56, H58, H95, H96, H97, H98, H101, L30, L31, L32, L34, L50, L52, L53, L55, L91, L92, L93, L94 and L96;

f) combining, in the parent antibody, or antigen-binding portion thereof, at least two individual activity enhancing amino acid residues shown to have improved activity and not to affect at least one other property or characteristic, to form combination antibodies, or antigen-binding portions thereof; and g) evaluating the activity and retention of at least one property or characteristic of the combination antibodies, or antigen-binding portions thereof with two activity enhancing amino acid residues, relative to the parent antibody or antigen-binding portion thereof until an antibody, or antigen-binding portion thereof, with an improved activity and at least one other retained characteristic or property, relative to the parent antibody, or antigen-binding portion thereof, is obtained.

V. Expression of Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To obtain a DNA fragment encoding the heavy chain variable region of Joe 9 wt or a Joe 9 wt-related antibody, antibodies specific for human IL-12 were screened from human libraries and mutated, as described in section II. Once DNA fragments encoding Joe 9 wt or Joe 9 wt-related VH and VL segments are obtained, mutagenesis of these sequences is carried out by standard methods, such as PCR site directed mutagenesis (PCR-mediated mutagenesis in which the mutated nucleotides are incorporated into the PCR primers such that the PCR product contains the mutations) or other site-directed mutagenesis methods. Human IL-12 antibodies that displayed a level of activity and binding specificity/affinity that was desirable, for example J695, were further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region and any allotypic variant therein as described in Kabat (, Kabat, E. A., et al. (1991) *Sequences of Proteins of Immunological Interest, Fifth Edition*, U.S. Department of Health and Human Services, NIH Publication No. 91-3242), but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a lambda constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the J695 or J695-related light or heavy chain sequences, the expression vector may already carry antibody constant region sequences. For example, one approach to converting the J695 or J695-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., U.S. Pat. No. 5,464,758 by Bujard et al. and U.S. Pat. No. 5,654,168 by Bujard et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in $dhfr^-$ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hIL-12 The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hIL-12 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies or antigen-binding portions thereof of the invention can be expressed in an animal (e.g., a mouse) that is transgenic for human immunoglobulin genes (see e.g., Taylor, L. D. et al. (1992) Nucl. Acids Res. 20: 6287-6295). Plant cells can also be modified to create transgenic plants that express the antibody or antigen binding portion thereof, of the invention.

In view of the foregoing, another aspect of the invention pertains to nucleic acid, vector and host cell compositions that can be used for recombinant expression of the antibodies and antibody portions of the invention. Preferably, the invention features isolated nucleic acids that encode CDRs of J695, or the full heavy and/or light chain variable region of J695. Accordingly, in one embodiment, the invention features an isolated nucleic acid encoding an antibody heavy chain variable region that encodes the J695 heavy chain CDR3 comprising the amino acid sequence of SEQ ID NO: 25. Preferably, the nucleic acid encoding the antibody heavy chain variable region further encodes a J695 heavy chain CDR2 which comprises the amino acid sequence of SEQ ID NO: 27. More preferably, the nucleic acid encoding the antibody heavy chain variable region further encodes a J695 heavy chain CDR1 which comprises the amino acid sequence of SEQ ID NO: 29. Even more preferably, the isolated nucleic acid encodes an antibody heavy chain variable region comprising the amino acid sequence of SEQ ID NO: 31 (the full VH region of J695).

In other embodiments, the invention features an isolated nucleic acid encoding an antibody light chain variable region that encodes the J695 light chain CDR3 comprising the amino acid sequence of SEQ ID NO: 26. Preferably, the nucleic acid encoding the antibody light chain variable region further encodes a J695 light chain CDR2 which comprises the amino acid sequence of SEQ ID NO: 28. More preferably, the nucleic acid encoding the antibody light chain variable region further encodes a J695 light chain CDR1 which comprises the amino acid sequence of SEQ ID NO: 30. Even more preferably, the isolated nucleic acid encodes an antibody light chain variable region comprising the amino acid sequence of SEQ ID NO: 32 (the full VL region of J695).

The invention also provides recombinant expression vectors encoding both an antibody heavy chain and an antibody light chain. For example, in one embodiment, the invention provides a recombinant expression vector encoding:

a) an antibody heavy chain having a variable region comprising the amino acid sequence of SEQ ID NO: 31; and b) an antibody light chain having a variable region comprising the amino acid sequence of SEQ ID NO: 32.

The invention also provides host cells into which one or more of the recombinant expression vectors of the invention have been introduced. Preferably, the host cell is a mammalian host cell, more preferably the host cell is a CHO cell, an NS0 cell or a COS cell. Still further the invention provides a method of synthesizing a recombinant human antibody of the invention by culturing a host cell of the invention in a suitable culture medium until a recombinant human antibody of the invention is synthesized. The method can further comprise isolating the recombinant human antibody from the culture medium.

VI. Pharmaceutical Compositions and Pharmaceutical Administration

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In a preferred embodiment, the pharmaceutical composition includes the antibody at a dosage of about 100 mg-200 mg dose.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-12 activity is detrimental. For example, an anti-hIL-12 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

Interleukin 12 plays a critical role in the pathology associated with a variety of diseases involving immune and inflammatory elements. These diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes, autoimmune uveitis.

Preferably, the antibodies of the invention or antigen-binding portions thereof, are used to treat rheumatoid arthritis, Crohn's disease, multiple sclerosis, insulin dependent diabetes mellitus and psoriasis, as described in more detail in section VII.

A human antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the IL-12 antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function. Furthermore, additional agents described herein used in combination with an IL-12 antibody, are not limited to the disorder to which they are attributed for treatment.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-12 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF (including adalimumab/HUMIRA), LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (U.S. application Ser. No. 08/599,226 filed Feb. 9, 1996), cA2 (Remicade™), CDP 571, anti-TNF antibody fragments (e.g., CDP870), and soluble p55 or p75 TNF receptors, derivatives thereof, (p75TNFR1gG (Enbrel™) or p55TNFR1gG (Lenercept), soluble IL-13 receptor (sIL-13), and also TNFα converting enzyme (TACE) inhibitors; similarly IL-1 inhibitors (e.g., Interleukin-1-converting enzyme inhibitors, such as Vx740, or IL-1RA etc.) may be effective for the same reason. Other preferred combinations include Interleukin 11, anti-P7s and p-selectin glycoprotein ligand (PSGL). Yet another preferred combination are other key players of the autoimmune response which may act parallel to, dependent on or in concert with IL-12 function; especially preferred are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

Anti-IL12 antibodies, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R, soluble IL-13 receptor (sIL-13)) and antiinflammatory cytokines (e.g. IL-4, IL-10, IL-11, IL-13 and TGFβ). Preferred combinations include methotrexate or leflunomide and in moderate or severe rheumatoid arthritis cases, cyclosporine.

Non-limiting examples of therapeutic agents for inflammatory bowel disease with which an anti-IL-12 antibody, or antibody portion, can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF (including adalimumab/HUMIRA), LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-Iβ converting enzyme inhibitors (e.g., Vx740), anti-P7s, p-selectin glycoprotein ligand (PSGL), TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R, soluble IL-13 receptor (sIL-13)) and antiinflammatory cytokines (e.g. IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (adalimumab/HUMIRA), cA2 (Remicade™), CDP 571, anti-TNF antibody fragments (e.g., CDP870), TNFR-Ig constructs (p75TNFRIgG (Enbrel™) and p55TNFRIgG (Lenercept)), anti-P7s, p-selectin glycoprotein ligand (PSGL), soluble IL-13 receptor (sIL-13), and PDE4 inhibitors. Antibodies of the invention or antigen binding portions thereof, can be combined with corticosteroids, for example, budenoside and dexamethasone. Antibodies may also be combined with agents such as sulfasalazine, 5-aminosalicylic acid and olsalazine, and agents which interfere with synthesis or action of proinflammatory cytokines such as IL-1, for example, IL-Iβ converting enzyme inhibitors (e.g., Vx740) and IL-1ra. Antibodies or antigen binding portion thereof may also be used with T cell signaling inhibitors, for example, tyrosine kinase inhibitors 6-mercaptopurines. Antibodies or antigen binding portions thereof, can be combined with IL-11.

Non-limiting examples of therapeutic agents for multiple sclerosis with which an antibody, or antibody portion, can be combined include the following: corticosteroids; prednisolone; methylprednisolone; azathioprine; cyclophosphamide; cyclosporine; methotrexate; 4-aminopyridine; tizanidine; interferon-β1a (Avonex; Biogen); interferon-β1b (Betaseron; Chiron/Berlex); Copolymer 1 (Cop-1; Copaxone; Teva Pharmaceutical Industries, Inc.); hyperbaric oxygen; intravenous immunoglobulin; clabribine; antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors (e.g., Vx740), anti-P7s, p-selectin glycoprotein ligand (PSGL), TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R, soluble IL-13 receptor (sIL-13)) and anti-inflammatory cytokines (e.g. IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, IL-1 inhibitors, TNF inhibitors, and antibodies to CD40 ligand and CD80.

An antibody, antibody portion, may be used in combination with other agents to treat skin conditions. For example, an antibody, antibody portion, or other IL-12 inhibitor of the invention is combined with PUVA therapy. PUVA is a combination of psoralen (P) and long-wave ultraviolet radiation (UVA) that is used to treat many different skin conditions. The antibodies, antibody portions, or other IL-12 inhibitors of the invention can also be combined with pimecrolimus. In another embodiment, the antibodies of the invention are used to treat psoriasis, wherein the antibodies are administered in combination with tacrolimus. In a further embodiment, tacrolimus and IL-12 inhibitors are administered in combination with methotrexate and/or cyclosporine. In still another embodiment, the IL-12 inhibitor of the invention is administered with excimer laser treatment for treating psoriasis.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In one embodiment, the IL-12 antibody, or antigen-binding portion thereof, is administered on a biweekly dosing regimen, including, for example, a biweekly dosage ranging from about 50 to 300 mg, a dosage ranging from about 100 mg to about 200 mg, and a dosage from about 125 to about 175 mg. Alternatively, the IL-12 antibody may be administered as a one time dose, including, for example, a dose of about 200 mg dose, a dose of about 100 mg. In another embodiment, the IL-12 antibody is administered on a weekly dosing regimen, including, for example, a dose ranging from about 50 to 300 mg, a dosage ranging from about 100 mg to about 200 mg, and a dosage from about 125 to about 175 mg. It should be noted that doses within the specified ranges are also included herein, e.g., 85 mg, 97 mg, etc.

In another embodiment, a human IL-12 antibody, or antigen-binding portion thereof, is administered as a single dose to a subject having a disorder in which IL-12 activity is detrimental, e.g., psoriasis, which results in treatment. A response to the IL-12 antibody, or antigen-binding portion thereof, may be maintained for an extended period in a subject. Maintenance of a response may be monitored in accordance with the disorder being treated. For example, maintenance of a response with an IL-12 antibody, or antigen-binding portion thereof, for treating psoriasis may be determined by the subject's PASI 75 response over time. Maintenance of a response for treating psoriasis may also be determined by the subject's PASI 50 response or PASI 90 response over time. Maintenance of a response for treating psoriasis may alternatively be determined by the subject's achieving a PGA score of "clear" or "minimal", e.g., a PGA score of 0 or 1, over time.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

VII. Uses of the Invention

The invention provides a method for inhibiting IL-12 activity in a subject suffering from a disorder in which IL-12 activity is detrimental. In one embodiment, the invention provides a method treating psoriasis comprising administering a single dose of an IL-12 antibody, or antigen-binding portion thereof.

IL-12 has been implicated in the pathophysiology of a wide variety of disorders (Windhagen et al., (1995) *J. Exp. Med.* 182: 1985-1996; Morita et al. (1998) *Arthritis and Rheumatism.* 41: 306-314; Bucht et al., (1996) *Clin. Exp. Immunol.* 103: 347-367; Fais et al. (1994) *J. Interferon Res.* 14:235-238; Parronchi et al., (1997) *Am. J. Path.* 150:823-832; Monteleone et al., (1997) *Gastroenterology.* 112:1169-1178, and Berrebi et al., (1998) *Am. J. Path* 152:667-672; Parronchi et al (1997) *Am. J. Path.* 150:823-832). The invention provides methods for inhibiting IL-12 activity in a subject suffering from such a disorder, which method comprises administering to the subject an antibody or antibody portion of the invention such that IL-12 activity in the subject is inhibited. Preferably, the IL-12 is human IL-12 and the subject is a human subject. Alternatively, the subject can be a mammal expressing a IL-12 with which an antibody of the invention cross-reacts. Still further the subject can be a mammal into which has been introduced hIL-12 (e.g., by administration of hIL-12 or by expression of an hIL-12 transgene). An antibody of the invention can be administered to a human subject for therapeutic purposes (discussed further below). Moreover, an antibody of the invention can be administered to a non-human mammal expressing a IL-12 with which the antibody cross-reacts for veterinary purposes or as an animal model of human disease. Regarding the latter, such animal models may be useful for evaluating the therapeutic efficacy of antibodies of the invention (e.g., testing of dosages and time courses of administration).

As used herein, the phrase “a disorder in which IL-12 activity is detrimental” is intended to include diseases and other disorders in which the presence of IL-12 in a subject suffering from the disorder has been shown to be or is suspected of being either responsible for the pathophysiology of the disorder or a factor that contributes to a worsening of the disorder. Accordingly, a disorder in which IL-12 activity is detrimental is a disorder in which inhibition of IL-12 activity is expected to alleviate the symptoms and/or progression of the disorder. Such disorders may be evidenced, for example, by an increase in the concentration of IL-12 in a biological fluid of a subject suffering from the disorder (e.g., an increase in the concentration of IL-12 in serum, plasma, synovial fluid, etc. of the subject), which can be detected, for example, using an anti-IL-12 antibody as described above. There are numerous examples of disorders in which IL-12 activity is detrimental. In one embodiment, the antibodies or antigen binding portions thereof, can be used in therapy to treat the diseases or disorders described herein. In another embodiment, the antibodies or antigen binding portions thereof, can be used for the manufacture of a medicine for treating the diseases or disorders described herein. The use of the antibodies and antibody portions of the invention in the treatment of a few non-limiting specific disorders is discussed further below:

A. Rheumatoid Arthritis:

Interleukin-12 has been implicated in playing a role in inflammatory diseases such as rheumatoid arthritis. Inducible IL-12p40 message has been detected in synovia from rheumatoid arthritis patients and IL-12 has been shown to be present in the synovial fluids from patients with rheumatoid arthritis (see e.g., Morita et al., (1998) *Arthritis and Rheumatism* 41: 306-314). IL-12 positive cells have been found to be present in the sublining layer of the rheumatoid arthritis synovium. The human antibodies, and antibody portions of the invention can be used to treat, for example, rheumatoid arthritis, juvenile rheumatoid arthritis, Lyme arthritis, rheumatoid spondylitis, osteoarthritis and gouty arthritis. Typically, the antibody, or antibody portion, is administered systemically, although for certain disorders, local administration of the antibody or antibody portion may be beneficial. An antibody, or antibody portion, of the invention also can be administered with one or more additional therapeutic agents useful in the treatment of autoimmune diseases.

In the collagen induced arthritis (CIA) murine model for rheumatoid arthritis, treatment of mice with an anti-IL-12 mAb (rat anti-mouse IL-12 monoclonal antibody, C17.15) prior to arthritis profoundly suppressed the onset, and reduced the incidence and severity of disease. Treatment with the anti-IL-12 mAb early after onset of arthritis reduced severity, but later treatment of the mice with the anti-IL-12 mAb after the onset of disease had minimal effect on disease severity.

B. Crohn’s Disease

Interleukin-12 also plays a role in the inflammatory bowel disease, Crohn’s disease. Increased expression of IFN-γ and IL-12 occurs in the intestinal mucosa of patients with Crohn’s disease (see e.g., Fais et al., (1994) *J. Interferon Res.* 14: 235-238; Parronchi et al., (1997) *Amer. J. Pathol.* 150: 823-832; Monteleone et al., (1997) *Gastroenterology* 112: 1169-1178; Berrebi et al., (1998) *Amer. J. Pathol.* 152: 667-672). Anti-IL-12 antibodies have been shown to suppress disease in mouse models of colitis, e.g., TNBS induced colitis IL-2 knockout mice, and recently in IL-10 knock-out mice. Accordingly, the antibodies, and antibody portions, of the invention, can be used in the treatment of inflammatory bowel diseases.

C. Multiple Sclerosis

Interleukin-12 has been implicated as a key mediator of multiple sclerosis. Expression of the inducible IL-12 p40 message or IL-12 itself can be demonstrated in lesions of patients with multiple sclerosis (Windhagen et al., (1995) *J. Exp. Med.* 182: 1985-1996, Drulovic et al., (1997) *J. Neurol. Sci.* 147: 145-150). Chronic progressive patients with multiple sclerosis have elevated circulating levels of IL-12. Investigations with T-cells and antigen presenting cells (APCs) from patients with multiple sclerosis revealed a self-perpetuating series of immune interactions as the basis of progressive multiple sclerosis leading to a Th1-type immune response. Increased secretion of IFN-γ from the T cells led to increased IL-12 production by APCs, which perpetuated the cycle leading to a chronic state of a Th1-type immune activation and disease (Balashov et al., (1997) *Proc. Nat. Acad. Sci.* 94: 599-603). The role of IL-12 in multiple sclerosis has been investigated using mouse and rat experimental allergic encephalomyelitis (EAE) models of multiple sclerosis. In a relapsing-remitting EAE model of multiple sclerosis in mice, pretreatment with anti-IL-12 mAb delayed paralysis and reduced clinical scores. Treatment with anti-IL-12 mAb at the peak of paralysis or during the subsequent remission period reduced clinical scores. Accordingly, the antibodies or antigen binding portions thereof of the invention may serve to alleviate symptoms associated with multiple sclerosis in humans.

D. Insulin-Dependent Diabetes Mellitus

Interleukin-12 has been implicated as an important mediator of insulin-dependent diabetes mellitus (IDDM). IDDM was induced in NOD mice by administration of IL-12, and anti-IL-12 antibodies were protective in an adoptive transfer model of IDDM. Early onset IDDM patients often experience a so-called "honeymoon period" during which some residual islet cell function is maintained. These residual islet cells produce insulin and regulate blood glucose levels better than administered insulin. Treatment of these early onset patients with an anti-IL-12 antibody may prevent further destruction of islet cells, thereby maintaining an endogenous source of insulin.

E. Psoriasis

Interleukin-12 (IL-12) and the related cytokine IL-23 have been implicated as key mediators in psoriasis. Psoriasis involves acute and chronic skin lesions that are associated with a TH1-type cytokine expression profile (Hamid et al. (1996) J. Allergy Clin. Immunol. 1:225-231; Turka et al. (1995) Mol. Med. 1:690-699). Both IL-12 and IL-23 contribute to the development of the type 1T helper cell (Th1) immune response in psoriasis. Moreover, the IL-12 p40 and IL-23 p40 messenger RNA is overexpressed in psoriatic skin lesions. Accordingly, the antibodies or antigen binding portions thereof of the invention may serve to alleviate chronic skin disorders such psoriasis.

In one embodiment, the invention provides a method for treating psoriasis. Treatment for psoriasis often includes a topical corticosteroids, vitamin D analogs, and topical or oral retinoids, or combinations thereof. In one embodiment, an IL-12 and/or IL-23 antibody is administered in combination with or the presence of one of these common treatments. Additional therapeutic agents which can be combined with the IL-12 and/or IL-23 antibody for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

Improvements in psoriasis in a subject can be monitored by the subject's Psoriasis Area and Severity Index Score (PASI). The method for determining the PASI has been described in Fredriksson and Pettersson (1978) *Dermatologica* 157:238 and Marks et al. (1989) *Arch Dermatol* 125:235. Briefly, the index is based on evaluation of four anatomic sites, including the head, upper extremities, trunk, and lower extremities, for erythema, induration, and desquamation using a 5 point scale (0=no symptoms; 1=slight; 2=moderate; 3=marked; 4=very marked). Based on the extent of lesions in a given anatomic site, the area affected is assigned a numerical value (0=0; 1=<10%; 2=10-29%; 3=30-49%; 4=50-69%; 5=70=89%; 6=90-100%). The PASI score is then calculated, wherein the possible range of PASI score is 0.0 to 72.0 with the highest score representing complete erythroderma of the severest degree.

In one embodiment of the invention, an IL-12 and/or IL-23 antibody is used for the treatment of psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In another embodiment, an IL-12 and/or IL-23 antibody, such as J695/ABT-874, is used to treat subjects who have psoriasis in combination with PsA. Specific types of psoriasis included in the treatment methods of the invention are described in detail below:

a. Chronic Plaque Psoriasis

Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

Inverse psoriasis is a form of psoriasis in which the patient has smooth, usually moist areas of skin that are red and inflammed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

d. Pustular Psoriasis

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders which can be treated with the IL-12 and/or IL-23 antibody include erythrodermic psoriasis, vulgaris, psoriasis associated with IBD, and psoriasis associated with arthritis, including rheumatoid arthritis.

The present invention is further illustrated by the following examples which should not be construed as limiting in any way. The contents of all cited references, including literature references, issued patents, and published patent applications, as cited throughout this application are hereby expressly incorporated herein by reference. It should further be understood that the contents of all the tables attached hereto (see Appendix A attached hereto and Appendix A of U.S. Pat. No. 6,914,128) as well as the entire contents of U.S. Pat. No. 6,914,128 are incorporated herein by reference.

EXAMPLES

Example 1

Efficacy of the Fully Human IL-12/IL-23 Monoclonal Antibody, ABT-874, In the Treatment of Moderate to Severe Plaque Psoriasis ABT-874 is a fully human antibody against interleukin-12 (IL-12) and IL-23. It binds with great affinity to the p40 subunit common to both IL-12 and IL-23, both validated targets in the treatment of psoriasis (Ps).

The objective of the following study was to evaluate the efficacy of subcutaneous injections of ABT-874 in the treatment of patients with moderate to severe plaque Ps.

Adult patients with Ps affecting ≧10% body surface area (BSA) and a Psoriasis Area and Severity Index (PASI) score ≧12 at baseline were eligible for this 12-week, double-blind, placebo-controlled study. Patients were randomized to 1 of 6 arms: 1) 100-mg ABT-874 every other week (eow) for 12 weeks; 2) one 200-mg ABT-874 dose at Week 0; 3) 200-mg ABT-874 every week for 4 weeks; 4) 200-mg ABT-874 eow for 12 weeks; 5) 200-mg ABT-874 every week for 12 weeks; or 6) placebo. Primary endpoint was a ≧PAS175 response at Week 12. Other efficacy assessments included the PASI50 and Physician's Global Assessment (PGA). Patients who met the primary endpoint entered a 36-week blinded/retreatment phase and were monitored for time to loss of response.

A total of 180 patients enrolled in the study, 30 in each arm. Baseline characteristics were similar between arms and indicative of moderate to severe Ps (all mean values except % male): age, 46 yrs, 74% male; 21 yrs duration of Ps; PASI 19; and 25% BSA affected. At Week 12, the percentages of patients achieving ≧PAS175 were statistically significantly greater for patients in each of the 5 ABT-874 arms vs. placebo (93%, 63%, 90%, 93%, 90%, vs. 3%, respectively, p<0.001, ITT). In addition, the percentages of patients achieving ≧PASI50 were statistically significantly greater for patients in each of the 5 ABT-874 arms vs. placebo (100%, 77%, 97%, 97%, and 100%, vs. 17%, p<0.001). The mean percentage decreases (improvements) in PASI at Week 12 were 90%, 70%, 92%, 92%, and 90%, respectively, in the ABT-874 arms, and 26% for placebo. Similarly, the percentages of patients with a PGA of Clear/Minimal were 83%, 50%, 73%, 87% and 87%, respectively, in the ABT-874 arms, and 3% for placebo.

In conclusion, ABT-874 was significantly more efficacious than placebo in the treatment of moderate to severe plaque psoriasis.

Example 2

Safety and Efficacy of the Fully Human IL-12/-23 Monoclonal Antibody, ABT-874, in the Treatment of Moderate to Severe Plaque Psoriasis ABT-874 is a fully human antibody against interleukin 12 (IL-12) and IL-23. It binds with great affinity to the p40 subunit common to both IL-12 and IL-23, validated targets in the treatment of psoriasis (Ps). The objective of this Phase II study was to investigate the efficacy and safety of subcutaneous injections of ABT-874 in the treatment of moderate to severe plaque Ps.

Adults with Ps affecting ≧10% body surface area (BSA) and a PASI score ≧12 were eligible for this 12-wk, double-blind, placebo-controlled study. Patients were randomized to 1 of 6 arms: 1) 100-mg ABT-874 every other week (eow) for 12 wks; 2) one 200-mg ABT-874 dose at Wk 0; 3) 200-mg ABT-874 every wk for 4 wks; 4) 200-mg ABT-874 eow for 12 wks; 5) 200-mg ABT-874 every wk for 12 wks; or 6) placebo. The primary endpoint was a ≧PASI75 response at Wk 12. Patients who met the primary endpoint entered a 36-wk blinded/retreatment phase and were monitored for time to loss of response. All patients were evaluated for safety through Wk 54.

180 patients enrolled, 30 in each arm. Baseline characteristics were similar between arms (mean values presented except % male): age, 46 yrs, 74% male; 21 yrs duration of Ps; PASI=19; and 25% BSA affected. At Wk 12, the % s of patients with ≧PASI75 were statistically significantly greater in each of the 5 ABT-874 arms vs. placebo (93%, 63%, 90%, 93%, 90%, vs. 3%, respectively, p<0.001, ITT). During the 12-wk, DB phase, infectious AEs for the ABT-874 groups ranged from 23-43% and for the placebo group was 23%, with the most common being nasopharyngitis (7-17% for ABT-874; 3% for placebo). There were no statistically significant differences between arms. No serious infectious AEs were reported, and no deaths occurred.

In conclusion, ABT-874 was significantly more efficacious than placebo in the treatment of moderate to severe plaque Ps, and appears to have a favorable safety profile.

Example 3

Maintenance of Response with the Fully Human IL-12/-23 Monoclonal Antibody, ABT-874, in the Treatment of Moderate to Severe Plaque Psoriasis The efficacy and safety of ABT-874 was evaluated in a 12-week, Phase II, randomized controlled trial and 36-week follow-up phase. The objective of the following example was to analyze maintenance of response following discontinuation of therapy during the second 12 weeks of this Phase II study of subcutaneous injections of ABT-874 in the treatment of moderate to severe plaque Ps.

Adults with Ps affecting ≧10% body surface area (BSA) and a PASI score ≧12 were eligible for this 12-week, double-blind, placebo-controlled study. Patients were randomized to 1 of 6 arms:

1) 100-mg ABT-874 every other week (eow) for 12 wks;
2) one 200-mg ABT-874 dose at Wk 0;
3) 200-mg ABT-874 every wk for 4 wks;
4) 200-mg ABT-874 eow for 12 wks;
5) 200-mg ABT-874 every wk for 12 wks; or
6) placebo.

The primary endpoint was a ≧PASI75 response at Week 12. Patients who met the primary endpoint entered a 36-week blinded/retreatment phase. Treatment with study drug was discontinued, and patients were monitored for time to loss of response (a decrease in PASI score, any time during the 36-week follow-up period, to <PASI 50). Maintenance of PASI response was evaluated through Week 24.

A total of 180 patients enrolled, 30 in each arm. Baseline characteristics were similar between arms (mean values presented except % male): age, 46 years, 74% male; 21 years duration of Ps; PASI=19; and 25% BSA affected.

At Week 12, the percentages of patients with ≧PASI75 were statistically significantly greater in each of the 5 ABT-874 arms vs. placebo (Table 1). At Week 24, substantial percentages of PASI 75 responders in the active treatments arms had maintained at least a PASI 50 response.

TABLE 1

24-Week Efficacy of ABT-874

| | ≧PASI75 at Wk 12 | Maintenance of PASI Response: Wk 24 vs. Wk 12 |
|---|---|---|
| 100 mg eow for 12 wks | 28/30 (93%)* | 24/28 (86%) |
| 200 mg, one dose | 19/30 (63%)* | 15/19 (79%) |
| 200-mg every wk for 4 wks | 27/30 (90%)* | 23/27 (85%) |

TABLE 1-continued

24-Week Efficacy of ABT-874

| | ≧PASI75 at Wk 12 | Maintenance of PASI Response: Wk 24 vs. Wk 12 |
|---|---|---|
| 200-mg eow for 12 wks | 28/30 (93%)* | 26/28 (93%) |
| 200-mg every wk for 12 wks | 27/30 (90%)* | 26/27 (96%) |
| Placebo | 1/30 (3%) | — |

*p < 0.001 vs. placebo, NRI.

In conclusion, ABT-874 was significantly more efficacious than placebo in the treatment of moderate to severe plaque Ps. Substantial percentages of PASI 75 responders maintained these responses at Week 24, following discontinuation of active therapy.

Example 4

Safety and Efficacy of ABT-874, a Fully Human IL-12/-23 Monoclonal Antibody, in the Treatment of Moderate to Severe Chronic Plaque Psoriasis The objective of the following example was to demonstrate the efficacy and safety of a range of doses of a human IL-12/23 monoclonal antibody (ABT-874) compared with placebo in the treatment of patients with clinically stable moderate to severe chronic plaque psoriasis.

I. Materials and Methods

A. Study design: The following study was a 12-week, multicentre, randomised, double-blind, phase II, placebo-controlled trial that was conducted at 24 centres in the United States (16 sites) and Canada (8 sites). ABT-874 (Abbott Laboratories, Abbott Park, Ill.) is a human monoclonal antibody with genetically engineered complementarity-determining regions that have high affinity for the IL-12/23 p40 subunit protein. Patients were randomised in a 1:1:1:1:1:1 ratio to receive 1 of 6 treatments: 200 mg of ABT-874, 1 dose at week 0 (200 mg×1); 100 mg of ABT-874 every other week (eow) for 12 weeks (100 mg eow); 200 mg of ABT-874 weekly for the first 4 weeks (200 mg×4); 200 mg of ABT-874 eow for 12 weeks (200 mg eow); 200 mg of ABT-874 weekly for 12 weeks (200 mg weekly); or placebo. After week 12, all patients who achieved at least a 75% reduction in psoriasis area and severity index (PASI 75) response continued into a 36-week blinded observation/retreatment phase.

B. Patients: Patients were ≧18 years of age and had a clinical diagnosis of psoriasis for at least 6 months (determined by patient interview and confirmation of diagnosis through physical examination by the investigator), stable plaque psoriasis for at least 2 months before screening and at baseline visits as determined by subject interview, moderate to severe plaque psoriasis defined by ≧10% body surface area (BSA) involvement at the baseline visit, a PASI score of ≧12 at the baseline visit, and a physician's global assessment (PGA) of at least moderate disease at the baseline visit.

Patients were ineligible if they had previous exposure to systemic or biologic anti-IL-12 therapy; nonplaque psoriasis; inability to discontinue the following therapies before the baseline visit: topical psoriasis therapies at least 2 weeks before, ultraviolet B light phototherapy at least 2 weeks before, psoralen-ultraviolet-light phototherapy at least 4 weeks before, systemic therapies at least 4 weeks before, and biologic therapies at least 12 weeks before; required intake of oral or injectable corticosteroids during the study (inhaled corticosteroids for stable medical conditions were allowed); an exacerbation of asthma requiring hospitalization in the 10 years prior to screening; an infection or risk factors for severe infection; a history of malignancies other than successfully treated basal cell carcinoma (patients with a history of squamous cell carcinoma were excluded) or cervical carcinoma in situ; or a history of major immunologic reaction (e.g., serum sickness or anaphylactoid reaction) to an immunoglobulin G-containing agent (e.g., intravenous gamma globulin, a fusion protein, or monoclonal antibody).

Patients were allowed to continue treatment with medicated shampoos that did not contain corticosteroids, bland (without beta- or alpha-hydroxy acids) emollients, or Class VI or VII low-potency topical corticosteroids on their palms, soles, face, inframammary area, and groin area during the course of the study. Application of these topical psoriasis therapies was not to occur within 24 hours of a study visit. Vaccination with a live viral agent was not allowed within 1 month prior to dosing with ABT-874, during the study, or for 1 month after the last dose of study drug was administered.

Occurrence of any of the following clinically significant abnormal laboratory results led to immediate withdrawal of a patient from the study: aspartate transaminase or alanine transaminase >5 times the upper limit of normal; serum total bilirubin >3 times the upper limit of normal; serum creatinine >3 times the upper limit of normal; creatine phosphokinase >5 times the upper limit of normal; hemoglobin <8 g/dL; white blood cell count $<2\times10^9$/L; or platelet count $<75\times10^9$/L.

C. Efficacy assessments: The primary efficacy assessment was the percentage of patients achieving a PASI 75 response at week 12, defined as at least a 75% reduction in PASI score relative to the baseline score. PASI is a measure of the severity of psoriatic lesions (in terms of erythema, induration, and desquamation) and the extent of BSA involvement. The PASI score ranges from 0 (no psoriasis) to 72 (severe disease) (Fredriksson T, Pettersson U. *Dermatologica* 1978; 157: 238-44). Other efficacy measures included the percentage of patients who achieved at least PASI 75 at weeks 1, 2, 4, and 8; the percentage of patients who achieved at least PASI 50 or PASI 90 at weeks 1, 2, 4, 8, and 12; and the percentage of patients who attained a PGA of clear or minimal at week 12 and at weeks 1, 2, 4, and 8. The PGA measures the severity of disease on a 6-point scale, which ranges from 0 (no disease, or clear) to 5 (very severe) (Ko H-S. Clinical trial design in psoriasis. Presented at: 49th Meeting of the Dermatologic and Opthalmologic Advisory Committee; Mar. 20, 1998; Bethesda, Md.).

D. Safety assessments: Adverse events, laboratory data, and vital signs were assessed throughout the study. Patients were closely monitored for signs of infection, malignancy, and immunologic reaction. Treatment-emergent AEs were defined as those events that occurred between week 0 and the earlier of 45 days after the last nonmissing study drug dose or 1 day prior to the first retreatment dose (for those patients continuing on to the 36-week trial).

E. Statistical analysis: The sample size was calculated using nQuery Advisor® 4.0 (Statistical Solutions, Saugus, Mass.). With the assumption that 15% of the patients in the placebo group would achieve a PASI 75 response at week 12, the study designers determined that a sample size of 26 in each dosage group would be adequate to detect at least a 45% difference from a treated group using the Fisher exact test with 90% power at a 0.05 2-sided significance level. The study was designed to enroll approximately 180 patients, with 30 patients in each group.

The intention-to-treat population included all patients who were randomised at week 0 and received at least 1 injection of study drug; this population was used for the efficacy analyses. All tests were performed at $\alpha=0.05$. Nonresponder imputation was used for all efficacy analyses; any patient with a missing PASI or PGA score at any visit was considered a nonresponder at that visit. To assess the impact of the missing data, sensitivity analyses of week-12 data were completed using the last-observation-carried-forward method. The primary analysis of PASI 75 response at week 12 was performed using the following sequential order to adjust for multiplicity: 200 mg weekly versus placebo, 200 mg eow versus placebo, 100 mg eow versus placebo, 200 mg×4 versus placebo, and 200 mg×1 versus placebo. The treatment difference between each ABT-874 treatment group and the placebo group for mean percentage change in PASI score was assessed using analysis of variance, with baseline PASI score and treatment group as factors. The safety analyses were conducted using the safety population, which included all patients who received at least 1 injection of study drug.

II. Results

A. Patients: A total of 180 patients were enrolled and randomised to 1 of the 6 treatment groups (FIG. 1). The majority of patients (76.7% of placebo-treated patients and 98% of all ABT-874 treatment group patients) completed the 12-week portion of the study.

Patients were well balanced across treatment groups with respect to demographic characteristics and disease activity (table 1). Patients were predominantly male (74.4%) and white (92.2%). Mean BSA involvement was 25% and mean PASI score was 18.8.

Figure 2:
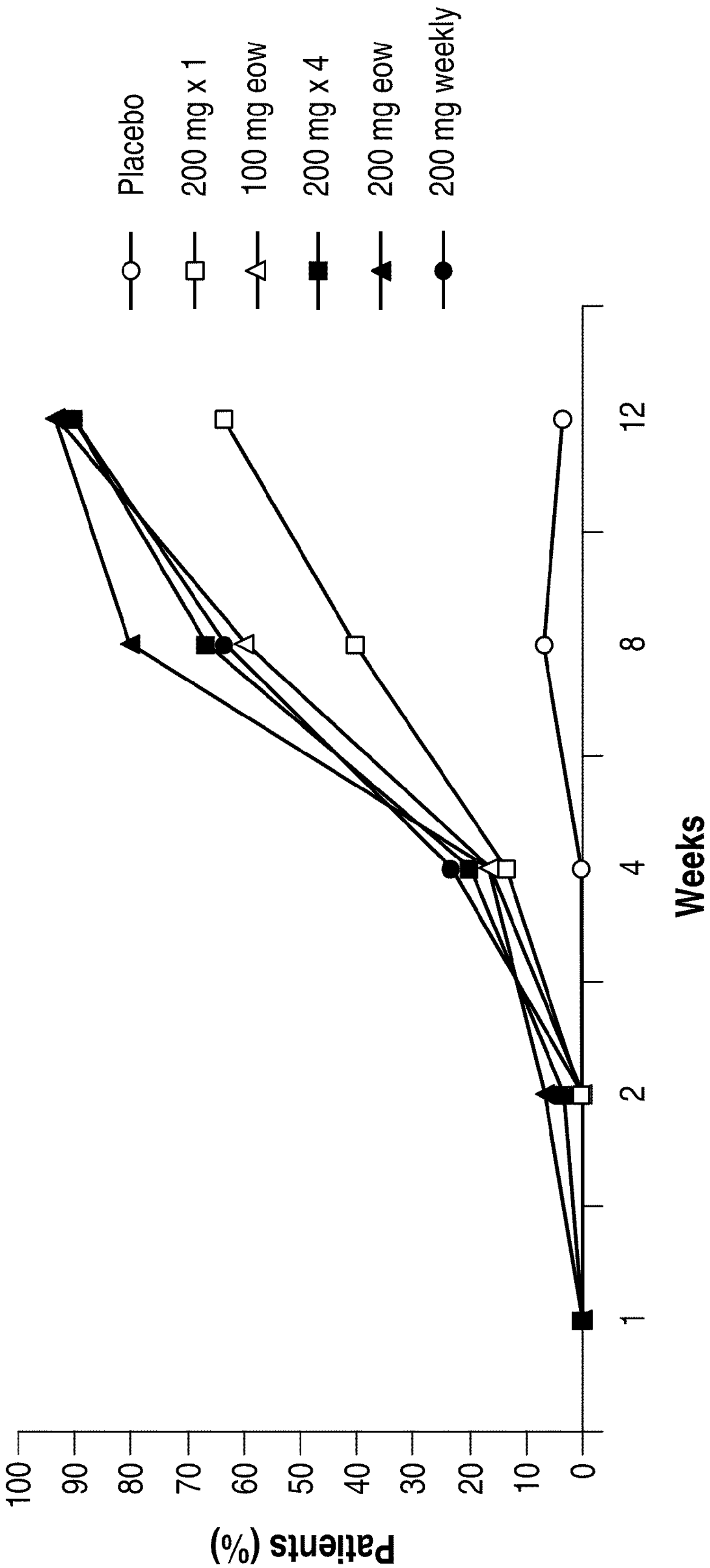
FIG. 2 shows the percentage of patients with at least a 75% improvement in the psoriasis area and severity index (PASI 75) during the 12-week portion of the trial By week 8, with the exception of the 200 mg×1 group, the percentage of patients who had a PASI 75 response was statistically significantly greater ($p<0.001$) in each ABT-874 treatment group for each comparison with placebo based on an analysis of variance of observed data for the intention-to-treat population. (The term "eow" refers to every other week dosing.)

B. Efficacy: The percentage of patients achieving the primary endpoint of PASI 75 response at week 12 was statistically significantly greater ($p<0.001$) in all of the ABT-874 treatment groups (200 mg×1: 63.3%, 19 of 30; 100 mg eow: 93.3%, 28 of 30; 200 mg×4:90.0%, 27 of 30; 200 mg eow: 93.3%, 28 of 30; 200 mg weekly: 90.0%, 27 of 30) compared with placebo (3.3%, 1 of 30). For the relatively short duration of this trial, PASI 75 responses in all ABT-874 treatment groups were similar with the exception of the 200 mg×1 treatment group (FIG. 2).

A subgroup analysis by demographics (gender, age, race, and weight), baseline disease characteristics (history of psoriatic arthritis, BSA, and PASI score), and baseline therapy for psoriasis within 12 months of receiving study treatment (systemic biologic and nonbiologic, topical, and phototherapy) demonstrated that ABT-874-treated patients within the various subgroups consistently achieved high levels of PASI 75 response at week 12.

Nearly 100% of the higher ABT-874 dosage groups attained at least a PASI 50 response by week 12 (200 mg×1: 76.7%, 23 of 30; 100 mg eow: 100.0%, 30 of 30; 200 mg×4: 96.7%, 29 of 30; 200 mg eow: 96.7%, 29 of 30; 200 mg weekly: 100.0%, 30 of 30; placebo: 16.7%, 5 of 30; $p<0.001$ for each comparison with placebo). The percentage of patients achieving at least a PASI 90 response at week 12 was statistically significantly greater ($p<0.001$) in all but 1 (200 mg×1) of the ABT-874 treatment groups when compared with placebo, as follows: 200 mg×1:16.7%, 5 of 30; 100 mg eow: 53.3%, 16 of 30; 200 mg×4:63.3%, 19 of 30; 200 mg eow: 76.6%, 23 of 30; 200 mg weekly: 53.3%, 16 of 30; and placebo: 0%, 0 of 30. In addition, by week 12, significantly more ($p<0.001$) patients in all ABT-874 treatment groups had attained a clear or minimal PGA rating compared with patients in the placebo group, as follows: 200 mg×1:50.0%, 15 of 30; 100 mg eow: 83.3%, 25 of 30; 200 mg×4:73.3%, 22 of 30; 200 mg eow: 86.7%, 26 of 30; 200 mg weekly: 86.7%, 26 of 30; versus placebo: 3.3%, 1 of 30.

The percentage of patients achieving the primary endpoint of PASI 100 response at week 12 was statistically significantly greater ($p<0.001$) in the following ABT-874 treatment groups (200 mg eow: 46.7%, 14 of 30; 200 mg weekly: 36.7%, 11 of 30) compared with placebo (0%, 0 of 30).

Figure 3:
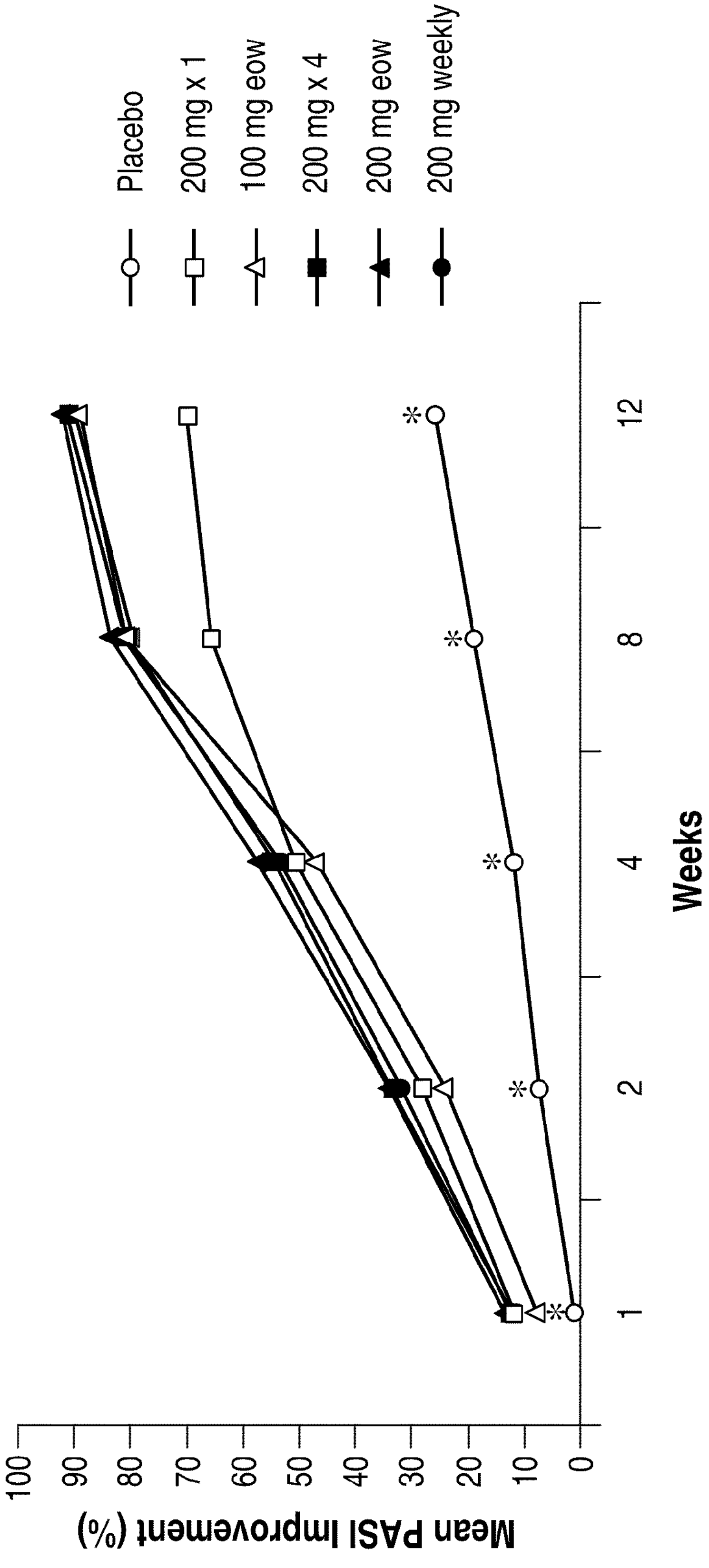
FIG. 3 shows the mean percentage improvement in psoriasis area and severity index (PASI) scores from baseline. The data show that *$p<0.001$ for each ABT-874 treatment group compared with placebo at all time points (except 100 mg eow at week 1, $p=0.023$) based on an analysis of variance of observed data for the intention-to-treat population. (The term "eow" refers to every other week dosing.)

Response to ABT-874 was rapid. The mean percentage improvement in PASI scores from baseline increased over time for all ABT-874 treatment groups (FIG. 3) and were statistically significantly greater for each ABT-874 treatment group compared with placebo at each time point ($p<0.001$, except for the 100 mg eow group at week 1, $p=0.023$).

C. Safety: ABT-874 therapy was generally well tolerated (table 2). One (0.7%) patient treated with ABT-874 discontinued the study owing to a localised skin discoloration; 2 (6.7%) patients treated with placebo discontinued the study, 1 for psoriatic arthropathy and 1 for ovarian cancer. Two (1.1%) patients experienced serious adverse effects (AEs); 1 placebo-treated patient was diagnosed with ovarian cancer on day 37, and 1 ABT-874-treated patient (200 mg×1) was diagnosed with costochondritis on day 10. No patients experienced myocardial or cerebral infarctions, and there were no deaths.

Patients receiving any dose of ABT-874 were significantly ($p=0.033$) more likely than patients receiving placebo to experience an AE at least possibly related to study drug (ABT-874:36.0%, 54 of 150; placebo: 10.0%, 3 of 30; table 2); most of these AEs were related to the injection site (injection-site reaction, erythema, pruritus, or irritation).

Most AEs were mild (mild AEs occurred in 46.0% [69 of 150] of ABT-874-treated patients and 30.0% [9 of 30] placebo-treated patients). The most common AE was injection-site reaction, occurring in 16.7% (25 of 150) of patients treated with any dose of ABT-874 (no reported injection-site reactions for placebo-treated patients; $p=0.028$; table 3). There were no statistically significant differences between the incidences of other AEs in the ABT-874-treated patients compared with placebo-treated patients. The next most frequently reported AEs were nasopharyngitis and upper respiratory tract infection.

Infectious AEs were reported by 32.8% (59 of 180) of all patients (placebo: 23.3%, 7 of 30; all ABT-874-treated patients: 34.7%, 52 of 150). The most common infectious AEs reported for any ABT-874 treatment group were nasopharyngitis (12.0%, 18 of 150), upper respiratory tract infection (10.7%, 16 of 150), and bronchitis and viral infection (both 2.7%, 4 of 150). No serious infectious AEs were reported.

Two patients reported malignancies during the study. One placebo-treated patient was diagnosed with ovarian cancer, which was ongoing as of day 129. One ABT-874-treated patient (200 mg×4) was diagnosed with a non-melanoma skin cancer (squamous cell carcinoma) that was removed on day 133. The medical history for this patient included removal of a benign skin growth in March 2005.

There were no clinically significant hematology, chemistry (including blood glucose concentrations), or vital sign changes compared with placebo.

TABLE 1

| Baseline demographics and clinical characteristics | | | | | | | |
|---|---|---|---|---|---|---|---|
| | Treatment Group | | | | | | |
| Characteristic | Placebo N = 30 | 200 mg × 1 N = 30 | 100 mg eow N = 30 | 200 mg × 4 N = 30 | 200 mg eow N = 30 | 200 mg weekly N = 30 | All ABT-874 N = 150 |
| Age, y | 49 ± 14.4 | 52 ± 12.0 | 45 ± 13.8 | 43 ± 13.8 | 44 ± 16.0 | 46 ± 14.0 | 46 ± 14.1 |
| Male, No. (%) | 22 (73.3) | 23 (76.7) | 22 (73.3) | 21 (70.0) | 23 (76.7) | 23 (76.7) | 112 (74.7) |
| White, No. (%) | 28 (93.3) | 25 (83.3) | 28 (93.3) | 27 (90.0) | 30 (100.0) | 28 (93.3) | 138 (92.0) |
| Weight, kg | 89 ± 17.6 | 94 ± 21.2 | 94 ± 17.9 | 92 ± 27.8 | 93 ± 24.1 | 95 ± 18.0 | 94 ± 21.9 |
| Duration of psoriasis, y | 21 ± 12.4 | 20 ± 13.2 | 24 ± 14.6 | 22 ± 14.2 | 18 ± 11.5 | 18 ± 10.9 | 21 ± 13.0 |
| PASI score | 16 ± 2.9 | 18 ± 6.7 | 20 ± 6.3 | 20 ± 7.6 | 20 ± 6.2 | 19 ± 6.3 | 19 ± 6.6 |
| BSA affected, % | 21 ± 9.2 | 24 ± 13.6 | 28 ± 15.7 | 24 ± 13.0 | 29 ± 16.8 | 23 ± 12.6 | 26 ± 14.5 |
| PGA, No. (%) | | | | | | | |
| Mild | 1 (3.3) | 0 | 0 | 0 | 0 | 0 | 0 |
| Moderate | 20 (66.7) | 19 (63.3) | 17 (56.7) | 13 (43.3) | 15 (50.0) | 17 (56.7) | 81 (54.0) |
| Severe | 9 (30.0) | 11 (36.7) | 12 (40.0) | 14 (46.7) | 13 (43.3) | 11 (36.7) | 61 (40.7) |
| History of PsA, No. (%) | 9 (30.0) | 7 (23.3) | 12 (40.0) | 9 (30.0) | 6 (20.0) | 9 (30.0) | 43 (28.7) |
| Previous psoriasis treatment,* No. (%) | | | | | | | |
| Topical therapy | 19 (63.3) | 21 (70.0) | 26 (86.7) | 15 (50.0) | 21 (70.0) | 23 (76.7) | 106 (70.7) |
| Phototherapy | 1 (3.3) | 6 (20.0) | 4 (13.3) | 4 (13.3) | 3 (10.0) | 5 (16.7) | 22 (14.7) |
| Systemic nonbiologic | 6 (20.0) | 4 (13.3) | 7 (23.3) | 5 (16.7) | 6 (20.0) | 8 (26.7) | 30 (20.0) |
| Systemic biologic | 3 (10.0) | 3 (10.0) | 7 (23.3) | 6 (20.0) | 4 (13.3) | 7 (23.3) | 27 (18.0) |

Values are mean ± SD unless otherwise noted.

*Within past 12 months prior to study treatment.

BSA = body surface area;

eow = every other week;

PASI = psoriasis area and severity index;

PGA = physician's global assessment;

PsA = psoriatic arthritis

TABLE 2

| Clinical treatment-emergent adverse events summary | | | | | | | |
|---|---|---|---|---|---|---|---|
| | Treatment Group | | | | | | |
| Event | Placebo N = 30 | 200 mg × 1 N = 30 | 100 mg eow N = 30 | 200 mg × 4 N = 30 No. (%) | 200 mg eow N = 30 | 200 mg weekly N = 30 | All ABT-874 N = 150 |
| Any AE | 18 (60.0) | 18 (60.0) | 22 (73.3) | 21 (70.0) | 21 (70.0) | 19 (63.3) | 101 (67.3) |
| Any AE at least possibly drug-related* | 3 (10.0) | 9 (30.0) | 12 (40.0) | 14 (46.7) | 11 (36.7) | 8 (26.7) | 54 (36.0) |
| Any severe AE | 3 (10.0) | 1 (3.3) | 0 | 0 | 0 | 1 (3.3) | 2 (1.3) |
| Any serious AE† | 1 (3.3) | 1 (3.3) | 0 | 0 | 0 | 0 | 1 (0.7) |
| Any AE leading to discontinuation of study drug | 2 (6.7) | 1 (3.3) | 0 | 0 | 0 | 0 | 1 (0.7) |
| Any AE at least possibly drug-related* and serious | 0 | 0 | 0 | 0 | 0 | 0 | 0 |
| Any infectious AE | 7 (23.3) | 7 (23.3) | 9 (30.0) | 13 (43.3) | 13 (43.3) | 10 (33.3) | 52 (34.7) |
| Any serious infectious AE | 0 | 0 | 0 | 0 | 0 | 0 | 0 |
| Any malignant neoplasms | 1 (3.3) | 0 | 0 | 1 (3.3) | 0 | 0 | 1 (0.7) |
| Deaths | 0 | 0 | 0 | 0 | 0 | 0 | 0 |

*As assessed by the investigator.

†Serious adverse events included the following: any event that resulted in death; any event that was life-threatening; any event that resulted in admission to the hospital for any length of time; any event that occurred while the patient was hospitalised and resulted in prolongation of hospital stay; any event that resulted in persistent or significant disability/incapacity; or any important medical event that required medical or surgical intervention to prevent serious outcome. AE = adverse event; eow = every other week.

TABLE 3

Treatment-emergent adverse events with an incidence ≧5% in any treatment group by descending frequency of patients treated with any dosage of ABT-874

| Event | Placebo N = 30 | 200 mg × 1 N = 30 | 100 mg eow N = 30 | 200 mg × 4 N = 30 | 200 mg eow N = 30 | 200 mg weekly N = 30 | All ABT-874 N = 150 |
|---|---|---|---|---|---|---|---|
| | Treatment Group No. (%) | | | | | | |
| Injection-site reaction | 0 | 2 (6.7) | 7 (23.3) | 5 (16.7) | 7 (23.3) | 4 (13.3) | 25 (16.7) |
| Nasopharyngitis | 1 (3.3) | 4 (13.3) | 4 (13.3) | 3 (10.0) | 2 (6.7) | 5 (16.7) | 18 (12.0) |
| Upper respiratory tract infection | 2 (6.7) | 2 (6.7) | 4 (13.3) | 3 (10.0) | 5 (16.7) | 2 (6.7) | 16 (10.7) |
| Headache | 2 (6.7) | 5 (16.7) | 0 | 1 (3.3) | 3 (10.0) | 2 (6.7) | 11 (7.3) |
| Injection site pruritus | 0 | 0 | 1 (3.3) | 2 (6.7) | 2 (6.7) | 2 (6.7) | 7 (4.7) |
| Injection site erythema | 0 | 0 | 0 | 4 (13.3) | 2 (6.7) | 1 (3.3) | 7 (4.7) |
| Injection site irritation | 0 | 1 (3.3) | 3 (10.0) | 2 (6.7) | 0 | 0 | 6 (4.0) |
| Fatigue | 0 | 2 (6.7) | 2 (6.7) | 0 | 0 | 1 (3.3) | 5 (3.3) |
| Pain in extremity | 0 | 1 (3.3) | 0 | 0 | 1 (3.3) | 2 (6.7) | 4 (2.7) |
| Arthralgia | 0 | 2 (6.7) | 0 | 0 | 0 | 2 (6.7) | 4 (2.7) |
| Viral infection | 0 | 0 | 0 | 2 (6.7) | 1 (3.3) | 1 (3.3) | 4 (2.7) |
| Bronchitis | 0 | 1 (3.3) | 0 | 1 (3.3) | 2 (6.7) | 0 | 4 (2.7) |
| Nausea | 1 (3.3) | 0 | 3 (10.0) | 0 | 0 | 0 | 3 (2.0) |
| Otitis externa | 0 | 0 | 0 | 0 | 2 (6.7) | 0 | 2 (1.3) |
| Vomiting | 1 (3.3) | 0 | 0 | 2 (6.7) | 0 | 0 | 2 (1.3) |
| Urinary tract infection | 2 (6.7) | 1 (3.3) | 0 | 1 (3.3) | 0 | 0 | 2 (1.3) |
| Herpes simplex | 0 | 0 | 2 (6.7) | 0 | 0 | 0 | 2 (1.3) |
| Limb injury | 0 | 2 (6.7) | 0 | 0 | 0 | 0 | 2 (1.3) |
| Pruritus | 2 (6.7) | 0 | 0 | 0 | 0 | 0 | 0 |

*As assessed by the investigator.

III. Conclusion

The phase II, multicentre, randomised, double-blind, placebo-controlled trial described in this Example demonstrated statistically and clinically significant efficacy of ABT-874 in the treatment of moderate to severe chronic plaque psoriasis. With the exception of the ABT-874 200 mg×1 treatment group, 90% or more of patients in all ABT-874 treatment groups achieved PASI 75 or greater by week 12, compared with 3.3% of placebo-treated patients. Even in the group that received only 1 dose of study drug (200 mg×1), a majority (63.3%) of patients had achieved at least PASI 75 by week 12. In addition, almost 100% of patients treated with ABT-874 reached PASI 50 or greater, which is considered to be a clinically significant improvement (Carlin C S, Feldman S R, Krueger J G, Menter A, Krueger G G. *J Am Acad Dermatol* 2004; 50: 859-66) by week 12. The results for other secondary endpoints, such as PASI 90 and PGA of clear or minimal, were consistent with and supported the primary efficacy analysis.

Response to ABT-874 was rapid. Statistically significant separation between placebo- and ABT-874-treated patients occurred as early as week 1 for the mean percentage improvement in PASI scores. Improvement was sustained for the 12-week duration of the trial, even for patients in the ABT-874 200 mg×1 and 200 mg×4 dosage groups.

ABT-874 was well tolerated, and most AEs were mild. Although ABT-874-treated patients were significantly more likely to experience an AE at least possibly related to study drug, most of these were injection site-related AEs (injection-site reaction, erythema, pruritus, or irritation). There was no apparent association between an increased dose of ABT-874 and an increased incidence of AEs. Of note, there were no myocardial or cerebral infarctions.

Immunologic-related events are of particular interest for patients receiving anti-IL-12/23 antibodies. The most frequently reported infectious AEs were nasopharyngitis, upper respiratory tract infection, bronchitis, and viral infection. There were no serious infectious AEs reported for the duration of this trial. Of the 2 malignancies diagnosed during the study, ovarian cancer was diagnosed in a placebo-treated patient, and non-melanoma skin cancer was diagnosed in an ABT-874-treated patient who had a history of a benign skin growth.

In summary, ABT-874 demonstrated statistically and clinically significant benefit for the treatment of patients with moderate to severe chronic plaque psoriasis, and was well tolerated.

Example 5

Maintenance of Response with the Fully Human IL-12/-23 Monoclonal Antibody, ABT-874, in the Treatment of Moderate to Severe Plaque Psoriasis The efficacy and safety of ABT-874 was evaluated in a 12-week, Phase II, randomized controlled trial and 36-week follow-up phase. The objective of the following example was to analyze maintenance of response following discontinuation of therapy during the second 12 weeks of this Phase II study of subcutaneous injections of ABT-874 in the treatment of moderate to severe plaque Ps.

Adults with Ps affecting ≧10% body surface area (BSA) and a PASI score ≧12 were eligible for this 12-week, double-blind, placebo-controlled study. Patients were randomized to 1 of 6 arms:

1) 100-mg ABT-874 every other week (eow) for 12 wks;
2) one 200-mg ABT-874 dose at Wk 0;
3) 200-mg ABT-874 every wk for 4 wks;
4) 200-mg ABT-874 eow for 12 wks;
5) 200-mg ABT-874 every wk for 12 wks; or
6) placebo.

The primary endpoint was a ≧PASI 75 response at Week 12. Patients who met the primary endpoint entered a 36-week blinded/retreatment phase. Treatment with study drug was discontinued, and patients were monitored for PASI score at various times during the 36-week follow-up period, including PASI 50, PASI 75 and PASI 90 responses. Maintenance of PASI response was evaluated through Week 24.

A total of 180 patients enrolled, 30 in each arm. Baseline characteristics were similar between arms (mean values presented except % male): age, 46 years, 74% male; 21 years duration of Ps; PASI=19; and 25% BSA affected.

Figure 4A:
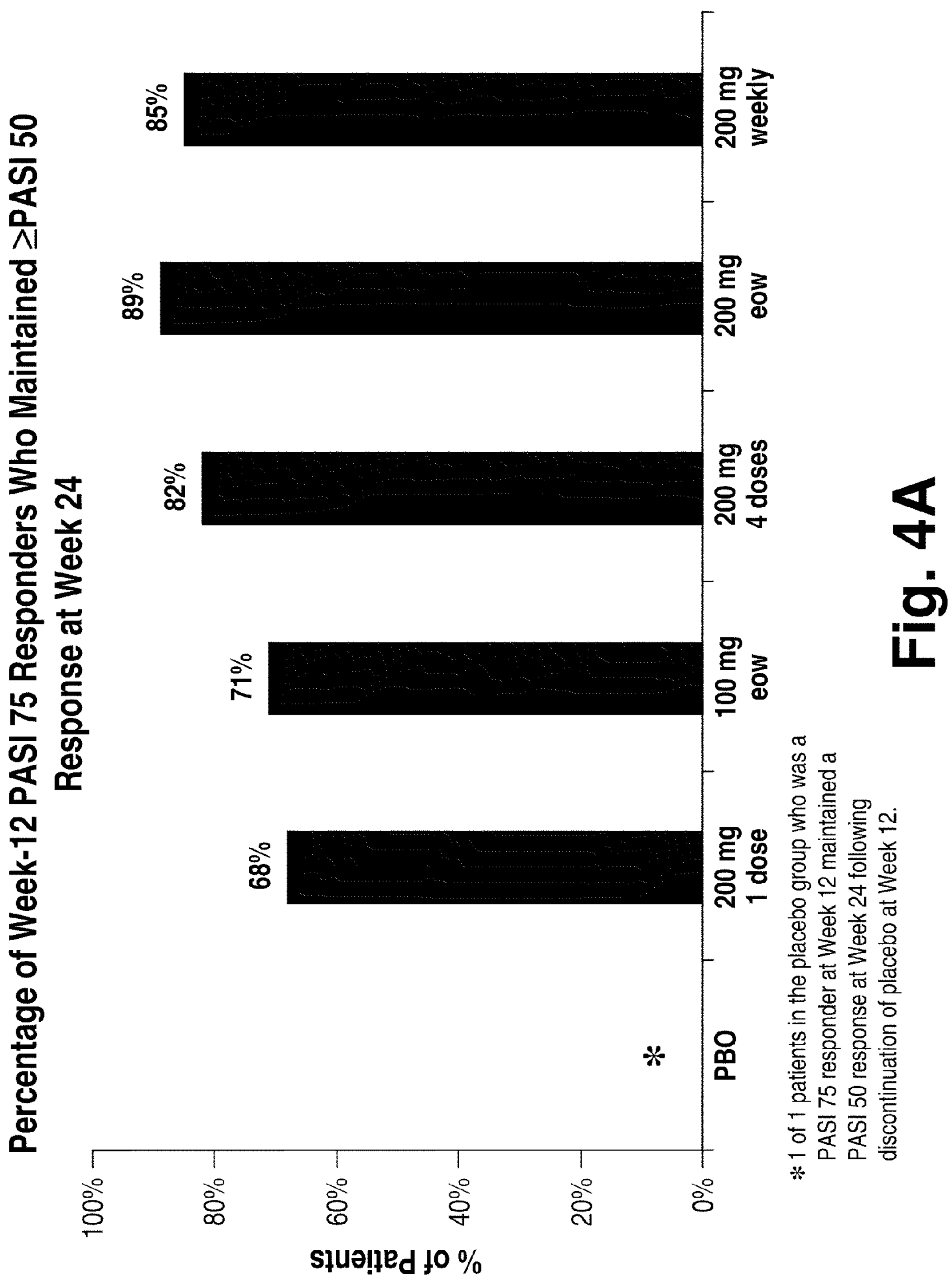
FIGS. 4A-C show the percentage of patients who maintained a PASI 50, PASI 75 and PASI 90 response, respectively, at week 24 of the trial, i.e., at 12 weeks following discontinuation of administration of the antibody.
Figure 4B:
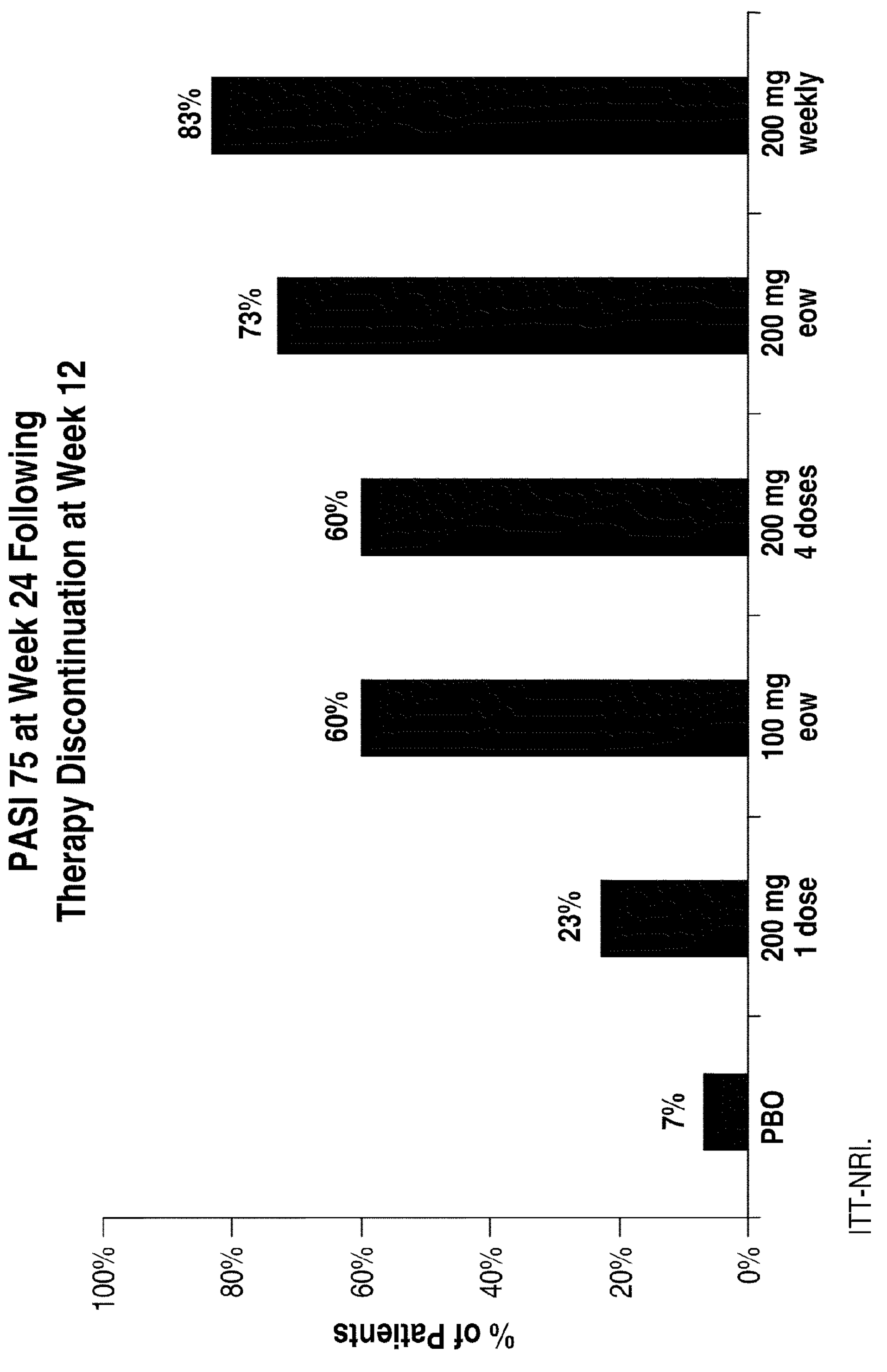
Figure 4C:
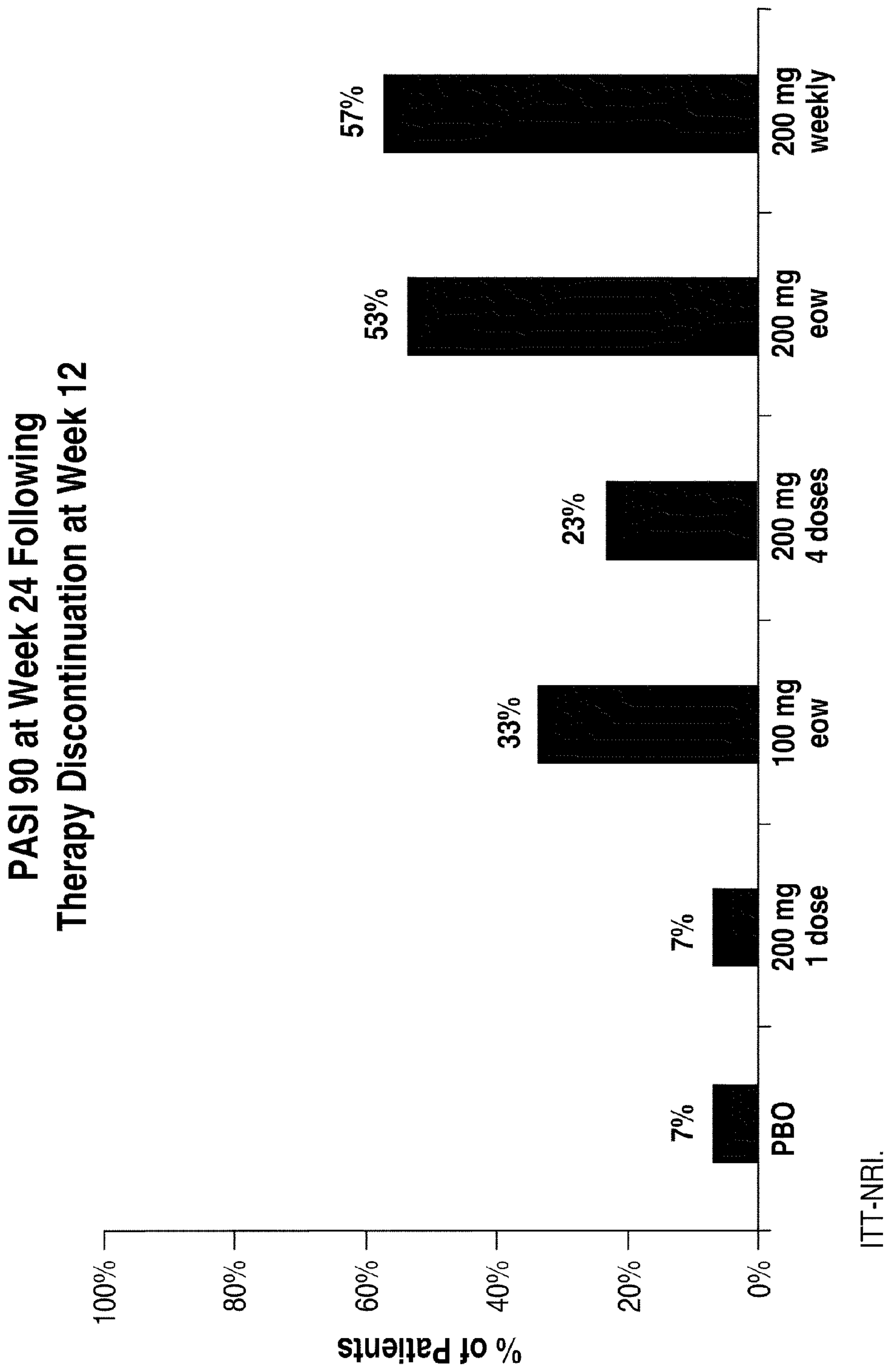
Figure 4D:
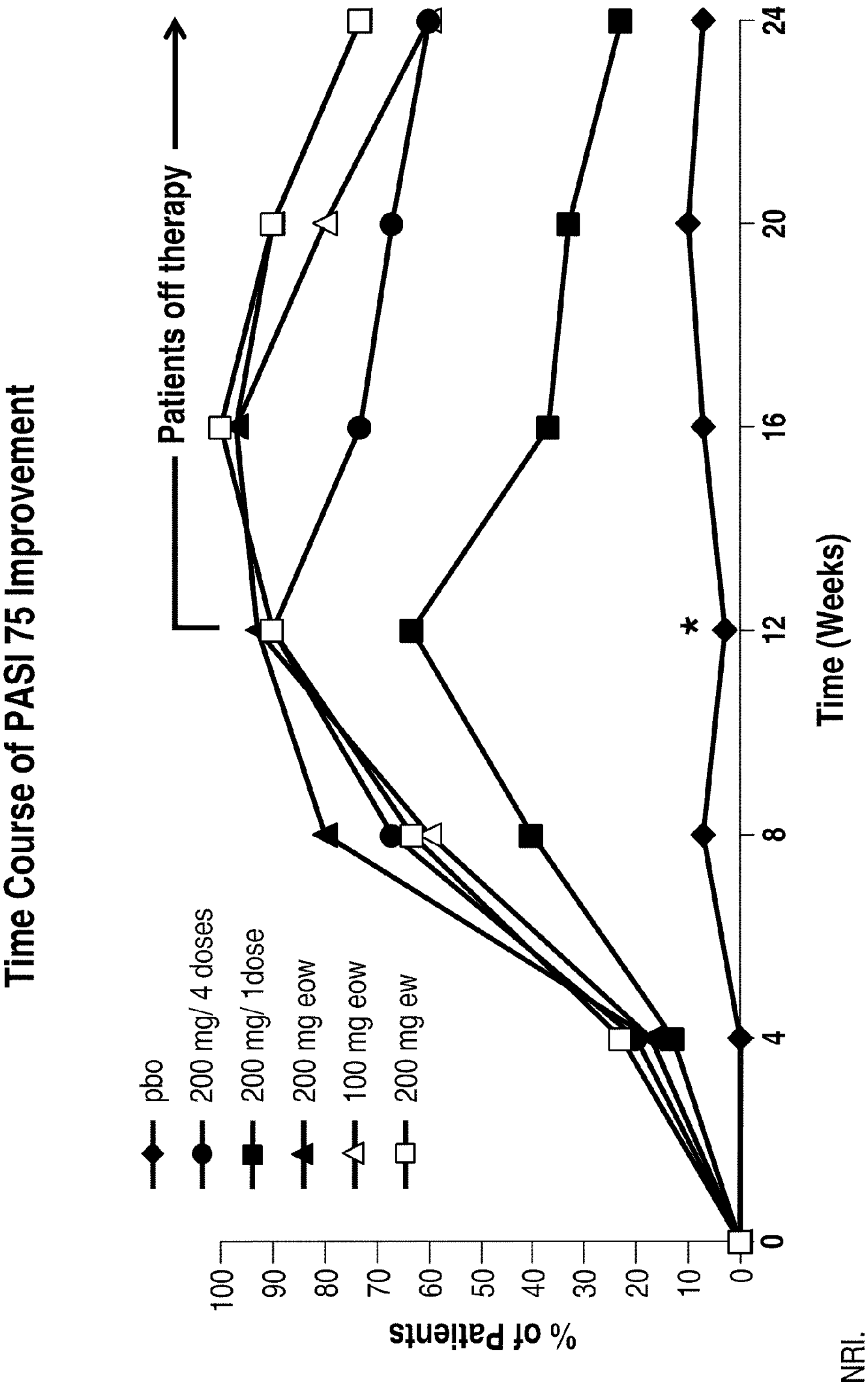
FIG. 4D shows the percentage of patients maintaining a PASI 75 response over time during the 24 week period of the trial.

At Week 12, the percentages of patients with ≧PASI 75 were statistically significantly greater in each of the 5 ABT-874 arms vs. placebo (Table 4). At Week 24, substantial percentages of PASI 75 responders in the active treatments arms had maintained at least a PASI score of ≧PASI 50. Further, substantial percentages of PASI 75 responders in the active treatments arms had also maintained at least a PASI score of ≧PASI 75, as well as a PASI score of ≧PASI 90 (Table 4 and FIGS. 4A-C). The percentage of patients maintaining a PASI 75 response over time during the 24 week period is depicted in FIG. 4D.

TABLE 4

24-Week Efficacy of ABT-874

| | ≧PASI 75 at Wk 12 | Maintenance of ≧PASI 50 Response: Wk 24 vs. Wk 12 | Maintenance of ≧PASI 75 Response: Wk 24 vs. Wk 12 | Maintenance of ≧PASI 90 Response: Wk 24 vs. Wk 12 |
|---|---|---|---|---|
| 100 mg eow for 12 wks | 93%* | 71% | 60% | 33% |
| 200 mg, one dose | 63%* | 68% | 23% | 7% |
| 200-mg every wk for 4 wks | 90%* | 82% | 60% | 23% |
| 200-mg eow for 12 wks | 93%* | 89% | 73% | 53% |
| 200-mg every wk for 12 wks | 90%* | 85% | 83% | 57% |
| Placebo | 3% | — | 7% | 7% |

*$p < 0.001$ vs. placebo, NRI.

In conclusion, ABT-874 was significantly more efficacious than placebo in the treatment of moderate to severe plaque Ps.

Substantial percentages of PASI 75 responders maintained a response of ≧PASI 50, ≧PASI 75, and ≧PASI 90 at Week 24, following discontinuation of active therapy.

Example 6

Maintenance of Re-treatment Response with the Fully Human IL-12/-23 Monoclonal Antibody, ABT-874, in the Treatment of Moderate to Severe Plaque Psoriasis The efficacy and safety of ABT-874 was evaluated in a 48-week, Phase II, randomized controlled trial that included a 12-week initial treatment phase and a 36-week re-treatment phase of patients responding to initial treatment. The initial 12-week efficacy results and maintenance of response results are described in the above examples. The objective of the following example was to examine the re-treatment response during the 36-week re-treatment/follow-up phase in patients who lost their initial responses of this Phase II study of subcutaneous injections of ABT-874 in the treatment of moderate to severe plaque Ps. The further objective of the following example was to examine safety of subcutaneous injections of ABT-874 in the treatment of moderate to severe plaque Ps through 48 weeks.

At baseline, demographics and clinical characteristics were similar across treatment groups (summarized in Table 5 below).

TABLE 5

Baseline Demographics and Clinical Characteristics

| | Treatment Group* | | | | | | |
|---|---|---|---|---|---|---|---|
| Characteristic | Placebo (n = 30) | 200 mg × 1 (n = 30) | 100 mg eow (n = 30) | 200 mg × 4 (n = 30) | 200 mg eow (n = 30) | 200 mg Weekly (n = 30) | All (N = 150) |
| Age, yrs | 49 (14.4) | 52 (12.0) | 45 (13.8) | 43 (13.8) | 44 (16.0) | 46 (14.0) | 46 (14.1) |
| Sex, n (%) male | 22 (73) | 23 (77) | 22 (73) | 21 (70) | 23 (77) | 23 (77) | 112 (75) |
| Race, n (%) white | 28 (93) | 25 (83) | 28 (93) | 27 (90) | 30 (100) | 28 (93) | 138 (92) |
| Weight, kg | 89 (17.6) | 94 (21.2) | 94 (17.9) | 92 (27.8) | 93 (24.1) | 95 (18.0) | 94 (21.9) |
| Duration of psoriasis, yrs | 21 (12.4) | 20 (13.2) | 24 (14.6) | 22 (14.2) | 18 (11.5) | 18 (10.9) | 21 (13.0) |
| PASI score | | | | | | | |
| Mean (SD) | 16 (2.9) | 18 (6.7) | 20 (6.3) | 20 (7.6) | 20 (6.2) | 19 (6.3) | 19 (6.6) |
| Median, IQ | 16.1, 3.8 | 15.0, 7.5 | 18.7, 7.4 | 17.0, 10.2 | 18.0, 10.0 | 16.8, 5.8 | 17.3, 8.0 |

TABLE 5-continued

Baseline Demographics and Clinical Characteristics

| Characteristic | Placebo (n = 30) | 200 mg × 1 (n = 30) | 100 mg eow (n = 30) | 200 mg × 4 (n = 30) | 200 mg eow (n = 30) | 200 mg Weekly (n = 30) | All (N = 150) |
|---|---|---|---|---|---|---|---|
| | Treatment Group* | | | | | | |
| BSA affected, % | | | | | | | |
| Mean (SD) | 21 (9.2) | 24 (13.6) | 28 (15.7) | 24 (13.0) | 29 (16.8) | 23 (12.6) | 26 (14.5) |
| Median, IQ | 17.5, 13.0 | 17.5, 16.0 | 22.5, 19.5 | 20.3, 17.0 | 22.0, 24.5 | 19.5, 17.0 | 20.0, 21.0 |
| PGA, n (%)† | | | | | | | |
| Mild | 1 (3) | 0 | 0 | 0 | 0 | 0 | 0 |
| Moderate | 20 (67) | 19 (63) | 17 (57) | 13 (43) | 15 (50) | 17 (57) | 81 (54) |
| Severe | 9 (30) | 11 (37) | 12 (40) | 14 (47) | 13 (43) | 11 (37) | 61 (41) |
| History of PsA, n (%) | 9 (30) | 7 (23) | 12 (40) | 9 (30) | 6 (20) | 9 (30) | 43 (29) |
| Previous psoriasis treatment,‡ n (%) | | | | | | | |
| Topical therapy | 19 (63) | 21 (70) | 26 (87) | 15 (50) | 21 (70) | 23 (77) | 106 (71) |
| Phototherapy | 1 (3) | 6 (20) | 4 (13) | 4 (13) | 3 (10) | 5 (17) | 22 (15) |
| Systemic nonbiologic | 6 (20) | 4 (13) | 7 (23) | 5 (17) | 6 (20) | 8 (27) | 30 (20) |
| Systemic biologic | 3 (10) | 3 (10) | 7 (23) | 6 (20) | 4 (13) | 7 (23) | 27 (18) |

BSA, body surface area, PsA, psoriatic arthritis.
*Values are mean (SD) unless otherwise noted.
†Data are presented for only 3 of 5 possible categories and therefore do not sum up to 30 for each group.
‡Within the 12 months before study treatment.

Adults with psoriasis affecting ≧10% body surface area and a Psoriasis Area and Severity Index (PASI) score ≧12 were randomized to 1 of 6 arms: 1) one 200-mg dose ABT-874 at Week 0; 2) 100 mg of ABT-874 every other wk (eow) for 12 weeks; 3) 200 mg of ABT-874 weekly for 4 weeks; 4) 200 mg of ABT-874 eow for 12 weeks; 5) 200 mg of ABT-874 weekly for 12 weeks; or 6) placebo. The primary endpoint was a ≧PASI 75 response at Week 12. Patients who met the primary endpoint entered a 36-week re-treatment phase. Treatment with study drug was discontinued, and patients who lost response (≦PASI 50) during weeks 12-36 received re-treatment with the same dosing regimen assigned during the initial 12-week period. Re-treatment lasted for 12 weeks. Regardless of disposition, all patients were monitored for the entire duration of the study, or until discontinuation.

Of the 180 patients initially enrolled, 130 (1 placebo) entered the retreatment phase and 58 (all ABT-874) were re-treated. The percentages of patients who achieved ≧PASI 75 at week 12 and then again at 12 weeks after re-treatment were as follows for each group: one 200-mg dose, 63% vs. 55%; 100 mg eow, 93% vs. 94%; 200 mg weekly 4 wks, 90% vs. 69%; 200 mg eow, 93% vs. 75%; and 200 mg weekly, 90% vs. 83%, respectively. Of the total 58 patients who were retreated, 76% achieved ≧PASI 75 at 12 weeks after re-treatment.

Figure 5A:
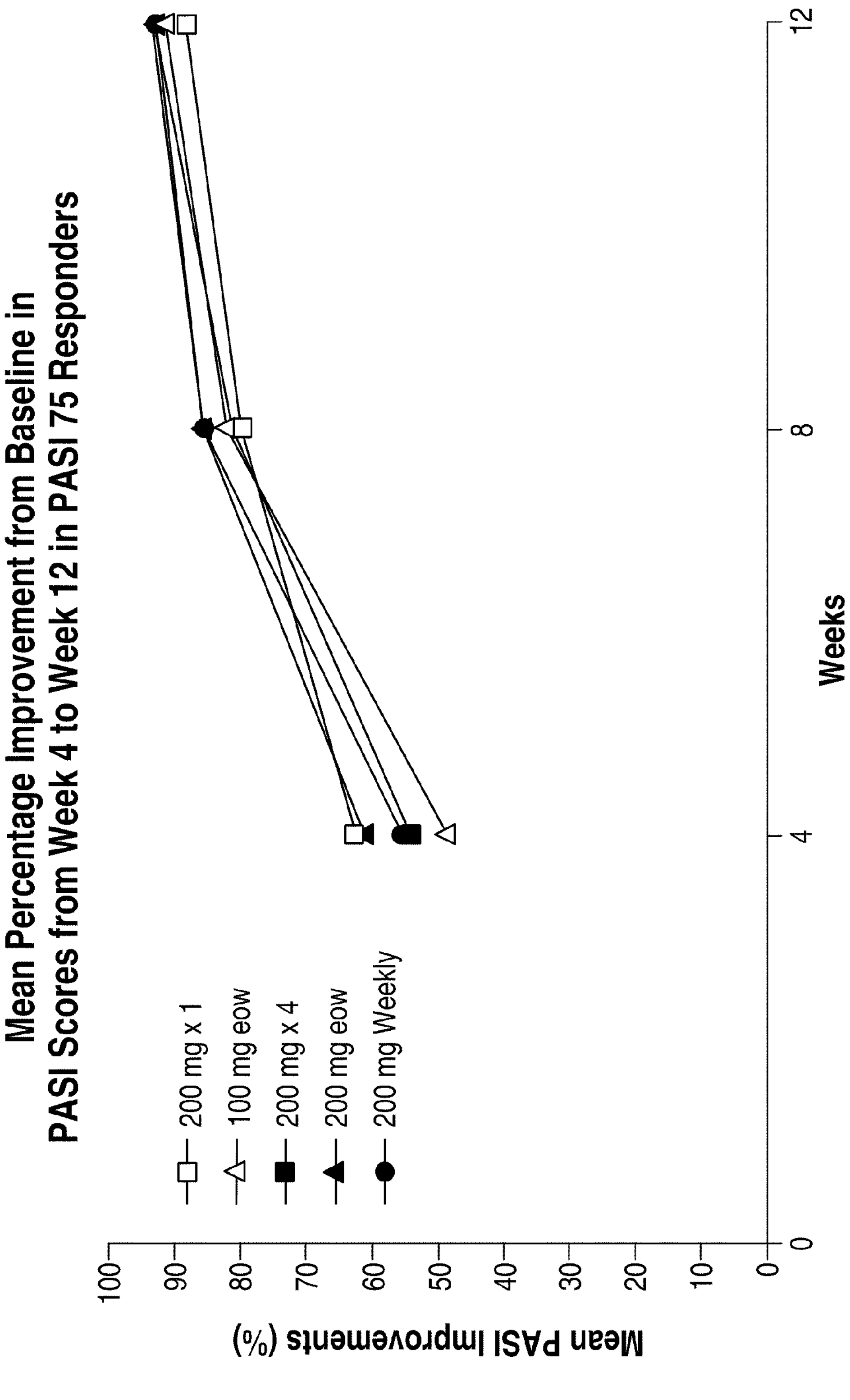
FIG. 5A displays the mean percentage improvement from baseline in PASI scores from Week 4 to Week 12.
Figure 5B:
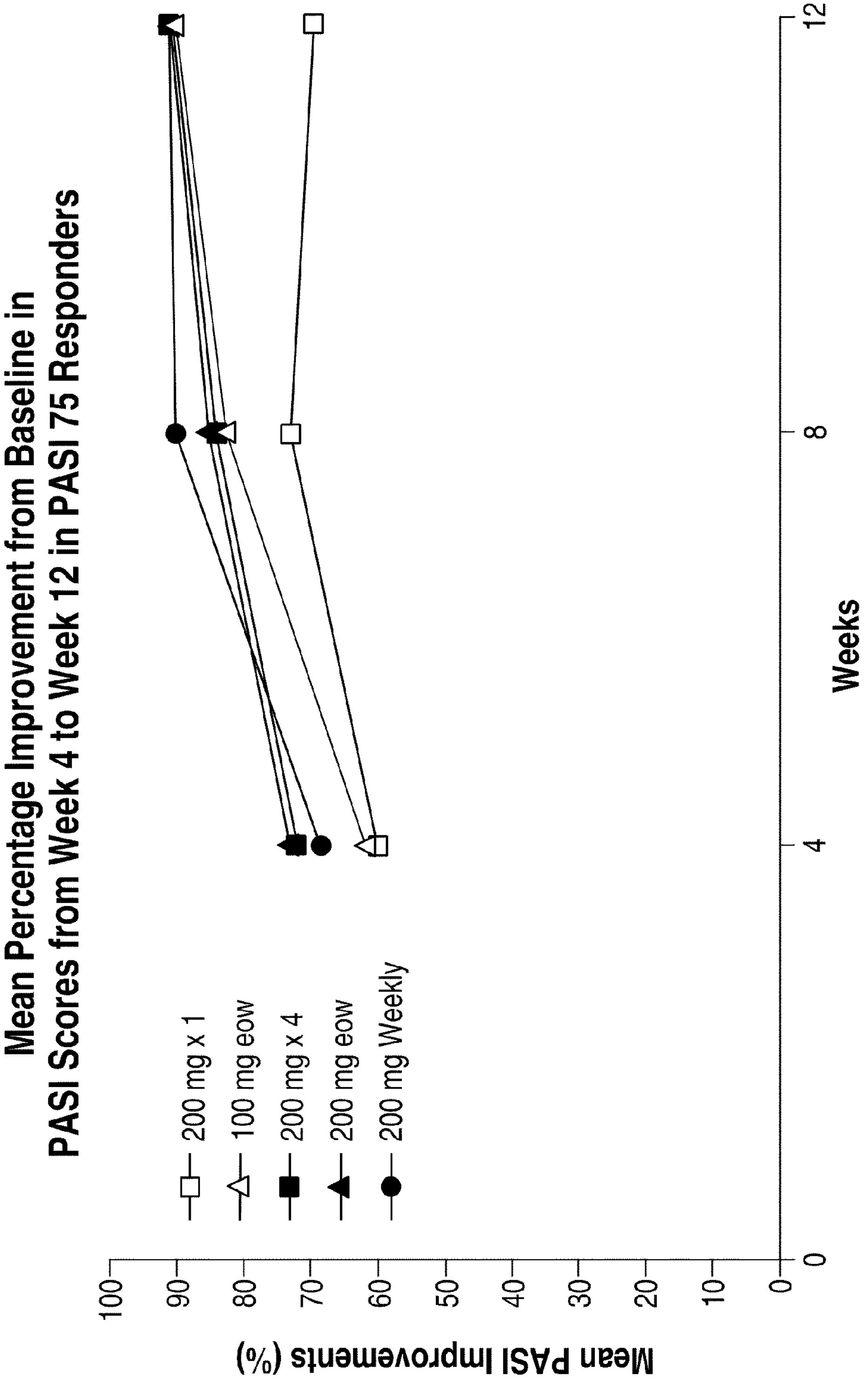
FIG. 5B displays the mean percentage improvement from baseline in PASI scores from Week 4 to Week 12 post retreatment.

The improvement in PASI scores over time for the re-treated patients is depicted in FIGS. 5A-B. Specifically, FIG. 5A displays the mean percentage improvement from baseline in PASI scores from weeks 4 to week 12 in PASI responders, and FIG. 5B displays the mean percentage improvement from baseline in PASI scores from weeks 4 to week 12 post retreatment in PASI 75 responders.

The percentages of patients who achieved ≧PASI 50 at 12 weeks after re-treatment were as follows for each group: one 200-mg dose, 82%; 100 mg eow, 100%; 200 mg weekly 4 wks, 77%; 200 mg eow, 83%; and 200 mg weekly, 100%. Of the total 58 patients who were retreated, 88% achieved ≧PASI 50 at 12 weeks after re-treatment.

The percentages of patients who achieved a PGA of "clear" or "minimal" at 12 weeks after re-treatment were as follows for each group: one 200-mg dose, 36%; 100 mg eow, 75%; 200 mg weekly 4 wks, 62%; 200 mg eow, 67%; and 200 mg weekly, 83%. Of the total 58 patients who were retreated, 64% achieved a PGA of "clear" or "minimal" at 12 weeks after re-treatment.

Adverse events (AEs) occurring ≧5% in at least 1 treatment group in descending order through week 48 were: nasopharyngitis, injection-site reaction, upper respiratory tract infection, headache, hypertension, and arthralgia. An overview of treatment-emergent adverse events through Week 48 is displayed in Table 6 below. An overview of treatment-emergent adverse events with an incidence ≧5% in any treatment group is displayed in Table 7 below.

TABLE 6

Overview of Treatment-Emergent Adverse Events Through Week 48*

| Event | Placebo* n = 30 n (%) | 200 mg × 1 n = 30 n (%) | 100 mg eow n = 30 n (%) | 200 mg × 4 n = 30 n (%) | 200 mg eow n = 30 n (%) | 200 mg Weekly n = 30 n (%) | All ABT N = 150 n (%) |
|---|---|---|---|---|---|---|---|
| Any AE | 18 (60.0) | 20 (66.7) | 25 (83.3) | 25 (83.3) | 25 (83.3) | 21 (70.0) | 116 (77.3) |
| Any AE at least possibly drug-related† | 4 (13.3) | 9 (30.0) | 16 (53.3) | 16 (53.3) | 13 (43.3) | 10 (33.3) | 64 (42.7) |
| Any severe AE | 4 (13.3) | 1 (3.3) | 0 | 2 (6.7) | 1 (3.3) | 1 (3.3) | 5 (3.3) |
| Any serious AE | 1 (3.3) | 1 (3.3) | 0 | 1 (3.3) | 2 (6.7) | 0 | 4 (2.7) |

TABLE 6-continued

Overview of Treatment-Emergent Adverse Events Through Week 48*

| Event | Placebo* n = 30 n (%) | 200 mg × 1 n = 30 n (%) | 100 mg eow n = 30 n (%) | 200 mg × 4 n = 30 n (%) | 200 mg eow n = 30 n (%) | 200 mg Weekly n = 30 n (%) | All ABT N = 150 n (%) |
|---|---|---|---|---|---|---|---|
| Any AE leading to discontinuation of study drug | 2 (6.7) | 1 (3.3) | 0 | 0 | 0 | 0 | 1 (0.7) |
| Any AE at least possibly drug-related and serious† | 0 | 0 | 0 | 0 | 1 (3.3) | 0 | 1 (0.7) |
| Any infectious AE | 7 (23.3) | 10 (33.3) | 12 (40.0) | 14 (46.7) | 16 (53.3) | 10 (33.3) | 62 (41.3) |
| Any serious infectious AE | 0 | 0 | 0 | 0 | 1 (3.3) | 0 | 1 (0.7) |
| Any malignant AE | 1 (3.3) | 0 | 0 | 1 (3.3) | 0 | 0 | 1 (0.7) |
| Any lymphomas | 0 | 0 | 0 | 0 | 0 | 0 | 0 |
| Any nonmelanoma skin cancer | 0 | 0 | 0 | 1 (3.3) | 0 | 0 | 1 (0.7) |
| Any injection-site reaction-related AE | 0 | 4 (13.3) | 11 (36.7) | 12 (40.0) | 11 (36.7) | 6 (20.0) | 44 (29.3) |
| Deaths | 0 | 0 | 0 | 0 | 0 | 0 | 0 |

*Placebo data are only for the first 12 weeks of the study: all 12-week data previously reported.

†As assessed by investigator.

AE adverse event.

TABLE 7

Treatment-Emergent Adverse Events With an Incidence of 5% or More in any Treatment Group Through Week 48*

| Event | Placebo* n = 30 n (%) | 200 mg × 1 n = 30 n (%) | 100 mg eow n = 30 n (%) | 200 mg × 4 n = 30 n (%) | 200 mg eow n = 30 n (%) | 200 mg Weekly n = 30 n (%) | All ABT N = 150 n (%) |
|---|---|---|---|---|---|---|---|
| Injection-site reaction | 0 | 2 (6.7) | 7 (23.3) | 8 (26.7) | 8 (26.7) | 4 (13.3) | 29 (19.3) |
| Nasopharyngitis | 1 (3.3) | 5 (16.7) | 5 (20.0) | 3 (10.0) | 4 (13.3) | 5 (16.7) | 23 (15.3) |
| Upper respiratory tract infection | 2 (6.7) | 2 (6.7) | 5 (16.7) | 3 (10.0) | 5 (16.7) | 2 (6.7) | 17 (11.3) |
| Headache | 2 (6.7) | 5 (16.7) | 1 (3.3) | 1 (3.3) | 3 (10.0) | 2 (6.7) | 12 (8.0) |
| Injection-site erythema | 0 | 0 | 1 (3.3) | 14 (13.3) | 2 (6.7) | 1 (3.3) | 8 (5.3) |
| Injection-site pruritus | 0 | 0 | 1 (3.3) | 2 (6.7) | 2 (6.7) | 2 (6.7) | 7 (4.7) |
| Injection-site irritation | 0 | 1 (3.3) | 3 (10.0) | 2 (6.7) | 0 | 0 | 6 (4.0) |
| Arthralgia | 1 (3.3) | 2 (6.7) | 1 (3.3) | 0 | 0 | 2 (6.7) | 5 (3.3) |
| Viral infection | 0 | 0 | 0 | 2 (6.7) | 2 (6.7) | 1 (3.3) | 5 (3.3) |
| Gastroenteritis viral | 0 | 1 (3.3) | 0 | 2 (6.7) | 1 (3.3) | 1 (3.3) | 5 (3.3) |
| Fatigue | 0 | 2 (6.7) | 2 (6.7) | 0 | 0 | 1 (3.3) | 5 (3.3) |
| Hypertriglyceridemia | 0 | 1 (3.3) | 2 (6.7) | 2 (6.7) | 0 | 0 | 5 (3.3) |
| Pain in extremity | 0 | 1 (3.3) | 0 | 0 | 1 (3.3) | 2 (6.7) | 4 (2.7) |
| Bronchitis | 0 | 1 (3.3) | 0 | 1 (3.3) | 2 (6.7) | 0 | 4 (2.7) |
| Pharyngolaryngeal pain | 0 | 2 (6.7) | 0 | 0 | 0 | 1 (3.3) | 3 (2.0) |
| Influenza | 1 (3.3) | 0 | 1 (3.3) | 0 | 2 (6.7) | 0 | 3 (2.0) |
| Back pain | 0 | 0 | 1 (3.3) | 0 | 2 (6.7) | 0 | 3 (2.0) |
| Blood triglycerides increased | 1 (3.3) | 0 | 0 | 2 (6.7) | 1 (3.3) | 0 | 3 (2.0) |
| Urinary tract infection | 2 (6.7) | 1 (3.3) | 0 | 1 (3.3) | 1 (3.3) | 0 | 3 (2.0) |
| Insomnia | 1 (3.3) | 2 (6.7) | 0 | 1 (3.3) | 1 (3.3) | 0 | 3 (2.0) |
| Nausea | 2 (6.7) | 0 | 3 (10.0) | 0 | 0 | 0 | 3 (2.0) |
| Cyst | 0 | 1 (3.3) | 2 (6.7) | 0 | 0 | 0 | 3 (2.0) |
| Gastroenteritis | 0 | 0 | 0 | 0 | 0 | 2 (6.7) | 2 (1.3) |
| Rhinorrhea | 0 | 0 | 0 | 0 | 0 | 2 (6.7) | 2 (1.3) |
| Otitis externa | 0 | 0 | 0 | 0 | 2 (6.7) | 0 | 2 (1.3) |
| Vomiting | 1 (3.3) | 0 | 0 | 2 (6.7) | 0 | 0 | 2 (1.3) |
| Hypercholesterolemia | 0 | 0 | 0 | 2 (6.7) | 0 | 0 | 2 (1.3) |
| Blood pressure increased | 0 | 0 | 2 (6.7) | 0 | 0 | 0 | 2 (1.3) |
| Procedural pain | 0 | 0 | 2 (6.7) | 0 | 0 | 0 | 2 (1.3) |
| Limb injury | 0 | 2 (6.7) | 0 | 0 | 0 | 0 | 2 (1.3) |
| Pruritis | 2 (6.7) | 0 | 0 | 0 | 0 | 1 (3.3) | 1 (0.7) |
| Psoriatic arthropathy | 2 (6.7) | 1 (3.3) | 0 | 0 | 0 | 0 | 1 (0.7) |

*Placebo data are only for the first 12 weeks fo the study; all 12 week data previously reported.

The foregoing data demonstrate that ABT-874 was highly efficacious in the treatment of moderate to severe psoriasis. Upon loss of response and re-treatment, a majority of patients were able to re-achieve a PASI 75 response. Moreover, ABT-874 appears to have a favorable safety profile in the long term.

Example 7

Pharmacokinetics of a Fully Human IL-12/-23 Monoclonal Antibody, ABT-874, in Normal Healthy Volunteers The tolerability, safety, and pharmacokinetics (PK) of a range of doses of ABT-874 were evaluated in a randomized, double-blind, placebo-controlled dose-ranging study. The objective of the following example was to investigate the pharmacokinetics of intravenous (IV) and subcutaneous (SC) injections of ABT-874 in healthy volunteers.

The main inclusion criteria were: (i) healthy male volunteers between 18 and 45 years of age; (ii) no clinically relevant abnormalities in any of the investigations of the screening examination (physical exam, vital signs, electrocardiogram, biochemistry, hematology, urinalysis, serology); and (iii) chest x-rays normal within 12 months prior to entering the study. The main exclusion criteria were: (i) smoking more than 10 cigarettes per day; (ii) drinking more than 30 g of alcohol per day; (iii) positive urine drug screen; (iv) chronic infections, especially by intracellular bacterial pathogens such as Mycobacterium tuberculosis; and (v) major infections requiring hospitalization or IV antibiotics within the previous 2 years.

Young (18-45 years of age), healthy male volunteers received 2 equal doses (1 IV and 1 SC administered 8 weeks apart) of 0.1, 0.3, 1.0, or 5.0 mg/kg ABT-874 in a 2-period crossover (2×2 Latin square) design. Blood samples for the determination of ABT-874 concentrations were collected before the first dose (0) and at 0.5, 1, 1.5, 2, 4, 8, 12, 24, 48, 72, 120, 168, 336, 504 and 672 hours after dosing. Serum concentrations of ABT-874 were measured by an enzyme-linked immunosorbent assay.

ABT-874 serum concentrations were tabulated individually, described by statistical characteristics (including geometric mean and geometric standard deviation) and displayed as individual as well as mean, median, and geometric mean concentration vs. time curves for IV and SC treatment and each treatment group. The following PK parameters were estimated using noncompartmental methods:

Cmax maximum serum concentration (μg/mL)

Tmax time to reach Cmax (hr)

AUC area under the serum concentration-time curve (μg×hr/mL)

t½ half-life (hr)

CL clearance (mL/hr) (for IV administration)

Vz volume of distribution (mL) (for IV administration)

CL/F apparent CL (mL/hr) (for SC administration)

V/F apparent Vz (mL) (for SC administration)

A total of 64 patients were randomized; 12 received ABT-874 and 4 received placebo for each dose group. ABT-874 appeared to follow bi-exponential kinetics following IV administration, entering the terminal phase approximately 7 days after administration. The mean±SD terminal half-lives for the 0.1-, 0.3-, 1.0-, and 3.0-mg IV doses were 81.2±55.6, 147±73.2, 208±79.2, and 196±55.4 hours, respectively. The mean±SD terminal half-lives for the 0.1-, 0.3-, 1.0-, and 3.0-mg SC doses were 221±103, 161±92.6, 210±90.9, and 208±79.2 hours, respectively. The mean terminal half-life for IV administration ranged from 81.2±55.6 hours to 208±79.2 hours. The mean terminal half-life for SC administration ranged from 161±92.6 hours to 221±103 hours. The overall mean terminal half-life was 8-9 days.

Figure 6A:
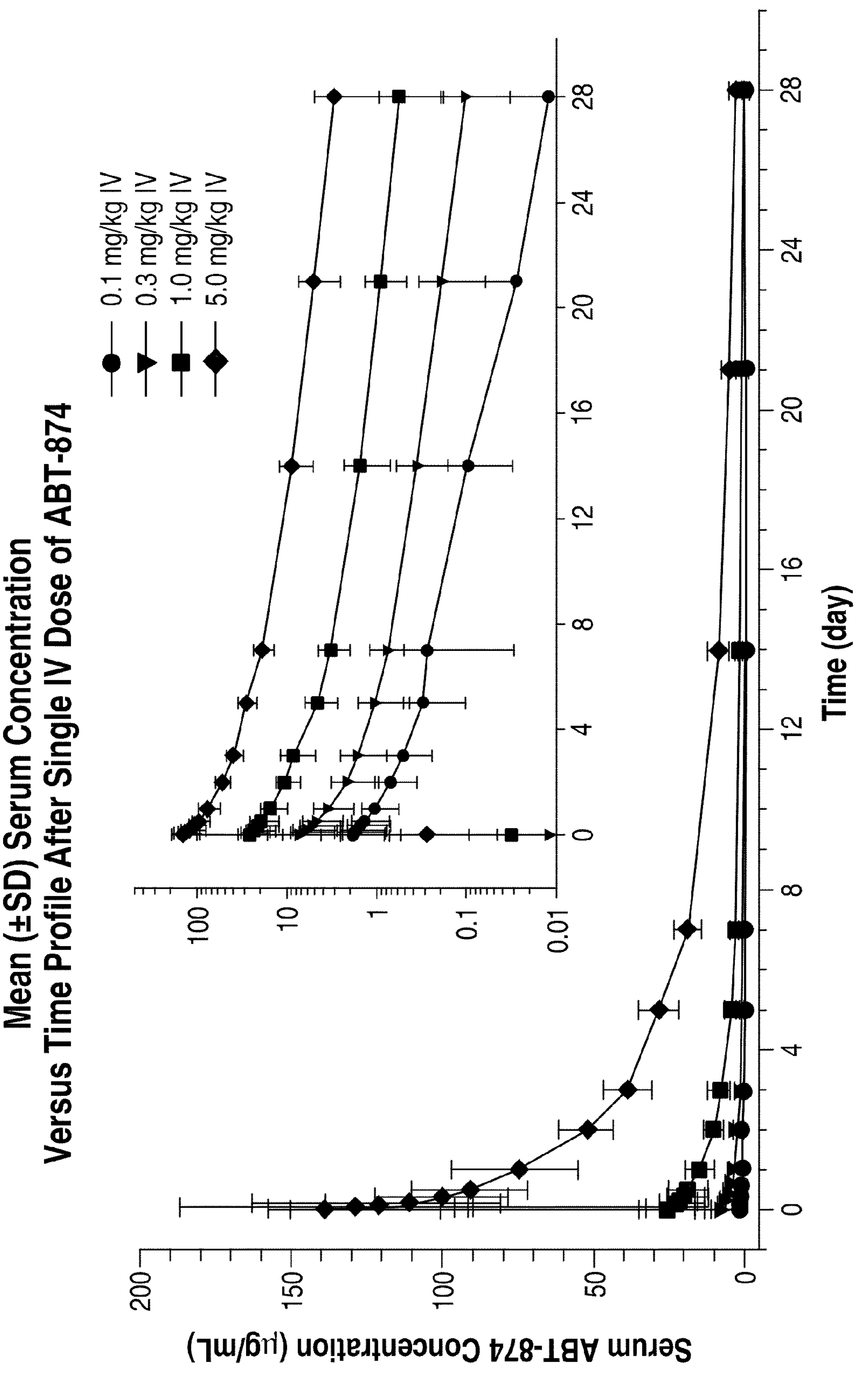
FIG. 6A displays the serum concentration-time curve for IV dosing of ABT-874.
Figure 6B:
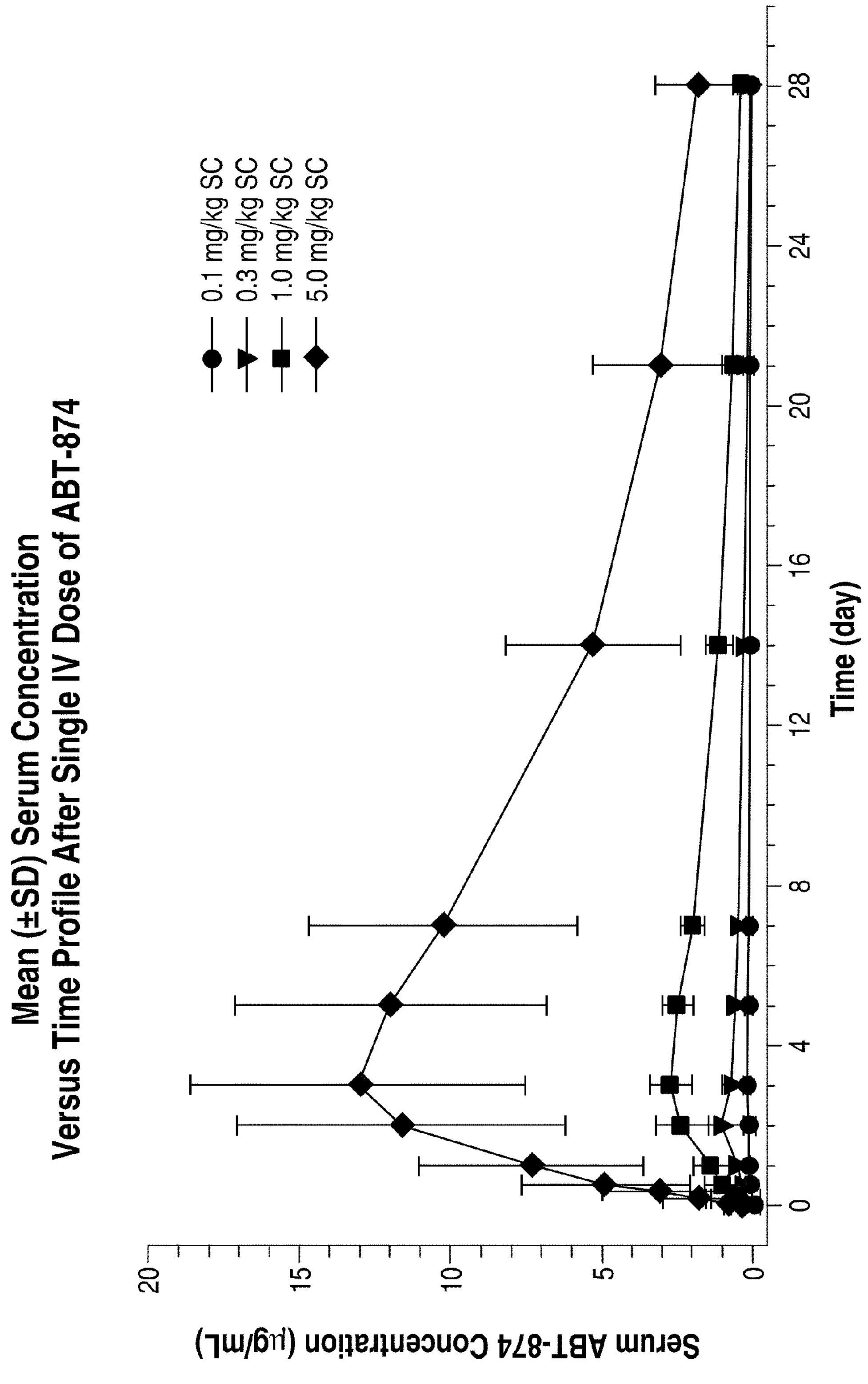
FIG. 6B displays the serum concentration-time curve for SC dosing of ABT-874.

The pharmacokinetics of ABT-874 (maximum concentration of drug [$C_{max}$] or area under the curve [AUC]) increased proportionally to dose after both IV and SC administrations. The serum concentration-time curve for IV and SC dosing is displayed in FIGS. 6A and 6B, respectively. The volume of distribution ranged from approximately 8-10 L after IV administration to 24-67 L after SC administration. After SC administration, the time to reach $C_{max}$ was approximately 3-4 days. Bioavailability after SC administration ranged between 42% and 62% for the doses evaluated. The pharmacokinetic parameters following IV or SC administration at each dose, including $C_{max}$ (the maximum serum concentration in μg/mL), AUC (area under the serum concentration-time curve in μg×hr/mL), $t_{max}$ (time to reach $C_{max}$ in hrs), $t_{1/2}$ (half-life in hrs), CL (clearance in mL/hr) and Vz (volume of distribution (mL)), are displayed in Table 8 below.

TABLE 8

PK Parameters (Mean ± SD) in Healthy Human Volunteers Following IV or SC Administration of ABT-874

| Cohort | Route | $C_{max}$ (μg/mL) | $t_{max}$ (hr) | $AUC_{0-\infty}$ (μg × hr/mL) | $t_{1/2}$ (hr) | CL* (mL/hr) | Vz† (mL) |
|---|---|---|---|---|---|---|---|
| 0.1 mg/kg | IV | 1.99 ± 0.931 | — | 146 ± 78.8 | 81.2 ± 55.6 | 596 ± 1,850 | 8,010 ± 7,600 |
| | SC | 0.245 ± 0.100 | 66.7 ± 10.6 | 84.4 ± 40.6 | 221 ± 103 | 183 ± 248 | 66,500 ± 135,000 |
| 0.3 mg/kg | IV | 7.99 ± 3.08 | — | 562 ± 202 | 147 ± 73.2 | 50.4 ± 32.7 | 8,512 ± 3,746 |
| | SC | 1.09 ± 1.12 | 90.0 ± 43.6 | 244 ± 150 | 161 ± 92.6 | 183 ± 196 | 24,800 ± 7,430 |
| 1.0 mg/kg | IV | 27.7 ± 8.33 | — | 2,410 ± 717 | 208 ± 79.2 | 36.2 ± 9.80 | 10,400 ± 3,840 |
| | SC | 2.83 ± 0.633 | 82.0 ± 23.9 | 1,000 ± 318 | 210 ± 90.9 | 91.1 ± 41.2 | 23,900 ± 8,590 |
| 5.0 mg/kg | IV | 150 ± 50.6 | — | 12,700 ± 3,390 | 196 ± 55.4 | 33.6 ± 9.26 | 9,360 ± 3,360 |
| | SC | 13.4 ± 5.34 | 82.0 ± 36.1 | 4,840 ± 2,420 | 208 ± 79.2 | 229 ± 480 | 31,800 ± 19,500 |

*For SC administration, CL/F

†For SC administration V/F

The foregoing data demonstrate that ABT-874 administered IV and SC in single doses between 0.1 and 5.0 mg/kg was well-tolerated by young healthy male individuals. The pharmacokinetic properties of ABT-874, with its half-life of 8-9 days, are as would be expected for an $IgG_1$ antibody.

Example 8

Maintenance of Re-treatment Response with the Fully Human IL-12/-23 Monoclonal Antibody, ABT-874, in the Treatment of Moderate to Severe Plaque Psoriasis The efficacy and safety of ABT-874 was evaluated in a 48-week, Phase II, randomized controlled trial that included a 12-week initial treatment phase and a 36-week re-treatment phase of patients responding to initial treatment. The initial 12-week efficacy results and maintenance of response results are described in examples 1-5 above. The objective of the following example was to examine the re-treatment response during the 36-week re-treatment/follow-up phase in patients who lost their initial responses of this Phase II study of subcutaneous injections of ABT-874 in the treatment of moderate to severe plaque Ps. The further objective of the following example was to examine safety of subcutaneous injections of ABT-874 in the treatment of moderate to severe plaque Ps through 48 weeks.

The main inclusion criteria for the trial were: (i) adults with clinical diagnosis of psoriasis for at least 6 months and stable plaque psoriasis for at least 2 months prior to screening; and (ii) moderate to severe plaque psoriasis (≧10% body surface area involvement, Psoriasis Area and Severity Index [PASI] score ≧12 and a Physician's Global Assessment [PGA] of at least moderate disease) at the baseline visit.

A first exclusion criteria for the trial was previous exposure to systemic or biologic anti-IL-12 therapy. A second exclusion criteria was inability to discontinue the following therapies before the baseline visit: topical psoriasis therapies ≧2 weeks prior; ultraviolet (UV)-B light phototherapy ≧2 weeks prior; psoralen-UV light phototherapy ≧4 weeks prior; systemic therapies ≧4 weeks prior; and biologic therapies ≧12 weeks prior.

At baseline, demographics and clinical characteristics were similar across treatment groups (summarized in Table 5 of Example 6, above).

Adults with psoriasis affecting ≧10% body surface area and a Psoriasis Area and Severity Index (PASI) score ≧12 were randomized to 1 of 6 arms: 1) one 200-mg dose ABT-874 at Week 0; 2) 100 mg of ABT-874 every other wk (eow) for 12 weeks; 3) 200 mg of ABT-874 weekly for 4 weeks; 4) 200 mg of ABT-874 eow for 12 weeks; 5) 200 mg of ABT-874 weekly for 12 weeks; or 6) placebo. The primary endpoint was a ≧PASI 75 response at Week 12. Patients who met the primary endpoint entered a 36-week re-treatment phase. Treatment with study drug was discontinued, and patients who lost response (≦PASI 50) during weeks 12-36 received re-treatment with the same dosing regimen assigned during the initial 12-week period. Re-treatment lasted for 12 weeks. Regardless of disposition, all patients were monitored for the entire duration of the study, or until discontinuation.

Outcome measurements included the following: (i) percentage of patients achieving PASI 75; (i) median time to achieve PASI 75 response after retreatment; (iii) median time to lose PASI 75 response (iii) percentage of patients with a PGA score of "Clear" or "Minimal" after retreatment.

Statistical analysis was carried out as follows. Intention-to-treat (ITT) analyses were performed by randomized treatment group. For PASI assessments obtained after retreatment with ABT-874, the assessments were assigned to study visits according to the number of days after the first dose of the retreatment. The proportion of patients achieving PASI response (yes/no) are presented according to the derived study visit. All statistical tests were 2-tailed with a significance value of 0.05

Figure 7A:
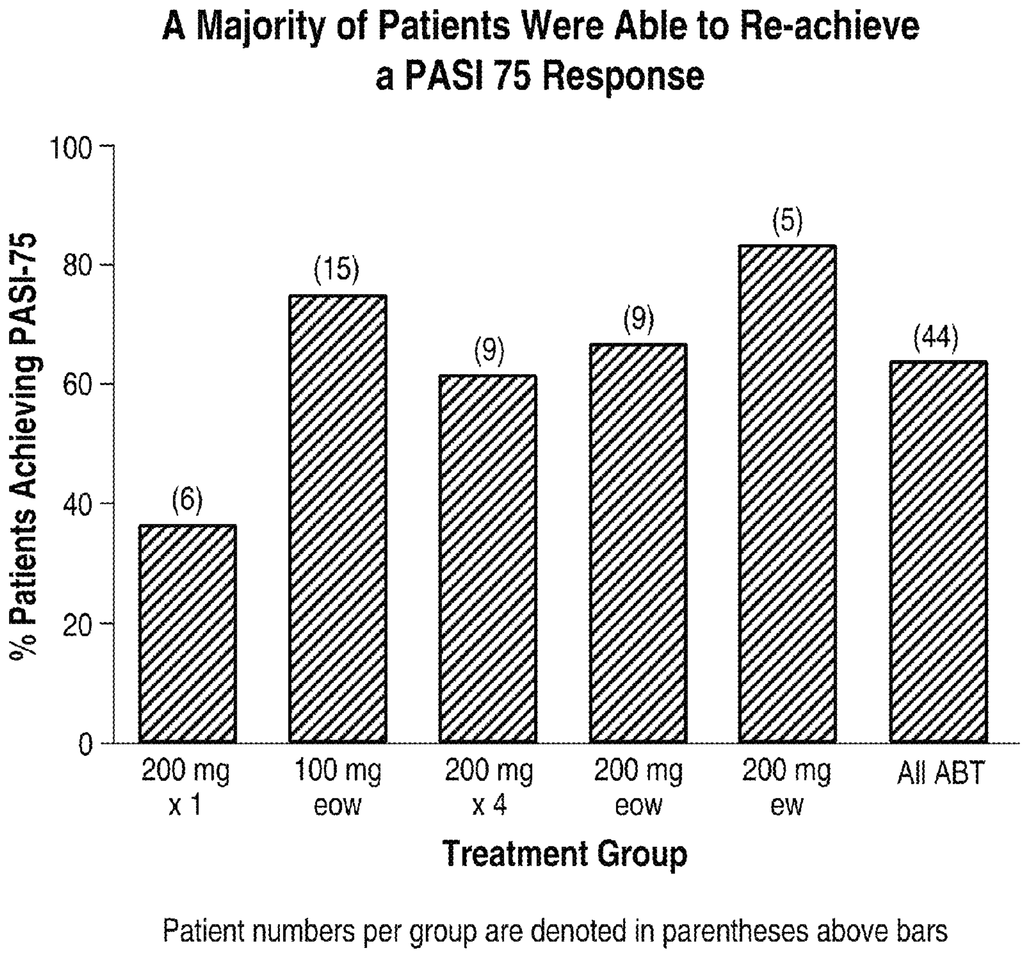
FIG. 7A displays the percentage of patients re-achieving a PASI 75 response following retreatment.

Of the 180 patients initially enrolled (30 patients per treatment group), 130 (1 placebo) entered the retreatment phase and 58 (all ABT-874) were re-treated. The percentages of patients who achieved ≧PASI 75 at week 12 and then again at 12 weeks after re-treatment were as follows for each group: one 200-mg dose, 63% vs. 55%; 100 mg eow, 93% vs. 94%; 200 mg weekly 4 wks, 90% vs. 69%; 200 mg eow, 93% vs. 75%; and 200 mg weekly, 90% vs. 83%, respectively. Of the total 58 patients who were retreated, 76% achieved ≧PASI 75 at 12 weeks after re-treatment. A majority of patients were able to re-achieve a PASI 75 response (FIG. 7A).

Figure 7B:
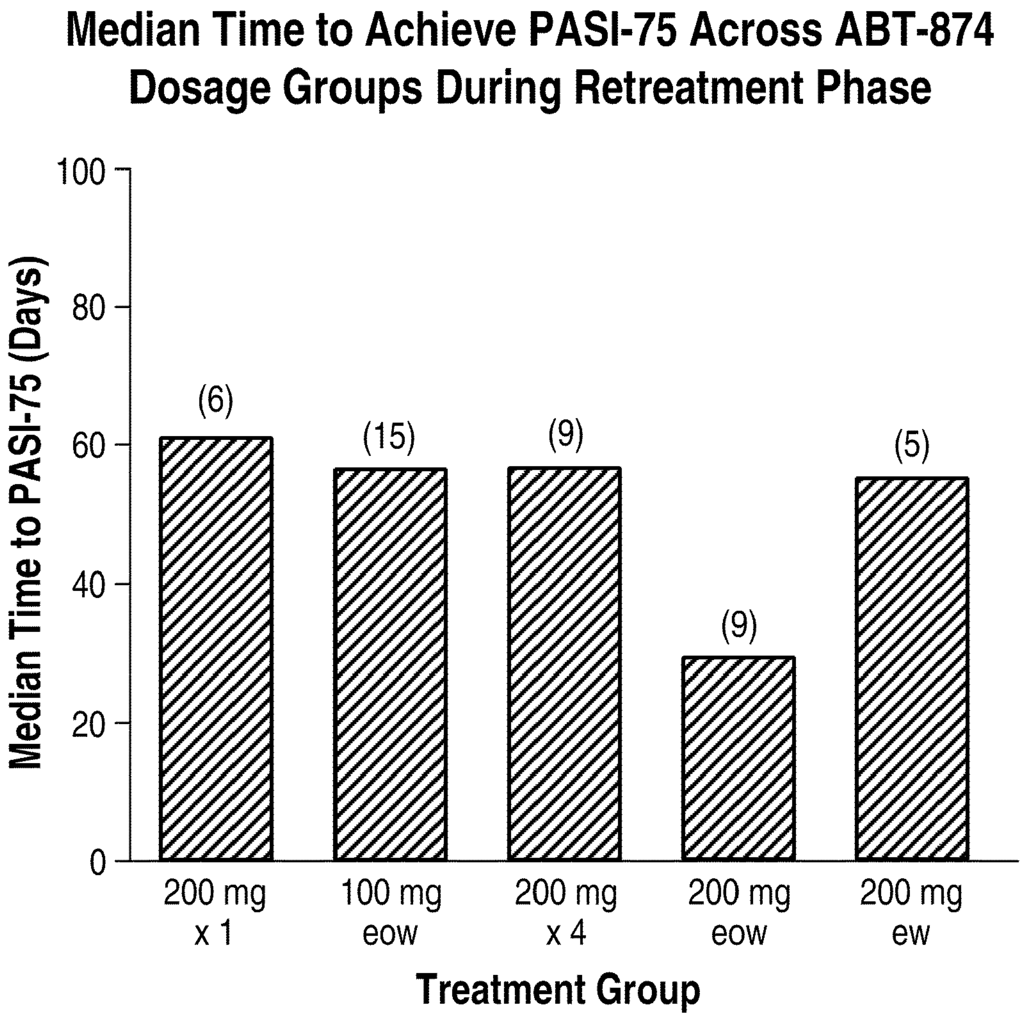
FIG. 7B displays the median time to achieve a PASI 75 response across all ABT-874 dosage groups during retreatment.

The median time (in days) to achieve PASI 75 during the retreatment phase across all ABT-874 dosage groups is depicted in FIG. 7B. The median time to achieve ≧PASI 75 during retreatment were as follows for each group: one 200-mg dose, between 60 and 65 days; 100 mg eow, between 55 and 60 days; 200 mg weekly 4 wks, between 55 and 60 days; 200 mg eow, between 25 and 35 days; and 200 mg weekly, between 55 and 60 days, respectively.

Figure 7C:
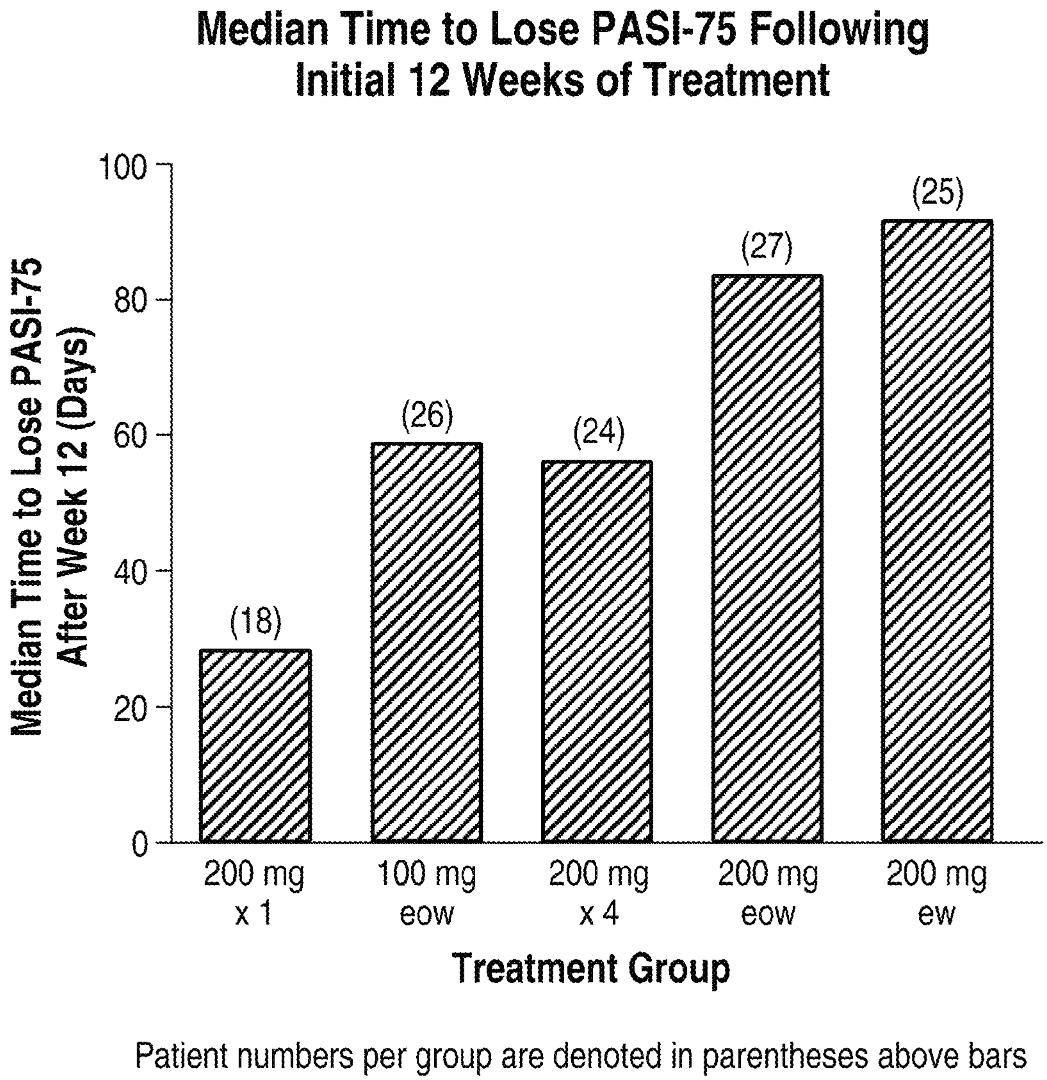
FIG. 7C displays the median time to loss of a PASI 75 response following the initial 12 weeks of treatment.

The median time (in days) to lose PASI 75 following the initial 12 weeks of treatment is depicted in FIG. 7C. The median time to lose PASI 75 following the initial 12 weeks of treatment were as follows for each group: one 200-mg dose, between 55 and 60 days; 100 mg eow, between 110 and 120 days; 200 mg weekly 4 wks, between 110 and 120 days; 200 mg eow, between 160 and 180 days; and 200 mg weekly, between 180 and 190 days, respectively.

Figure 7D:
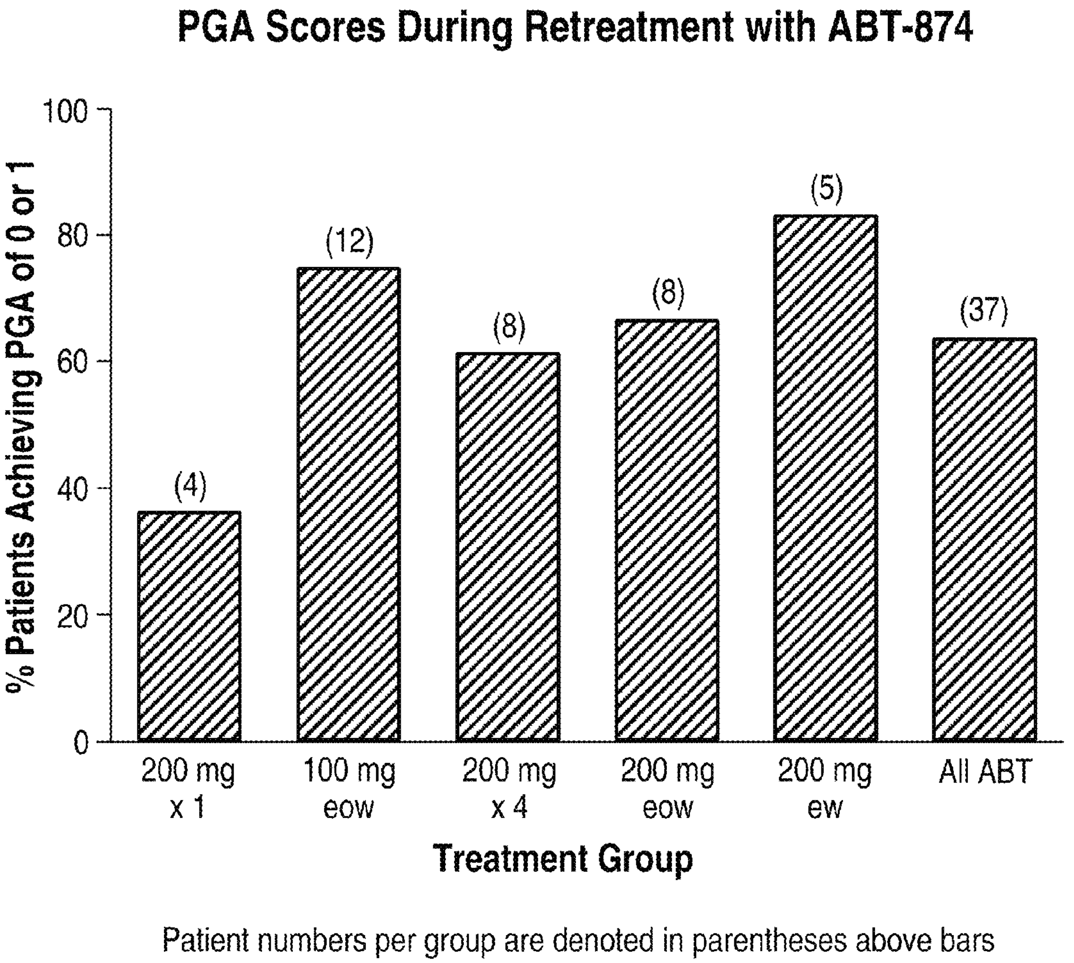
FIG. 7D displays the percentage of patients achieving a PGA score of 0 or 1 following retreatment.
Figures 1, 9A:
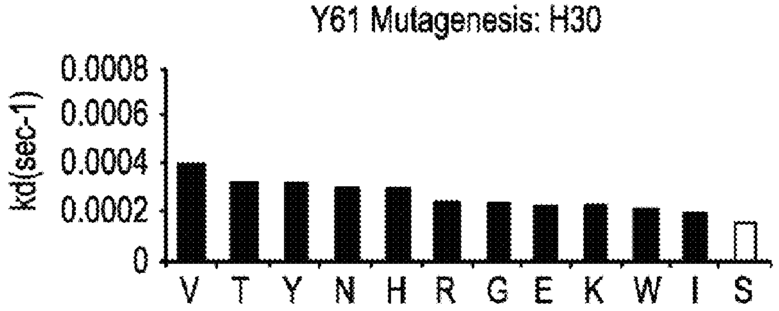
FIGS. 9A-9E show the CDR positions in the heavy chain of the Y61 antibody that were mutated by site-directed mutagenesis and the respective amino acid substitutions at each position. The graphs at the right of the figures show the off-rates for the substituted antibodies (black bars) as compared to unmutated Y61 (open bar).
Figures 2, 9A:
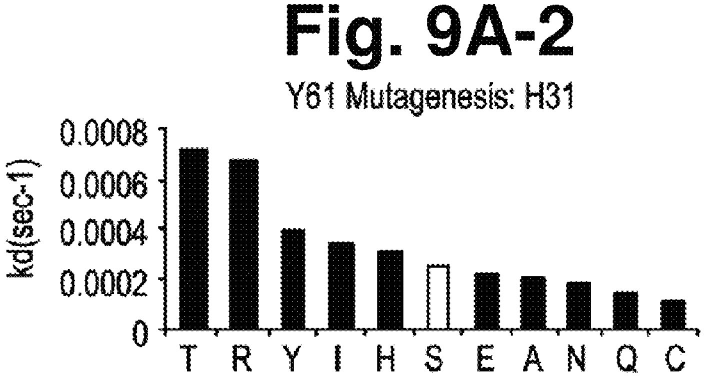
Figures 3, 9A:
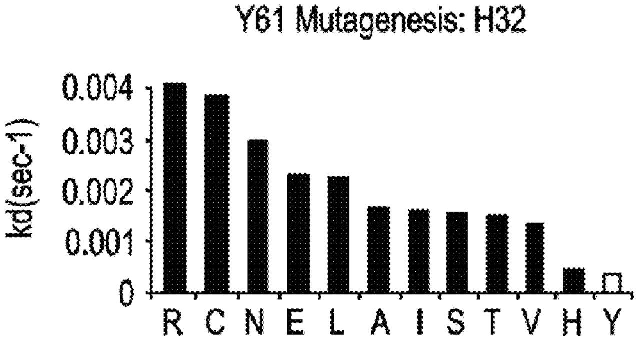
Figures 4, 9A:
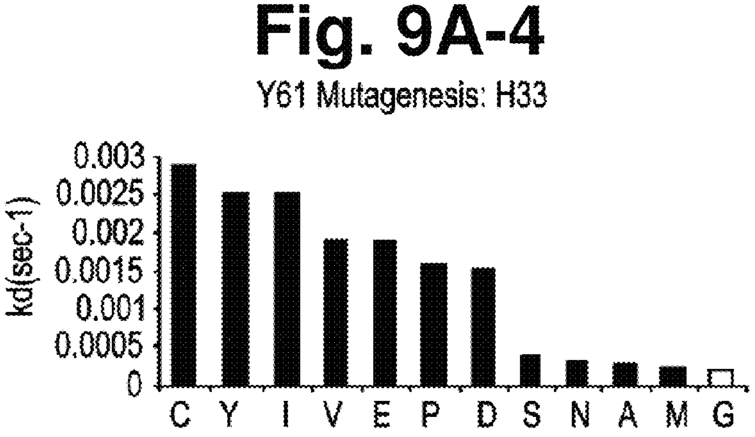
Figures 1, 9B:
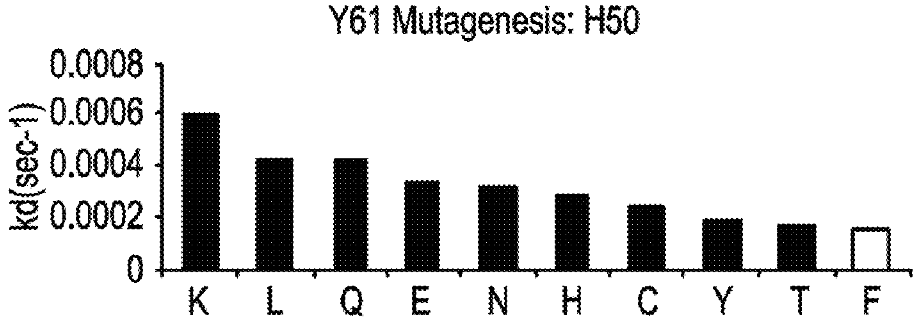
Figures 2, 9B:
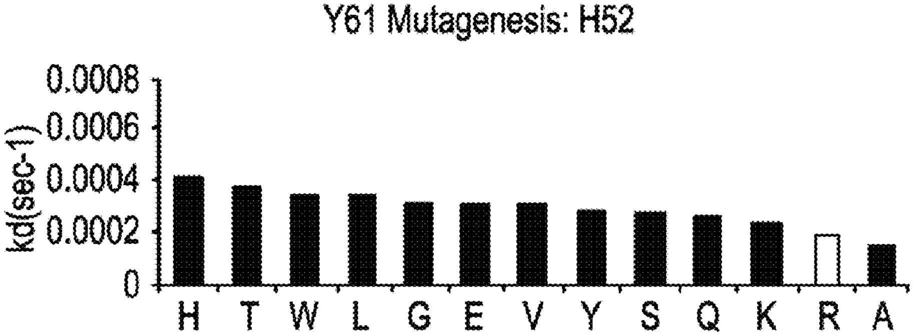
Figures 3, 9B:
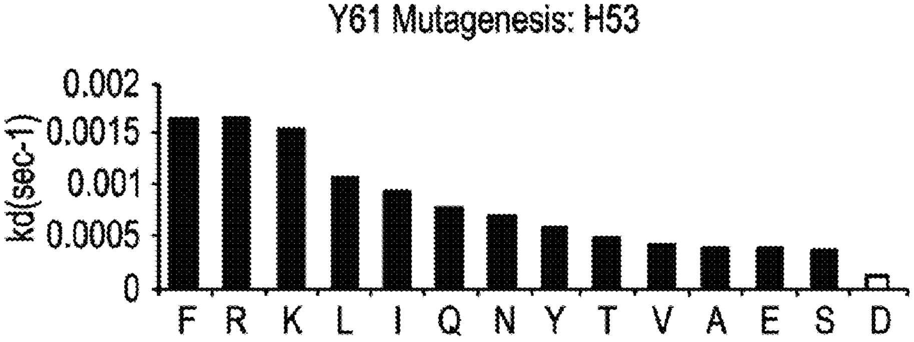
Figures 4, 9B:
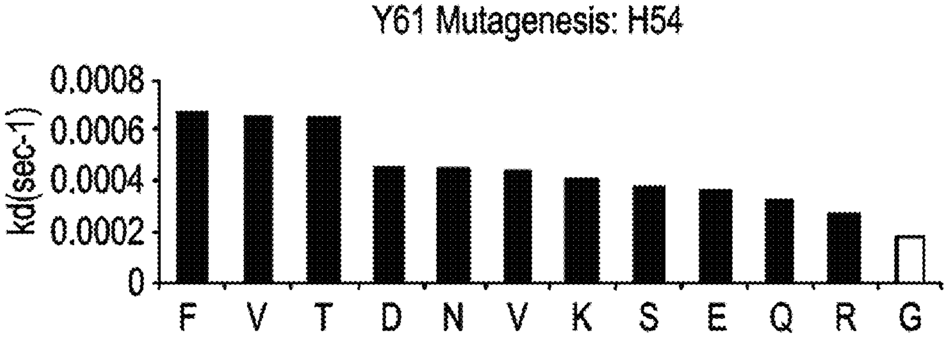
Figures 1, 9C:
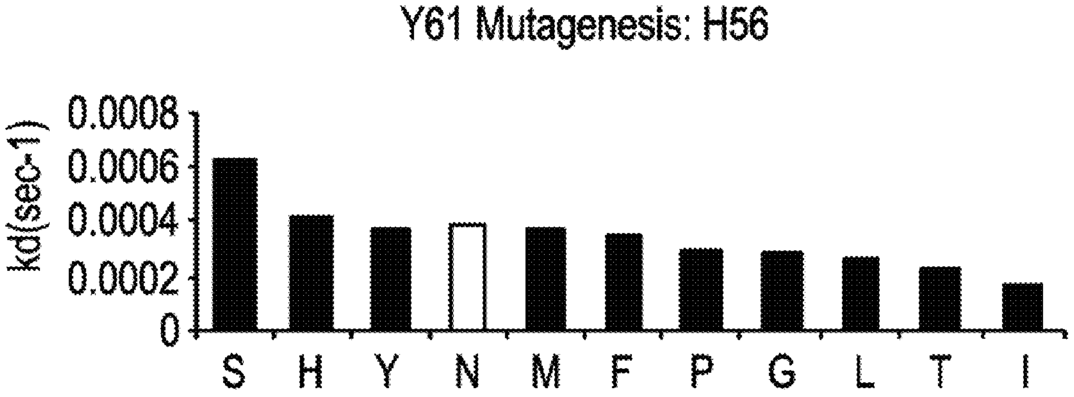
Figures 1, 9C:
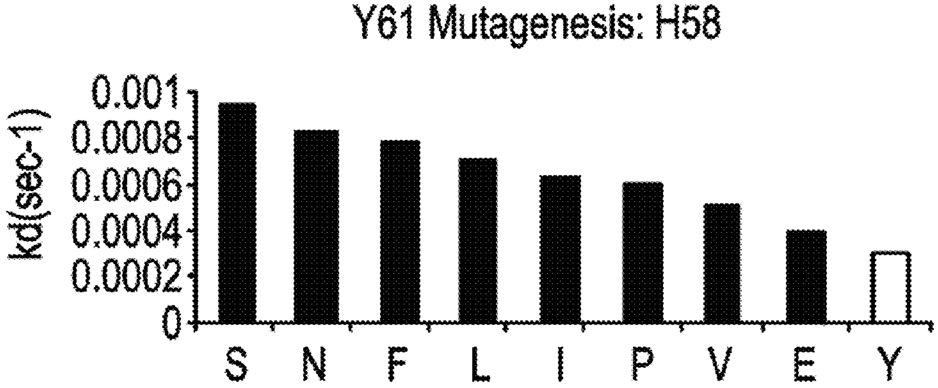
Figures 1, 9D:
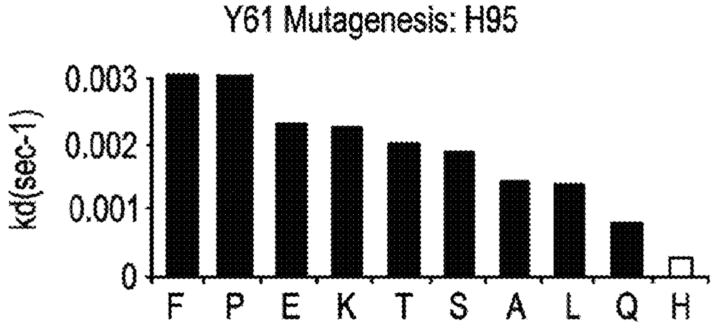
Figures 2, 9D:
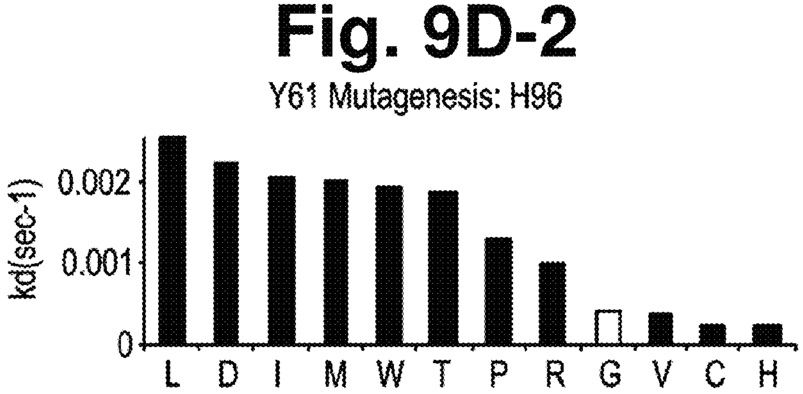
Figures 3, 9D:
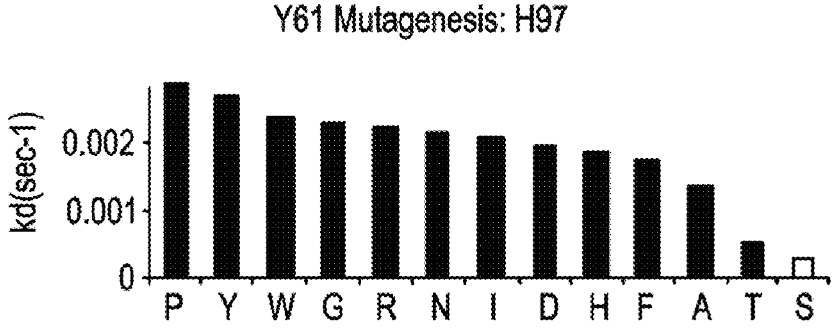
Figures 4, 9D:
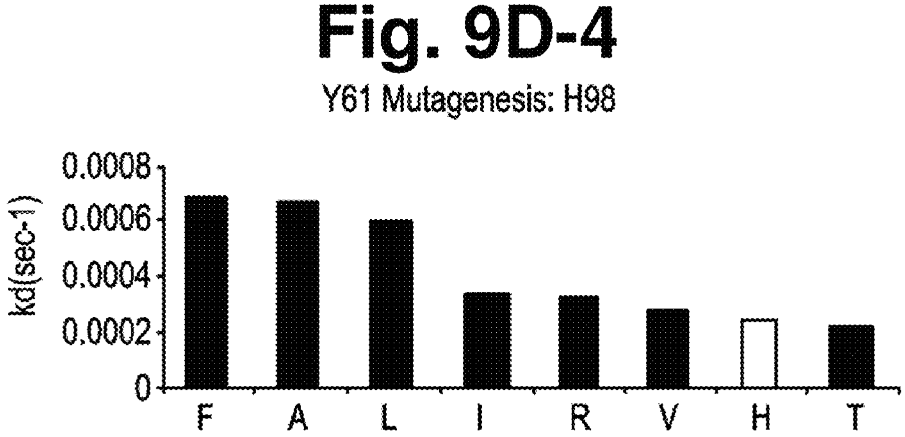
Figures 1, 9E:
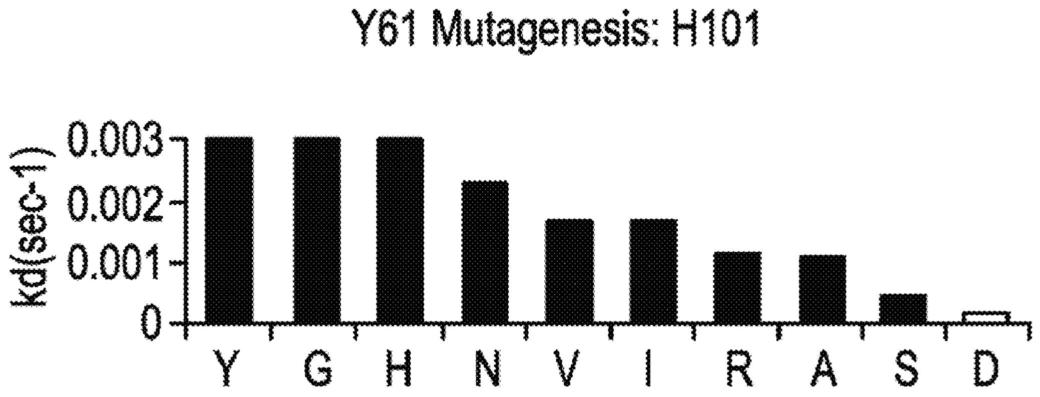
Figures 2, 9E:
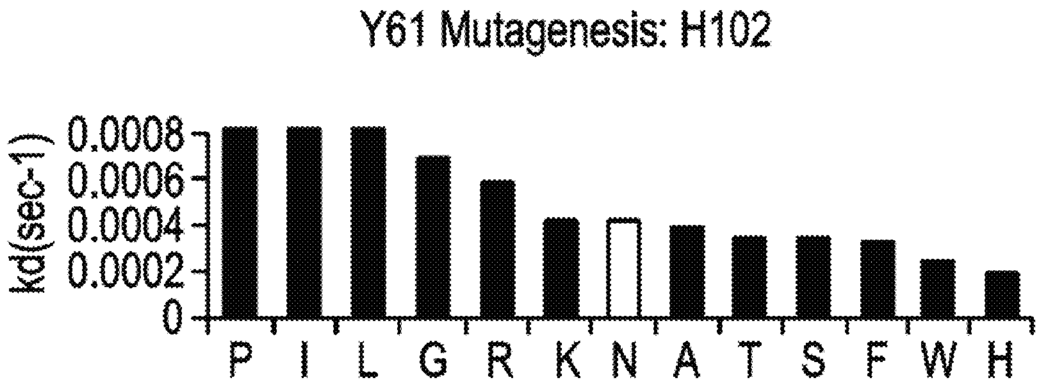
Figures 1, 9F:
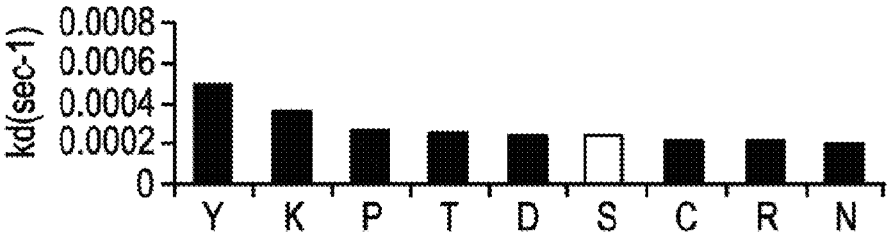
FIGS. 9F-9H show the CDR positions in the light chain of the Y61 antibody that were mutated by site-directed mutagenesis and the respective amino acid substitutions at each position. The graphs at the right of the figures show the off-rates for the substituted antibodies (black bars) as compared to unmutated Y61 (open bar).
Figures 2, 9F:
Figures 3, 9F:
Figures 1, 9G:
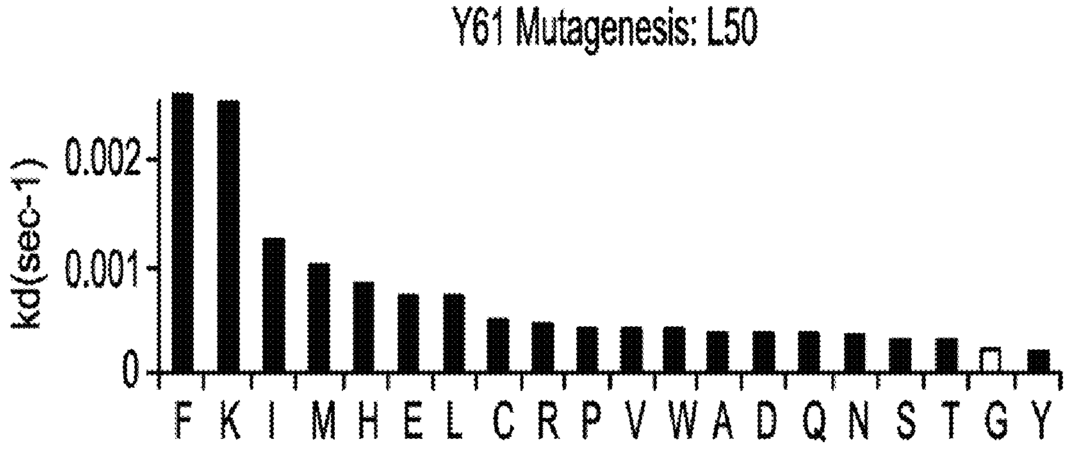
Figures 2, 9G:
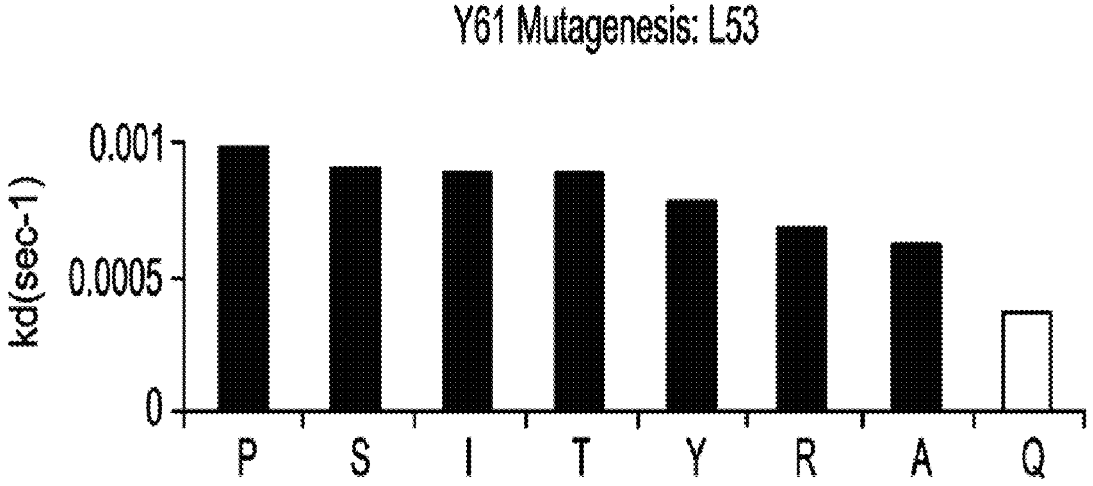
Figures 1, 9H:
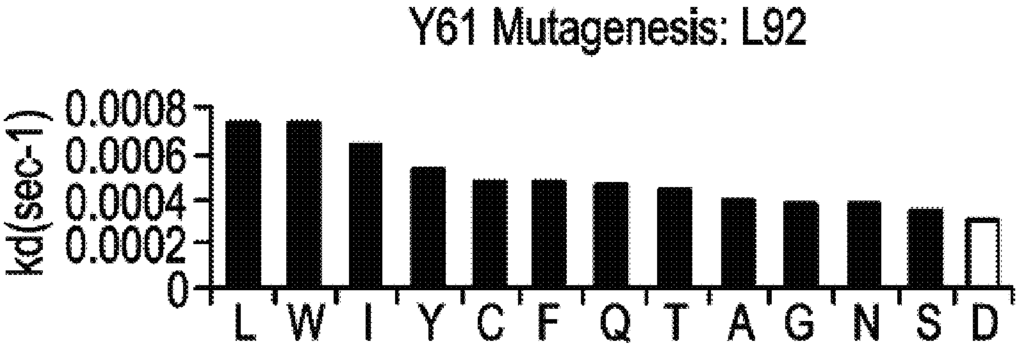
Figures 2, 9H:
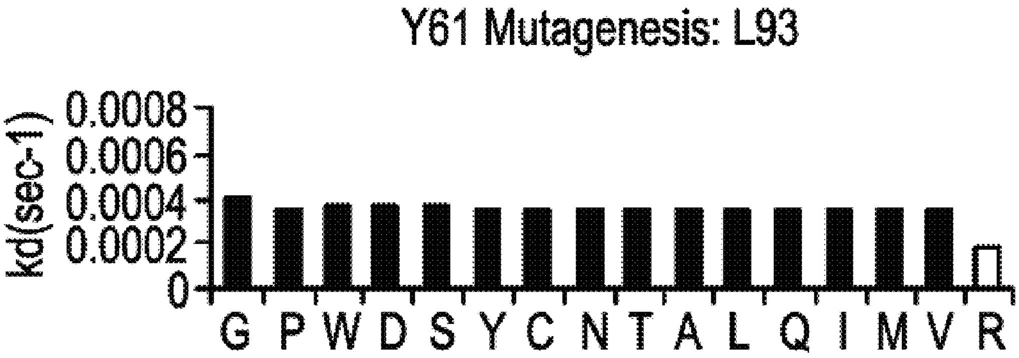
Figures 3, 9H:
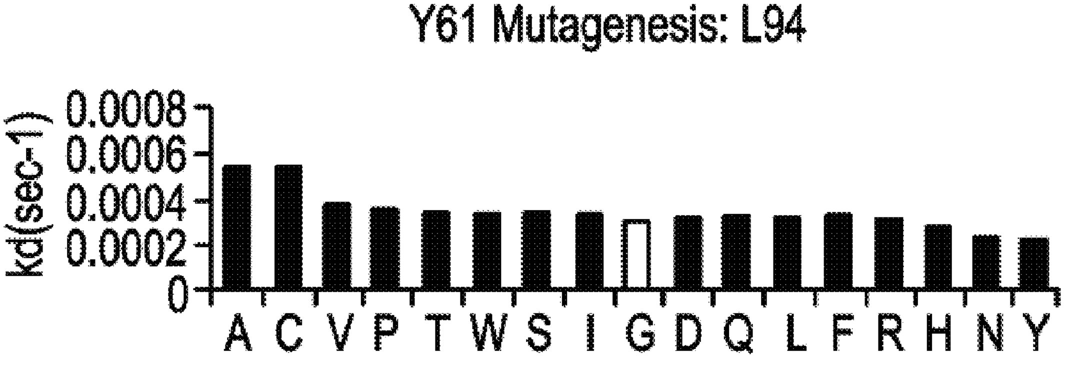

The percentages of patients who achieved a PGA of "clear" or "minimal" (e.g., PGA of 0 or 1) at 12 weeks after re-treatment are depicted in FIG. 7D. The percentages of patients who achieved a PGA of 0 or 1 during re-treatment were as follows for each group: one 200-mg dose, between 35% and 40%; 100 mg eow, between 70% and 80%; 200 mg weekly 4 wks, between 60% and 65%; 200 mg eow, between 60% and 70%; and 200 mg weekly, between 80% and 90%, respectively. Of the total patients who were retreated, between 60 and 65% achieved a PGA of 0 or 1 after re-treatment.

Adverse events (AEs) occurring ≧5% in at least 1 treatment group in descending order through week 48 were: nasopharyngitis, injection-site reaction, upper respiratory tract infection, headache, hypertension, and arthralgia. An overview of treatment-emergent adverse events through Week 48 is displayed in Table 6 of Example 6, above. An overview of treatment-emergent adverse events with an incidence ≧5% in any treatment group is displayed in Table 7 of Example 6, above.

The foregoing data demonstrate that ABT-874 was highly efficacious in the treatment of moderate to severe psoriasis. Upon loss of response and re-treatment, a majority of patients were able to re-achieve a PASI 75 response. Moreover, ABT-874 appears to have a favorable safety profile in the long term.

EQUIVALENTS

Those skilled in the art will recognize, or be able to ascertain using no more than routine experimentation, many equivalents to the specific embodiments of the invention described herein. Such equivalents are intended to be encompassed by the following claims.

Table 1 VH3 Family Germline Amino Acid Sequences

Numbering according to Kabat
(Joe9 VH included for comparison)

| SEQ ID NO: | germline VH | | CDR H1 | | CDR H2 | |
|---|---|---|---|---|---|---|
| 594 | dp-29 | EVQLVESGGGLVQPGGSLRLSCAASGFTFS | DHYMD | WVRQAPGKGLEWVG | RTRNKANSYTTEYAASVKG | RFTISRDDSKNSLYLQMNSLKTEDTAVYYCAR |
| 595 | DP-30 | EVQLVESGGGLVQPGGSLRLSCAASGFTFS | DHYMS | WVRQAQGKGLELVG | LIRNKANSYTTEYAASVKG | RLTISREDSKNTLYLQMSSLKTEDLAVYYCAR |
| 596 | HC15-7 | EVQLVESGGGLVQPGGSLRLSCAASGFTFS | DHYMS | WVRQAQGKGLELVG | LIRNKANSYTTEYAASVKG | RLTISREDSKNTMYLQMSNLKTEDLAVYYCAR |
| 597 | VHD26 | EVQLLESGGGLVQPGGSLRLSCAASGFTFS | DHYMS | WVRQAQGKGLELVG | LIRNKANSYTTEYAASVKG | RLTISREDSKNTLYLQMSSLKTEDLAVYYCAR |
| 598 | DP-31 | EVQLVESGGGLVQPGRSLRLSCAASGFTFD | DYAMH | WVRQAPGKGLEWVS | GISW..NSGSIGYADSVKG | RFTISRDNAKNSLYLQMNSLRAEDTALYYCAK |
| 599 | DP-32 | EVQLVESGGGVVRPGGSLRLSCAASGFTFD | DYGMS | WVRQAPGKGLEWVS | GINW..NGGSTGYADSVKG | RFTISRDNAKNSLYLQMNSLRAEDTALYHCAR |
| 600 | DP-33 | EVQLVESGGVVVQPGGSLRLSCAASGFTFD | DYTMH | WVRQAPGKGLEWVS | LISW..DGGSTYYADSVKG | RFTISRDNSKNSLYLQMNSLRTEDTALYYCAK |
| 601 | dp-35 | QVQLVESGGGLVKPGGSLRLSCAASGFTFS | DYYMS | WIRQAPGKGLEWVS | YI..SSSGSTIYYADSVKG | RFTISRDNAKNSLYLQMNSLRAEDTAVYYCAR |
| 602 | VH3-8 | QVQLLESGGGLVKPGGSLRLSCAASGFTFS | EYYMS | WIRQAPGKGLEWVS | YI..SSSSSYTNYADSVKG | RFTISRDNAKNSLYLQMNSLRAEDTAVYYCAR |
| 603 | ysc-9 | EVQLVESGGGLVQPGGSLKLSCAASGFTFS | GSAMH | WVRQASGKGLEWVG | RIRSKANSYATAYAASVKG | RFTISRDDSKNTAYLQMNSLKTEDTAVYYCTR |
| 604 | dp-38 | EVQLVESGGGLVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 605 | LSG2 | EVQLVESGGGLVKPGGSLRLSCAASGFTFS | NAWMS | WVRQAPGKGLEWVG | RIESKTDGGTTDYAAPVKG | RFTISRDDSKNTLYLQMNSLKTEDTAVYYCTT |
| 606 | LSG3 | EVQLVESGGGLVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 607 | LSG4 | EVQLVESGGGLVKPGGSLRLSCAASGFTFS | NAWMS | WVRQAPGKGLEWVG | RIKSKTDGGTTNYAAPVKG | RFTISRDDSKNTLYLQMNSLKTEDTAVYYCTT |
| 608 | LSG6 | EVQLVESGGGLVKPGGSLRLSCAASGFTFS | NAWMN | WVRQAPGKGLEWVG | RIKSKTDGGTTDYAAPVKG | RFTISRDDSKNTLYLQMNSLKTEDTAVYYCTT |
| 609 | v3-15 | EVQLVESGGALVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 610 | dp-39 | EVQLVESGGGLVQPGGSLRLSCPASGFTFS | NHYMS | WVRQAPGKGLEWVS | YI..SGDSGYTNYADSVKG | RFTISRDNANNSPYLQMNSLRAEDTAVYYCVK |
| 611 | dp-40 | EVQLVESGGGLVQPGGSLRLSCAASGFTFS | NHYTS | WVRQAPGKGLEWVS | YS..SGNSGYTNYADSVKG | RFTISRDNAKNSLYLQMNSLRAEDTAVYYCVK |
| 612 | dp-59 | EVQLVESGGGLVQPGGSLRLSCAASGFTFS | NSDMN | WVHQAPGKGLEWVS | GV..SWNGSRTHYADSVKG | RFIISRDNSRNTLYLQTNSLRAEDTAVYYCVR |
| 613 | v3-16p | EVQLVESGGGLVQPGGSLRLSCAASGFTFS | NSDMN | WARKAPGKGLEWVS | GV..SWNGSRTHYVDSVKR | RFIISRDNSRNSLYLQKNRRRAEDMAVYYCVR |
| 614 | v3-19p | TVQLVESGGGLVEPGGSLRLSCAASGFTFS | NSDMN | WVRQAPGKGLEWVS | GV..SWNGSRTHYADSVKG | RFIISRDNSRNFLYQQMNSLRPEDMAVYYCVR |
| 615 | v3-13 | EVHLVESGGGLVQPGGALRLSCAASGFTFS | NYDMH | WVRQATGKGLEWVS | AN..GTAG.DTYYPGSVKG | RFTISRENAKNSLYLQMNSLRAGDTAVYYCAR |
| 616 | DP-42 | EVQLVETGGGLIQPGGSLRLSCAASGFTVS | SNYMS | WVRQAPGKGLEWVS | VI.Y..SGGSTYYADSVKG | RFTISRDNSKNTLYLQMNSLRAEDTAVYYCAR |
| 617 | dp-44 | EVQLVQSGGGLVHPGGSLRLSCAGSGFTFS | SYAMH | WVRQAPGKGLEWVS | AI...GTGGGTYYADSVKG | RFTISRDNAKNSLYLQMNSLRAEDMAVYYCAR |
| 618 | DP-45 | EVQLVQSGGGLVQPGGSLRLSCAGSGFTFS | SYAMH | WVRQAPGKGLEWVS | AI...GTGGGTYYADSVKG | RFTISRDNAKNSLYLQMNSLRAEDMAVYYCAR |
| 619 | dp-47 | EVQLLESGGGLVQPGGSLRLSCAASGFTFS | SYAMS | WVRQAPGKGLEWVS | AI..SGSGGSTYYADSVKG | RFTISRDNSKNTLYLQMNSLRAEDTAVYYCAK |
| 620 | f1m | EVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 621 | F1 | EVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 622 | v3-64 | EVQLVESGGGLVQPGGSLRLSCAASGFTFS | SYAMH | WVRQAPGKGLEYVS | AI..SSNGGSTYYANSVKG | RFTISRDNSKNTLYLQMGSLRAEDMAVYYCAR |
| 623 | vh26 | EVQLLESGGGLVQPGGSLRLSCAASGFTFS | SYAMS | WVRQAPGKGLEWVS | AI..SGSGGSTYYGDSVKG | RFTISRDNSKNTLYLQMNSLRAEDTAVYYCAK |
| 624 | B25 | QVQLVESGGGVVQPGRSLRLSCAASGFTFS | SYAMH | WVRQAPGKGLEWVA | VI..SYDGSNKYYTDSVKG | RFTISRDNSKNTLYLQMNSLRAEDTAVYYCAR |
| 625 | b32e | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 626 | B37 | QVQLVESGGGVVQPGRSLRLSCAASGFTFS | SYAMH | WVRQAPGKGLEWVA | VI..SYDGSNKYYADSVKG | RFTISRDNSKNTLYLQMSSLRAEDTAVYYCAR |
| 627 | B43 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 628 | B48 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 629 | B52 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 630 | B54 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 631 | cos-8 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 632 | dp-46 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 633 | F2M | QVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 634 | F3 | QVQLVESGGGLVQPGGSLRLSCSASGFTFS | SYAMH | WVRQAPGKGLEYVS | AI..SSNGGSTYYADSVKG | RFTISRDNSKNTLYLQMNSLRAEDTAVYYCAR |
| 635 | F7 | QVQLVESGGGVVQPGRSLRLSCAASGFTFS | SYAMH | WVRQAPGKGLEWVA | VI..SYDGSNKYYADSVKG | RFAISRDNSKNTLYLQMNSLRAEDTAVYYCAR |
| 636 | hv3005 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 637 | F2 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 638 | dp-48 | EVQLVESGGGLVQPGGSLRLSCAASGFTFS | SYDMH | WVRQATGKGLEWVS | AI..GTAG.DTYYPGSVKG | RFTISRENAKNSLYLQMNSLRAGDTAVYYCAR |
| 639 | dp-38 | EVQLVESGGGLVQPGGSLRLSCAASGFTFS | SYEMN | WVRQAPGKGLEWVS | YI..SSSGSTIYYADSVKG | RFTISRDNAKNSLYLQMNSLRAEDTAVYYCAR |

Table 1 VH3 Family Germline Amino Acid Sequences
Numbering according to Kabat
(Joe9 VH included for comparison)

| SEQ ID NO: | germline VH | | CDR H1 | | CDR H2 | |
|---|---|---|---|---|---|---|
| 640 | B1 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRLRARLCITVRE |
| 641 | B13 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 642 | B18 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 643 | B26 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 644 | B28E | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 645 | B29E | QVQLVESGGGVVQPGRSLRLSCAASGFTFS | SYGMH | WVRQAPGKGLEWVA | VI..SYDGSNKYYADSVKG | RFTISRDNSKNRLYLQMNSLRAEDTAVYYCAR |
| 646 | B29M | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 647 | B30 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAR |
| 648 | B32M | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEGTAVYYCAR |
| 649 | cos-3 | QVQLVESGGGVVQPGGSLRLSCAASGFTFS | SYGMH | WVRQAPGKGLEWVA | FI..RYDGSNKYYADSVKG | RFTISRDNSKNTLYLQMNSLRAEDTAVYYCAK |
| 650 | dp-49 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAK |
| 651 | dp-50 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAR |
| 652 | F6 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAK |
| 653 | P9E | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVRK--- |
| 654 | v3-30 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 655 | v3-33 | QVQLVESGGGVVQPGRSLRLSCAASGFTFS | SYGMH | WVRQAPGKGLEWVA | VI..WYDGSNKYYADSAKG | RFTISRDNSTNTLFLQMNSLRAEDTAVYYCAR |
| 656 | dp-51 | EVQLVESGGGLVQPGGSLRLSCAASGFTFS | SYSMN | WVRQAPGKGLEWVS | YI..SSSSSTIYYADSVKG | RFTISRDNAKNSLYLQMNSLRDEDTAVYYCAR |
| 657 | dp-77 | EVQLVESGGGLVKPGGSLRLSCAASGFTFS | SYSMN | WVRQAPGKGLEWVS | SI..SSSSSYIYYADSVKG | RFTISRDNAKNSLYLQMNSLRAEDTAVYYCAR |
| 658 | HHG4 | EVQLVESGGGLVKPGGSLRLSCAASGFTFS | SYSMN | WVRQAPGKGLEWVS | SI...SSSSYIYYADSVKG | RFTISRDNAKNSLYLQMNSLRAEDTAVYYCAR |
| 659 | v3-21 | EVQLVESGGGLVKPGGSLRLSCAASGFTFS | SYSMN | WVRQAPGKGLEWVS | SI..SSSSSYIYYADSVKG | RFTISRDNAKNSLYLQMNSLRAEDTAVYYCAR |
| 660 | v3-48 | EVQLVESGGGLVQPGGSLRLSCAASGFTFS | SYSMN | WVRQAPGKGLEWVS | YI..SSSSSTIYYADSVKG | RFTISRDNAKNSLYLQMNSLRAEDTAVYYCAR |
| 661 | DP-52 | EDQLVESGGGLVQPGGSLRPSCAASGFAFS | SYVLH | WVRRAPGKGPEWVS | AIG...TGGDTYYADSVMG | RFTISRDNAKKSLYLQMNSLIAEDMAVYYCAR |
| 662 | cos-6 | EVQLVESGGGLVQPGGSLRLSCAASGFTFS | SYWMH | WVRQAPGKGLVWVS | RI..NSDGSSTSYADSVKG | RFTISRDNAKNTLYLQMNSLRAEDTAVYYCAR |
| 663 | dp-53 | EVQLVESGGGLVQPGGSLRLSCAASGFTFS | SYWMH | WVRQAPGKGLVWVS | RI..NSDGSSTSYADSVKG | RFTISRDNAKNTLYLQMNSLRAEDTAVYYCAR |
| 664 | dp-54 | EVQLVESGGGLVQPGGSLRLSCAASGFTFS | SYWMS | WVRQAPGKGLEWVA | NI..KQDGSEKYYVDSVKG | RFTISRDNAKNSLYLQMNSLRAEDTAVYYCAR |
| 665 | dp-87 | EVQLVESGGGLVQPGGSLRLSCAASGFTFS | SYWMH | WVRQAPGKGLVWVS | KI..NSDGSSTSYADSMKG | QFTISRDNAKNTLYLQMNSLRAEDMAVYYCTR |
| 666 | VH3-11 | EVQLVESGGGLVQPGGSLRLSCAASGFTFS | SYWMS | WVRQAPGKGLEWVA | NI..KQDGSEKYYVDSVKG | RFTISRDNAKNSLYLQMNSLRAEDTAVYYCAR |
| 667 | JOE9 VH | QVQLVQSGGGVVQPGRSLRLSCAASGFTFS | SYGMH | WVRQAPGKGLEWVA | FI..RYDGSNKYYADSVKG | RFTISRDNSKNTLYLQMKSLRAEDTAVYYCTT |

Appendix A

BBI-329

Table 1 Vλ1 Family Germline Amino Acid Sequences

Numbering according to Kabat.
(Joe9 VL included for comparison)

| SEQ ID NO: | gene* | VL | | CDR L1 | | CDR L2 | | CDR L3 |
|---|---|---|---|---|---|---|---|---|
| | | | [illegible] | [illegible] | [illegible] | [illegible] | [illegible] | [illegible] |
| 668 | 1b | DPL5 | QSVLTQPPSVSAAPGQKVTISC | SGSSSNIGNNY.VS | WYQQLPGTAPKLLIY | DNNKRPS | GIPDRFSGSKSGTSATLGITGLQTGDEADYYC | GTWDSSLSA |
| 669 | 1d | DPL4 | QSVLTQPPSVSAAPGQKVTISC | SGSSSDMGNYA.VS | WYQQLPGTAPKLLIY | ENNKRPS | GIPDRFSGSKSGTSATLGITGLWPEDEADYYC | LAWDTSPRA |
| 670 | 1c | DPL2 | QSVLTQPPSASGTPGQRVTISC | SGSSSNIGSNT.VN | WYQQLPGTAPKLLIY | SNNQRPS | GVPDRFSGSKSGTSASLAISGLQSEDEADYYC | AAWDDSLNG |
| 671 | 1g | DPL3 | QSVLTQPPSASGTPGQRVTISC | SGSSSNIGSNY.VY | WYQQLPGTAPKLLIY | RNNQRPS | GVPDRFSGSKSGTSASLAISGLRSEDEADYYC | AAWDDSLSG |
| 672 | 1a | DPL1 | QSVLTQPPSVSEAPRQRVTISC | SGSSSNIGNN.AVN | WYQQLPGKAPKLLIY | YDDLLPS | GVSDRFSGSKSGTSASLAISGLQSEDEADYYC | AAWDDSLNG |
| 673 | 1f | DPL9 | QSVLTQPPSVSGAPGQRVTISC | TGSSSNIGAGYVVH | WYQQLPGTAPKLLIY | GNSNRPS | GVPDQFSGSKSGTSASLAITGLQSEDEADYYC | KAWDNSLNA |
| 674 | 1e | DPL8 | QSVVTQPPSVSGAPGQRVTISC | TGSSSNIGAGYDVH | WYQQLPGTAPKLLIY | GNSNRPS | GVPDRFSGSKSGTSASLAITGLQAEDEADYYC | QSYDSSLSG |
| 675 | | JOE9 VL | SYVLTQPPSVSGTPGQRVTISC | SGGRSNIGSNT.VK | WYQQLPGTAPKLLIY | GNDQRPS | GVPDRFSGSKSGTSASLAITGVQAEDEADYYC | QSYDSSLRG |

*Williams, JMB, 1996, 264, 220-232

Appendix A BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| Joe9 wt | 77 | SGSYDY | 110 | QSYDSSLRGSRV | 1.00E-01 | 1.50E-06 | 1.00E-06 | |
| Joe9 wt IgG1 | 77 | SGSYDY | 110 | QSYDSSLRGSRV | | | 5.00E-07 | |
| 70-1 | 78 | HGSHDN | 110 | Joe9 wt | 1.34 e-2 | | 2.00E-07 | |
| 70-1 IgG1 | 78 | HGSHDN | 110 | Joe9 wt | | | 2.00E-07 | |
| 70-2 | 79 | HGSYDY | 110 | Joe9 wt | 3.30E-02 | | 3-5.0E-7 | |
| 70-7 | 80 | RRRSNY | 110 | Joe9 wt | 1.29E-01 | | 3-5.0E-7 | |
| 70-13 | 81 | SGSIDY | 110 | Joe9 wt | 7.20E-02 | | 3-5.0E-7 | |
| 78-34 | 77 | wt | 111 | QSYDRGFTGSRV | 1.64 e-2 | 2.00E-07 | 6.00E-07 | |
| 78-25 | 77 | wt | 112 | QSYDSSLRGSRV | 5.00E-02 | | | |
| 78-28 | 77 | wt | 112 | QSYDSSLRGSRV | 4.66E-02 | | | |
| 78-35 | 77 | wt | 113 | QSYDSSLTGSRV | 4.99E-02 | 4.00E-07 | | |
| 79-1 | 77 | wt | 114 | QSYDSSLWGSRV | | 2.00E-07 | 6.00E-07 | |
| 101-14 | 79 | 70-2 | 111 | 78-34 | 7.52E-03 | | | |
| 101-9 | 79 | 70-2 | 113 | 78-35 | 8.54E-03 | | | |
| 101-19 | 81 | 70-13 | 111 | 78-34 | 4.56E-02 | | | |
| 101-8 | 81 | 70-13 | 111 | 78-34 | 1.01E-02 | | | |
| 101-4 | 81 | 70-13 | 113 | 78-35 | 9.76E-03 | | | |
| 101-5 | 81 | 70-13 | 113 | 78-35 | 4.45E-02 | | | |
| 101-11 (12) | 78 | 70-1 | 111 | 78-34 | 4.5 e-3 | | 3.00E-08 | |
| 101-11 IgG1 | 78 | 70-1 | 111 | 78-34 | | 1.60E-09 | | |
| 26-1 (2,3) | 78 | 70-1 | 114 | 79-1 | 7.4 e-3 | | 6.00E-08 | |
| 136-9 | 82 | HGSHDD | 115 | QTYDISESGSRV | 3.20E-03 | | | |
| 136-10 | 82 | HGSHDD | 116 | QSYDRGFTGSRV | 1.40E-03 | 2.00E-09 | | |
| 136-14 | 83 | HGSHDN | 117 | QTYDRGFTGSRV | 1.10E-03 | 3.00E-10 | 1.00E-07 | |
| 136-15 | 83 | HGSHDN | 118 | QTYDKGFTGSSV | 7.4 e-4 | 1.00E-10 | 2.00E-09 | |
| 136-15 germline | 83 | HGSHDN | 118 | QTYDKGFTGSSV | 4.60E-04 | | 6.00E-09 | |
| 136-16 | 83 | HGSHDN | 119 | QSYDRRFTGSRV | 6.10E-04 | 3.00E-10 | 5.00E-09 | |
| 136-17 | 83 | HGSHDN | 120 | QSYDWNFTGSRV | 2.90E-05 | 2.00E-09 | 7.00E-09 | |
| 136-18 | 83 | HGSHDN | 121 | QSYDRGFTGSRV | 1.10E-03 | 8.00E-10 | | |
| 136-21 | 83 | HGSHDN | 122 | QSYDNGFTGSRV | 4.20E-04 | 2.00E-09 | | |
| 136-24 | 83 | HGSHDN | 123 | QSYDNAVTASKV | 8.90E-04 | 1.00E-09 | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| 101-11 | 84 | TT HGSHDN WGQG | 124 | QSYDRGFTGSRV | 4.5x10-3 | 2X10-9 | 2.00E-08 | |
| 136-15M1 | 85 | AK ...... .... | 124 | QSYDRGFTGSRV | | 4.00E-10 | | |
| 149-4 | 86 | .. ...... .S.. | 124 | ............ | 1.37x10-3 | 8x10-11 | 3.00E-09 | |
| 149-5 | 87 | .. .....T .... | 125 | QSYDSSLWGTRV | 1.02x10-3 | 1.2x10-10 | 3.00E-09 | |
| 149-6 | 84 | .. ...... .... | 124 | ............ | 2.73x10-3 | 6x10-10 | 2.00E-09 | |
| 149-7 | 84 | .. ...... .... | 126 | .....D...... | 1.13x10-3 | 9x10-10 | 3.00E-09 | |
| 149-8 | 88 | K. ...... .... | | | 2.33x10-3 | 3x10-9 | | |
| 149-9 | 89 | K. ...... ..H. | 127 | ...E.....M. | 3.54x10-3 | 1.8x10-10 | | |
| 149-11 | 90 | .. ...... .S.. | 128 | ....N...A.. | 1.43x10-2 | 2x10-10 | 4.00E-09 | |
| 149-12 | 84 | .. ...... .... | | | 3.73x10-3 | neutralising | | |
| 149-13 | 84 | .. ...... .... | | | 2.22x10-3 | 5x10-10 | | |
| 149-14 | 91 | .. .R..N. .... | | | | 1.5x10-10 | 6.00E-09 | |
| | | | | | | | | |
| | 92 | TT HGSHDN | 124 | QSYDRGFTGSRV | | | | |
| 156-1 | 93 | .. .....T | 126 | .....D...... | 5.00E-03 | | | |
| 156-2 | 93 | .. .....T | 129 | .....R...... | | | | |
| 156-3 | 93 | .. .....T | 128 | ....N...A.. | 9.00E-03 | | | |
| 156-4 | 93 | .. .....T | 127 | ...E.....SM. | | | | |
| 156-5 | 93 | .. .....T | 130 | .T..K.....S. | | | | |
| 156-6 | 92 | .. ...... | 126 | .....D...... | 3.00E-03 | | | |
| 156-7 | 92 | .. ...... | 129 | .....R...... | | | | |
| 156-8 | 92 | .. ...... | 128 | ....N...A.. | | | | |
| 156-9 | 92 | .. ...... | 127 | ...E.....SM. | | | | |
| 156-10 | 92 | .. ...... | 130 | .T..K.....S. | | | | |
| 156-11 | 94 | .K ...... | 126 | .....D...... | | | | |
| 156-12 | 94 | .K ...... | 129 | .....R...... | | | | |
| 156-13 | 94 | .K ...... | 128 | ....N...A.. | | | | |
| 156-14 | 94 | .K ...... | 127 | ...E.....SM. | | | | |
| 156-15 | 94 | .K ...... | 130 | .T..K.....S. | | | | |
| 156-16 | 93 | .. .....T | 124 | ............ | | | | |
| 156-17 | 92 | .. ...... | 125 | ....SSLW.T.. | 6.00E-03 | | | |
| 156-18 | 93 | .. .....T | 125 | ....SSLW.T.. | | | | |
| | | | | | | | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | 92 | TT HGSHDN | 124 | QSYDRGFTGSRV | | | | |
| 103-1 | 95 | .. Q.R... | 124 | ............ | 2.9x10-3 | | | |
| 103-2 | 96 | K. R.R... | 130 | .T..K.....S. | 7.3x10-4 | 7.00E-11 | 1.00E-09 | |
| 103-3 | 97 | .. .....K | 124 | ............ | 2.5x10-3 | | | |
| 103-6 | | | 131 | .....D...T.. | 4.5x10-4 | | | |
| 103-7 | 98 | .. .....D | 131 | .....D...T.. | 3.7x10-4 | 1.40E-10 | 1.00E-09 | |
| 103-8 | 99 | K. ...... | 130 | .T..K.....S. | 3.3x10-4 | 6.00E-11 | 1.50E-09 | |
| 103-14 & 9 | 100 | KT HGSHDN | 132 | QSYDRGFTGSMV | 6.7 e-4 | 4.00E-11 | 1.20E-09 | |
| 103-8 & 2 | 100 | KT HGSHDN | 133 | QTYDKGFTGSSV | 5.3 e-4 | | 1.50E-09 | |
| 103-4 | 101 | TT HGSHDN | 134 | QSYDRGFTGARV | 1.6 e-4 | 8.60E-11 | 9.00E-10 | |
| 103-152 | 101 | TT HGSHDN | 135 | QSYERGFTGARV | | 8.60E-11 | | |
| | | | | | | | | |
| | 102 | TT SGSYDY | 136 | QSYDRGFTGSRVF | | | | |
| 170-1 | 102 | .. ...... | 137 | .........FK.. | 2.35E-03 | | | |
| 170-2 | 102 | .. ...... | 138 | .......VSAY.. | 8.80E-04 | | | |
| 170-3 | 102 | .. ...... | 139 | ......L.VTK.. | 1.11E-03 | | | |
| 170-4 | 102 | .. ...... | 140 | ......Y.A.... | 8.11E-04 | | | |
| 170-7 | 102 | .. ...... | 141 | ..........K.. | 5.30E-04 | | | |
| 170-11 | 102 | .. ...... | 142 | ......L..F... | 4.40E-04 | | | |
| 170-13 | 102 | .. ...... | 143 | .........YK.. | 1.59E-03 | | | |
| 170-15 | 102 | .. ...... | 144 | ......L..Y.L. | 4.43E-03 | | | |
| 170-19 | 103 | .. H..H.N | 145 | ........DYK.. | 1.00E-03 | | | |
| 170-21 | 104 | .. H..Q.N | 146 | .........P.L. | 3.89E-03 | | | |
| 170-22 | 102 | .. ...... | 147 | ......L...... | 5.60E-04 | | | |
| 170-23 | 103 | .. H..H.N | 148 | ..........A..W | 1.00E-03 | 2.00E-10 | | |
| 170-24 | 104 | .. H..Q.N | 149 | ..........Y... | 2.80E-04 | 5.00E-10 | | |
| 170-35 | 105 | A. H..Q.N | 136 | ............. | 1.00E-05 | | | |
| 170-38 | | | 150 | ..........P... | 2.10E-04 | | | |
| 170-39 | | | 151 | .......M.S.... | 2.79E-03 | | | |
| 170-36 | 83 | HGSHDN | 152 | QSYDRDSTGSRVF | 4.00E-04 | 2.00E-10 | | |
| 170-25 | 106 | HGSQDT | 153 | QSYDSSLRGSRVF | 5.00E-04 | 5.00E-11 | | |
| | | | | | | | | |

Appendix A BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | 106 | SGSYDY | 136 | QSYDRGFTGSRVF | | | | |
| 73-B1 | 107 | SGSYDY | 154 | H...SD....... | 3.25E-03 | >1E-8 | | |
| 73-B2 | 107 | SGSYDY | 155 | H.SES........ | 2.07E-03 | | | |
| 73-B6 | 107 | SGSYDY | 156 | H...NR....... | 2.51E-03 | >1E-8 | | |
| 73-C1 | 107 | SGSYDY | 157 | H...SR....... | 2.71E-03 | >1E-8 | | |
| 73-C2 | 107 | SGSYDY | 158 | ....SE....... | 3.79E-03 | | | |
| 73-C6 | 107 | SGSYDY | 159 | ....T........ | 3.96E-03 | | | |
| 73-D1 | 107 | SGSYDY | 160 | H...S........ | 3.99E-03 | | | |
| 73-D2 | 107 | SGSYDY | 161 | ....T........ | 3.56E-03 | | | |
| 73-D4 | 107 | SGSYDY | 162 | H...TK....... | 5.36E-03 | | | |
| 73-D5 | 107 | SGSYDY | 163 | H.S.S........ | 3.57E-03 | | | |
| 73-E3 | 107 | SGSYDY | 164 | ....SD....... | 4.98E-03 | | | |
| 73-E6 | 107 | SGSYDY | 165 | H..ES........ | 4.17E-03 | | | |
| 73-F3 | 107 | SGSYDY | 166 | ....APWS..... | 7.08E-03 | | | |
| 73-F5 | 107 | SGSYDY | 167 | ...DSD....K.. | 3.74E-03 | | | |
| 73-G2 | 107 | SGSYDY | 168 | HTN.S........ | 3.98E-03 | | | |
| 73-G3 | 107 | SGSYDY | 169 | H...TR....... | 3.50E-03 | | | |
| 73-G4 | 107 | SGSYDY | 170 | ....MR....... | 6.58E-03 | | | |
| 73-G5 | 107 | SGSYDY | 171 | H.S.SDS...... | 6.01E-03 | | | |
| 73-G6 | 107 | SGSYDY | 172 | ...NTD....... | 6.30E-03 | | | |
| 73-H2 | 107 | SGSYDY | 173 | ....S........ | 5.93E-03 | | | |
| 73-F6 | 107 | SGSYDY | 174 | H...M........ | 5.87E-03 | | | |
| 73-H3 | 107 | SGSYDY | 175 | H...N........ | 6.85E-03 | | | |
| 73-C5 | 107 | SGSYDY | 176 | H.H..D....... | 4.84E-03 | | | |
| 73-B7 | 108 | HGSQDN | 177 | QSYDSSLRGSRV | 2.50E-03 | 7.00E-09 | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 136 | QSYDRGFTGSRVF | | | | |
| M2 A2 | 83 | HGSHDN | 178 | ......IH..... | 4.00E-02 | | | |
| M2 A4 | 83 | HGSHDN | 179 | ....S..P..... | 8.49E-03 | | | |
| M2 A5 | 83 | HGSHDN | 180 | ....I.S...... | 4.01E-02 | | | |
| M2 B1 | 83 | HGSHDN | 181 | ....S.L...... | 7.97E-03 | | | |
| M2 B3 | 83 | HGSHDN | 182 | ....I.M...... | 4.60E-02 | | | |
| M2 B4 | 83 | HGSHDN | 183 | ....I.L...... | 4.42E-02 | | | |
| M2 B5 | 83 | HGSHDN | 184 | ....S.V...... | 8.38E-03 | | | |
| M2 B6 | 83 | HGSHDN | 185 | ......L.A.... | 2.81E-02 | | | |
| M2 C2 | 83 | HGSHDN | 181 | ....S.L...... | 4.85E-02 | | | |
| M2 C3 | 83 | HGSHDN | 186 | ....T.L...... | 4.62E-02 | | | |
| M2 C4 | 83 | HGSHDN | 181 | ....S.L...... | 8.16E-03 | | | |
| M2 C5 | 83 | HGSHDN | 187 | ....TAL...... | 4.71E-02 | | | |
| M2 D1 | 83 | HGSHDN | 188 | ....IR....... | 3.71E-02 | | | |
| M2 D2 | 83 | HGSHDN | 189 | ....IRS...... | 3.85E-02 | | | |
| M2 D3 | 83 | HGSHDN | 190 | ....NPL...... | 3.33E-02 | | | |
| M2 D4 | 83 | HGSHDN | 191 | ...ETS....... | 5.81E-02 | | | |
| M2 D5 | 83 | HGSHDN | 192 | ....SSS...... | 5.18E-02 | | | |
| M2 D6 | 83 | HGSHDN | 193 | ....S...A.... | 5.01E-02 | | | |
| M2 E1 | 83 | HGSHDN | 194 | .T..K.....S.. | 5.32E-02 | | | |
| M2 E2 | 83 | HGSHDN | 195 | ....N........ | 4.77E-02 | | | |
| M2 E6 | 83 | HGSHDN | 196 | ....T..K..... | 9.77E-03 | | | |
| M2 F1 | 83 | HGSHDN | 197 | ....SDV...... | 6.16E-02 | | | |
| M2 H5 | 83 | HGSHDN | 198 | ....A........ | 9.90E-03 | | | |
| | | | | | | | | |

Appendix A BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 124 | QSYDRGFTGSRV | | | | |
| A5 | 83 | HGSHDN | 199 | ......THPSML | 1.12E-03 | | | |
| A12 | 83 | HGSHDN | 200 | ......TTPRPM | 1.43E-03 | | | |
| A4 | 83 | HGSHDN | 201 | ......RNPALT | 1.47E-03 | | | |
| A6 | 83 | HGSHDN | 202 | ......THPWLE | 1.87E-03 | | | |
| A10 | 83 | HGSHDN | 203 | ......NSPATV | 1.87E-03 | | | |
| A11 | 83 | HGSHDN | 204 | ......TFPSPQ | 2.07E-03 | | | |
| C2 | 83 | HGSHDN | 205 | ......LNFSAT | 2.23E-03 | | | |
| A8 | 83 | HGSHDN | 206 | ......KSNKML | 2.37E-03 | | | |
| B8 | 83 | HGSHDN | 207 | ......HTAHLY | 2.40E-03 | | | |
| C6 | 83 | HGSHDN | 208 | ......QTPSIT | 2.42E-03 | | | |
| A3 | 83 | HGSHDN | 209 | ......YPRNIL | 2.51E-03 | | | |
| B11 | 83 | HGSHDN | 210 | ......ITPGLA | 2.95E-03 | | | |
| B5 | 83 | HGSHDN | 211 | ......QPHAVL | 3.04E-03 | | | |
| C10 | 83 | HGSHDN | 212 | ......NSPIPT | 3.10E-03 | | | |
| C4 | 83 | HGSHDN | 213 | ......TPNNSF | 3.23E-03 | | | |
| C3 | 83 | HGSHDN | 214 | ....S.VDPGPY | 3.34E-03 | | | |
| B2 | 83 | HGSHDN | 215 | ......RPRHAL | 3.61E-03 | | | |
| A2 | 83 | HGSHDN | 216 | ......PYHPIR | 3.80E-03 | | | |
| C5 | 83 | HGSHDN | 217 | ......PHTQPT | 3.91E-03 | | | |
| A7 | 83 | HGSHDN | 218 | ......HNNFSP | 3.95E-03 | | | |
| C9 | 83 | HGSHDN | 219 | ......PTHLPH | 3.97E-03 | | | |
| B3 | 83 | HGSHDN | 220 | ......TPSYPT | 4.12E-03 | | | |
| C8 | 83 | HGSHDN | 221 | ....S.TSNLLP | 5.36E-03 | | | |
| B7 | 83 | HGSHDN | 222 | ......DSNHDL | 5.45E-03 | | | |
| A1 | 83 | HGSHDN | 223 | ......LPRLTH | 5.66E-03 | | | |
| C7 | 83 | HGSHDN | 224 | ......IPTSYL | 5.83E-03 | | | |
| C12 | 83 | HGSHDN | 225 | ......LRVQAP | 5.85E-03 | | | |
| B10 | 83 | HGSHDN | 226 | ......LSDSPL | 6.04E-03 | | | |
| B6 | 83 | HGSHDN | 227 | ....S.SLRRIL | 7.58E-03 | | | |
| A9 | 83 | HGSHDN | 228 | ......PARTSP | 7.98E-03 | | | |
| B9 | 83 | HGSHDN | 229 | ......RAAHPQ | 8.66E-03 | | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 124 | QSYDRGFTGSRV | | | | |
| 177-D7 | 83 | HGSHDN | 230 | ......TQPABI | 4.07E-04 | | | |
| 177-G6 | 83 | HGSHDN | 231 | ......THPTMI | 5.50E-04 | | | |
| 177-D9 | 83 | HGSHDN | 232 | ......RIPABT | 6.32E-04 | | | |
| 177-C6 | 83 | HGSHDN | 233 | ......THPVPA | 7.94E-04 | | | |
| 177-H5 | 83 | HGSHDN | 234 | ......SBPIPA | 1.32E-03 | | | |
| 177-H9 | 83 | HGSHDN | 235 | ......THPVPA | 1.58E-03 | | | |
| 177-H10 | 83 | HGSHDN | 236 | ......THPTMY | 3.44E-03 | | | |
| 144-F1 | 83 | HGSHDN | 237 | ......HHYTTF | 5.80E-04 | | | |
| 43-E3 | 83 | HGSHDN | 238 | ......SHPAAE | 8.00E-04 | | | |
| 43-E9 | 83 | HGSHDN | 239 | ......TIPSIE | 8.00E-04 | | | |
| 43-G2 | 83 | HGSHDN | 240 | ......SSPAIM | 7.00E-04 | | | |
| 43-G3 | 83 | HGSHDN | 241 | ......IWPNLN | 9.00E-04 | | | |
| 31-A6 | 83 | HGSHDN | 242 | ......THPNLN | 5.00E-04 | | | |
| 31-B5 | 83 | HGSHDN | 243 | ......THPSIS | 5.00E-04 | | | |
| | | | | | | | | |
| | | | 124 | QSYDRGFTGSRV | | | | |
| Y17 | 83 | HGSHDN | 244 | QSYDRGSAPMIN | 8.90E-05 | 4.50E-10 | >1E-8 | |
| Y19 | 83 | HGSHDN | 245 | QSYDRGHHPAMS | 2.26E-04 | 3.00E-11 | >1E-8 | |
| Y38 | 83 | HGSHDN | 246 | ......THPSIT | 5.08E-04 | 5.50E-11 | 2.60E-09 | |
| Y45 | 83 | HGSHDN | 247 | ......TDPAIV | 6.17E-04 | 4.00E-11 | 4.30E-09 | |
| Y61 | 83 | HGSHDN | 248 | ......THPALL | 2.75 e-4 | 4E-11 | 1.40E-10 | |
| Y61 IgG | 83 | HGSHDN | 248 | ......THPALL | 1.50E-04 | 1.60E-11 | 1.30E-10 | |
| Y61 IgG germline | 83 | HGSHDN | 248 | ......THPALL | 1.50E-04 | 1.60E-11 | 1.30E-10 | 1.60E-10 |
| Y139 | 83 | HGSHDN | 249 | ......SHPALT | 5.92E-04 | 3E-11 | 4.50E-10 | |
| Y139 IgG1 | 83 | HGSHDN | 249 | ......SHPALT | | | 1.00E-09 | |
| Y174 | 83 | HGSHDN | 250 | ......TTPAPE | 7.55E-04 | 6E-11 | 2.00E-09 | |
| Y177 | 83 | HGSHDN | 251 | ......SHPTLI | 6.61E-04 | 5E-11 | 1.00E-09 | |
| A5 | 83 | HGSHDN | 252 | ......THPSML | 4.50E-04 | 6.60E-11 | | |
| A12 | 83 | HGSHDN | 253 | ......TTPRPM | 5.57E-04 | 2.50E-10 | | |
| D9 | 83 | HGSHDN | 254 | ......RLPAQT | 8.21E-04 | 3.5E-09 | >> | |
| G6 | 83 | HGSHDN | 255 | ......THPLTI | 5.08E-04 | 1E-10 | 1.00E-09 | |
| G6 IgG1 | 83 | HGSHDN | 255 | ......THPLTI | | | 1.00E-09 | |
| C6 | 83 | HGSHDN | 256 | QSYDRGQTPSIT | 1.07E-03 | 3.5E-10 | 1.00E-08 | |
| Y55 | 83 | HGSHDN | 257 | QSYDRGTHFQMY | 1.08E-03 | 1.40E-10 | >1E-8 | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| A4 | 83 | HGSHDN | 258 | QSYDRGRNPALT | 6.30E-04 | 2.50E-10 | | |
| | | | | | | | | |
| AO3 | 83 | HGSHDN | 259 | QSYDRGTHPLTM | 3.04E-04 | 3.00E-11 | 4.00E-10 | |
| AO3 IgG1 | 83 | HGSHDN | 260 | QSYDRGTHPLTM | 3.04 e-4 | 2.90E-11 | 3.80E-10 | |
| A03 IgG germline | 83 | HGSHDN | 260 | QSYDRGTHPLTM | 2.50E-04 | 3.50E-11 | 1.75E-10 | |
| | | | | | | | | |
| 99-B11 | 83 | HGSHDN | 261 | QSYDSGYTGSRV | 5.40E-03 | | | |
| 99-C11 | 83 | HGSHDN | 262 | QSYDSGFTGSRV | 5.70E-03 | | | |
| 99-H4 | 83 | HGSHDN | 263 | QSYDSRFTGSRV | 4.80E-03 | | | |
| 99-E9 | 83 | HGSHDN | 262 | QSYDSGFTGSRV | 5.40E-03 | | | |
| 99-H7 | 83 | HGSHDN | 264 | QSYPDGTPASRV | 3.30E-03, | | | |
| 99-H11 | 83 | HGSHDN | 265 | QSYSTHMPISRV | 4.90E-03 | | | |
| 99-F6 | 83 | HGSHDN | 266 | QSYDSGSTGSRV | 4.90E-03 | | | |
| 99-F7 | 83 | HGSHDN | 267 | QSYPNSYPISRV | 4.80E-03 | | | |
| 99-F8 | 83 | HGSHDN | 268 | QSYIRAPQQV | 3.70E-03 | | | |
| 99-F11 | 83 | HGSHDN | 262 | QSYDSGFTGSRV | 5.40E-03 | | | |
| 99-G7 | 83 | HGSHDN | 269 | QSYLKSRAFSRV | 4.80E-03 | | | |
| 99-G11 | 83 | HGSHDN | 270 | QSYDSRFTGSRV | 4.30E-03 | | | |
| | | | | | | | | |
| | | | 124 | QSYDRGFTGSRV | | | | |
| L3.3R3M-B1 | 83 | HGSHDN | 271 | ......FTGSMV | 5.46E+00 | | | |
| L3.3R3M-B3 | 83 | HGSHDN | 272 | ......FTGSMV | 5.51E+00 | | | |
| L3.3R3M-C6 | 83 | HGSHDN | 273 | ......FTGFDG | 6.17E+00 | | | |
| L3.3R3M-F9 | 83 | HGSHDN | 274 | ......TAPALS | 4.99E+00 | | | |
| L3.3R3M-G8 | 83 | HGSHDN | 275 | ......SYPALR | 5.55E+00 | | | |
| L3.3R3M-H6 | 83 | HGSHDN | 276 | ......NWPNSN | 5.69E+00 | | | |
| L3.3R3M-H10 | 83 | HGSHDN | 277 | ......TAPSLL | 5.35E+00 | | | |
| L3.3R3M-A3 | 83 | HGSHDN | 278 | ......FTGSMV | 5.37E+00 | | | |
| L3.3R3M-F8 | 83 | HGSHDN | 279 | ......TTPRIR | 4.99E+00 | | | |
| L3.3R3M-G1 | 83 | HGSHDN | 280 | ......FTGSMV | 4.21E+00 | | | |
| L3.3R3M-G7 | 83 | HGSHDN | 281 | ......FTGSMV | 4.24E+00 | | | |
| L3.3R3M-H11 | 83 | HGSHDN | 282 | ......MIPALT | 3.95E+00 | | | |
| | | | | | | | | |

Appendix A BBI-329

| Table 2 | | | | | | | | |
|---|---|---|---|---|---|---|---|---|
| Clone | H3 SEQ ID NO: | H3 | L3 SEQ ID NO: | L3 | koff | RB assay IC50 (M) | PHA assay IC50 (M) | IFN gamma IC50 (M) |
| Y61-L94N | 109 | CKT HGSHDN | 283 | QSYDRNTHPALL | | | 8.00E-11 | |
| Y61-L94F | 109 | CKT HGSHDN | 284 | QSYDRFTHPALL | | | 6.00E-11 | |
| Y61-L94Y | 109 | CKT HGSHDN | 285 | QSYDRYTHPALL | | 2.00E-11 | 2.00E-11 | |
| Y61-L94Y IgG | 109 | CKT HGSHDN | 285 | QSYDRYTHPALL | 1.27E-04 | 6.00E-11 | 5.00E-11 | 4.00E-11 |
| Y61-L50Y | 109 | CKT HGSHDN | 286 | QSYDRGTHPALL | | 2.00E-11 | | 2.00E-11 |
| Y61-L50Y* IgG | 109 | CKT HGSHDN | 286 | QSYDRGTHPALL | 6.98E-05 | | 2.00E-11 | 3.00E-11 |
| Y61-L50Y-H31E** IgG | 109 | CKT HGSHDN | 286 | QSYDRGTHPALL | 2.99E-05 | | 6.00E-11 | 2.00E-11 |
| Y61-L50Y-H31E-L94Y** IgG | 109 | CKT HGSHDN | 287 | QSYDRYTHPALL | 4.64E-05 | | 1.00E-11 | 1.00E-11 |
| J695 (Y61-L94Y-L50Y IgG*) | 109 | CKT HGSHDN | 287 | QSYDRYTHPALL | 5.14E-05 | 5.00E-11 | 1.00E-11 | 5.00E-12 |

*CDR L2: L50G to Y

**CDR L2: L50G to Y; CDR H1: H31S to E

Appendix A BBI-329

Table 3

| | CDR H1 | | | | | | | | | CDR H2 | | | | | | | | | | | | | | | | | CDR H3 | | | | | |
|---|---|---|---|---|---|---|---|---|---|---|---|---|---|---|---|---|---|---|---|---|---|---|---|---|---|---|---|---|---|---|---|---|
| Kabat Number | 27 | 28 | 29 | 30 | 31 | 32 | 33 | 34 | 35 | 50 | 51 | 52 | 52A | 53 | 54 | 55 | 56 | 57 | 58 | 59 | 60 | 61 | 62 | 63 | 64 | 65 | 95 | 96 | 97 | 98 | 101 | 102 |
| Y61 VH | F | T | F | S | S | Y | G | M | H | F | I | R | Y | D | G | S | N | K | Y | Y | A | D | S | V | K | G | H | G | S | H | D | N |
| Contact Positions | | | | x̲ | x̲ | x̲ | x̲ | | x | x̲ | | x̲ | x̲ | x̲ | x̲ | | x̲ | | x̲ | | | | | | | | x̲ | x̲ | x̲ | x̲ | x̲ | |
| Hypermutation Positions | | | | x̲ | x̲ | x̲ | | | | | | x̲ | | | | | x̲ | | x̲ | | | | | | | | | | | | | |

| | CDR L1 | | | | | | | | | | | | | CDR L2 | | | | | | | CDR L3 | | | | | | | | | | | |
|---|---|---|---|---|---|---|---|---|---|---|---|---|---|---|---|---|---|---|---|---|---|---|---|---|---|---|---|---|---|---|---|---|
| Kabat number | 24 | 25 | 26 | 27 | 27A | 27B | 28 | 29 | 30 | 31 | 32 | 33 | 34 | 50 | 51 | 52 | 53 | 54 | 55 | 56 | 89 | 90 | 91 | 92 | 93 | 94 | 95 | 95A | 95B | 95C | 96 | 97 |
| Y61 VL | S | G | G | R | S | N | I | G | S | N | T | V | K | G | N | D | Q | R | P | S | Q | S | Y | D | R | G | T | H | P | A | L | L |
| Contact Positions | | | | | | | | | x̲ | x̲ | x̲ | | x | x̲ | | x | x̲ | | x | | | | x | x̲ | x̲ | x̲ | | | | | x | |
| Hypermutation Positions | | | | | | | | | x̲ | x̲ | x̲ | | | | | | x̲ | | | | | | | | x̲ | | | | | | | |

x contact and/or hypermutation position
x̲ contact and/or hypermutation position mutated in Y61

Appendix A BBI-329

Table 4. Neutralization Activity in the Presence of Excess Free IL-12 p40

| SEQ ID NO: | Clone | PHA assay IC50 (M) p70:p40 1:0 | PHA assay IC50 (M) p70:p40 1:20 | PHA assay IC50 (M) p70:p40 1:50 |
|---|---|---|---|---|
| VH: 47<br>VL: 48 | 136-15 | 2.00E-09 | 5.00E-09 | 4.00E-09 |
| VH: 51<br>VL: 52 | 149-5 | 6.50E-09 | 7.00E-09 | 4.00E-09 |
| VH: 53<br>VL: 54 | 149-6 | 9.00E-10 | 1.00E-09 | 1.00E-09 |
| VH: 84<br>VL: 126 | 149-7 | 3.50E-09 | 2.50E-09 | 4.00E-09 |
| VH: 23<br>VL: 24 | Y61 IgG | 1.80E-10 | | 1.80E-10 |
| VH: 65<br>VL: 66 | AO3 IgG1 | 2.50E-10 | | 2.20E-10 |
| VH: 31<br>VL: 32 | J695 | 1.00E-11 | | 3.50E-11 |

Appendix A

BBI-329

Table 1 VH3 Family Germline Amino Acid Sequences
Numbering according to Kabat
(Joe9 VH included for comparison)

| SEQ ID NO: | germline VH | | CDR H1 | | CDR H2 | |
|---|---|---|---|---|---|---|
| 594 | dp-29 | EVQLVESGGGLVQPGGSLRLSCAASGFTFS | DHYMD | WVRQAPGKGLEWVG | RTRNKANSYTTEYAASVKG | RFTISRDDSKNSLYLQMNSLKTEDTAVYYCAR |
| 595 | DP-30 | EVQLVESGGGLVQPGGSLRLSCAASGFTFS | DHYMS | WVRQAQGKGLELVG | LIRNKANSYTTEYAASVKG | RLTISREDSKNTLYLQMSSLKTEDLAVYYCAR |
| 596 | HC15-7 | EVQLVESGGGLVQPGGSLRLSCAASGFTFS | DHYMS | WVRQAQGKGLELVG | LIRNKANSYTTEYAASVKG | RLTISREDSKNTMYLQMSNLKTEDLAVYYCAR |
| 597 | VHD26 | EVQLLESGGGLVQPGGSLRLSCAASGFTFS | DHYMS | WVRQAQGKGLELVG | LIRNKANSYTTEYAASVKG | RLTISREDSKNTLYLQMSSLKTEDLAVYYCAR |
| 598 | DP-31 | EVQLVESGGGLVQPGRSLRLSCAASGFTFD | DYAMH | WVRQAPGKGLEWVS | GISW..NSGSIGYADSVKG | RFTISRDNAKNSLYLQMNSLRAEDTALYYCAK |
| 599 | DP-32 | EVQLVESGGGVVRPGGSLRLSCAASGFTFD | DYGMS | WVRQAPGKGLEWVS | GINW..NGGSTGYADSVKG | RFTISRDNAKNSLYLQMNSLRAEDTALYHCAR |
| 600 | DP-33 | EVQLVESGGVVVQPGGSLRLSCAASGFTFD | DYTMH | WVRQAPGKGLEWVS | LISW..DGGSTYYADSVKG | RFTISRDNSKNSLYLQMNSLRTEDTALYYCAK |
| 601 | dp-35 | QVQLVESGGGLVKPGGSLRLSCAASGFTFS | DYYMS | WIRQAPGKGLEWVS | YI..SSSGSTIYYADSVKG | RFTISRDNAKNSLYLQMNSLRAEDTAVYYCAR |
| 602 | VH3-8 | QVQLLESGGGLVKPGGSLRLSCAASGFTFS | DYYMS | WIRQAPGKGLEWVS | YI..SSSSSYTNYADSVKG | RFTISRDNAKNSLYLQMNSLRAEDTAVYYCAR |
| 603 | yac-9 | EVQLVESGGGLVQPGGSLKLSCAASGFTFS | GSAMH | WVRQASGKGLEWVG | RIRSKANSYATAYAASVKG | RFTISRDDSKNTAYLQMNSLKTEDTAVYYCTR |
| 604 | dp-38 | EVQLVESGGGLVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 605 | LSG2 | EVQLVESGGGLVKPGGSLRLSCAASGFTFS | NAWMS | WVRQAPGKGLEWVG | RIESKTDGGTTDYAAPVKG | RFTISRDDSKNTLYLQMNSLKTEDTAVYYCTT |
| 606 | LSG3 | EVQLVESGGGLVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 607 | LSG4 | EVQLVESGGGLVKPGGSLRLSCAASGFTFS | NAWMS | WVRQAPGKGLEWVG | RIKSKTDGGTTNYAAPVKG | RFTISRDDSKNTLYLQMNSLKTEDTAVYYCTT |
| 608 | LSG6 | EVQLVESGGGLVKPGGSLRLSCAASGFTFS | NAWMN | WVRQAPGKGLEWVG | RIKSKTDGGTTDYAAPVKG | RFTISRDDSKNTLYLQMNSLKTEDTAVYYCTT |
| 609 | v3-15 | EVQLVESGGALVKPGGSLRLSCAASGFTFS | NAWMS | WVRQAPGKGLEWVG | RIKSKTDGGTTDYAAPVKG | RFTISRDDSKNTLYLQMNSLKTEDTAVYYCTT |
| 610 | dp-39 | EVQLVESGGGLVQPGGSLRLSCPASGFTFS | NHYMS | WVRQAPGKGLEWVS | YI..SGDSGYTNYADSVKG | RFTISRDNANNSPYLQMNSLRAEDTAVYYCVK |
| 611 | dp-40 | EVQLVESGGGLVQPGGSLRLSCAASGFTFS | NHYTS | WVRQAPGKGLEWVS | YS..SGNSGYTNYADSVKG | RFTISRDNAKNSLYLQMNSLRAEDTAVYYCVK |
| 612 | dp-59 | EVQLVESGGGLVQPGGSLRLSCAASGFTFS | NSDMN | WVHQAPGKGLEWVS | GV..SWNGSRTHYADSVKG | RFIISRDNSRNTLYLQTNSLRAEDTAVYYCVR |
| 613 | v3-16p | EVQLVESGGGLVQPGGSLRLSCAASGFTFS | NSDMN | WARKAPGKGLEWVS | GV..SWNGSRTHYVDSVKR | RFIISRDNSRNSLYLQKNRRRAEDMAVYYCVR |
| 614 | v3-19p | TVQLVESGGGLVEPGGSLRLSCAASGFTFS | NSDMN | WVRQAPGKGLEWVS | GV..SWNGSRTHYADSVKG | RFIISRDNSRNFLYQQMNSLRPEDMAVYYCVR |
| 615 | v3-13 | EVHLVESGGGLVQPGGALRLSCAASGFTFS | NYDMH | WVRQATGKGLEWVS | AN..GTAG.DTYYPGSVKG | RFTISRENAKNSLYLQMNSLRAGDTAVYYCAR |
| 616 | DP-42 | EVQLVETGGGLIQPGGSLRLSCAASGFTVS | SNYMS | WVRQAPGKGLEWVS | VI.Y..SGGSTYYADSVKG | RFTISRDNSKNTLYLQMNSLRAEDTAVYYCAR |
| 617 | dp-44 | EVQLVQSGGGLVHPGGSLRLSCAGSGFTFS | SYAMH | WVRQAPGKGLEWVS | AI...GTGGGTYYADSVKG | RFTISRDNAKNSLYLQMNSLRAEDMAVYYCAR |
| 618 | DP-45 | EVQLVQSGGGLVQPGGSLRLSCAGSGFTFS | SYAMH | WVRQAPGKGLEWVS | AI...GTGGGTYYADSVKG | RFTISRDNAKNSLYLQMNSLRAEDMAVYYCAR |
| 619 | dp-47 | EVQLLESGGGLVQPGGSLRLSCAASGFTFS | SYAMS | WVRQAPGKGLEWVS | AI..SGSGGSTYYADSVKG | RFTISRDNSKNTLYLQMNSLRAEDTAVYYCAK |
| 620 | f1m | EVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 621 | P1 | EVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 622 | v3-64 | EVQLVESGGGLVQPGGSLRLSCAASGFTFS | SYAMH | WVRQAPGKGLEYVS | AI..SSNGGSTYYANSVKG | RFTISRDNSKNTLYLQMGSLRAEDMAVYYCAR |
| 623 | vh26 | EVQLLESGGGLVQPGGSLRLSCAASGFTFS | SYAMS | WVRQAPGKGLEWVS | AI..SGSGGSTYYGDSVKG | RFTISRDNSKNTLYLQMNSLRAEDTAVYYCAK |
| 624 | B25 | QVQLVESGGGVVQPGRSLRLSCAASGFTFS | SYAMH | WVRQAPGKGLEWVA | VI..SYDGSNKYYTDSVKG | RFTISRDNSKNTLYLQMNSLRAEDTAVYYCAR |
| 625 | b32e | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 626 | B37 | QVQLVESGGGVVQPGRSLRLSCAASGFTFS | SYAMH | WVRQAPGKGLEWVA | VI..SYDGSNKYYADSVKG | RFTISRDNSKNTLYLQMSSLRAEDTAVYYCAR |
| 627 | B43 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 628 | B48 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 629 | B52 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 630 | B54 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 631 | cos-8 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 632 | dp-46 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 633 | F2M | QVQLVESGGGLVQPGGSLRLSCSASGFTFS | SYAMH | WVRQAPGKGLEYVS | AI..SSNGGSTYYADSVKG | RFTISRDNSKNTLYVQMSSLRAEDTAVYYCVK |
| 634 | F3 | QVQLVESGGGLVQPGGSLRLSCSASGFTFS | SYAMH | WVRQAPGKGLEYVS | AI..SSNGGSTYYADSVKG | RFTISRDNSKNTLYLQMNSLRAEDTAVYYCAR |
| 635 | F7 | QVQLVESGGGVVQPGRSLRLSCAASGFTFS | SYAMH | WVRQAPGKGLEWVA | VI..SYDGSNKYYADSVKG | RFAISRDNSKNTLYLQMNSLRAEDTAVYYCAR |
| 636 | hv3005 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAR |
| 637 | P2 | QVQLVESGGGVVQPGRSLRLSCAASGFTFS | SYAMH | WVRQAPGKGLEWVA | VI..SYDGSNKYYADSVKG | RFTISRDNSKNTLYLQMNSLRAEDTAVYYCAK |
| 638 | dp-48 | EVQLVESGGGLVQPGGSLRLSCAASGFTFS | SYDMH | WVRQATGKGLEWVS | AI..GTAG.DTYYPGSVKG | RFTISRENAKNSLYLQMNSLRAGDTAVYYCAR |
| 639 | dp-58 | EVQLVESGGGLVQPGGSLRLSCAASGFTFS | SYEMN | WVRQAPGKGLEWVS | YI..SSSGSTIYYADSVKG | RFTISRDNAKNSLYLQMNSLRAEDTAVYYCAR |

Appendix A

BBI-329

Table 1 VH3 Family Germline Amino Acid Sequences
Numbering according to Kabat
(Joe9 VH included for comparison)

| SEQ ID NO: | germline VH | | CDR H1 | | CDR H2 | |
|---|---|---|---|---|---|---|
| 640 | B1 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRLRARLCITVRE |
| 641 | B13 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 642 | B18 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 643 | B26 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 644 | B28E | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 645 | B29E | QVQLVESGGGVVQPGRSLRLSCAASGFTFS | SYGMH | WVRQAPGKGLEWVA | VI..SYDGSNKYYADSVKG | RFTISRDNSKNRLYLQMNSLRAEDTAVYYCAR |
| 646 | B29M | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 647 | B30 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAR |
| 648 | B32M | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEGTAVYYCAR |
| 649 | cos-3 | QVQLVESGGGVVQPGGSLRLSCAASGFTFS | SYGMH | WVRQAPGKGLEWVA | FI..RYDGSNKYYADSVKG | RFTISRDNSKNTLYLQMNSLRAEDTAVYYCAK |
| 650 | dp-49 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAK |
| 651 | dp-50 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAR |
| 652 | P6 | QVQLVESGGGVVQPGRSLRLSCAASGFTFS | SYGMH | WVRQAPGKGLEWVA | VI..WYDGSNKYYADSVKG | RFTISRDNSKNTLYLQMNSLRAEDTAVYYCAK |
| 653 | P9E | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVRK--- |
| 654 | v3-30 | QVQLVESGGGVVQPGRSLRLSCAASGFTFS | SYGMH | WVRQAPGKGLEWVA | VI..SYDGSNKYYADSVKG | RFTISRDNSKNTLYLQMNSLRAEDTAVYYCAR |
| 655 | v3-33 | QVQLVESGGGVVQPGRSLRLSCAASGFTFS | SYGMH | WVRQAPGKGLEWVA | VI..WYDGSNKYYADSAKG | RFTISRDNSTNTLFLQMNSLRAEDTAVYYCAR |
| 656 | dp-51 | EVQLVESGGGLVQPGGSLRLSCAASGFTFS | SYSMN | WVRQAPGKGLEWVS | YI..SSSSTIYYADSVKG | RFTISRDNAKNSLYLQMNSLRDEDTAVYYCAR |
| 657 | dp-77 | EVQLVESGGGLVKPGGSLRLSCAASGFTFS | SYSMN | WVRQAPGKGLEWVS | SI..SSSSYIYYADSVKG | RFTISRDNAKNSLYLQMNSLRAEDTAVYYCAR |
| 658 | HHG4 | EVQLVESGGGLVKPGGSLRLSCAASGFTFS | SYSMN | WVRQAPGKGLEWVS | SI...SSSYIYYADSVKG | RFTISRDNAKNSLYLQMNSLRAEDTAVYYCAR |
| 659 | v3-21 | EVQLVESGGGLVKPGGSLRLSCAASGFTFS | SYSMN | WVRQAPGKGLEWVS | SI..SSSSYIYYADSVKG | RFTISRDNAKNSLYLQMNSLRAEDTAVYYCAR |
| 660 | v3-48 | EVQLVESGGGLVQPGGSLRLSCAASGFTFS | SYSMN | WVRQAPGKGLEWVS | YI..SSSSTIYYADSVKG | RFTISRDNAKNSLYLQMNSLRAEDTAVYYCAR |
| 661 | DP-52 | EDQLVESGGGLVQPGGSLRPSCAASGFAFS | SYVLH | WVRRAPGKGPEWVS | AIG...TGGDTYYADSVMG | RFTISRDNAKKSLYLQMNSLIAEDMAVYYCAR |
| 662 | cos-6 | EVQLVESGGGLVQPGGSLRLSCAASGFTFS | SYWMH | WVRQAPGKGLVWVS | RI..NSDGSSTSYADSVKG | RFTISRDNAKNTLYLQMNSLRAEDTAVYYCAR |
| 663 | dp-53 | EVQLVESGGGLVQPGGSLRLSCAASGFTFS | SYWMH | WVRQAPGKGLVWVS | RI..NSDGSSTSYADSVKG | RFTISRDNAKNTLYLQMNSLRAEDTAVYYCAR |
| 664 | dp-54 | EVQLVESGGGLVQPGGSLRLSCAASGFTFS | SYWMS | WVRQAPGKGLEWVA | NI..KQDGSEKYYVDSVKG | RFTISRDNAKNSLYLQMNSLRAEDTAVYYCAR |
| 665 | dp-87 | EVQLVESGGGLVQPGGSLRLSCAASGFTFS | SYWMH | WVRQAPGKGLVWVS | RI..NSDGSSTSYADSMKG | QFTISRDNAKNTLYLQMNSLRAEDMAVYYCTR |
| 666 | VH3-11 | EVQLVESGGGLVQPGGSLRLSCAASGFTFS | SYWMS | WVRQAPGKGLEWVA | NI..KQDGSEKYYVDSVKG | RFTISRDNAKNSLYLQMNSLRAEDTAVYYCAR |
| 667 | JOE9 VH | QVQLVQSGGGVVQPGRSLRLSCAASGFTFS | SYGMH | WVRQAPGKGLEWVA | FI..RYDGSNKYYADSVKG | RFTISRDNSKNTLYLQMKSLRAEDTAVYYCTT |

Table 1 Vλ1 Family Germline Amino Acid Sequences

Numbering according to Kabat.
(Joe9 VL included for comparison)

| SEQ ID NO: | gene* | VL | | CDR L1 | | CDR L2 | | CDR L3 |
|---|---|---|---|---|---|---|---|---|
| 668 | 1b | DPL5 | QSVLTQPPSVSAAPGQKVTISC | SGSSSNIGNNY.VS | WYQQLPGTAPKLLIY | DNNKRPS | GIPDRFSGSKSGTSATLGITGLQTGDEADYYC | GTWDSSLSA |
| 669 | 1d | DPL4 | QSVLTQPPSVSAAPGQKVTISC | SGSSSDMGNYA.VS | WYQQLPGTAPKLLIY | ENNKRPS | GIPDRFSGSKSGTSATLGITGLWPEDEADYYC | LAWDTSPRA |
| 670 | 1c | DPL2 | QSVLTQPPSASGTPGQRVTISC | SGSSSNIGSNT.VN | WYQQLPGTAPKLLIY | SNNQRPS | GVPDRFSGSKSGTSASLAISGLQSEDEADYYC | AAWDDSLNG |
| 671 | 1g | DPL3 | QSVLTQPPSASGTPGQRVTISC | SGSSSNIGSNY.VY | WYQQLPGTAPKLLIY | RNNQRPS | GVPDRFSGSKSGTSASLAISGLRSEDEADYYC | AAWDDSLSG |
| 672 | 1a | DPL1 | QSVLTQPPSVSEAPRQRVTISC | SGSSSNIGNN.AVN | WYQQLPGKAPKLLIY | YDDLLPS | GVSDRFSGSKSGTSASLAISGLQSEDEADYYC | AAWDDSLNG |
| 673 | 1f | DPL9 | QSVLTQPPSVSGAPGQRVTISC | TGSSSNIGAGYVVH | WYQQLPGTAPKLLIY | GNSNRPS | GVPDQFSGSKSGTSASLAITGLQSEDEADYYC | KAWDNSLNA |
| 674 | 1e | DPL8 | QSVVTQPPSVSGAPGQRVTISC | TGSSSNIGAGYDVH | WYQQLPGTAPKLLIY | GNSNRPS | GVPDRFSGSKSGTSASLAITGLQAEDEADYYC | QSYDSSLSG |
| 675 | | JOE9 VL | SYVLTQPPSVSGTPGQRVTISC | SGGRSNIGSNT.VK | WYQQLPGTAPKLLIY | GNDQRPS | GVPDRFSGSKSGTSASLAITGVQAEDEADYYC | QSYDSSLRG |

*Williams, JMB, 1996, 264, 220-232

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| Joe9 wt | 77 | SGSYDY | 110 | QSYDSSLRGSRV | 1.00E-01 | 1.50E-06 | 1.00E-06 | |
| Joe9 wt IgG1 | 77 | SGSYDY | 110 | QSYDSSLRGSRV | | | 5.00E-07 | |
| 70-1 | 78 | HGSHDN | 110 | Joe9 wt | 1.34 e-2 | | 2.00E-07 | |
| 70-1 IgG1 | 78 | HGSHDN | 110 | Joe9 wt | | | 2.00E-07 | |
| 70-2 | 79 | HGSYDY | 110 | Joe9 wt | 3.30E-02 | | 3-5.0E-7 | |
| 70-7 | 80 | RRRSNY | 110 | Joe9 wt | 1.29E-01 | | 3-5.0E-7 | |
| 70-13 | 81 | SGSIDY | 110 | Joe9 wt | 7.20E-02 | | 3-5.0E-7 | |
| 78-34 | 77 | wt | 111 | QSYDRGFTGSRV | 1.64 e-2 | 2.00E-07 | 6.00E-07 | |
| 78-25 | 77 | wt | 112 | QSYDSSLRGSRV | 5.00E-02 | | | |
| 78-28 | 77 | wt | 112 | QSYDSSLRGSRV | 4.66E-02 | | | |
| 78-35 | 77 | wt | 113 | QSYDSSLTGSRV | 4.99E-02 | 4.00E-07 | | |
| 79-1 | 77 | wt | 114 | QSYDSSLWGSRV | | 2.00E-07 | 6.00E-07 | |
| 101-14 | 79 | 70-2 | 111 | 78-34 | 7.52E-03 | | | |
| 101-9 | 79 | 70-2 | 113 | 78-35 | 8.54E-03 | | | |
| 101-19 | 81 | 70-13 | 111 | 78-34 | 4.56E-02 | | | |
| 101-8 | 81 | 70-13 | 111 | 78-34 | 1.01E-02 | | | |
| 101-4 | 81 | 70-13 | 113 | 78-35 | 9.76E-03 | | | |
| 101-5 | 81 | 70-13 | 113 | 78-35 | 4.45E-02 | | | |
| 101-11 (12) | 78 | 70-1 | 111 | 78-34 | 4.5 e-3 | | 3.00E-08 | |
| 101-11 IgG1 | 78 | 70-1 | 111 | 78-34 | | 1.60E-09 | | |
| 26-1 (2,3) | 78 | 70-1 | 114 | 79-1 | 7.4 e-3 | | 6.00E-08 | |
| 136-9 | 82 | HGSHDD | 115 | QTYDISESGSRV | 3.20E-03 | | | |
| 136-10 | 82 | HGSHDD | 116 | QSYDRGFTGSRV | 1.40E-03 | 2.00E-09 | | |
| 136-14 | 83 | HGSHDN | 117 | QTYDRGFTGSRV | 1.10E-03 | 3.00E-10 | 1.00E-07 | |
| 136-15 | 83 | HGSHDN | 118 | QTYDKGFTGSSV | 7.4 e-4 | 1.00E-10 | 2.00E-09 | |
| 136-15 germline | 83 | HGSHDN | 118 | QTYDKGFTGSSV | 4.60E-04 | | 6.00E-09 | |
| 136-16 | 83 | HGSHDN | 119 | QSYDRRFTGSRV | 6.10E-04 | 3.00E-10 | 5.00E-09 | |
| 136-17 | 83 | HGSHDN | 120 | QSYDWNFTGSRV | 2.90E-05 | 2.00E-09 | 7.00E-09 | |
| 136-18 | 83 | HGSHDN | 121 | QSYDRGFTGSRV | 1.10E-03 | 8.00E-10 | | |
| 136-21 | 83 | HGSHDN | 122 | QSYDNGFTGSRV | 4.20E-04 | 2.00E-09 | | |
| 136-24 | 83 | HGSHDN | 123 | QSYDNAVTASKV | 8.90E-04 | 1.00E-09 | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| 101-11 | 84 | TT HGSHDN WGQG | 124 | QSYDRGFTGSRV | 4.5x10-3 | 2X10-9 | 2.00E-08 | |
| 136-15M1 | 85 | AK ...... .... | 124 | QSYDRGFTGSRV | | 4.00E-10 | | |
| 149-4 | 86 | .. ...... .S.. | 124 | ............ | 1.37x10-3 | 8x10-11 | 3.00E-09 | |
| 149-5 | 87 | .. .....T .... | 125 | QSYDSSLWGTRV | 1.02x10-3 | 1.2x10-10 | 3.00E-09 | |
| 149-6 | 84 | .. ...... .... | 124 | ............ | 2.73x10-3 | 6x10-10 | 2.00E-09 | |
| 149-7 | 84 | .. ...... .... | 126 | .....D...... | 1.13x10-3 | 9x10-10 | 3.00E-09 | |
| 149-8 | 88 | K. ...... .... | | | 2.33x10-3 | 3x10-9 | | |
| 149-9 | 89 | K. ...... ..H. | 127 | ...E.....M. | 3.54x10-3 | 1.8x10-10 | | |
| 149-11 | 90 | .. ...... .S.. | 128 | ....N....A.. | 1.43x10-2 | 2x10-10 | 4.00E-09 | |
| 149-12 | 84 | .. ...... .... | | | 3.73x10-3 | neutralising | | |
| 149-13 | 84 | .. ...... .... | | | 2.22x10-3 | 5x10-10 | | |
| 149-14 | 91 | .. .R..N. .... | | | | 1.5x10-10 | 6.00E-09 | |
| | | | | | | | | |
| | 92 | TT HGSHDN | 124 | QSYDRGFTGSRV | | | | |
| 156-1 | 93 | .. .....T | 126 | .....D...... | 5.00E-03 | | | |
| 156-2 | 93 | .. .....T | 129 | .....R...... | | | | |
| 156-3 | 93 | .. .....T | 128 | ....N....A.. | 9.00E-03 | | | |
| 156-4 | 93 | .. .....T | 127 | ...E.....SM. | | | | |
| 156-5 | 93 | .. .....T | 130 | .T..K.....S. | | | | |
| 156-6 | 92 | .. ...... | 126 | .....D...... | 3.00E-03 | | | |
| 156-7 | 92 | .. ...... | 129 | .....R...... | | | | |
| 156-8 | 92 | .. ...... | 128 | ....N....A.. | | | | |
| 156-9 | 92 | .. ...... | 127 | ...E.....SM. | | | | |
| 156-10 | 92 | .. ...... | 130 | .T..K.....S. | | | | |
| 156-11 | 94 | .K ...... | 126 | .....D...... | | | | |
| 156-12 | 94 | .K ...... | 129 | .....R...... | | | | |
| 156-13 | 94 | .K ...... | 128 | ....N....A.. | | | | |
| 156-14 | 94 | .K ...... | 127 | ...E.....SM. | | | | |
| 156-15 | 94 | .K ...... | 130 | .T..K.....S. | | | | |
| 156-16 | 93 | .. .....T | 124 | ............ | | | | |
| 156-17 | 92 | .. ...... | 125 | ....SSLW.T.. | 6.00E-03 | | | |
| 156-18 | 93 | .. .....T | 125 | ....SSLW.T.. | | | | |
| | | | | | | | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | 92 | <u>TT HGSHDN</u> | 124 | <u>QSYDRGFTGSRV</u> | | | | |
| 103-1 | 95 | .. Q.R... | 124 | ............ | 2.9x10-3 | | | |
| 103-2 | 96 | K. R.R... | 130 | .T..K.....S. | 7.3x10-4 | 7.00E-11 | 1.00E-09 | |
| 103-3 | 97 | .. .....K | 124 | ............ | 2.5x10-3 | | | |
| 103-6 | | | 131 | .....D...T.. | 4.5x10-4 | | | |
| 103-7 | 98 | .. .....D | 131 | .....D...T.. | 3.7x10-4 | 1.40E-10 | 1.00E-09 | |
| 103-8 | 99 | K. ...... | 130 | .T..K.....S. | 3.3x10-4 | 6.00E-11 | 1.50E-09 | |
| 103-14 & 9 | 100 | KT HGSHDN | 132 | QSYDRGFTGSMV | 6.7 e-4 | 4.00E-11 | 1.20E-09 | |
| 103-8 & 2 | 100 | KT HGSHDN | 133 | QTYDKGFTGSSV | 5.3 e-4 | | 1.50E-09 | |
| 103-4 | 101 | TT HGSHDN | 134 | QSYDRGFTGARV | 1.6 e-4 | 8.60E-11 | 9.00E-10 | |
| 103-152 | 101 | TT HGSHDN | 135 | QSYERGFTGARV | | 8.60E-11 | | |
| | | | | | | | | |
| | 102 | <u>TT SGSYDY</u> | 136 | <u>QSYDRGFTGSRVF</u> | | | | |
| 170-1 | 102 | .. ...... | 137 | .........FK.. | 2.35E-03 | | | |
| 170-2 | 102 | .. ...... | 138 | .......VSAY.. | 8.80E-04 | | | |
| 170-3 | 102 | .. ...... | 139 | ......L.VTK.. | 1.11E-03 | | | |
| 170-4 | 102 | .. ...... | 140 | ......Y.A.... | 8.11E-04 | | | |
| 170-7 | 102 | .. ...... | 141 | ..........K.. | 5.30E-04 | | | |
| 170-11 | 102 | .. ...... | 142 | ......L..F... | 4.40E-04 | | | |
| 170-13 | 102 | .. ...... | 143 | .........YK.. | 1.59E-03 | | | |
| 170-15 | 102 | .. ...... | 144 | ......L..Y.L. | 4.43E-03 | | | |
| 170-19 | 103 | .. H..H.N | 145 | ........DYK.. | 1.00E-03 | | | |
| 170-21 | 104 | .. H..Q.N | 146 | .........P.L. | 3.89E-03 | | | |
| 170-22 | 102 | .. ...... | 147 | ......L...... | 5.60E-04 | | | |
| 170-23 | 103 | .. H..H.N | 148 | .........A..W | 1.00E-03 | 2.00E-10 | | |
| 170-24 | 104 | .. H..Q.N | 149 | .........Y... | 2.80E-04 | 5.00E-10 | | |
| 170-35 | 105 | A. H..Q.N | 136 | ............. | 1.00E-05 | | | |
| 170-38 | | | 150 | .........P... | 2.10E-04 | | | |
| 170-39 | | | 151 | ......M.S.... | 2.79E-03 | | | |
| 170-36 | 83 | HGSHDN | 152 | QSYDRDSTGSRVF | 4.00E-04 | 2.00E-10 | | |
| 170-25 | 106 | HGSQDT | 153 | QSYDSSLRGSRVF | 5.00E-04 | 5.00E-11 | | |
| | | | | | | | | |

Appendix A

BBI-329

| Table 2 | | | | | | | | |
|---|---|---|---|---|---|---|---|---|
| Clone | H3 SEQ ID NO: | H3 | L3 SEQ ID NO: | L3 | koff | RB assay IC50 (M) | PHA assay IC50 (M) | IFN gamma IC50 (M) |
| | 106 | SGSYDY | 136 | QSYDRGFTGSRVF | | | | |
| 73-B1 | 107 | SGSYDY | 154 | H...SD....... | 3.25E-03 | >1E-8 | | |
| 73-B2 | 107 | SGSYDY | 155 | H.SES........ | 2.07E-03 | | | |
| 73-B6 | 107 | SGSYDY | 156 | H...NR....... | 2.51E-03 | >1E-8 | | |
| 73-C1 | 107 | SGSYDY | 157 | H...SR....... | 2.71E-03 | >1E-8 | | |
| 73-C2 | 107 | SGSYDY | 158 | ....SE....... | 3.79E-03 | | | |
| 73-C6 | 107 | SGSYDY | 159 | ....T........ | 3.96E-03 | | | |
| 73-D1 | 107 | SGSYDY | 160 | H...S........ | 3.99E-03 | | | |
| 73-D2 | 107 | SGSYDY | 161 | ....T........ | 3.56E-03 | | | |
| 73-D4 | 107 | SGSYDY | 162 | H...TK....... | 5.36E-03 | | | |
| 73-D5 | 107 | SGSYDY | 163 | H.S.S........ | 3.57E-03 | | | |
| 73-E3 | 107 | SGSYDY | 164 | ....SD....... | 4.98E-03 | | | |
| 73-E6 | 107 | SGSYDY | 165 | H..ES........ | 4.17E-03 | | | |
| 73-F3 | 107 | SGSYDY | 166 | ....APWS..... | 7.08E-03 | | | |
| 73-F5 | 107 | SGSYDY | 167 | ...DSD....K.. | 3.74E-03 | | | |
| 73-G2 | 107 | SGSYDY | 168 | HTN.S........ | 3.98E-03 | | | |
| 73-G3 | 107 | SGSYDY | 169 | H...TR....... | 3.50E-03 | | | |
| 73-G4 | 107 | SGSYDY | 170 | ....MR....... | 6.58E-03 | | | |
| 73-G5 | 107 | SGSYDY | 171 | H.S.SDS...... | 6.01E-03 | | | |
| 73-G6 | 107 | SGSYDY | 172 | ...NTD....... | 6.30E-03 | | | |
| 73-H2 | 107 | SGSYDY | 173 | ....S........ | 5.93E-03 | | | |
| 73-F6 | 107 | SGSYDY | 174 | H...M........ | 5.87E-03 | | | |
| 73-H3 | 107 | SGSYDY | 175 | H...N........ | 6.85E-03 | | | |
| 73-C5 | 107 | SGSYDY | 176 | H.H..D....... | 4.84E-03 | | | |
| 73-B7 | 108 | HGSQDN | 177 | QSYDSSLRGSRV | 2.50E-03 | 7.00E-09 | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 136 | QSYDRGFTGSRVF | | | | |
| M2 A2 | 83 | HGSHDN | 178 | ......IH..... | 4.00E-02 | | | |
| M2 A4 | 83 | HGSHDN | 179 | ....S..P..... | 8.49E-03 | | | |
| M2 A5 | 83 | HGSHDN | 180 | ....I.S...... | 4.01E-02 | | | |
| M2 B1 | 83 | HGSHDN | 181 | ....S.L...... | 7.97E-03 | | | |
| M2 B3 | 83 | HGSHDN | 182 | ....I.M...... | 4.60E-02 | | | |
| M2 B4 | 83 | HGSHDN | 183 | ....I.L...... | 4.42E-02 | | | |
| M2 B5 | 83 | HGSHDN | 184 | ....S.V...... | 8.38E-03 | | | |
| M2 B6 | 83 | HGSHDN | 185 | ......L.A.... | 2.81E-02 | | | |
| M2 C2 | 83 | HGSHDN | 181 | ....S.L...... | 4.85E-02 | | | |
| M2 C3 | 83 | HGSHDN | 186 | ....T.L...... | 4.62E-02 | | | |
| M2 C4 | 83 | HGSHDN | 181 | ....S.L...... | 8.16E-03 | | | |
| M2 C5 | 83 | HGSHDN | 187 | ....TAL...... | 4.71E-02 | | | |
| M2 D1 | 83 | HGSHDN | 188 | ....IR....... | 3.71E-02 | | | |
| M2 D2 | 83 | HGSHDN | 189 | ....IRS...... | 3.85E-02 | | | |
| M2 D3 | 83 | HGSHDN | 190 | ....NRL...... | 3.33E-02 | | | |
| M2 D4 | 83 | HGSHDN | 191 | ...ETS....... | 5.81E-02 | | | |
| M2 D5 | 83 | HGSHDN | 192 | ....SSS...... | 5.18E-02 | | | |
| M2 D6 | 83 | HGSHDN | 193 | ....S...A.... | 5.01E-02 | | | |
| M2 E1 | 83 | HGSHDN | 194 | .T..K.....S.. | 5.32E-02 | | | |
| M2 E2 | 83 | HGSHDN | 195 | ....N........ | 4.77E-02 | | | |
| M2 E6 | 83 | HGSHDN | 196 | ....T...K.... | 9.77E-03 | | | |
| M2 F1 | 83 | HGSHDN | 197 | ....SDV...... | 6.16E-02 | | | |
| M2 H5 | 83 | HGSHDN | 198 | ....A........ | 9.90E-03 | | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 124 | QSYDRGFTGSRV | | | | |
| A5 | 83 | HGSHDN | 199 | ......THPSML | 1.12E-03 | | | |
| A12 | 83 | HGSHDN | 200 | ......TTPRPM | 1.43E-03 | | | |
| A4 | 83 | HGSHDN | 201 | ......RNPALT | 1.47E-03 | | | |
| A6 | 83 | HGSHDN | 202 | ......THPWLH | 1.87E-03 | | | |
| A10 | 83 | HGSHDN | 203 | ......NSPATV | 1.87E-03 | | | |
| A11 | 83 | HGSHDN | 204 | ......TFPSPQ | 2.07E-03 | | | |
| C2 | 83 | HGSHDN | 205 | ......LNPSAT | 2.23E-03 | | | |
| A8 | 83 | HGSHDN | 206 | ......KSNKML | 2.37E-03 | | | |
| B8 | 83 | HGSHDN | 207 | ......HTAHLY | 2.40E-03 | | | |
| C6 | 83 | HGSHDN | 208 | ......QTPSIT | 2.42E-03 | | | |
| A3 | 83 | HGSHDN | 209 | ......YPRNIL | 2.51E-03 | | | |
| B11 | 83 | HGSHDN | 210 | ......ITPGLA | 2.95E-03 | | | |
| B5 | 83 | HGSHDN | 211 | ......QPHAVL | 3.04E-03 | | | |
| C10 | 83 | HGSHDN | 212 | ......NSPIPT | 3.10E-03 | | | |
| C4 | 83 | HGSHDN | 213 | ......TPNNSF | 3.23E-03 | | | |
| C3 | 83 | HGSHDN | 214 | ....S.VDPGPY | 3.34E-03 | | | |
| B2 | 83 | HGSHDN | 215 | ......RPRHAL | 3.61E-03 | | | |
| A2 | 83 | HGSHDN | 216 | ......PYHPIR | 3.80E-03 | | | |
| C5 | 83 | HGSHDN | 217 | ......PHTQPT | 3.91E-03 | | | |
| A7 | 83 | HGSHDN | 218 | ......HNNFSP | 3.95E-03 | | | |
| C9 | 83 | HGSHDN | 219 | ......PTHLPH | 3.97E-03 | | | |
| B3 | 83 | HGSHDN | 220 | ......TPSYPT | 4.12E-03 | | | |
| C8 | 83 | HGSHDN | 221 | ....S.TSNLLP | 5.36E-03 | | | |
| B7 | 83 | HGSHDN | 222 | ......DSNHDL | 5.45E-03 | | | |
| A1 | 83 | HGSHDN | 223 | ......LPRLTH | 5.66E-03 | | | |
| C7 | 83 | HGSHDN | 224 | ......IPTSYL | 5.83E-03 | | | |
| C12 | 83 | HGSHDN | 225 | ......LRVQAP | 5.85E-03 | | | |
| B10 | 83 | HGSHDN | 226 | ......LSDSPL | 6.04E-03 | | | |
| B6 | 83 | HGSHDN | 227 | ....S.SLRRIL | 7.58E-03 | | | |
| A9 | 83 | HGSHDN | 228 | ......PARTSP | 7.98E-03 | | | |
| B9 | 83 | HGSHDN | 229 | ......RAAHPQ | 8.66E-03 | | | |
| | | | | | | | | |

Appendix A BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| | | | 124 | QSYDRGFTGSRV | | | | |
| 177-D7 | 83 | HGSHDN | 230 | ......TQPABI | 4.07E-04 | | | |
| 177-G6 | 83 | HGSHDN | 231 | ......THPTMI | 5.50E-04 | | | |
| 177-D9 | 83 | HGSHDN | 232 | ......RIPABT | 6.32E-04 | | | |
| 177-C6 | 83 | HGSHDN | 233 | ......THPVPA | 7.94E-04 | | | |
| 177-H5 | 83 | HGSHDN | 234 | ......SBPIPA | 1.32E-03 | | | |
| 177-H9 | 83 | HGSHDN | 235 | ......THPVPA | 1.58E-03 | | | |
| 177-H10 | 83 | HGSHDN | 236 | ......THPTMY | 3.44E-03 | | | |
| 144-F1 | 83 | HGSHDN | 237 | ......HHYTTF | 5.80E-04 | | | |
| 43-E3 | 83 | HGSHDN | 238 | ......SHPAAE | 8.00E-04 | | | |
| 43-E9 | 83 | HGSHDN | 239 | ......TIPSIE | 8.00E-04 | | | |
| 43-G2 | 83 | HGSHDN | 240 | ......SSPAIM | 7.00E-04 | | | |
| 43-G3 | 83 | HGSHDN | 241 | ......IWPNLN | 9.00E-04 | | | |
| 31-A6 | 83 | HGSHDN | 242 | ......THPNLN | 5.00E-04 | | | |
| 31-B5 | 83 | HGSHDN | 243 | ......THPSIS | 5.00E-04 | | | |
| | | | | | | | | |
| | | | 124 | QSYDRGFTGSRV | | | | |
| Y17 | 83 | HGSHDN | 244 | QSYDRGSAPMIN | 8.90E-05 | 4.50E-10 | >1E-8 | |
| Y19 | 83 | HGSHDN | 245 | QSYDRGHHPAMS | 2.26E-04 | 3.00E-11 | >1E-8 | |
| Y38 | 83 | HGSHDN | 246 | ......THPSIT | 5.08E-04 | 5.50E-11 | 2.60E-09 | |
| Y45 | 83 | HGSHDN | 247 | ......TDPAIV | 6.17E-04 | 4.00E-11 | 4.30E-09 | |
| Y61 | 83 | HGSHDN | 248 | ......THPALL | 2.75 e-4 | 4E-11 | 1.40E-10 | |
| Y61 IgG | 83 | HGSHDN | 248 | ......THPALL | 1.50E-04 | 1.60E-11 | 1.30E-10 | |
| Y61 IgG germline | 83 | HGSHDN | 248 | ......THPALL | 1.50E-04 | 1.60E-11 | 1.30E-10 | 1.60E-10 |
| Y139 | 83 | HGSHDN | 249 | ......SHPALT | 5.92E-04 | 3E-11 | 4.50E-10 | |
| Y139 IgG1 | 83 | HGSHDN | 249 | ......SHPALT | | | 1.00E-09 | |
| Y174 | 83 | HGSHDN | 250 | ......TTPAPE | 7.55E-04 | 6E-11 | 2.00E-09 | |
| Y177 | 83 | HGSHDN | 251 | ......SHPTLI | 6.61E-04 | 5E-11 | 1.00E-09 | |
| A5 | 83 | HGSHDN | 252 | ......THPSML | 4.50E-04 | 6.60E-11 | | |
| A12 | 83 | HGSHDN | 253 | ......TTPRPM | 5.57E-04 | 2.50E-10 | | |
| D9 | 83 | HGSHDN | 254 | ......RLPAQT | 8.21E-04 | 3.5E-09 | >> | |
| G6 | 83 | HGSHDN | 255 | ......THPLTI | 5.08E-04 | 1E-10 | 1.00E-09 | |
| G6 IgG1 | 83 | HGSHDN | 255 | ......THPLTI | | | 1.00E-09 | |
| C6 | 83 | HGSHDN | 256 | QSYDRGQTPSIT | 1.07E-03 | 3.5E-10 | 1.00E-08 | |
| Y55 | 83 | HGSHDN | 257 | QSYDRGTHFQMY | 1.06E-03 | 1.40E-10 | >1E-8 | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| A4 | 83 | HGSHDN | 258 | QSYDRGRNPALT | 6.30E-04 | 2.50E-10 | | |
| | | | | | | | | |
| A03 | 83 | HGSHDN | 259 | QSYDRGTHPLTM | 3.04E-04 | 3.00E-11 | 4.00E-10 | |
| A03 IgG1 | 83 | HGSHDN | 260 | QSYDRGTHPLTM | 3.04 e-4 | 2.90E-11 | 3.80E-10 | |
| A03 IgG germline | 83 | HGSHDN | 260 | QSYDRGTHPLTM | 2.50E-04 | 3.50E-11 | 1.75E-10 | |
| | | | | | | | | |
| 99-B11 | 83 | HGSHDN | 261 | QSYDSGYTGSRV | 5.40E-03 | | | |
| 99-C11 | 83 | HGSHDN | 262 | QSYDSGFTGSRV | 5.70E-03 | | | |
| 99-H4 | 83 | HGSHDN | 263 | QSYDSRFTGSRV | 4.80E-03 | | | |
| 99-E9 | 83 | HGSHDN | 262 | QSYDSGFTGSRV | 5.40E-03 | | | |
| 99-H7 | 83 | HGSHDN | 264 | QSYPDGTPASRV | 3.30E-03 | | | |
| 99-H11 | 83 | HGSHDN | 265 | QSYSTHMPISRV | 4.90E-03 | | | |
| 99-F6 | 83 | HGSHDN | 266 | QSYDSGSTGSRV | 4.90E-03 | | | |
| 99-F7 | 83 | HGSHDN | 267 | QSYPNSYPISRV | 4.80E-03 | | | |
| 99-F8 | 83 | HGSHDN | 268 | QSYIRAPQQV | 3.70E-03 | | | |
| 99-F11 | 83 | HGSHDN | 262 | QSYDSGFTGSRV | 5.40E-03 | | | |
| 99-G7 | 83 | HGSHDN | 269 | QSYLKSRAFSRV | 4.80E-03 | | | |
| 99-G11 | 83 | HGSHDN | 270 | QSYDSRFTGSRV | 4.30E-03 | | | |
| | | | | | | | | |
| | | | 124 | QSYDRGFTGSRV | | | | |
| L3.3R3M-B1 | 83 | HGSHDN | 271 | ......FTGSMV | 5.46E+00 | | | |
| L3.3R3M-B3 | 83 | HGSHDN | 272 | ......FTGSMV | 5.51E+00 | | | |
| L3.3R3M-C6 | 83 | HGSHDN | 273 | ......FTGFDG | 6.17E+00 | | | |
| L3.3R3M-F9 | 83 | HGSHDN | 274 | ......TAPALS | 4.99E+00 | | | |
| L3.3R3M-G8 | 83 | HGSHDN | 275 | ......SYPALR | 5.55E+00 | | | |
| L3.3R3M-H6 | 83 | HGSHDN | 276 | ......NWPNSN | 5.69E+00 | | | |
| L3.3R3M-H10 | 83 | HGSHDN | 277 | ......TAPSLL | 5.35E+00 | | | |
| L3.3R3M-A3 | 83 | HGSHDN | 278 | ......FTGSMV | 5.37E+00 | | | |
| L3.3R3M-F8 | 83 | HGSHDN | 279 | ......TTPRIR | 4.99E+00 | | | |
| L3.3R3M-G1 | 83 | HGSHDN | 280 | ......FTGSMV | 4.21E+00 | | | |
| L3.3R3M-G7 | 83 | HGSHDN | 281 | ......FTGSMV | 4.24E+00 | | | |
| L3.3R3M-H11 | 83 | HGSHDN | 282 | ......MIPALT | 3.95E+00 | | | |
| | | | | | | | | |

Appendix A

BBI-329

Table 2

| Clone | H3 SEQ ID NO: | H3 | L3 SEQ ID NO: | L3 | koff | RB assay IC50 (M) | PHA assay IC50 (M) | IFN gamma IC50 (M) |
|---|---|---|---|---|---|---|---|---|
| Y61-L94N | 109 | CKT HGSHDN | 283 | QSYDRNTHPALL | | | 8.00E-11 | |
| Y61-L94F | 109 | CKT HGSHDN | 284 | QSYDRFTHPALL | | | 6.00E-11 | |
| Y61-L94Y | 109 | CKT HGSHDN | 285 | QSYDRYTHPALL | | 2.00E-11 | 2.00E-11 | |
| Y61-L94Y IgG | 109 | CKT HGSHDN | 285 | QSYDRYTHPALL | 1.27E-04 | 6.00E-11 | 5.00E-11 | 4.00E-11 |
| Y61-L50Y | 109 | CKT HGSHDN | 286 | QSYDRGTHPALL | | 2.00E-11 | | 2.00E-11 |
| Y61-L50Y* IgG | 109 | CKT HGSHDN | 286 | QSYDRGTHPALL | 6.98E-05 | | 2.00E-11 | 3.00E-11 |
| Y61-L50Y-H31E** IgG | 109 | CKT HGSHDN | 286 | QSYDRGTHPALL | 2.99E-05 | | 6.00E-11 | 2.00E-11 |
| Y61-L50Y-H31E-L94Y** IgG | 109 | CKT HGSHDN | 287 | QSYDRYTHPALL | 4.64E-05 | | 1.00E-11 | 1:00E-11 |
| J695 (Y61-L94Y-L50Y IgG*) | 109 | CKT HGSHDN | 287 | QSYDRYTHPALL | 5.14E-05 | 5.00E-11 | 1.00E-11 | 5.00E-12 |

*CDR L2: L50G to Y

**CDR L2: L50G to Y; CDR H1: H31S to E

Appendix A BBI-329

Table 3

| | CDR H1 | | | | | | | | | CDR H2 | | | | | | | | | | | | | | | | | CDR H3 | | | | | |
|---|---|---|---|---|---|---|---|---|---|---|---|---|---|---|---|---|---|---|---|---|---|---|---|---|---|---|---|---|---|---|---|---|
| Kabat Number | 27 | 28 | 29 | 30 | 31 | 32 | 33 | 34 | 35 | 50 | 51 | 52 | 52A | 53 | 54 | 55 | 56 | 57 | 58 | 59 | 60 | 61 | 62 | 63 | 64 | 65 | 95 | 96 | 97 | 98 | 101 | 102 |
| Y61 VH | F | T | F | S | S | Y | G | M | H | F | I | R | Y | D | G | S | N | K | Y | Y | A | D | S | V | K | G | H | G | S | H | D | N |
| Contact Positions | | | | X | X | X | X | | x | X | | X | X | X | X | | X | | X | | | | | | | | X | X | X | X | X | |
| Hypermutation Positions | | | | X | X | X | | | | | | X | | | | | X | | X | | | | | | | | | | | | | |

| | CDR L1 | | | | | | | | | | | | | CDR L2 | | | | | | | CDR L3 | | | | | | | | | | | |
|---|---|---|---|---|---|---|---|---|---|---|---|---|---|---|---|---|---|---|---|---|---|---|---|---|---|---|---|---|---|---|---|---|
| Kabat number | 24 | 25 | 26 | 27 | 27A | 27B | 28 | 29 | 30 | 31 | 32 | 33 | 34 | 50 | 51 | 52 | 53 | 54 | 55 | 56 | 89 | 90 | 91 | 92 | 93 | 94 | 95 | 95A | 95B | 95C | 96 | 97 |
| Y61 VL | S | G | G | R | S | N | I | G | S | N | T | V | K | G | N | D | Q | R | P | S | Q | S | Y | D | R | G | T | H | P | A | L | L |
| Contact Positions | | | | | | | | | X | X | X | | x | X | | x | X | | x | | | | x | X | X | X | | | | | x | |
| Hypermutation Positions | | | | | | | | | X | X | X | | | | | | X | | | | | | | | X | | | | | | | |

x contact and/or hypermutation position

X contact and/or hypermutation position mutated in Y61

Appendix A BBI-329

Table 4. Neutralization Activity in the Presence of Excess Free IL-12 p40

| SEQ ID NO: | Clone | PHA assay IC50 (M) p70:p40 1:0 | PHA assay IC50 (M) p70:p40 1:20 | PHA assay IC50 (M) p70:p40 1:50 |
|---|---|---|---|---|
| VH: 47<br>VL: 48 | 136-15 | 2.00E-09 | 5.00E-09 | 4.00E-09 |
| VH: 51<br>VL: 52 | 149-5 | 6.50E-09 | 7.00E-09 | 4.00E-09 |
| VH: 53<br>VL: 54 | 149-6 | 9.00E-10 | 1.00E-09 | 1.00E-09 |
| VH: 84<br>VL: 126 | 149-7 | 3.50E-09 | 2.50E-09 | 4.00E-09 |
| VH: 23<br>VL: 24 | Y61 IgG | 1.80E-10 | | 1.80E-10 |
| VH: 65<br>VL: 66 | AO3 IgG1 | 2.50E-10 | | 2.20E-10 |
| VH: 31<br>VL: 32 | J695 | 1.00E-11 | | 3.50E-11 |

The invention claimed is:

1. A method of treating psoriasis in a subject comprising administering to the subject an antibody, or antigen-binding portion thereof, which is capable of binding to an epitope of the p40 subunit of IL-12 and/or IL-23, for a first extended period of at least 12 weeks, wherein the subject achieves at least a Psoriasis Area and Severity Index (PASI) 75 response by week 12 of the first extended period, discontinuing administration of the antibody, or antigen-binding portion thereof, for at least 12 weeks following the first extended period of administration of the antibody, or antigen-binding portion thereof, wherein the subject exhibits a loss of response by a decrease in PASI score to less than PASI 50 following discontinuation, and re-administering to the subject the antibody, or antigen-binding portion thereof, for a second extended period of at least 12 weeks, wherein the subject achieves at least a PASI 50 response by week 12 of the second extended period, thereby treating psoriasis in the subject.

2. The method of claim 1, wherein the antibody, or antigen-binding portion thereof, is administered or re-administered biweekly.

3. The method of claim 1, wherein the antibody, or antigen-binding portion thereof, is administered or re-administered weekly.

4. The method of claim 1, wherein the antibody, or antigen-binding portion thereof, is administered or re-administered in a single dose.

5. The method of claim 1, wherein the antibody, or antigen-binding portion thereof, is administered or re-administered in a dose of about 200 mg.

6. The method of claim 1, wherein the antibody, or antigen-binding portion thereof, is administered or re-administered in a dose of about 100 mg.

7. The method of claim 1, wherein the psoriasis is chronic psoriasis.

8. The method of claim 1, wherein the subject achieves at least a PASI 75 response by week 12 of the second extended period.

* * * * *

UNITED STATES PATENT AND TRADEMARK OFFICE

CERTIFICATE OF CORRECTION

PATENT NO. : 8,178,092 B2
APPLICATION NO. : 12/402342
DATED : May 15, 2012
INVENTOR(S) : Valdes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

Signed and Sealed this
Eighteenth Day of September, 2012

David J. Kappos
*Director of the United States Patent and Trademark Office*

SEQUENCE LISTING

<160> NUMBER OF SEQ ID NOS: 675

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either His or Ser
<220> FEATURE:
<221> NAME/KEY: MISC_FEATURE
<222> LOCATION: (4)..(4)
<223> OTHER INFORMATION: Xaa at position 4 could be either Tyr or His
<220> FEATURE:
<221> NAME/KEY: MISC_FEATURE
<222> LOCATION: (6)..(6)
<223> OTHER INFORMATION: Xaa at position 6 could be either Tyr, Asn or Thr

<400> SEQUENCE: 1

Xaa Gly Ser Xaa Asp Xaa
1               5

<210> SEQ ID NO 2
<211> LENGTH: 12
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa at position 2 could be either Ser or Thr
<220> FEATURE:
<221> NAME/KEY: MISC_FEATURE
<222> LOCATION: (4)..(4)
<223> OTHER INFORMATION: Xaa at position 4 could be either Asp or Glu
<220> FEATURE:
<221> NAME/KEY: MISC_FEATURE
<222> LOCATION: (5)..(5)
<223> OTHER INFORMATION: Xaa at position 5 could be either Ser, Arg or Lys
<220> FEATURE:
<221> NAME/KEY: MISC_FEATURE
<222> LOCATION: (6)..(6)
<223> OTHER INFORMATION: Xaa at position 6 could be either Ser, Gly or Tyr
<220> FEATURE:
<221> NAME/KEY: MISC_FEATURE
<222> LOCATION: (7)..(7)
<223> OTHER INFORMATION: Xaa at position 7 could be either Leu, Phe, Thr or Ser
<220> FEATURE:
<221> NAME/KEY: MISC_FEATURE
<222> LOCATION: (8)..(8)
<223> OTHER INFORMATION: Xaa at position 8 could be either Arg, Ser, Thr, Trp or His
<220> FEATURE:
<221> NAME/KEY: MISC_FEATURE
<222> LOCATION: (9)..(9)
<223> OTHER INFORMATION: Xaa at position 9 could be either Gly or Pro
<220> FEATURE:
<221> NAME/KEY: MISC_FEATURE
<222> LOCATION: (10)..(10)
<223> OTHER INFORMATION: Xaa at position 10 could be either Ser, Thr, Ala or Leu
<220> FEATURE:
<221> NAME/KEY: MISC_FEATURE
<222> LOCATION: (11)..(11)
<223> OTHER INFORMATION: Xaa at position 11 could be either Arg, Ser, Met, Thr or Leu
<220> FEATURE:
<221> NAME/KEY: MISC_FEATURE
<222> LOCATION: (12)..(12)
<223> OTHER INFORMATION: Xaa at position 12 could be either Val, Ile, Thr, Met or Leu

<400> SEQUENCE: 2

Gln Xaa Tyr Xaa Xaa Xaa Xaa Xaa Xaa Xaa Xaa Xaa
1 5 10

<210> SEQ ID NO 3
<211> LENGTH: 17
<212> TYPE: PRT
<213> ORGANISM: Homo sapiens

<400> SEQUENCE: 3

Phe Ile Arg Tyr Asp Gly Ser Asn Lys Tyr Tyr Ala Asp Ser Val Lys
1 5 10 15

Gly

<210> SEQ ID NO 4
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Gly or Tyr
<220> FEATURE:
<221> NAME/KEY: MISC_FEATURE
<222> LOCATION: (3)..(3)
<223> OTHER INFORMATION: Xaa at position 3 could be either Asp or Ser
<220> FEATURE:
<221> NAME/KEY: MISC_FEATURE
<222> LOCATION: (4)..(4)
<223> OTHER INFORMATION: Xaa at position 4 could be either Gln or Asn

<400> SEQUENCE: 4

Xaa Asn Xaa Xaa Arg Pro Ser
1 5

<210> SEQ ID NO 5
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa represents either Ser or Glu

<400> SEQUENCE: 5

Phe Thr Phe Ser Xaa Tyr Gly Met His
1 5

<210> SEQ ID NO 6
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Ser or Thr
<220> FEATURE:
<221> NAME/KEY: MISC_FEATURE
<222> LOCATION: (3)..(3)
<223> OTHER INFORMATION: Xaa at position 3 could be either Ser or Gly
<220> FEATURE:
<221> NAME/KEY: MISC_FEATURE
<222> LOCATION: (4)..(4)
<223> OTHER INFORMATION: Xaa at position 4 could be either Arg or Ser
<220> FEATURE:
<221> NAME/KEY: MISC_FEATURE
<222> LOCATION: (8)..(8)
<223> OTHER INFORMATION: Xaa at position 8 could be either Gly or Val
<220> FEATURE:
<221> NAME/KEY: MISC_FEATURE
<222> LOCATION: (9)..(9)
<223> OTHER INFORMATION: Xaa at position 9 could be either Ser or Ala
<220> FEATURE:
<221> NAME/KEY: MISC_FEATURE
<222> LOCATION: (10)..(10)
<223> OTHER INFORMATION: Xaa at position 10 could be either Asn, Gly or Tyr
<220> FEATURE:
<221> NAME/KEY: MISC_FEATURE
<222> LOCATION: (11)..(11)
<223> OTHER INFORMATION: Xaa at position 11 could be either Thr or Asp
<220> FEATURE:
<221> NAME/KEY: MISC_FEATURE
<222> LOCATION: (13)..(13)
<223> OTHER INFORMATION: Xaa at position 13 could be either Lys or His

<400> SEQUENCE: 6

```
Xaa Gly Xaa Xaa Ser Asn Ile Xaa Xaa Xaa Xaa Val Xaa
1               5                   10
```

<210> SEQ ID NO 7
<211> LENGTH: 115
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa at position 6 could be either Gln or Glu
<220> FEATURE:
<221> NAME/KEY: MISC_FEATURE
<222> LOCATION: (16)..(16)
<223> OTHER INFORMATION: Xaa at position 16 could be either Arg or Gly
<220> FEATURE:
<221> NAME/KEY: MISC_FEATURE
<222> LOCATION: (31)..(31)
<223> OTHER INFORMATION: Xaa at position 31 could be either Ser or Glu
<220> FEATURE:
<221> NAME/KEY: MISC_FEATURE
<222> LOCATION: (84)..(84)
<223> OTHER INFORMATION: Xaa at position 84 could be either Lys or Asn
<220> FEATURE:
<221> NAME/KEY: MISC_FEATURE
<222> LOCATION: (97)..(97)
<223> OTHER INFORMATION: Xaa at position 97 could be either Thr, Ala or Lys
<220> FEATURE:
<221> NAME/KEY: MISC_FEATURE
<222> LOCATION: (98)..(98)
<223> OTHER INFORMATION: Xaa at position 98 could be either Thr or Lys
<220> FEATURE:
<221> NAME/KEY: MISC_FEATURE
<222> LOCATION: (99)..(99)
<223> OTHER INFORMATION: Xaa at position 99 could be either Ser or His
<220> FEATURE:
<221> NAME/KEY: MISC_FEATURE
<222> LOCATION: (102)..(102)
<223> OTHER INFORMATION: Xaa at position 102 could be either Tyr or His
<220> FEATURE:
<221> NAME/KEY: MISC_FEATURE
<222> LOCATION: (104)..(104)
<223> OTHER INFORMATION: Xaa at position 104 could be either Tyr, Asn or Thr

<400> SEQUENCE: 7

```
Gln Val Gln Leu Val Xaa Ser Gly Gly Gly Val Val Gln Pro Gly Xaa
1               5                   10                  15

Ser Leu Arg Leu Ser Cys Ala Ala Ser Gly Phe Thr Phe Ser Xaa Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Asx
    50                  55                  60

Lys Gly Arg Phe Thr Ile Ser Arg Asp Asn Ser Lys Asn Thr Leu Tyr
```

```
65                  70                  75                  80

Leu Gln Met Xaa Ser Leu Arg Ala Glu Asp Thr Ala Val Tyr Tyr Cys
                85                  90                  95

Xaa Xaa Xaa Gly Ser Xaa Asp Xaa Trp Gly Gln Gly Thr Met Val Thr
            100                 105                 110

Val Ser Ser
        115


<210> SEQ ID NO 8
<211> LENGTH: 112
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Ser or Gln
<220> FEATURE:
<221> NAME/KEY: MISC_FEATURE
<222> LOCATION: (2)..(2)
<223> OTHER INFORMATION: Xaa at position 2 could be either Tyr or Ser
<220> FEATURE:
<221> NAME/KEY: MISC_FEATURE
<222> LOCATION: (13)..(13)
<223> OTHER INFORMATION: Xaa at position 13 could be either Thr or Ala
<220> FEATURE:
<221> NAME/KEY: MISC_FEATURE
<222> LOCATION: (23)..(23)
<223> OTHER INFORMATION: Xaa at position 23 could be either Ser or Thr
<220> FEATURE:
<221> NAME/KEY: MISC_FEATURE
<222> LOCATION: (25)..(25)
<223> OTHER INFORMATION: Xaa at position 25 could be either Gly or Ser
<220> FEATURE:
<221> NAME/KEY: MISC_FEATURE
<222> LOCATION: (26)..(26)
<223> OTHER INFORMATION: Xaa at position 26 could be either Arg or Ser
<220> FEATURE:
<221> NAME/KEY: MISC_FEATURE
<222> LOCATION: (30)..(30)
<223> OTHER INFORMATION: Xaa at position 30 could be either Gly or Val
<220> FEATURE:
<221> NAME/KEY: MISC_FEATURE
<222> LOCATION: (31)..(31)
<223> OTHER INFORMATION: Xaa at position 31 could be either Ser or Ala
<220> FEATURE:
<221> NAME/KEY: MISC_FEATURE
<222> LOCATION: (32)..(32)
<223> OTHER INFORMATION: Xaa at position 32 could be either Asn, Gly or
      Tyr
<220> FEATURE:
<221> NAME/KEY: MISC_FEATURE
<222> LOCATION: (33)..(33)
<223> OTHER INFORMATION: Xaa at position 33 could be either Thr or Asp
<220> FEATURE:
<221> NAME/KEY: MISC_FEATURE
<222> LOCATION: (35)..(35)
<223> OTHER INFORMATION: Xaa at position 35 could be either Lys or His
<220> FEATURE:
<221> NAME/KEY: MISC_FEATURE
<222> LOCATION: (51)..(51)
<223> OTHER INFORMATION: Xaa at position 51 could be either Gly or Lys
<220> FEATURE:
<221> NAME/KEY: MISC_FEATURE
<222> LOCATION: (53)..(53)
<223> OTHER INFORMATION: Xaa at position 53 could be either Asp or Ser
<220> FEATURE:
<221> NAME/KEY: MISC_FEATURE
<222> LOCATION: (54)..(54)
<223> OTHER INFORMATION: Xaa at position 54 could be either Gln or Asn
<220> FEATURE:
<221> NAME/KEY: MISC_FEATURE
<222> LOCATION: (79)..(79)
<223> OTHER INFORMATION: Xaa at position 79 could be either Val or Leu
<220> FEATURE:
<221> NAME/KEY: MISC_FEATURE
<222> LOCATION: (91)..(91)
```

<223> OTHER INFORMATION: Xaa at 91 could be either Ser or Thr
<220> FEATURE:
<221> NAME/KEY: MISC_FEATURE
<222> LOCATION: (93)..(93)
<223> OTHER INFORMATION: Xaa at position 93 could be either Asp or Glu
<220> FEATURE:
<221> NAME/KEY: MISC_FEATURE
<222> LOCATION: (94)..(94)
<223> OTHER INFORMATION: Xaa at position 94 could be either Ser, Arg or Lys
<220> FEATURE:
<221> NAME/KEY: MISC_FEATURE
<222> LOCATION: (95)..(95)
<223> OTHER INFORMATION: Xaa at position 95 could be either Ser, Gly or Tyr
<220> FEATURE:
<221> NAME/KEY: MISC_FEATURE
<222> LOCATION: (96)..(96)
<223> OTHER INFORMATION: Xaa at position 96 could be either Leu, Phe, Thr or Ser
<220> FEATURE:
<221> NAME/KEY: MISC_FEATURE
<222> LOCATION: (97)..(97)
<223> OTHER INFORMATION: Xaa at position 97 could be either Arg, Ser, Thr, Trp or His
<220> FEATURE:
<221> NAME/KEY: MISC_FEATURE
<222> LOCATION: (98)..(98)
<223> OTHER INFORMATION: Xaa at position 98 could be either Gly or Pro
<220> FEATURE:
<221> NAME/KEY: MISC_FEATURE
<222> LOCATION: (99)..(99)
<223> OTHER INFORMATION: Xaa at position 99 could be either Ser, Thr, Ala or Leu
<220> FEATURE:
<221> NAME/KEY: MISC_FEATURE
<222> LOCATION: (100)..(100)
<223> OTHER INFORMATION: Xaa at position 100 could be either Arg, Ser, Met, Thr or Leu
<220> FEATURE:
<221> NAME/KEY: MISC_FEATURE
<222> LOCATION: (101)..(101)
<223> OTHER INFORMATION: Xaa at position 101 could be either Val, Ile, Thr, Met or Leu

<400> SEQUENCE: 8

```
Xaa Xaa Val Leu Thr Gln Pro Pro Ser Val Ser Gly Xaa Pro Gly Gln
1               5                   10                  15

Arg Val Thr Ile Ser Cys Xaa Gly Xaa Xaa Ser Asn Ile Xaa Xaa Xaa
            20                  25                  30

Xaa Val Xaa Trp Tyr Gln Gln Leu Pro Gly Thr Ala Pro Lys Leu Leu
        35                  40                  45

Ile Tyr Xaa Asn Xaa Xaa Arg Pro Ser Gly Val Pro Asp Arg Phe Ser
    50                  55                  60

Gly Ser Lys Ser Gly Thr Ser Ala Ser Leu Ala Ile Thr Gly Xaa Gln
65                  70                  75                  80

Ala Glu Asp Glu Ala Asp Tyr Tyr Cys Gln Xaa Tyr Xaa Xaa Xaa Xaa
                85                  90                  95

Xaa Xaa Xaa Xaa Xaa Phe Gly Thr Gly Thr Lys Val Thr Val Leu Gly
            100                 105                 110
```

<210> SEQ ID NO 9
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa at position 2 could be either Gly, Val, Cys or His
<220> FEATURE:
<221> NAME/KEY: MISC_FEATURE

```
<222> LOCATION: (3)..(3)
<223> OTHER INFORMATION: Xaa at position 3 could be either Ser or Thr
<220> FEATURE:
<221> NAME/KEY: MISC_FEATURE
<222> LOCATION: (4)..(4)
<223> OTHER INFORMATION: Xaa at position 4 could be either His, Thr,
      Val, Arg, or Ile
<220> FEATURE:
<221> NAME/KEY: MISC_FEATURE
<222> LOCATION: (5)..(5)
<223> OTHER INFORMATION: Xaa at position 5 could be either Asp or Ser
<220> FEATURE:
<221> NAME/KEY: MISC_FEATURE
<222> LOCATION: (6)..(6)
<223> OTHER INFORMATION: Xaa at position 6 could be either Asn, Lys,
      Ala, Thr, Ser, Phe, Trp, or His

<400> SEQUENCE: 9

His Xaa Xaa Xaa Xaa Xaa
1               5


<210> SEQ ID NO 10
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa at position 4 could be either Asp or Ser
<220> FEATURE:
<221> NAME/KEY: MISC_FEATURE
<222> LOCATION: (5)..(5)
<223> OTHER INFORMATION: Xaa at position 5 represents any amino acid
<220> FEATURE:
<221> NAME/KEY: MISC_FEATURE
<222> LOCATION: (6)..(6)
<223> OTHER INFORMATION: Xaa at position 6 could be either Gly, Asp,
      Gln, Leu, Phe, Arg, His, Asn or Tyr

<400> SEQUENCE: 10

Gln Ser Tyr Xaa Xaa Xaa Thr His Pro Ala Leu Leu
1               5                   10


<210> SEQ ID NO 11
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Phe, Thr or
      Tyr
<220> FEATURE:
<221> NAME/KEY: MISC_FEATURE
<222> LOCATION: (3)..(3)
<223> OTHER INFORMATION: Xaa at position 3 could be either Arg or Ala
<220> FEATURE:
<221> NAME/KEY: MISC_FEATURE
<222> LOCATION: (5)..(5)
<223> OTHER INFORMATION: Xaa at position 5 could be either Asp, Ser, Glu
      or Ala
<220> FEATURE:
<221> NAME/KEY: MISC_FEATURE
<222> LOCATION: (6)..(6)
<223> OTHER INFORMATION: Xaa at position 6 could be either Gly or Arg
<220> FEATURE:
<221> NAME/KEY: MISC_FEATURE
<222> LOCATION: (8)..(8)
<223> OTHER INFORMATION: Xaa at position 8 represents any amino acid
<220> FEATURE:
<221> NAME/KEY: MISC_FEATURE
<222> LOCATION: (10)..(10)
<223> OTHER INFORMATION: Xaa at position 10 could be either Tyr or Glu

<400> SEQUENCE: 11
```

```
Xaa Ile Xaa Tyr Xaa Xaa Ser Xaa Lys Xaa Tyr Ala Asp Ser Val Lys
1               5                   10                  15

Gly


<210> SEQ ID NO 12
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Gly, Tyr,
      Ser, Thr, Asn or Gln

<400> SEQUENCE: 12

Xaa Asn Asp Gln Arg Pro Ser
1               5


<210> SEQ ID NO 13
<211> LENGTH: 9
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: Xaa at position 4 and 5 represents any amino
      acid
<220> FEATURE:
<221> NAME/KEY: MISC_FEATURE
<222> LOCATION: (6)..(6)
<223> OTHER INFORMATION: Xaa at position 6 could be either Tyr or His
<220> FEATURE:
<221> NAME/KEY: MISC_FEATURE
<222> LOCATION: (7)..(7)
<223> OTHER INFORMATION: Xaa at position 7 could be either Gly, Met,
      Ala, Asn or Ser

<400> SEQUENCE: 13

Phe Thr Phe Xaa Xaa Xaa Xaa Met His
1               5


<210> SEQ ID NO 14
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa at position 9 could be either Ser, Cys,
      Arg, Asn, Asp or Thr
<220> FEATURE:
<221> NAME/KEY: MISC_FEATURE
<222> LOCATION: (10)..(10)
<223> OTHER INFORMATION: Xaa at position 10 could be either Asn, Met or
      Ile
<220> FEATURE:
<221> NAME/KEY: MISC_FEATURE
<222> LOCATION: (11)..(11)
<223> OTHER INFORMATION: Xaa at position 11 could be either Thr, Tyr,
      Asp, His, Lys or Pro

<400> SEQUENCE: 14

Ser Gly Gly Arg Ser Asn Ile Gly Xaa Xaa Xaa Val Lys
1               5                   10


<210> SEQ ID NO 15
<211> LENGTH: 114
<212> TYPE: PRT
<213> ORGANISM: Homo sapiens
<220> FEATURE:
<221> NAME/KEY: MISC_FEATURE
<222> LOCATION: (5)..(5)
```

<223> OTHER INFORMATION: Xaa at position 5 could be either Gln or Glu
<220> FEATURE:
<221> NAME/KEY: MISC_FEATURE
<222> LOCATION: (30)..(30)
<223> OTHER INFORMATION: Xaa at position 30 could be Ser or Glu
<220> FEATURE:
<221> NAME/KEY: MISC_FEATURE
<222> LOCATION: (83)..(83)
<223> OTHER INFORMATION: Xaa at position 83 could be Lys or Asn

<400> SEQUENCE: 15

```
Gln Val Gln Val Xaa Ser Gly Gly Gly Val Val Gln Pro Gly Arg Ser
1               5                   10                  15

Leu Arg Leu Ser Cys Ala Ala Ser Gly Phe Thr Phe Ser Xaa Tyr Gly
            20                  25                  30

Met His Trp Val Arg Gln Ala Pro Gly Lys Gly Leu Glu Trp Val Ala
        35                  40                  45

Phe Ile Arg Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Xaa Ser Leu Arg Ala Glu Asp Thr Ala Val Tyr Tyr Cys Lys
                85                  90                  95

Thr His Gly Ser His Asp Asn Trp Gly Gln Gly Thr Met Val Thr Val
            100                 105                 110

Ser Ser
```

<210> SEQ ID NO 16
<211> LENGTH: 112
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 could be either Ser or Gln
<220> FEATURE:
<221> NAME/KEY: MISC_FEATURE
<222> LOCATION: (2)..(2)
<223> OTHER INFORMATION: Xaa at position 2 could be Tyr or Ser
<220> FEATURE:
<221> NAME/KEY: MISC_FEATURE
<222> LOCATION: (13)..(13)
<223> OTHER INFORMATION: Xaa at position 13 could be either Thr or Ala
<220> FEATURE:
<221> NAME/KEY: MISC_FEATURE
<222> LOCATION: (25)..(25)
<223> OTHER INFORMATION: Xaa at position 25 could be either Gly or Ser
<220> FEATURE:
<221> NAME/KEY: MISC_FEATURE
<222> LOCATION: (51)..(51)
<223> OTHER INFORMATION: Xaa at position 51 could be either Gly or Tyr
<220> FEATURE:
<221> NAME/KEY: MISC_FEATURE
<222> LOCATION: (79)..(79)
<223> OTHER INFORMATION: Xaa at position 79 could be either Val or Leu
<220> FEATURE:
<221> NAME/KEY: MISC_FEATURE
<222> LOCATION: (95)..(95)
<223> OTHER INFORMATION: Xaa at position 95 could be either Gly or Tyr

<400> SEQUENCE: 16

```
Xaa Xaa Val Leu Thr Gln Pro Pro Ser Val Ser Gly Xaa Pro Gly Gln
1               5                   10                  15

Arg Val Thr Ile Ser Cys Ser Gly Xaa Arg Ser Asn Ile Gly Ser Asn
            20                  25                  30

Thr Val Lys Trp Tyr Gln Gln Leu Pro Gly Thr Ala Pro Lys Leu Leu
        35                  40                  45
```

```
Ile Tyr Xaa Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Xaa Gln
65                  70                  75                  80

Ala Glu Asp Glu Ala Asp Tyr Tyr Cys Gln Ser Tyr Asp Arg Xaa Thr
                85                  90                  95

His Pro Ala Leu Leu Phe Gly Thr Gly Thr Lys Val Thr Val Leu Gly
            100                 105                 110


<210> SEQ ID NO 17
<211> LENGTH: 6
<212> TYPE: PRT
<213> ORGANISM: Homo sapiens

<400> SEQUENCE: 17

His Gly Ser His Asp Asn
1               5


<210> SEQ ID NO 18
<211> LENGTH: 12
<212> TYPE: PRT
<213> ORGANISM: Homo sapiens

<400> SEQUENCE: 18

Gln Ser Tyr Asp Arg Gly Thr His Pro Ala Leu Leu
1               5                   10


<210> SEQ ID NO 19
<211> LENGTH: 17
<212> TYPE: PRT
<213> ORGANISM: Homo sapiens

<400> SEQUENCE: 19

Phe Ile Arg Tyr Asp Gly Ser Asn Lys Tyr Tyr Ala Asp Ser Val Lys
1               5                   10                  15

Gly


<210> SEQ ID NO 20
<211> LENGTH: 7
<212> TYPE: PRT
<213> ORGANISM: Homo sapiens

<400> SEQUENCE: 20

Gly Asn Asp Gln Arg Pro Ser
1               5


<210> SEQ ID NO 21
<211> LENGTH: 9
<212> TYPE: PRT
<213> ORGANISM: Homo sapiens

<400> SEQUENCE: 21

Phe Thr Phe Ser Ser Tyr Gly Met His
1               5


<210> SEQ ID NO 22
<211> LENGTH: 13
<212> TYPE: PRT
<213> ORGANISM: Homo sapiens

<400> SEQUENCE: 22

Ser Gly Gly Arg Ser Asn Ile Gly Ser Asn Thr Val Lys
1               5                   10
```

<210> SEQ ID NO 23
<211> LENGTH: 115
<212> TYPE: PRT
<213> ORGANISM: Homo sapiens

<400> SEQUENCE: 23

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115
```

<210> SEQ ID NO 24
<211> LENGTH: 112
<212> TYPE: PRT
<213> ORGANISM: Homo sapiens

<400> SEQUENCE: 24

```
Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Trp Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Thr
                85                  90                  95

His Pro Ala Leu Leu Phe Gly Thr Gly Thr Lys Val Thr Val Leu Gly
            100                 105                 110
```

<210> SEQ ID NO 25
<211> LENGTH: 6
<212> TYPE: PRT
<213> ORGANISM: Homo sapiens

<400> SEQUENCE: 25

```
His Gly Ser His Asp Asn
1               5
```

<210> SEQ ID NO 26
<211> LENGTH: 12
<212> TYPE: PRT
<213> ORGANISM: Homo sapiens

<400> SEQUENCE: 26

Gln Ser Tyr Asp Arg Tyr Thr His Pro Ala Leu Leu
1               5                   10

<210> SEQ ID NO 27
<211> LENGTH: 17
<212> TYPE: PRT
<213> ORGANISM: Homo sapiens

<400> SEQUENCE: 27

Phe Ile Arg Tyr Asp Gly Ser Asn Lys Tyr Tyr Ala Asp Ser Val Lys
1               5                   10                  15

Gly

<210> SEQ ID NO 28
<211> LENGTH: 7
<212> TYPE: PRT
<213> ORGANISM: Homo sapiens

<400> SEQUENCE: 28

Tyr Asn Asp Gln Arg Pro Ser
1               5

<210> SEQ ID NO 29
<211> LENGTH: 9
<212> TYPE: PRT
<213> ORGANISM: Homo sapiens

<400> SEQUENCE: 29

Phe Thr Phe Ser Ser Tyr Gly Met His
1               5

<210> SEQ ID NO 30
<211> LENGTH: 13
<212> TYPE: PRT
<213> ORGANISM: Homo sapiens

<400> SEQUENCE: 30

Ser Gly Ser Arg Ser Asn Ile Gly Ser Asn Thr Val Lys
1               5                   10

<210> SEQ ID NO 31
<211> LENGTH: 115
<212> TYPE: PRT
<213> ORGANISM: Homo sapiens

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 32
<211> LENGTH: 112
<212> TYPE: PRT
<213> ORGANISM: Homo sapiens

<400> SEQUENCE: 32

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110
```

<210> SEQ ID NO 33
<211> LENGTH: 115
<212> TYPE: PRT
<213> ORGANISM: Homo sapiens

<400> SEQUENCE: 33

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr Ser Gly Ser Tyr Asp Tyr Trp Gly Gln Gly Thr Met Val Thr
            100                 105                 110

Val Ser Ser
        115
```

<210> SEQ ID NO 34
<211> LENGTH: 112
<212> TYPE: PRT
<213> ORGANISM: Homo sapiens

<400> SEQUENCE: 34

```
Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
```

```
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Arg Gly Ser Arg Val Phe Gly Thr Gly Thr Lys Val Thr Val Leu Gly
            100                 105                 110


<210> SEQ ID NO 35
<211> LENGTH: 115
<212> TYPE: PRT
<213> ORGANISM: Homo sapiens

<400> SEQUENCE: 35

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Ser Tyr Asp Tyr Trp Gly Gln Gly Thr Met Val Thr
            100                 105                 110

Val Ser Ser
        115


<210> SEQ ID NO 36
<211> LENGTH: 112
<212> TYPE: PRT
<213> ORGANISM: Homo sapiens
<220> FEATURE:
<221> NAME/KEY: MISC_FEATURE
<222> LOCATION: (32)..(32)
<223> OTHER INFORMATION: Xaa at position 32 represents either Gly or Tyr

<400> SEQUENCE: 36

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Xaa
            20                  25                  30

Asp Val His Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Ser Arg Val Phe Gly Thr Gly Thr Lys Val Thr Val Leu Gly
            100                 105                 110


<210> SEQ ID NO 37
<211> LENGTH: 115
<212> TYPE: PRT
```

<213> ORGANISM: Homo sapiens

<400> SEQUENCE: 37

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Thr Thr His Gly Ser His Asp Asn Trp Gly Gln Gly Thr Met Val Thr
100 105 110

Val Ser Ser
115

<210> SEQ ID NO 38
<211> LENGTH: 112
<212> TYPE: PRT
<213> ORGANISM: Homo sapiens

<400> SEQUENCE: 38

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln
65 70 75 80

Ala Glu Asp Glu Ala Asp Tyr Tyr Cys Gln Ser Tyr Asp Ser Ser Leu
85 90 95

Arg Gly Ser Arg Val Phe Gly Thr Gly Thr Lys Val Thr Val Leu Gly
100 105 110

<210> SEQ ID NO 39
<211> LENGTH: 115
<212> TYPE: PRT
<213> ORGANISM: Homo sapiens

<400> SEQUENCE: 39

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Lys Ser Leu Arg Ala Glu Asp Thr Ala Val Tyr Tyr Cys
                85                  90                  95

Thr Thr Ser Gly Ser Tyr Asp Tyr Trp Gly Gln Gly Thr Met Val Thr
            100                 105                 110

Val Ser Ser
        115


<210> SEQ ID NO 40
<211> LENGTH: 112
<212> TYPE: PRT
<213> ORGANISM: Homo sapiens

<400> SEQUENCE: 40

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Phe
                85                  90                  95

Thr Gly Ser Arg Val Phe Gly Thr Gly Thr Lys Val Thr Val Leu Gly
            100                 105                 110


<210> SEQ ID NO 41
<211> LENGTH: 115
<212> TYPE: PRT
<213> ORGANISM: Homo sapiens

<400> SEQUENCE: 41

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr Ser Gly Ser Tyr Asp Tyr Trp Gly Gln Gly Thr Met Val Thr
            100                 105                 110

Val Ser Ser
        115


<210> SEQ ID NO 42
<211> LENGTH: 112
<212> TYPE: PRT
<213> ORGANISM: Homo sapiens

<400> SEQUENCE: 42

Ser Tyr Val Leu Thr Gln Pro Pro Ser Val Ser Gly Thr Pro Gly Gln
1               5                   10                  15
```

```
Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Trp Gly Ser Arg Val Phe Gly Thr Gly Thr Lys Val Thr Val Leu Gly
            100                 105                 110


<210> SEQ ID NO 43
<211> LENGTH: 115
<212> TYPE: PRT
<213> ORGANISM: Homo sapiens

<400> SEQUENCE: 43

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr His Gly Ser His Asp Asn Trp Gly Gln Gly Thr Met Val Thr
            100                 105                 110

Val Ser Ser
        115


<210> SEQ ID NO 44
<211> LENGTH: 112
<212> TYPE: PRT
<213> ORGANISM: Homo sapiens

<400> SEQUENCE: 44

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Phe
                85                  90                  95

Thr Gly Ser Arg Val Phe Gly Thr Gly Thr Lys Val Thr Val Leu Gly
            100                 105                 110
```

<210> SEQ ID NO 45
<211> LENGTH: 115
<212> TYPE: PRT
<213> ORGANISM: Homo sapiens

<400> SEQUENCE: 45

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Thr Thr His Gly Ser His Asp Asn Trp Gly Gln Gly Thr Met Val Thr
100 105 110

Val Ser Ser
115

<210> SEQ ID NO 46
<211> LENGTH: 112
<212> TYPE: PRT
<213> ORGANISM: Homo sapiens

<400> SEQUENCE: 46

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln
65 70 75 80

Ala Glu Asp Glu Ala Asp Tyr Tyr Cys Gln Ser Tyr Asp Ser Ser Leu
85 90 95

Trp Gly Ser Arg Val Phe Gly Thr Gly Thr Lys Val Thr Val Leu Gly
100 105 110

<210> SEQ ID NO 47
<211> LENGTH: 115
<212> TYPE: PRT
<213> ORGANISM: Homo sapiens

<400> SEQUENCE: 47

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 48
<211> LENGTH: 112
<212> TYPE: PRT
<213> ORGANISM: Homo sapiens

<400> SEQUENCE: 48

Ser Tyr Val Leu Thr Gln Pro Pro Ser Val Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Thr Tyr Asp Lys Gly Phe
                85                  90                  95

Thr Gly Ser Ser Val Phe Gly Thr Gly Thr Lys Val Thr Val Leu Gly
            100                 105                 110


<210> SEQ ID NO 49
<211> LENGTH: 115
<212> TYPE: PRT
<213> ORGANISM: Homo sapiens

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 50
<211> LENGTH: 112
<212> TYPE: PRT
<213> ORGANISM: Homo sapiens
```

<400> SEQUENCE: 50

Gln Ser Val Leu Thr Gln Pro Pro Ser Val Ser Gly Ala Pro Gly Gln
1 5 10 15

Arg Val Thr Ile Ser Cys Ser Gly Ser Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Thr Tyr Asp Lys Gly Phe
85 90 95

Thr Gly Ser Ser Val Phe Gly Thr Gly Thr Lys Val Thr Val Leu Gly
100 105 110

<210> SEQ ID NO 51
<211> LENGTH: 115
<212> TYPE: PRT
<213> ORGANISM: Homo sapiens

<400> SEQUENCE: 51

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Thr Thr His Gly Ser His Asp Thr Trp Gly Gln Gly Thr Met Val Thr
100 105 110

Val Ser Ser
115

<210> SEQ ID NO 52
<211> LENGTH: 112
<212> TYPE: PRT
<213> ORGANISM: Homo sapiens

<400> SEQUENCE: 52

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln
65 70 75 80

Ala Glu Asp Glu Ala Asp Tyr Tyr Cys Gln Ser Tyr Asp Ser Ser Leu
85 90 95

Trp Gly Thr Arg Val Phe Gly Thr Gly Thr Lys Val Thr Val Leu Gly
100 105 110

<210> SEQ ID NO 53
<211> LENGTH: 115
<212> TYPE: PRT
<213> ORGANISM: Homo sapiens

<400> SEQUENCE: 53

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Thr Thr His Gly Ser His Asp Asn Trp Gly Gln Gly Thr Met Val Thr
100 105 110

Val Ser Ser
115

<210> SEQ ID NO 54
<211> LENGTH: 112
<212> TYPE: PRT
<213> ORGANISM: Homo sapiens

<400> SEQUENCE: 54

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Val Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln
65 70 75 80

Ala Glu Asp Glu Ala Asp Tyr Tyr Cys Gln Ser Tyr Asp Arg Gly Phe
85 90 95

Thr Gly Ser Arg Val Phe Gly Thr Gly Thr Lys Val Thr Val Leu Gly
100 105 110

<210> SEQ ID NO 55
<211> LENGTH: 115
<212> TYPE: PRT
<213> ORGANISM: Homo sapiens

<400> SEQUENCE: 55

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val

```
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr His Gly Ser His Asp Asn Trp Gly Gln Gly Thr Met Val Thr
            100                 105                 110

Val Ser Ser
        115


<210> SEQ ID NO 56
<211> LENGTH: 112
<212> TYPE: PRT
<213> ORGANISM: Homo sapiens

<400> SEQUENCE: 56

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Val Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Phe
                85                  90                  95

Thr Gly Ala Arg Val Phe Gly Thr Gly Thr Lys Val Thr Val Leu Gly
            100                 105                 110


<210> SEQ ID NO 57
<211> LENGTH: 115
<212> TYPE: PRT
<213> ORGANISM: Homo sapiens

<400> SEQUENCE: 57

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 58
```

<211> LENGTH: 112
<212> TYPE: PRT
<213> ORGANISM: Homo sapiens

<400> SEQUENCE: 58

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln
65 70 75 80

Ala Glu Asp Glu Ala Asp Tyr Tyr Cys Gln Thr Tyr Asp Lys Gly Phe
85 90 95

Thr Gly Ser Ser Val Phe Gly Thr Gly Thr Lys Val Thr Val Leu Gly
100 105 110

<210> SEQ ID NO 59
<211> LENGTH: 115
<212> TYPE: PRT
<213> ORGANISM: Homo sapiens

<400> SEQUENCE: 59

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Lys Thr His Gly Ser His Asp Asn Trp Gly Gln Gly Thr Met Val Thr
100 105 110

Val Ser Ser
115

<210> SEQ ID NO 60
<211> LENGTH: 112
<212> TYPE: PRT
<213> ORGANISM: Homo sapiens

<400> SEQUENCE: 60

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Val Gln

```
65                  70                  75                  80

Ala Glu Asp Glu Ala Asp Tyr Tyr Cys Gln Ser Tyr Glu Arg Gly Phe
                85                  90                  95

Thr Gly Ser Met Val Phe Gly Thr Gly Thr Lys Val Thr Val Leu Gly
            100                 105                 110


<210> SEQ ID NO 61
<211> LENGTH: 115
<212> TYPE: PRT
<213> ORGANISM: Homo sapiens

<400> SEQUENCE: 61

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 62
<211> LENGTH: 112
<212> TYPE: PRT
<213> ORGANISM: Homo sapiens

<400> SEQUENCE: 62

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Thr
                85                  90                  95

His Pro Leu Thr Ile Phe Gly Thr Gly Thr Lys Val Thr Val Leu Gly
            100                 105                 110


<210> SEQ ID NO 63
<211> LENGTH: 115
<212> TYPE: PRT
<213> ORGANISM: Homo sapiens

<400> SEQUENCE: 63

Gln Val Gln Leu Val Gln Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 64
<211> LENGTH: 112
<212> TYPE: PRT
<213> ORGANISM: Homo sapiens

<400> SEQUENCE: 64

Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Ser
                85                  90                  95

His Pro Ala Leu Thr Phe Gly Thr Gly Thr Lys Val Thr Val Leu Gly
            100                 105                 110


<210> SEQ ID NO 65
<211> LENGTH: 115
<212> TYPE: PRT
<213> ORGANISM: Homo sapiens

<400> SEQUENCE: 65

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
```

115

<210> SEQ ID NO 66
<211> LENGTH: 112
<212> TYPE: PRT
<213> ORGANISM: Homo sapiens

<400> SEQUENCE: 66

```
Ser Tyr Val Leu Thr Gln Pro Pro Ser Val Ser Gly Thr Pro Gly Gln
1               5                   10                  15

Arg Val Thr Ile Ser Cys Ser Gly Gly Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Gly Thr
                85                  90                  95

His Pro Leu Thr Met Phe Gly Thr Gly Thr Lys Val Thr Val Leu Gly
            100                 105                 110
```

<210> SEQ ID NO 67
<211> LENGTH: 115
<212> TYPE: PRT
<213> ORGANISM: Homo sapiens

<400> SEQUENCE: 67

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115
```

<210> SEQ ID NO 68
<211> LENGTH: 112
<212> TYPE: PRT
<213> ORGANISM: Homo sapiens

<400> SEQUENCE: 68

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45
```

-continued

```
Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Gly Thr
                85                  90                  95

His Pro Leu Thr Met Phe Gly Thr Gly Thr Lys Val Thr Val Leu Gly
            100                 105                 110


<210> SEQ ID NO 69
<211> LENGTH: 115
<212> TYPE: PRT
<213> ORGANISM: Homo sapiens

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115


<210> SEQ ID NO 70
<211> LENGTH: 112
<212> TYPE: PRT
<213> ORGANISM: Homo sapiens

<400> SEQUENCE: 70

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Gly Thr
                85                  90                  95

His Pro Ala Leu Leu Phe Gly Thr Gly Thr Lys Val Thr Val Leu Gly
            100                 105                 110


<210> SEQ ID NO 71
<211> LENGTH: 115
<212> TYPE: PRT
<213> ORGANISM: Homo sapiens

<400> SEQUENCE: 71
```

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Glu Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Lys Thr His Gly Ser His Asp Asn Trp Gly Gln Gly Thr Met Val Thr
100 105 110

Val Ser Ser
115

<210> SEQ ID NO 72
<211> LENGTH: 112
<212> TYPE: PRT
<213> ORGANISM: Homo sapiens

<400> SEQUENCE: 72

Gln Ser Val Leu Thr Gln Pro Pro Ser Val Ser Gly Ala Pro Gly Gln
1 5 10 15

Arg Val Thr Ile Ser Cys Ser Gly Ser Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Ser Tyr Asp Arg Gly Thr
85 90 95

His Pro Ala Leu Leu Phe Gly Thr Gly Thr Lys Val Thr Val Leu Gly
100 105 110

<210> SEQ ID NO 73
<211> LENGTH: 115
<212> TYPE: PRT
<213> ORGANISM: Homo sapiens

<400> SEQUENCE: 73

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Lys Thr His Gly Ser His Asp Asn Trp Gly Gln Gly Thr Met Val Thr
100 105 110

Val Ser Ser
115

<210> SEQ ID NO 74
<211> LENGTH: 112
<212> TYPE: PRT
<213> ORGANISM: Homo sapiens

<400> SEQUENCE: 74

Gln Ser Val Leu Thr Gln Pro Pro Ser Val Ser Gly Ala Pro Gly Gln
1 5 10 15

Arg Val Thr Ile Ser Cys Ser Gly Ser Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Tyr Asn Asp Gln Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Ser Tyr Asp Arg Gly Thr
85 90 95

His Pro Ala Leu Leu Phe Gly Thr Gly Thr Lys Val Thr Val Leu Gly
100 105 110

<210> SEQ ID NO 75
<211> LENGTH: 115
<212> TYPE: PRT
<213> ORGANISM: Homo sapiens

<400> SEQUENCE: 75

Gln Val Gln Leu Val Gln Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Lys Ser Leu Arg Ala Glu Asp Thr Ala Val Tyr Tyr Cys
85 90 95

Lys Thr His Gly Ser His Asp Asn Trp Gly Gln Gly Thr Met Val Thr
100 105 110

Val Ser Ser
115

<210> SEQ ID NO 76
<211> LENGTH: 112
<212> TYPE: PRT
<213> ORGANISM: Homo sapiens

<400> SEQUENCE: 76

Gln Ser Val Leu Thr Gln Pro Pro Ser Val Ser Gly Ala Pro Gly Gln
1 5 10 15

Arg Val Thr Ile Ser Cys Ser Gly Ser Arg Ser Asn Ile Gly Ser Asn
20 25 30

```
Thr Val Lys Trp Tyr Gln Gln Leu Pro Gly Thr Ala Pro Lys Leu Leu
        35                  40                  45

Ile Tyr Gly Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110


<210> SEQ ID NO 77
<211> LENGTH: 6
<212> TYPE: PRT
<213> ORGANISM: Homo sapiens

<400> SEQUENCE: 77

Ser Gly Ser Tyr Asp Tyr
1               5


<210> SEQ ID NO 78
<211> LENGTH: 6
<212> TYPE: PRT
<213> ORGANISM: Homo sapiens

<400> SEQUENCE: 78

His Gly Ser His Asp Asn
1               5


<210> SEQ ID NO 79
<211> LENGTH: 6
<212> TYPE: PRT
<213> ORGANISM: Homo sapiens

<400> SEQUENCE: 79

His Gly Ser Tyr Asp Tyr
1               5


<210> SEQ ID NO 80
<211> LENGTH: 6
<212> TYPE: PRT
<213> ORGANISM: Homo sapiens

<400> SEQUENCE: 80

Arg Arg Arg Ser Asn Tyr
1               5


<210> SEQ ID NO 81
<211> LENGTH: 6
<212> TYPE: PRT
<213> ORGANISM: Homo sapiens

<400> SEQUENCE: 81

Ser Gly Ser Ile Asp Tyr
1               5


<210> SEQ ID NO 82
<211> LENGTH: 6
<212> TYPE: PRT
<213> ORGANISM: Homo sapiens

<400> SEQUENCE: 82

His Gly Ser His Asp Asp
```

1 5

<210> SEQ ID NO 83
<211> LENGTH: 6
<212> TYPE: PRT
<213> ORGANISM: Homo sapiens

<400> SEQUENCE: 83

His Gly Ser His Asp Asn
1 5

<210> SEQ ID NO 84
<211> LENGTH: 12
<212> TYPE: PRT
<213> ORGANISM: Homo sapiens

<400> SEQUENCE: 84

Thr Thr His Gly Ser His Asp Asn Trp Gly Gln Gly
1 5 10

<210> SEQ ID NO 85
<211> LENGTH: 12
<212> TYPE: PRT
<213> ORGANISM: Homo sapiens

<400> SEQUENCE: 85

Ala Lys His Gly Ser His Asp Asn Trp Gly Gln Gly
1 5 10

<210> SEQ ID NO 86
<211> LENGTH: 12
<212> TYPE: PRT
<213> ORGANISM: Homo sapiens

<400> SEQUENCE: 86

Thr Thr His Gly Ser His Asp Asn Trp Ser Gln Gly
1 5 10

<210> SEQ ID NO 87
<211> LENGTH: 12
<212> TYPE: PRT
<213> ORGANISM: Homo sapiens

<400> SEQUENCE: 87

Thr Thr His Gly Ser His Asp Thr Trp Gly Gln Gly
1 5 10

<210> SEQ ID NO 88
<211> LENGTH: 12
<212> TYPE: PRT
<213> ORGANISM: Homo sapiens

<400> SEQUENCE: 88

Lys Thr His Gly Ser His Asp Asn Trp Gly Gln Gly
1 5 10

<210> SEQ ID NO 89
<211> LENGTH: 12
<212> TYPE: PRT
<213> ORGANISM: Homo sapiens

<400> SEQUENCE: 89

Lys Thr His Gly Ser His Asp Asn Trp Gly His Gly
1 5 10

<210> SEQ ID NO 90
<211> LENGTH: 12
<212> TYPE: PRT
<213> ORGANISM: Homo sapiens

<400> SEQUENCE: 90

Thr Thr His Gly Ser His Asp Asn Trp Ser Gln Gly
1 5 10

<210> SEQ ID NO 91
<211> LENGTH: 12
<212> TYPE: PRT
<213> ORGANISM: Homo sapiens

<400> SEQUENCE: 91

Thr Thr His Arg Ser His Asn Asn Trp Gly Gln Gly
1 5 10

<210> SEQ ID NO 92
<211> LENGTH: 8
<212> TYPE: PRT
<213> ORGANISM: Homo sapiens

<400> SEQUENCE: 92

Thr Thr His Gly Ser His Asp Asn
1 5

<210> SEQ ID NO 93
<211> LENGTH: 8
<212> TYPE: PRT
<213> ORGANISM: Homo sapiens

<400> SEQUENCE: 93

Thr Thr His Gly Ser His Asp Thr
1 5

<210> SEQ ID NO 94
<211> LENGTH: 8
<212> TYPE: PRT
<213> ORGANISM: Homo sapiens

<400> SEQUENCE: 94

Thr Lys His Gly Ser His Asp Asn
1 5

<210> SEQ ID NO 95
<211> LENGTH: 8
<212> TYPE: PRT
<213> ORGANISM: Homo sapiens

<400> SEQUENCE: 95

Thr Thr Gln Gly Arg His Asp Asn
1 5

<210> SEQ ID NO 96
<211> LENGTH: 8
<212> TYPE: PRT
<213> ORGANISM: Homo sapiens

<400> SEQUENCE: 96

Lys Thr Arg Gly Arg His Asp Asn
1 5

<210> SEQ ID NO 97
<211> LENGTH: 8
<212> TYPE: PRT

<213> ORGANISM: Homo sapiens

<400> SEQUENCE: 97

Thr Thr His Gly Ser His Asp Lys
1 5

<210> SEQ ID NO 98
<211> LENGTH: 8
<212> TYPE: PRT
<213> ORGANISM: Homo sapiens

<400> SEQUENCE: 98

Thr Thr His Gly Ser His Asp Asp
1 5

<210> SEQ ID NO 99
<211> LENGTH: 8
<212> TYPE: PRT
<213> ORGANISM: Homo sapiens

<400> SEQUENCE: 99

Lys Thr His Gly Ser His Asp Asn
1 5

<210> SEQ ID NO 100
<211> LENGTH: 8
<212> TYPE: PRT
<213> ORGANISM: Homo sapiens

<400> SEQUENCE: 100

Lys Thr His Gly Ser His Asp Asn
1 5

<210> SEQ ID NO 101
<211> LENGTH: 8
<212> TYPE: PRT
<213> ORGANISM: Homo sapiens

<400> SEQUENCE: 101

Thr Thr His Gly Ser His Asp Asn
1 5

<210> SEQ ID NO 102
<211> LENGTH: 8
<212> TYPE: PRT
<213> ORGANISM: Homo sapiens

<400> SEQUENCE: 102

Thr Thr Ser Gly Ser Tyr Asp Tyr
1 5

<210> SEQ ID NO 103
<211> LENGTH: 8
<212> TYPE: PRT
<213> ORGANISM: Homo sapiens

<400> SEQUENCE: 103

Thr Thr His Gly Ser His Asp Asn
1 5

<210> SEQ ID NO 104
<211> LENGTH: 8
<212> TYPE: PRT
<213> ORGANISM: Homo sapiens

<400> SEQUENCE: 104

Thr Thr His Gly Ser Gln Asp Asn
1 5

<210> SEQ ID NO 105
<211> LENGTH: 8
<212> TYPE: PRT
<213> ORGANISM: Homo sapiens

<400> SEQUENCE: 105

Ala Thr His Gly Ser Gln Asp Asn
1 5

<210> SEQ ID NO 106
<211> LENGTH: 6
<212> TYPE: PRT
<213> ORGANISM: Homo sapiens

<400> SEQUENCE: 106

His Gly Ser Gln Asp Thr
1 5

<210> SEQ ID NO 107
<211> LENGTH: 6
<212> TYPE: PRT
<213> ORGANISM: Homo sapiens

<400> SEQUENCE: 107

Ser Gly Ser Tyr Asp Tyr
1 5

<210> SEQ ID NO 108
<211> LENGTH: 6
<212> TYPE: PRT
<213> ORGANISM: Homo sapiens

<400> SEQUENCE: 108

His Gly Ser Gln Asp Asn
1 5

<210> SEQ ID NO 109
<211> LENGTH: 9
<212> TYPE: PRT
<213> ORGANISM: Homo sapiens

<400> SEQUENCE: 109

Cys Lys Thr His Gly Ser His Asp Asn
1 5

<210> SEQ ID NO 110
<211> LENGTH: 12
<212> TYPE: PRT
<213> ORGANISM: Homo sapiens

<400> SEQUENCE: 110

Gln Ser Tyr Asp Ser Ser Leu Arg Gly Ser Arg Val
1 5 10

<210> SEQ ID NO 111
<211> LENGTH: 12
<212> TYPE: PRT
<213> ORGANISM: Homo sapiens

<400> SEQUENCE: 111

Gln Ser Tyr Asp Arg Gly Phe Thr Gly Ser Arg Val
1 5 10

<210> SEQ ID NO 112
<211> LENGTH: 12
<212> TYPE: PRT
<213> ORGANISM: Homo sapiens

<400> SEQUENCE: 112

Gln Ser Tyr Asp Ser Ser Leu Arg Gly Ser Arg Val
1 5 10

<210> SEQ ID NO 113
<211> LENGTH: 12
<212> TYPE: PRT
<213> ORGANISM: Homo sapiens

<400> SEQUENCE: 113

Gln Ser Tyr Asp Ser Ser Leu Thr Gly Ser Arg Val
1 5 10

<210> SEQ ID NO 114
<211> LENGTH: 12
<212> TYPE: PRT
<213> ORGANISM: Homo sapiens

<400> SEQUENCE: 114

Gln Ser Tyr Asp Ser Ser Leu Trp Gly Ser Arg Val
1 5 10

<210> SEQ ID NO 115
<211> LENGTH: 12
<212> TYPE: PRT
<213> ORGANISM: Homo sapiens

<400> SEQUENCE: 115

Gln Thr Tyr Asp Ile Ser Glu Ser Gly Ser Arg Val
1 5 10

<210> SEQ ID NO 116
<211> LENGTH: 12
<212> TYPE: PRT
<213> ORGANISM: Homo sapiens

<400> SEQUENCE: 116

Gln Ser Tyr Asp Arg Gly Phe Thr Gly Ser Arg Val
1 5 10

<210> SEQ ID NO 117
<211> LENGTH: 12
<212> TYPE: PRT
<213> ORGANISM: Homo sapiens

<400> SEQUENCE: 117

Gln Thr Tyr Asp Arg Gly Phe Thr Gly Ser Arg Val
1 5 10

<210> SEQ ID NO 118
<211> LENGTH: 12
<212> TYPE: PRT
<213> ORGANISM: Homo sapiens

<400> SEQUENCE: 118

Gln Thr Tyr Asp Lys Gly Phe Thr Gly Ser Ser Val
1 5 10

<210> SEQ ID NO 119

<211> LENGTH: 12
<212> TYPE: PRT
<213> ORGANISM: Homo sapiens

<400> SEQUENCE: 119

Gln Ser Tyr Asp Arg Arg Phe Thr Gly Ser Arg Val
1 5 10

<210> SEQ ID NO 120
<211> LENGTH: 12
<212> TYPE: PRT
<213> ORGANISM: Homo sapiens

<400> SEQUENCE: 120

Gln Ser Tyr Asp Trp Asn Phe Thr Gly Ser Arg Val
1 5 10

<210> SEQ ID NO 121
<211> LENGTH: 12
<212> TYPE: PRT
<213> ORGANISM: Homo sapiens

<400> SEQUENCE: 121

Gln Ser Tyr Asp Arg Gly Phe Thr Gly Ser Arg Val
1 5 10

<210> SEQ ID NO 122
<211> LENGTH: 12
<212> TYPE: PRT
<213> ORGANISM: Homo sapiens

<400> SEQUENCE: 122

Gln Ser Tyr Asp Asn Gly Phe Thr Gly Ser Arg Val
1 5 10

<210> SEQ ID NO 123
<211> LENGTH: 12
<212> TYPE: PRT
<213> ORGANISM: Homo sapiens

<400> SEQUENCE: 123

Gln Ser Tyr Asp Asn Ala Val Thr Ala Ser Lys Val
1 5 10

<210> SEQ ID NO 124
<211> LENGTH: 12
<212> TYPE: PRT
<213> ORGANISM: Homo sapiens

<400> SEQUENCE: 124

Gln Ser Tyr Asp Arg Gly Phe Thr Gly Ser Arg Val
1 5 10

<210> SEQ ID NO 125
<211> LENGTH: 12
<212> TYPE: PRT
<213> ORGANISM: Homo sapiens

<400> SEQUENCE: 125

Gln Ser Tyr Asp Ser Ser Leu Trp Gly Thr Arg Val
1 5 10

<210> SEQ ID NO 126
<211> LENGTH: 12
<212> TYPE: PRT
<213> ORGANISM: Homo sapiens

<400> SEQUENCE: 126

Gln Ser Tyr Asp Arg Asp Phe Thr Gly Ser Arg Val
1 5 10

<210> SEQ ID NO 127
<211> LENGTH: 12
<212> TYPE: PRT
<213> ORGANISM: Homo sapiens

<400> SEQUENCE: 127

Gln Ser Tyr Glu Arg Gly Phe Thr Gly Ser Met Val
1 5 10

<210> SEQ ID NO 128
<211> LENGTH: 12
<212> TYPE: PRT
<213> ORGANISM: Homo sapiens

<400> SEQUENCE: 128

Gln Ser Tyr Asp Asn Gly Phe Thr Gly Ala Arg Val
1 5 10

<210> SEQ ID NO 129
<211> LENGTH: 12
<212> TYPE: PRT
<213> ORGANISM: Homo sapiens

<400> SEQUENCE: 129

Gln Ser Tyr Asp Arg Arg Phe Thr Gly Ser Arg Val
1 5 10

<210> SEQ ID NO 130
<211> LENGTH: 12
<212> TYPE: PRT
<213> ORGANISM: Homo sapiens

<400> SEQUENCE: 130

Gln Thr Tyr Asp Lys Gly Phe Thr Gly Ser Ser Val
1 5 10

<210> SEQ ID NO 131
<211> LENGTH: 12
<212> TYPE: PRT
<213> ORGANISM: Homo sapiens

<400> SEQUENCE: 131

Gln Ser Tyr Asp Arg Asp Phe Thr Gly Thr Arg Val
1 5 10

<210> SEQ ID NO 132
<211> LENGTH: 12
<212> TYPE: PRT
<213> ORGANISM: Homo sapiens

<400> SEQUENCE: 132

Gln Ser Tyr Asp Arg Gly Phe Tyr Gly Ser Met Val
1 5 10

<210> SEQ ID NO 133
<211> LENGTH: 12
<212> TYPE: PRT
<213> ORGANISM: Homo sapiens

<400> SEQUENCE: 133

Gln Thr Tyr Asp Lys Gly Phe Thr Gly Ser Ser Val
1 5 10

<210> SEQ ID NO 134
<211> LENGTH: 12
<212> TYPE: PRT
<213> ORGANISM: Homo sapiens

<400> SEQUENCE: 134

Gln Ser Tyr Asp Arg Gly Phe Thr Gly Ala Arg Val
1 5 10

<210> SEQ ID NO 135
<211> LENGTH: 12
<212> TYPE: PRT
<213> ORGANISM: Homo sapiens

<400> SEQUENCE: 135

Gln Ser Tyr Glu Arg Gly Phe Thr Gly Ala Arg Val
1 5 10

<210> SEQ ID NO 136
<211> LENGTH: 13
<212> TYPE: PRT
<213> ORGANISM: Homo sapiens

<400> SEQUENCE: 136

Gln Ser Tyr Asp Arg Gly Phe Thr Gly Ser Arg Val Phe
1 5 10

<210> SEQ ID NO 137
<211> LENGTH: 13
<212> TYPE: PRT
<213> ORGANISM: Homo sapiens

<400> SEQUENCE: 137

Gln Ser Tyr Asp Arg Gly Phe Thr Gly Phe Lys Val Phe
1 5 10

<210> SEQ ID NO 138
<211> LENGTH: 13
<212> TYPE: PRT
<213> ORGANISM: Homo sapiens

<400> SEQUENCE: 138

Gln Ser Tyr Asp Arg Gly Phe Val Ser Ala Tyr Val Phe
1 5 10

<210> SEQ ID NO 139
<211> LENGTH: 13
<212> TYPE: PRT
<213> ORGANISM: Homo sapiens

<400> SEQUENCE: 139

Gln Ser Tyr Asp Arg Gly Leu Thr Val Thr Lys Val Phe
1 5 10

<210> SEQ ID NO 140
<211> LENGTH: 13
<212> TYPE: PRT
<213> ORGANISM: Homo sapiens

<400> SEQUENCE: 140

Gln Ser Tyr Asp Arg Gly Tyr Thr Ala Ser Arg Val Phe
1 5 10

<210> SEQ ID NO 141
<211> LENGTH: 13
<212> TYPE: PRT
<213> ORGANISM: Homo sapiens

<400> SEQUENCE: 141

Gln Ser Tyr Asp Arg Gly Phe Thr Gly Ser Lys Val Phe
1               5                   10

<210> SEQ ID NO 142
<211> LENGTH: 13
<212> TYPE: PRT
<213> ORGANISM: Homo sapiens

<400> SEQUENCE: 142

Gln Ser Tyr Asp Arg Gly Leu Thr Gly Phe Arg Val Phe
1               5                   10

<210> SEQ ID NO 143
<211> LENGTH: 13
<212> TYPE: PRT
<213> ORGANISM: Homo sapiens

<400> SEQUENCE: 143

Gln Ser Tyr Asp Arg Gly Phe Thr Gly Tyr Lys Val Phe
1               5                   10

<210> SEQ ID NO 144
<211> LENGTH: 13
<212> TYPE: PRT
<213> ORGANISM: Homo sapiens

<400> SEQUENCE: 144

Gln Ser Tyr Asp Arg Gly Leu Thr Gly Tyr Arg Leu Phe
1               5                   10

<210> SEQ ID NO 145
<211> LENGTH: 13
<212> TYPE: PRT
<213> ORGANISM: Homo sapiens

<400> SEQUENCE: 145

Gln Ser Tyr Asp Arg Gly Phe Thr Asp Tyr Lys Val Phe
1               5                   10

<210> SEQ ID NO 146
<211> LENGTH: 13
<212> TYPE: PRT
<213> ORGANISM: Homo sapiens

<400> SEQUENCE: 146

Gln Ser Tyr Asp Arg Gly Phe Thr Gly Pro Arg Leu Phe
1               5                   10

<210> SEQ ID NO 147
<211> LENGTH: 13
<212> TYPE: PRT
<213> ORGANISM: Homo sapiens

<400> SEQUENCE: 147

Gln Ser Tyr Asp Arg Gly Leu Thr Gly Ser Arg Val Phe
1               5                   10

<210> SEQ ID NO 148
<211> LENGTH: 13

<212> TYPE: PRT
<213> ORGANISM: Homo sapiens

<400> SEQUENCE: 148

Gln Ser Tyr Asp Arg Gly Phe Thr Gly Ala Arg Val Trp
1 5 10

<210> SEQ ID NO 149
<211> LENGTH: 13
<212> TYPE: PRT
<213> ORGANISM: Homo sapiens

<400> SEQUENCE: 149

Gln Ser Tyr Asp Arg Gly Phe Thr Gly Tyr Arg Val Phe
1 5 10

<210> SEQ ID NO 150
<211> LENGTH: 13
<212> TYPE: PRT
<213> ORGANISM: Homo sapiens

<400> SEQUENCE: 150

Gln Ser Tyr Asp Arg Gly Phe Thr Gly Pro Arg Val Phe
1 5 10

<210> SEQ ID NO 151
<211> LENGTH: 13
<212> TYPE: PRT
<213> ORGANISM: Homo sapiens

<400> SEQUENCE: 151

Gln Ser Tyr Asp Arg Gly Met Thr Ser Ser Arg Val Phe
1 5 10

<210> SEQ ID NO 152
<211> LENGTH: 13
<212> TYPE: PRT
<213> ORGANISM: Homo sapiens

<400> SEQUENCE: 152

Gln Ser Tyr Asp Arg Asp Ser Thr Gly Ser Arg Val Phe
1 5 10

<210> SEQ ID NO 153
<211> LENGTH: 13
<212> TYPE: PRT
<213> ORGANISM: Homo sapiens

<400> SEQUENCE: 153

Gln Ser Tyr Asp Ser Ser Leu Arg Gly Ser Arg Val Phe
1 5 10

<210> SEQ ID NO 154
<211> LENGTH: 13
<212> TYPE: PRT
<213> ORGANISM: Homo sapiens

<400> SEQUENCE: 154

His Ser Tyr Asp Ser Asp Phe Thr Gly Ser Arg Val Phe
1 5 10

<210> SEQ ID NO 155
<211> LENGTH: 13
<212> TYPE: PRT
<213> ORGANISM: Homo sapiens

<400> SEQUENCE: 155

His Ser Ser Glu Ser Gly Phe Thr Gly Ser Arg Val Phe
1 5 10

<210> SEQ ID NO 156
<211> LENGTH: 13
<212> TYPE: PRT
<213> ORGANISM: Homo sapiens

<400> SEQUENCE: 156

His Ser Tyr Asp Asn Arg Phe Thr Gly Ser Arg Val Phe
1 5 10

<210> SEQ ID NO 157
<211> LENGTH: 13
<212> TYPE: PRT
<213> ORGANISM: Homo sapiens

<400> SEQUENCE: 157

His Ser Tyr Asp Ser Arg Phe Thr Gly Ser Arg Val Phe
1 5 10

<210> SEQ ID NO 158
<211> LENGTH: 13
<212> TYPE: PRT
<213> ORGANISM: Homo sapiens

<400> SEQUENCE: 158

Gln Ser Tyr Asp Ser Glu Phe Thr Gly Ser Arg Val Phe
1 5 10

<210> SEQ ID NO 159
<211> LENGTH: 13
<212> TYPE: PRT
<213> ORGANISM: Homo sapiens

<400> SEQUENCE: 159

Gln Ser Tyr Asp Thr Gly Phe Thr Gly Ser Arg Val Phe
1 5 10

<210> SEQ ID NO 160
<211> LENGTH: 13
<212> TYPE: PRT
<213> ORGANISM: Homo sapiens

<400> SEQUENCE: 160

His Ser Tyr Asp Ser Gly Phe Thr Gly Ser Arg Val Phe
1 5 10

<210> SEQ ID NO 161
<211> LENGTH: 13
<212> TYPE: PRT
<213> ORGANISM: Homo sapiens

<400> SEQUENCE: 161

Gln Ser Tyr Asp Thr Gly Phe Thr Gly Ser Arg Val Phe
1 5 10

<210> SEQ ID NO 162
<211> LENGTH: 13
<212> TYPE: PRT
<213> ORGANISM: Homo sapiens

<400> SEQUENCE: 162

His Ser Tyr Asp Thr Lys Phe Thr Gly Ser Arg Val Phe

-continued 1 5 10

<210> SEQ ID NO 163
<211> LENGTH: 13
<212> TYPE: PRT
<213> ORGANISM: Homo sapiens

<400> SEQUENCE: 163

His Ser Ser Asp Ser Gly Phe Thr Gly Ser Arg Val Phe
1 5 10

<210> SEQ ID NO 164
<211> LENGTH: 13
<212> TYPE: PRT
<213> ORGANISM: Homo sapiens

<400> SEQUENCE: 164

Gln Ser Tyr Asp Ser Asp Phe Thr Gly Ser Arg Val Phe
1 5 10

<210> SEQ ID NO 165
<211> LENGTH: 13
<212> TYPE: PRT
<213> ORGANISM: Homo sapiens

<400> SEQUENCE: 165

His Ser Tyr Glu Ser Gly Phe Thr Gly Ser Arg Val Phe
1 5 10

<210> SEQ ID NO 166
<211> LENGTH: 13
<212> TYPE: PRT
<213> ORGANISM: Homo sapiens

<400> SEQUENCE: 166

Gln Ser Tyr Asp Ala Pro Trp Ser Gly Ser Arg Val Phe
1 5 10

<210> SEQ ID NO 167
<211> LENGTH: 13
<212> TYPE: PRT
<213> ORGANISM: Homo sapiens

<400> SEQUENCE: 167

Gln Ser Tyr Asp Ser Asp Phe Thr Gly Ser Lys Val Phe
1 5 10

<210> SEQ ID NO 168
<211> LENGTH: 13
<212> TYPE: PRT
<213> ORGANISM: Homo sapiens

<400> SEQUENCE: 168

His Thr Asn Asp Ser Gly Phe Thr Gly Ser Arg Val Phe
1 5 10

<210> SEQ ID NO 169
<211> LENGTH: 13
<212> TYPE: PRT
<213> ORGANISM: Homo sapiens

<400> SEQUENCE: 169

His Ser Tyr Asp Thr Arg Phe Thr Gly Ser Arg Val Phe
1 5 10

<210> SEQ ID NO 170
<211> LENGTH: 13
<212> TYPE: PRT
<213> ORGANISM: Homo sapiens

<400> SEQUENCE: 170

Gln Ser Tyr Asp Met Arg Phe Thr Gly Ser Arg Val Phe
1 5 10

<210> SEQ ID NO 171
<211> LENGTH: 13
<212> TYPE: PRT
<213> ORGANISM: Homo sapiens

<400> SEQUENCE: 171

His Ser Ser Asp Ser Asp Ser Thr Gly Ser Arg Val Phe
1 5 10

<210> SEQ ID NO 172
<211> LENGTH: 13
<212> TYPE: PRT
<213> ORGANISM: Homo sapiens

<400> SEQUENCE: 172

Gln Ser Tyr Asn Thr Asp Phe Thr Gly Ser Arg Val Phe
1 5 10

<210> SEQ ID NO 173
<211> LENGTH: 13
<212> TYPE: PRT
<213> ORGANISM: Homo sapiens

<400> SEQUENCE: 173

Gln Ser Tyr Asp Ser Gly Phe Thr Gly Ser Arg Val Phe
1 5 10

<210> SEQ ID NO 174
<211> LENGTH: 13
<212> TYPE: PRT
<213> ORGANISM: Homo sapiens

<400> SEQUENCE: 174

His Ser Tyr Asp Met Gly Phe Thr Gly Ser Arg Val Phe
1 5 10

<210> SEQ ID NO 175
<211> LENGTH: 13
<212> TYPE: PRT
<213> ORGANISM: Homo sapiens

<400> SEQUENCE: 175

His Ser Tyr Asp Asn Gly Phe Thr Gly Ser Arg Val Phe
1 5 10

<210> SEQ ID NO 176
<211> LENGTH: 13
<212> TYPE: PRT
<213> ORGANISM: Homo sapiens

<400> SEQUENCE: 176

His Ser His Asp Arg Asp Phe Thr Gly Ser Arg Val Phe
1 5 10

<210> SEQ ID NO 177
<211> LENGTH: 12
<212> TYPE: PRT

<213> ORGANISM: Homo sapiens

<400> SEQUENCE: 177

Gln Ser Tyr Asp Ser Ser Leu Arg Gly Ser Arg Val
1 5 10

<210> SEQ ID NO 178
<211> LENGTH: 13
<212> TYPE: PRT
<213> ORGANISM: Homo sapiens

<400> SEQUENCE: 178

Gln Ser Tyr Asp Arg Gly Ile His Gly Ser Arg Val Phe
1 5 10

<210> SEQ ID NO 179
<211> LENGTH: 13
<212> TYPE: PRT
<213> ORGANISM: Homo sapiens

<400> SEQUENCE: 179

Gln Ser Tyr Asp Ser Gly Phe Pro Gly Ser Arg Val Phe
1 5 10

<210> SEQ ID NO 180
<211> LENGTH: 13
<212> TYPE: PRT
<213> ORGANISM: Homo sapiens

<400> SEQUENCE: 180

Gln Ser Tyr Asp Ile Gly Ser Thr Gly Ser Arg Val Phe
1 5 10

<210> SEQ ID NO 181
<211> LENGTH: 13
<212> TYPE: PRT
<213> ORGANISM: Homo sapiens

<400> SEQUENCE: 181

Gln Ser Tyr Asp Ser Gly Leu Thr Gly Ser Arg Val Phe
1 5 10

<210> SEQ ID NO 182
<211> LENGTH: 13
<212> TYPE: PRT
<213> ORGANISM: Homo sapiens

<400> SEQUENCE: 182

Gln Ser Tyr Asp Ile Gly Met Thr Gly Ser Arg Val Phe
1 5 10

<210> SEQ ID NO 183
<211> LENGTH: 13
<212> TYPE: PRT
<213> ORGANISM: Homo sapiens

<400> SEQUENCE: 183

Gln Ser Tyr Asp Ile Gly Leu Thr Gly Ser Arg Val Phe
1 5 10

<210> SEQ ID NO 184
<211> LENGTH: 13
<212> TYPE: PRT
<213> ORGANISM: Homo sapiens

<400> SEQUENCE: 184

-continued

Gln Ser Tyr Asp Ser Gly Val Thr Gly Ser Arg Val Phe
1 5 10

<210> SEQ ID NO 185
<211> LENGTH: 13
<212> TYPE: PRT
<213> ORGANISM: Homo sapiens

<400> SEQUENCE: 185

Gln Ser Tyr Asp Arg Gly Leu Thr Ala Ser Arg Val Phe
1 5 10

<210> SEQ ID NO 186
<211> LENGTH: 13
<212> TYPE: PRT
<213> ORGANISM: Homo sapiens

<400> SEQUENCE: 186

Gln Ser Tyr Asp Thr Gly Leu Thr Gly Ser Arg Val Phe
1 5 10

<210> SEQ ID NO 187
<211> LENGTH: 13
<212> TYPE: PRT
<213> ORGANISM: Homo sapiens

<400> SEQUENCE: 187

Gln Ser Tyr Asp Thr Ala Leu Thr Gly Ser Arg Val Phe
1 5 10

<210> SEQ ID NO 188
<211> LENGTH: 13
<212> TYPE: PRT
<213> ORGANISM: Homo sapiens

<400> SEQUENCE: 188

Gln Ser Tyr Asp Ile Arg Phe Thr Gly Ser Arg Val Phe
1 5 10

<210> SEQ ID NO 189
<211> LENGTH: 13
<212> TYPE: PRT
<213> ORGANISM: Homo sapiens

<400> SEQUENCE: 189

Gln Ser Tyr Asp Ile Arg Ser Thr Gly Ser Arg Val Phe
1 5 10

<210> SEQ ID NO 190
<211> LENGTH: 13
<212> TYPE: PRT
<213> ORGANISM: Homo sapiens

<400> SEQUENCE: 190

Gln Ser Tyr Asp Asn Arg Leu Thr Gly Ser Arg Val Phe
1 5 10

<210> SEQ ID NO 191
<211> LENGTH: 13
<212> TYPE: PRT
<213> ORGANISM: Homo sapiens

<400> SEQUENCE: 191

Gln Ser Tyr Glu Thr Ser Phe Thr Gly Ser Arg Val Phe
1 5 10

<210> SEQ ID NO 192
<211> LENGTH: 13
<212> TYPE: PRT
<213> ORGANISM: Homo sapiens

<400> SEQUENCE: 192

Gln Ser Tyr Asp Ser Ser Ser Thr Gly Ser Arg Val Phe
1 5 10

<210> SEQ ID NO 193
<211> LENGTH: 13
<212> TYPE: PRT
<213> ORGANISM: Homo sapiens

<400> SEQUENCE: 193

Gln Ser Tyr Asp Ser Gly Phe Thr Ala Ser Arg Val Phe
1 5 10

<210> SEQ ID NO 194
<211> LENGTH: 13
<212> TYPE: PRT
<213> ORGANISM: Homo sapiens

<400> SEQUENCE: 194

Gln Thr Tyr Asp Lys Gly Phe Thr Gly Ser Ser Val Phe
1 5 10

<210> SEQ ID NO 195
<211> LENGTH: 13
<212> TYPE: PRT
<213> ORGANISM: Homo sapiens

<400> SEQUENCE: 195

Gln Ser Tyr Asp Asn Gly Phe Thr Gly Ser Arg Val Phe
1 5 10

<210> SEQ ID NO 196
<211> LENGTH: 13
<212> TYPE: PRT
<213> ORGANISM: Homo sapiens

<400> SEQUENCE: 196

Gln Ser Tyr Asp Thr Gly Phe Thr Lys Ser Arg Val Phe
1 5 10

<210> SEQ ID NO 197
<211> LENGTH: 13
<212> TYPE: PRT
<213> ORGANISM: Homo sapiens

<400> SEQUENCE: 197

Gln Ser Tyr Asp Ser Asp Val Thr Gly Ser Arg Val Phe
1 5 10

<210> SEQ ID NO 198
<211> LENGTH: 13
<212> TYPE: PRT
<213> ORGANISM: Homo sapiens

<400> SEQUENCE: 198

Gln Ser Tyr Asp Ala Gly Phe Thr Gly Ser Arg Val Phe
1 5 10

<210> SEQ ID NO 199

<211> LENGTH: 12
<212> TYPE: PRT
<213> ORGANISM: Homo sapiens

<400> SEQUENCE: 199

Gln Ser Tyr Asp Arg Gly Thr His Pro Ser Met Leu
1 5 10

<210> SEQ ID NO 200
<211> LENGTH: 12
<212> TYPE: PRT
<213> ORGANISM: Homo sapiens

<400> SEQUENCE: 200

Gln Ser Tyr Asp Arg Gly Thr Thr Pro Arg Pro Met
1 5 10

<210> SEQ ID NO 201
<211> LENGTH: 12
<212> TYPE: PRT
<213> ORGANISM: Homo sapiens

<400> SEQUENCE: 201

Gln Ser Tyr Asp Arg Gly Arg Asn Pro Ala Leu Thr
1 5 10

<210> SEQ ID NO 202
<211> LENGTH: 12
<212> TYPE: PRT
<213> ORGANISM: Homo sapiens

<400> SEQUENCE: 202

Gln Ser Tyr Asp Arg Gly Thr His Pro Trp Leu His
1 5 10

<210> SEQ ID NO 203
<211> LENGTH: 12
<212> TYPE: PRT
<213> ORGANISM: Homo sapiens

<400> SEQUENCE: 203

Gln Ser Tyr Asp Arg Gly Asn Ser Pro Ala Thr Val
1 5 10

<210> SEQ ID NO 204
<211> LENGTH: 12
<212> TYPE: PRT
<213> ORGANISM: Homo sapiens

<400> SEQUENCE: 204

Gln Ser Tyr Asp Arg Gly Thr Phe Pro Ser Pro Gln
1 5 10

<210> SEQ ID NO 205
<211> LENGTH: 12
<212> TYPE: PRT
<213> ORGANISM: Homo sapiens

<400> SEQUENCE: 205

Gln Ser Tyr Asp Arg Gly Leu Asn Pro Ser Ala Thr
1 5 10

<210> SEQ ID NO 206
<211> LENGTH: 12
<212> TYPE: PRT
<213> ORGANISM: Homo sapiens

<400> SEQUENCE: 206

Gln Ser Tyr Asp Arg Gly Lys Ser Asn Lys Met Leu
1 5 10

<210> SEQ ID NO 207
<211> LENGTH: 12
<212> TYPE: PRT
<213> ORGANISM: Homo sapiens

<400> SEQUENCE: 207

Gln Ser Tyr Asp Arg Gly His Thr Ala His Leu Tyr
1 5 10

<210> SEQ ID NO 208
<211> LENGTH: 12
<212> TYPE: PRT
<213> ORGANISM: Homo sapiens

<400> SEQUENCE: 208

Gln Ser Tyr Asp Arg Gly Gln Thr Pro Ser Ile Thr
1 5 10

<210> SEQ ID NO 209
<211> LENGTH: 12
<212> TYPE: PRT
<213> ORGANISM: Homo sapiens

<400> SEQUENCE: 209

Gln Ser Tyr Asp Arg Gly Tyr Pro Arg Asn Ile Leu
1 5 10

<210> SEQ ID NO 210
<211> LENGTH: 12
<212> TYPE: PRT
<213> ORGANISM: Homo sapiens

<400> SEQUENCE: 210

Gln Ser Tyr Asp Arg Gly Ile Thr Pro Gly Leu Ala
1 5 10

<210> SEQ ID NO 211
<211> LENGTH: 12
<212> TYPE: PRT
<213> ORGANISM: Homo sapiens

<400> SEQUENCE: 211

Gln Ser Tyr Asp Arg Gly Gln Pro His Ala Val Leu
1 5 10

<210> SEQ ID NO 212
<211> LENGTH: 12
<212> TYPE: PRT
<213> ORGANISM: Homo sapiens

<400> SEQUENCE: 212

Gln Ser Tyr Asp Arg Gly Asn Ser Pro Ile Pro Thr
1 5 10

<210> SEQ ID NO 213
<211> LENGTH: 12
<212> TYPE: PRT
<213> ORGANISM: Homo sapiens

<400> SEQUENCE: 213

Gln Ser Tyr Asp Arg Gly Thr Pro Asn Asn Ser Phe
1 5 10

<210> SEQ ID NO 214
<211> LENGTH: 12
<212> TYPE: PRT
<213> ORGANISM: Homo sapiens

<400> SEQUENCE: 214

Gln Ser Tyr Asp Ser Gly Val Asp Pro Gly Pro Tyr
1 5 10

<210> SEQ ID NO 215
<211> LENGTH: 12
<212> TYPE: PRT
<213> ORGANISM: Homo sapiens

<400> SEQUENCE: 215

Gln Ser Tyr Asp Arg Gly Arg Pro Arg His Ala Leu
1 5 10

<210> SEQ ID NO 216
<211> LENGTH: 12
<212> TYPE: PRT
<213> ORGANISM: Homo sapiens

<400> SEQUENCE: 216

Gln Ser Tyr Asp Arg Gly Pro Tyr His Pro Ile Arg
1 5 10

<210> SEQ ID NO 217
<211> LENGTH: 12
<212> TYPE: PRT
<213> ORGANISM: Homo sapiens

<400> SEQUENCE: 217

Gln Ser Tyr Asp Arg Gly Pro His Thr Gln Pro Thr
1 5 10

<210> SEQ ID NO 218
<211> LENGTH: 12
<212> TYPE: PRT
<213> ORGANISM: Homo sapiens

<400> SEQUENCE: 218

Gln Ser Tyr Asp Arg Gly His Asn Asn Phe Ser Pro
1 5 10

<210> SEQ ID NO 219
<211> LENGTH: 12
<212> TYPE: PRT
<213> ORGANISM: Homo sapiens

<400> SEQUENCE: 219

Gln Ser Tyr Asp Arg Gly Pro Thr His Leu Pro His
1 5 10

<210> SEQ ID NO 220
<211> LENGTH: 12
<212> TYPE: PRT
<213> ORGANISM: Homo sapiens

<400> SEQUENCE: 220

Gln Ser Tyr Asp Arg Gly Thr Pro Ser Tyr Pro Thr
1 5 10

<210> SEQ ID NO 221
<211> LENGTH: 12
<212> TYPE: PRT
<213> ORGANISM: Homo sapiens

<400> SEQUENCE: 221

Gln Ser Tyr Asp Ser Gly Thr Ser Asn Leu Leu Pro
1 5 10

<210> SEQ ID NO 222
<211> LENGTH: 12
<212> TYPE: PRT
<213> ORGANISM: Homo sapiens

<400> SEQUENCE: 222

Gln Ser Tyr Asp Arg Gly Asp Ser Asn His Asp Leu
1 5 10

<210> SEQ ID NO 223
<211> LENGTH: 12
<212> TYPE: PRT
<213> ORGANISM: Homo sapiens

<400> SEQUENCE: 223

Gln Ser Tyr Asp Arg Gly Leu Pro Arg Leu Thr His
1 5 10

<210> SEQ ID NO 224
<211> LENGTH: 12
<212> TYPE: PRT
<213> ORGANISM: Homo sapiens

<400> SEQUENCE: 224

Gln Ser Tyr Asp Arg Gly Ile Pro Thr Ser Tyr Leu
1 5 10

<210> SEQ ID NO 225
<211> LENGTH: 12
<212> TYPE: PRT
<213> ORGANISM: Homo sapiens

<400> SEQUENCE: 225

Gln Ser Tyr Asp Arg Gly Leu Arg Val Gln Ala Pro
1 5 10

<210> SEQ ID NO 226
<211> LENGTH: 12
<212> TYPE: PRT
<213> ORGANISM: Homo sapiens

<400> SEQUENCE: 226

Gln Ser Tyr Asp Arg Gly Leu Ser Asp Ser Pro Leu
1 5 10

<210> SEQ ID NO 227
<211> LENGTH: 12
<212> TYPE: PRT
<213> ORGANISM: Homo sapiens

<400> SEQUENCE: 227

Gln Ser Tyr Asp Ser Gly Ser Leu Arg Arg Ile Leu
1 5 10

<210> SEQ ID NO 228
<211> LENGTH: 12

<212> TYPE: PRT
<213> ORGANISM: Homo sapiens

<400> SEQUENCE: 228

Gln Ser Tyr Asp Arg Gly Pro Ala Arg Thr Ser Pro
1 5 10

<210> SEQ ID NO 229
<211> LENGTH: 12
<212> TYPE: PRT
<213> ORGANISM: Homo sapiens

<400> SEQUENCE: 229

Gln Ser Tyr Asp Arg Gly Arg Ala Ala His Pro Gln
1 5 10

<210> SEQ ID NO 230
<211> LENGTH: 12
<212> TYPE: PRT
<213> ORGANISM: Homo sapiens

<400> SEQUENCE: 230

Gln Ser Tyr Asp Arg Gly Thr Gln Pro Ala Asx Ile
1 5 10

<210> SEQ ID NO 231
<211> LENGTH: 12
<212> TYPE: PRT
<213> ORGANISM: Homo sapiens

<400> SEQUENCE: 231

Gln Ser Tyr Asp Arg Gly Thr His Pro Thr Met Ile
1 5 10

<210> SEQ ID NO 232
<211> LENGTH: 12
<212> TYPE: PRT
<213> ORGANISM: Homo sapiens

<400> SEQUENCE: 232

Gln Ser Tyr Asp Arg Gly Arg Ile Pro Ala Asx Thr
1 5 10

<210> SEQ ID NO 233
<211> LENGTH: 12
<212> TYPE: PRT
<213> ORGANISM: Homo sapiens

<400> SEQUENCE: 233

Gln Ser Tyr Asp Arg Gly Thr His Pro Val Pro Ala
1 5 10

<210> SEQ ID NO 234
<211> LENGTH: 12
<212> TYPE: PRT
<213> ORGANISM: Homo sapiens

<400> SEQUENCE: 234

Gln Ser Tyr Asp Arg Gly Ser Asx Pro Ile Pro Ala
1 5 10

<210> SEQ ID NO 235
<211> LENGTH: 12
<212> TYPE: PRT
<213> ORGANISM: Homo sapiens

<400> SEQUENCE: 235

Gln Ser Tyr Asp Arg Gly Thr His Pro Val Pro Ala
1 5 10

<210> SEQ ID NO 236
<211> LENGTH: 12
<212> TYPE: PRT
<213> ORGANISM: Homo sapiens

<400> SEQUENCE: 236

Gln Ser Tyr Asp Arg Gly Thr His Pro Thr Met Tyr
1 5 10

<210> SEQ ID NO 237
<211> LENGTH: 12
<212> TYPE: PRT
<213> ORGANISM: Homo sapiens

<400> SEQUENCE: 237

Gln Ser Tyr Asp Arg Gly His His Tyr Thr Thr Phe
1 5 10

<210> SEQ ID NO 238
<211> LENGTH: 12
<212> TYPE: PRT
<213> ORGANISM: Homo sapiens

<400> SEQUENCE: 238

Gln Ser Tyr Asp Arg Gly Ser His Pro Ala Ala Glu
1 5 10

<210> SEQ ID NO 239
<211> LENGTH: 12
<212> TYPE: PRT
<213> ORGANISM: Homo sapiens

<400> SEQUENCE: 239

Gln Ser Tyr Asp Arg Gly Thr Ile Pro Ser Ile Glu
1 5 10

<210> SEQ ID NO 240
<211> LENGTH: 12
<212> TYPE: PRT
<213> ORGANISM: Homo sapiens

<400> SEQUENCE: 240

Gln Ser Tyr Asp Arg Gly Ser Ser Pro Ala Ile Met
1 5 10

<210> SEQ ID NO 241
<211> LENGTH: 12
<212> TYPE: PRT
<213> ORGANISM: Homo sapiens

<400> SEQUENCE: 241

Gln Ser Tyr Asp Arg Gly Ile Trp Pro Asn Leu Asn
1 5 10

<210> SEQ ID NO 242
<211> LENGTH: 12
<212> TYPE: PRT
<213> ORGANISM: Homo sapiens

<400> SEQUENCE: 242

Gln Ser Tyr Asp Arg Gly Thr His Pro Asn Leu Asn 1 5 10

<210> SEQ ID NO 243
<211> LENGTH: 12
<212> TYPE: PRT
<213> ORGANISM: Homo sapiens

<400> SEQUENCE: 243

Gln Ser Tyr Asp Arg Gly Thr His Pro Ser Ile Ser
1 5 10

<210> SEQ ID NO 244
<211> LENGTH: 12
<212> TYPE: PRT
<213> ORGANISM: Homo sapiens

<400> SEQUENCE: 244

Gln Ser Tyr Asp Arg Gly Ser Ala Pro Met Ile Asn
1 5 10

<210> SEQ ID NO 245
<211> LENGTH: 12
<212> TYPE: PRT
<213> ORGANISM: Homo sapiens

<400> SEQUENCE: 245

Gln Ser Tyr Asp Arg Gly His His Pro Ala Met Ser
1 5 10

<210> SEQ ID NO 246
<211> LENGTH: 12
<212> TYPE: PRT
<213> ORGANISM: Homo sapiens

<400> SEQUENCE: 246

Gln Ser Tyr Asp Arg Gly Thr His Pro Ser Ile Thr
1 5 10

<210> SEQ ID NO 247
<211> LENGTH: 12
<212> TYPE: PRT
<213> ORGANISM: Homo sapiens

<400> SEQUENCE: 247

Gln Ser Tyr Asp Arg Gly Thr Asp Pro Ala Ile Val
1 5 10

<210> SEQ ID NO 248
<211> LENGTH: 12
<212> TYPE: PRT
<213> ORGANISM: Homo sapiens

<400> SEQUENCE: 248

Gln Ser Tyr Asp Arg Gly Thr His Pro Ala Leu Leu
1 5 10

<210> SEQ ID NO 249
<211> LENGTH: 12
<212> TYPE: PRT
<213> ORGANISM: Homo sapiens

<400> SEQUENCE: 249

Gln Ser Tyr Asp Arg Gly Ser His Pro Ala Leu Thr
1 5 10

<210> SEQ ID NO 250
<211> LENGTH: 12
<212> TYPE: PRT
<213> ORGANISM: Homo sapiens

<400> SEQUENCE: 250

Gln Ser Tyr Asp Arg Gly Thr Thr Pro Ala Pro Glu
1 5 10

<210> SEQ ID NO 251
<211> LENGTH: 12
<212> TYPE: PRT
<213> ORGANISM: Homo sapiens

<400> SEQUENCE: 251

Gln Ser Tyr Asp Arg Gly Ser His Pro Thr Leu Ile
1 5 10

<210> SEQ ID NO 252
<211> LENGTH: 12
<212> TYPE: PRT
<213> ORGANISM: Homo sapiens

<400> SEQUENCE: 252

Gln Ser Tyr Asp Arg Gly Thr His Pro Ser Met Leu
1 5 10

<210> SEQ ID NO 253
<211> LENGTH: 12
<212> TYPE: PRT
<213> ORGANISM: Homo sapiens

<400> SEQUENCE: 253

Gln Ser Tyr Asp Arg Gly Thr Thr Pro Arg Pro Met
1 5 10

<210> SEQ ID NO 254
<211> LENGTH: 12
<212> TYPE: PRT
<213> ORGANISM: Homo sapiens

<400> SEQUENCE: 254

Gln Ser Tyr Asp Arg Gly Arg Leu Pro Ala Gln Thr
1 5 10

<210> SEQ ID NO 255
<211> LENGTH: 12
<212> TYPE: PRT
<213> ORGANISM: Homo sapiens

<400> SEQUENCE: 255

Gln Ser Tyr Asp Arg Gly Thr His Pro Leu Thr Ile
1 5 10

<210> SEQ ID NO 256
<211> LENGTH: 12
<212> TYPE: PRT
<213> ORGANISM: Homo sapiens

<400> SEQUENCE: 256

Gln Ser Tyr Asp Arg Gly Gln Thr Pro Ser Ile Thr
1 5 10

<210> SEQ ID NO 257
<211> LENGTH: 12
<212> TYPE: PRT

<213> ORGANISM: Homo sapiens

<400> SEQUENCE: 257

Gln Ser Tyr Asp Arg Gly Thr His Phe Gln Met Tyr
1               5                   10

<210> SEQ ID NO 258
<211> LENGTH: 12
<212> TYPE: PRT
<213> ORGANISM: Homo sapiens

<400> SEQUENCE: 258

Gln Ser Tyr Asp Arg Gly Arg Asn Pro Ala Leu Thr
1               5                   10

<210> SEQ ID NO 259
<211> LENGTH: 12
<212> TYPE: PRT
<213> ORGANISM: Homo sapiens

<400> SEQUENCE: 259

Gln Ser Tyr Asp Arg Gly Thr His Pro Leu Thr Met
1               5                   10

<210> SEQ ID NO 260
<211> LENGTH: 12
<212> TYPE: PRT
<213> ORGANISM: Homo sapiens

<400> SEQUENCE: 260

Gln Ser Tyr Asp Arg Gly Thr His Pro Leu Thr Met
1               5                   10

<210> SEQ ID NO 261
<211> LENGTH: 12
<212> TYPE: PRT
<213> ORGANISM: Homo sapiens

<400> SEQUENCE: 261

Gln Ser Tyr Asp Ser Gly Tyr Thr Gly Ser Arg Val
1               5                   10

<210> SEQ ID NO 262
<211> LENGTH: 12
<212> TYPE: PRT
<213> ORGANISM: Homo sapiens

<400> SEQUENCE: 262

Gln Ser Tyr Asp Ser Gly Phe Thr Gly Ser Arg Val
1               5                   10

<210> SEQ ID NO 263
<211> LENGTH: 12
<212> TYPE: PRT
<213> ORGANISM: Homo sapiens

<400> SEQUENCE: 263

Gln Ser Tyr Asp Ser Arg Phe Thr Gly Ser Arg Val
1               5                   10

<210> SEQ ID NO 264
<211> LENGTH: 12
<212> TYPE: PRT
<213> ORGANISM: Homo sapiens

<400> SEQUENCE: 264

Gln Ser Tyr Pro Asp Gly Thr Pro Ala Ser Arg Val
1 5 10

<210> SEQ ID NO 265
<211> LENGTH: 12
<212> TYPE: PRT
<213> ORGANISM: Homo sapiens

<400> SEQUENCE: 265

Gln Ser Tyr Ser Thr His Met Pro Ile Ser Arg Val
1 5 10

<210> SEQ ID NO 266
<211> LENGTH: 12
<212> TYPE: PRT
<213> ORGANISM: Homo sapiens

<400> SEQUENCE: 266

Gln Ser Tyr Asp Ser Gly Ser Thr Gly Ser Arg Val
1 5 10

<210> SEQ ID NO 267
<211> LENGTH: 12
<212> TYPE: PRT
<213> ORGANISM: Homo sapiens

<400> SEQUENCE: 267

Gln Ser Tyr Pro Asn Ser Tyr Pro Ile Ser Arg Val
1 5 10

<210> SEQ ID NO 268
<211> LENGTH: 10
<212> TYPE: PRT
<213> ORGANISM: Homo sapiens

<400> SEQUENCE: 268

Gln Ser Tyr Ile Arg Ala Pro Gln Gln Val
1 5 10

<210> SEQ ID NO 269
<211> LENGTH: 12
<212> TYPE: PRT
<213> ORGANISM: Homo sapiens

<400> SEQUENCE: 269

Gln Ser Tyr Leu Lys Ser Arg Ala Phe Ser Arg Val
1 5 10

<210> SEQ ID NO 270
<211> LENGTH: 12
<212> TYPE: PRT
<213> ORGANISM: Homo sapiens

<400> SEQUENCE: 270

Gln Ser Tyr Asp Ser Arg Phe Thr Gly Ser Arg Val
1 5 10

<210> SEQ ID NO 271
<211> LENGTH: 12
<212> TYPE: PRT
<213> ORGANISM: Homo sapiens

<400> SEQUENCE: 271

Gln Ser Tyr Asp Arg Gly Phe Thr Gly Ser Met Val
1 5 10

<210> SEQ ID NO 272
<211> LENGTH: 12
<212> TYPE: PRT
<213> ORGANISM: Homo sapiens

<400> SEQUENCE: 272

Gln Ser Tyr Asp Arg Gly Phe Thr Gly Ser Met Val
1 5 10

<210> SEQ ID NO 273
<211> LENGTH: 12
<212> TYPE: PRT
<213> ORGANISM: Homo sapiens

<400> SEQUENCE: 273

Gln Ser Tyr Asp Arg Gly Phe Thr Gly Phe Asp Gly
1 5 10

<210> SEQ ID NO 274
<211> LENGTH: 12
<212> TYPE: PRT
<213> ORGANISM: Homo sapiens

<400> SEQUENCE: 274

Gln Ser Tyr Asp Arg Gly Thr Ala Pro Ala Leu Ser
1 5 10

<210> SEQ ID NO 275
<211> LENGTH: 12
<212> TYPE: PRT
<213> ORGANISM: Homo sapiens

<400> SEQUENCE: 275

Gln Ser Tyr Asp Arg Gly Ser Tyr Pro Ala Leu Arg
1 5 10

<210> SEQ ID NO 276
<211> LENGTH: 12
<212> TYPE: PRT
<213> ORGANISM: Homo sapiens

<400> SEQUENCE: 276

Gln Ser Tyr Asp Arg Gly Asn Trp Pro Asn Ser Asn
1 5 10

<210> SEQ ID NO 277
<211> LENGTH: 12
<212> TYPE: PRT
<213> ORGANISM: Homo sapiens

<400> SEQUENCE: 277

Gln Ser Tyr Asp Arg Gly Thr Ala Pro Ser Leu Leu
1 5 10

<210> SEQ ID NO 278
<211> LENGTH: 12
<212> TYPE: PRT
<213> ORGANISM: Homo sapiens

<400> SEQUENCE: 278

Gln Ser Tyr Asp Arg Gly Phe Thr Gly Ser Met Val
1 5 10

<210> SEQ ID NO 279

<211> LENGTH: 12
<212> TYPE: PRT
<213> ORGANISM: Homo sapiens

<400> SEQUENCE: 279

Gln Ser Tyr Asp Arg Gly Thr Thr Pro Arg Ile Arg
1               5                   10

<210> SEQ ID NO 280
<211> LENGTH: 12
<212> TYPE: PRT
<213> ORGANISM: Homo sapiens

<400> SEQUENCE: 280

Gln Ser Tyr Asp Arg Gly Phe Thr Gly Ser Met Val
1               5                   10

<210> SEQ ID NO 281
<211> LENGTH: 12
<212> TYPE: PRT
<213> ORGANISM: Homo sapiens

<400> SEQUENCE: 281

Gln Ser Tyr Asp Arg Gly Phe Thr Gly Ser Met Val
1               5                   10

<210> SEQ ID NO 282
<211> LENGTH: 12
<212> TYPE: PRT
<213> ORGANISM: Homo sapiens

<400> SEQUENCE: 282

Gln Ser Tyr Asp Arg Gly Met Ile Pro Ala Leu Thr
1               5                   10

<210> SEQ ID NO 283
<211> LENGTH: 12
<212> TYPE: PRT
<213> ORGANISM: Homo sapiens

<400> SEQUENCE: 283

Gln Ser Tyr Asp Arg Asn Thr His Pro Ala Leu Leu
1               5                   10

<210> SEQ ID NO 284
<211> LENGTH: 12
<212> TYPE: PRT
<213> ORGANISM: Homo sapiens

<400> SEQUENCE: 284

Gln Ser Tyr Asp Arg Phe Thr His Pro Ala Leu Leu
1               5                   10

<210> SEQ ID NO 285
<211> LENGTH: 12
<212> TYPE: PRT
<213> ORGANISM: Homo sapiens

<400> SEQUENCE: 285

Gln Ser Tyr Asp Arg Tyr Thr His Pro Ala Leu Leu
1               5                   10

<210> SEQ ID NO 286
<211> LENGTH: 12
<212> TYPE: PRT
<213> ORGANISM: Homo sapiens

<400> SEQUENCE: 286

Gln Ser Tyr Asp Arg Gly Thr His Pro Ala Leu Leu
1 5 10

<210> SEQ ID NO 287
<211> LENGTH: 12
<212> TYPE: PRT
<213> ORGANISM: Homo sapiens

<400> SEQUENCE: 287

Gln Ser Tyr Asp Arg Tyr Thr His Pro Ala Leu Leu
1 5 10

<210> SEQ ID NO 288
<211> LENGTH: 9
<212> TYPE: PRT
<213> ORGANISM: Homo sapiens

<400> SEQUENCE: 288

Phe Thr Phe Glu Ser Tyr Gly Met His
1 5

<210> SEQ ID NO 289
<211> LENGTH: 9
<212> TYPE: PRT
<213> ORGANISM: Homo sapiens

<400> SEQUENCE: 289

Phe Thr Phe Ser Ser Tyr Gly Met His
1 5

<210> SEQ ID NO 290
<211> LENGTH: 9
<212> TYPE: PRT
<213> ORGANISM: Homo sapiens

<400> SEQUENCE: 290

Phe Thr Phe Tyr Ser Tyr Gly Met His
1 5

<210> SEQ ID NO 291
<211> LENGTH: 9
<212> TYPE: PRT
<213> ORGANISM: Homo sapiens

<400> SEQUENCE: 291

Phe Thr Phe His Ser Tyr Gly Met His
1 5

<210> SEQ ID NO 292
<211> LENGTH: 9
<212> TYPE: PRT
<213> ORGANISM: Homo sapiens

<400> SEQUENCE: 292

Phe Thr Phe Lys Ser Tyr Gly Met His
1 5

<210> SEQ ID NO 293
<211> LENGTH: 9
<212> TYPE: PRT
<213> ORGANISM: Homo sapiens

<400> SEQUENCE: 293

-continued

Phe Thr Phe Arg Ser Tyr Gly Met His
1 5

<210> SEQ ID NO 294
<211> LENGTH: 9
<212> TYPE: PRT
<213> ORGANISM: Homo sapiens

<400> SEQUENCE: 294

Phe Thr Phe Asn Ser Tyr Gly Met His
1 5

<210> SEQ ID NO 295
<211> LENGTH: 9
<212> TYPE: PRT
<213> ORGANISM: Homo sapiens

<400> SEQUENCE: 295

Phe Thr Phe Thr Ser Tyr Gly Met His
1 5

<210> SEQ ID NO 296
<211> LENGTH: 9
<212> TYPE: PRT
<213> ORGANISM: Homo sapiens

<400> SEQUENCE: 296

Phe Thr Phe Gly Ser Tyr Gly Met His
1 5

<210> SEQ ID NO 297
<211> LENGTH: 9
<212> TYPE: PRT
<213> ORGANISM: Homo sapiens

<400> SEQUENCE: 297

Phe Thr Phe Val Ser Tyr Gly Met His
1 5

<210> SEQ ID NO 298
<211> LENGTH: 9
<212> TYPE: PRT
<213> ORGANISM: Homo sapiens

<400> SEQUENCE: 298

Phe Thr Phe Ile Ser Tyr Gly Met His
1 5

<210> SEQ ID NO 299
<211> LENGTH: 9
<212> TYPE: PRT
<213> ORGANISM: Homo sapiens

<400> SEQUENCE: 299

Phe Thr Phe Trp Ser Tyr Gly Met His
1 5

<210> SEQ ID NO 300
<211> LENGTH: 9
<212> TYPE: PRT
<213> ORGANISM: Homo sapiens

<400> SEQUENCE: 300

Phe Thr Phe Ser Glu Tyr Gly Met His
1 5

<210> SEQ ID NO 301
<211> LENGTH: 9
<212> TYPE: PRT
<213> ORGANISM: Homo sapiens

<400> SEQUENCE: 301

Phe Thr Phe Ser Cys Tyr Gly Met His
1               5

<210> SEQ ID NO 302
<211> LENGTH: 9
<212> TYPE: PRT
<213> ORGANISM: Homo sapiens

<400> SEQUENCE: 302

Phe Thr Phe Ser Ser Tyr Gly Met His
1               5

<210> SEQ ID NO 303
<211> LENGTH: 9
<212> TYPE: PRT
<213> ORGANISM: Homo sapiens

<400> SEQUENCE: 303

Phe Thr Phe Ser Tyr Tyr Gly Met His
1               5

<210> SEQ ID NO 304
<211> LENGTH: 9
<212> TYPE: PRT
<213> ORGANISM: Homo sapiens

<400> SEQUENCE: 304

Phe Thr Phe Ser His Tyr Gly Met His
1               5

<210> SEQ ID NO 305
<211> LENGTH: 9
<212> TYPE: PRT
<213> ORGANISM: Homo sapiens

<400> SEQUENCE: 305

Phe Thr Phe Ser Arg Tyr Gly Met His
1               5

<210> SEQ ID NO 306
<211> LENGTH: 9
<212> TYPE: PRT
<213> ORGANISM: Homo sapiens

<400> SEQUENCE: 306

Phe Thr Phe Ser Asn Tyr Gly Met His
1               5

<210> SEQ ID NO 307
<211> LENGTH: 9
<212> TYPE: PRT
<213> ORGANISM: Homo sapiens

<400> SEQUENCE: 307

Phe Thr Phe Ser Gln Tyr Gly Met His
1               5

<210> SEQ ID NO 308
<211> LENGTH: 9

<212> TYPE: PRT
<213> ORGANISM: Homo sapiens

<400> SEQUENCE: 308

Phe Thr Phe Ser Thr Tyr Gly Met His
1               5

<210> SEQ ID NO 309
<211> LENGTH: 9
<212> TYPE: PRT
<213> ORGANISM: Homo sapiens

<400> SEQUENCE: 309

Phe Thr Phe Ser Ala Tyr Gly Met His
1               5

<210> SEQ ID NO 310
<211> LENGTH: 9
<212> TYPE: PRT
<213> ORGANISM: Homo sapiens

<400> SEQUENCE: 310

Phe Thr Phe Ser Ile Tyr Gly Met His
1               5

<210> SEQ ID NO 311
<211> LENGTH: 9
<212> TYPE: PRT
<213> ORGANISM: Homo sapiens

<400> SEQUENCE: 311

Phe Thr Phe Ser Ser Glu Gly Met His
1               5

<210> SEQ ID NO 312
<211> LENGTH: 9
<212> TYPE: PRT
<213> ORGANISM: Homo sapiens

<400> SEQUENCE: 312

Phe Thr Phe Ser Ser Cys Gly Met His
1               5

<210> SEQ ID NO 313
<211> LENGTH: 9
<212> TYPE: PRT
<213> ORGANISM: Homo sapiens

<400> SEQUENCE: 313

Phe Thr Phe Ser Ser Ser Gly Met His
1               5

<210> SEQ ID NO 314
<211> LENGTH: 9
<212> TYPE: PRT
<213> ORGANISM: Homo sapiens

<400> SEQUENCE: 314

Phe Thr Phe Ser Ser Tyr Gly Met His
1               5

<210> SEQ ID NO 315
<211> LENGTH: 9
<212> TYPE: PRT
<213> ORGANISM: Homo sapiens

<400> SEQUENCE: 315

Phe Thr Phe Ser Ser His Gly Met His
1 5

<210> SEQ ID NO 316
<211> LENGTH: 9
<212> TYPE: PRT
<213> ORGANISM: Homo sapiens

<400> SEQUENCE: 316

Phe Thr Phe Ser Ser Arg Gly Met His
1 5

<210> SEQ ID NO 317
<211> LENGTH: 9
<212> TYPE: PRT
<213> ORGANISM: Homo sapiens

<400> SEQUENCE: 317

Phe Thr Phe Ser Ser Asn Gly Met His
1 5

<210> SEQ ID NO 318
<211> LENGTH: 9
<212> TYPE: PRT
<213> ORGANISM: Homo sapiens

<400> SEQUENCE: 318

Phe Thr Phe Ser Ser Thr Gly Met His
1 5

<210> SEQ ID NO 319
<211> LENGTH: 9
<212> TYPE: PRT
<213> ORGANISM: Homo sapiens

<400> SEQUENCE: 319

Phe Thr Phe Ser Ser Ala Gly Met His
1 5

<210> SEQ ID NO 320
<211> LENGTH: 9
<212> TYPE: PRT
<213> ORGANISM: Homo sapiens

<400> SEQUENCE: 320

Phe Thr Phe Ser Ser Val Gly Met His
1 5

<210> SEQ ID NO 321
<211> LENGTH: 9
<212> TYPE: PRT
<213> ORGANISM: Homo sapiens

<400> SEQUENCE: 321

Phe Thr Phe Ser Ser Leu Gly Met His
1 5

<210> SEQ ID NO 322
<211> LENGTH: 9
<212> TYPE: PRT
<213> ORGANISM: Homo sapiens

<400> SEQUENCE: 322

Phe Thr Phe Ser Ser Ile Gly Met His 1 5

<210> SEQ ID NO 323
<211> LENGTH: 9
<212> TYPE: PRT
<213> ORGANISM: Homo sapiens

<400> SEQUENCE: 323

Phe Thr Phe Ser Ser Tyr Asp Met His
1 5

<210> SEQ ID NO 324
<211> LENGTH: 9
<212> TYPE: PRT
<213> ORGANISM: Homo sapiens

<400> SEQUENCE: 324

Phe Thr Phe Ser Ser Tyr Glu Met His
1 5

<210> SEQ ID NO 325
<211> LENGTH: 9
<212> TYPE: PRT
<213> ORGANISM: Homo sapiens

<400> SEQUENCE: 325

Phe Thr Phe Ser Ser Tyr Cys Met His
1 5

<210> SEQ ID NO 326
<211> LENGTH: 9
<212> TYPE: PRT
<213> ORGANISM: Homo sapiens

<400> SEQUENCE: 326

Phe Thr Phe Ser Ser Tyr Ser Met His
1 5

<210> SEQ ID NO 327
<211> LENGTH: 9
<212> TYPE: PRT
<213> ORGANISM: Homo sapiens

<400> SEQUENCE: 327

Phe Thr Phe Ser Ser Tyr Tyr Met His
1 5

<210> SEQ ID NO 328
<211> LENGTH: 9
<212> TYPE: PRT
<213> ORGANISM: Homo sapiens

<400> SEQUENCE: 328

Phe Thr Phe Ser Ser Tyr Asn Met His
1 5

<210> SEQ ID NO 329
<211> LENGTH: 9
<212> TYPE: PRT
<213> ORGANISM: Homo sapiens

<400> SEQUENCE: 329

Phe Thr Phe Ser Ser Tyr Gly Met His
1 5

<210> SEQ ID NO 330
<211> LENGTH: 9
<212> TYPE: PRT
<213> ORGANISM: Homo sapiens

<400> SEQUENCE: 330

Phe Thr Phe Ser Ser Tyr Ala Met His
1 5

<210> SEQ ID NO 331
<211> LENGTH: 9
<212> TYPE: PRT
<213> ORGANISM: Homo sapiens

<400> SEQUENCE: 331

Phe Thr Phe Ser Ser Tyr Val Met His
1 5

<210> SEQ ID NO 332
<211> LENGTH: 9
<212> TYPE: PRT
<213> ORGANISM: Homo sapiens

<400> SEQUENCE: 332

Phe Thr Phe Ser Ser Tyr Met Met His
1 5

<210> SEQ ID NO 333
<211> LENGTH: 9
<212> TYPE: PRT
<213> ORGANISM: Homo sapiens

<400> SEQUENCE: 333

Phe Thr Phe Ser Ser Tyr Ile Met His
1 5

<210> SEQ ID NO 334
<211> LENGTH: 9
<212> TYPE: PRT
<213> ORGANISM: Homo sapiens

<400> SEQUENCE: 334

Phe Thr Phe Ser Ser Tyr Pro Met His
1 5

<210> SEQ ID NO 335
<211> LENGTH: 17
<212> TYPE: PRT
<213> ORGANISM: Homo sapiens

<400> SEQUENCE: 335

Glu Ile Arg Tyr Asp Gly Ser Asn Lys Tyr Tyr Ala Asp Ser Val Lys
1 5 10 15

Gly

<210> SEQ ID NO 336
<211> LENGTH: 17
<212> TYPE: PRT
<213> ORGANISM: Homo sapiens

<400> SEQUENCE: 336

Cys Ile Arg Tyr Asp Gly Ser Asn Lys Tyr Tyr Ala Asp Ser Val Lys
1 5 10 15

Gly

<210> SEQ ID NO 337
<211> LENGTH: 17
<212> TYPE: PRT
<213> ORGANISM: Homo sapiens

<400> SEQUENCE: 337

Tyr Ile Arg Tyr Asp Gly Ser Asn Lys Tyr Tyr Ala Asp Ser Val Lys
1 5 10 15

Gly

<210> SEQ ID NO 338
<211> LENGTH: 17
<212> TYPE: PRT
<213> ORGANISM: Homo sapiens

<400> SEQUENCE: 338

His Ile Arg Tyr Asp Gly Ser Asn Lys Tyr Tyr Ala Asp Ser Val Lys
1 5 10 15

Gly

<210> SEQ ID NO 339
<211> LENGTH: 17
<212> TYPE: PRT
<213> ORGANISM: Homo sapiens

<400> SEQUENCE: 339

Lys Ile Arg Tyr Asp Gly Ser Asn Lys Tyr Tyr Ala Asp Ser Val Lys
1 5 10 15

Gly

<210> SEQ ID NO 340
<211> LENGTH: 17
<212> TYPE: PRT
<213> ORGANISM: Homo sapiens

<400> SEQUENCE: 340

Asn Ile Arg Tyr Asp Gly Ser Asn Lys Tyr Tyr Ala Asp Ser Val Lys
1 5 10 15

Gly

<210> SEQ ID NO 341
<211> LENGTH: 17
<212> TYPE: PRT
<213> ORGANISM: Homo sapiens

<400> SEQUENCE: 341

Gln Ile Arg Tyr Asp Gly Ser Asn Lys Tyr Tyr Ala Asp Ser Val Lys
1 5 10 15

Gly

<210> SEQ ID NO 342
<211> LENGTH: 17
<212> TYPE: PRT
<213> ORGANISM: Homo sapiens

<400> SEQUENCE: 342

Thr Ile Arg Tyr Asp Gly Ser Asn Lys Tyr Tyr Ala Asp Ser Val Lys
1 5 10 15

Gly

<210> SEQ ID NO 343

<211> LENGTH: 17
<212> TYPE: PRT
<213> ORGANISM: Homo sapiens

<400> SEQUENCE: 343

Leu Ile Arg Tyr Asp Gly Ser Asn Lys Tyr Tyr Ala Asp Ser Val Lys
1 5 10 15

Gly

<210> SEQ ID NO 344
<211> LENGTH: 17
<212> TYPE: PRT
<213> ORGANISM: Homo sapiens

<400> SEQUENCE: 344

Phe Ile Arg Tyr Asp Gly Ser Asn Lys Tyr Tyr Ala Asp Ser Val Lys
1 5 10 15

Gly

<210> SEQ ID NO 345
<211> LENGTH: 17
<212> TYPE: PRT
<213> ORGANISM: Homo sapiens

<400> SEQUENCE: 345

Phe Ile Glu Tyr Asp Gly Ser Asn Lys Tyr Tyr Ala Asp Ser Val Lys
1 5 10 15

Gly

<210> SEQ ID NO 346
<211> LENGTH: 17
<212> TYPE: PRT
<213> ORGANISM: Homo sapiens

<400> SEQUENCE: 346

Phe Ile Ser Tyr Asp Gly Ser Asn Lys Tyr Tyr Ala Asp Ser Val Lys
1 5 10 15

Gly

<210> SEQ ID NO 347
<211> LENGTH: 17
<212> TYPE: PRT
<213> ORGANISM: Homo sapiens

<400> SEQUENCE: 347

Phe Ile Tyr Tyr Asp Gly Ser Asn Lys Tyr Tyr Ala Asp Ser Val Lys
1 5 10 15

Gly

<210> SEQ ID NO 348
<211> LENGTH: 17
<212> TYPE: PRT
<213> ORGANISM: Homo sapiens

<400> SEQUENCE: 348

Phe Ile His Tyr Asp Gly Ser Asn Lys Tyr Tyr Ala Asp Ser Val Lys
1 5 10 15

Gly

<210> SEQ ID NO 349
<211> LENGTH: 17
<212> TYPE: PRT

<213> ORGANISM: Homo sapiens

<400> SEQUENCE: 349

Phe Ile Lys Tyr Asp Gly Ser Asn Lys Tyr Tyr Ala Asp Ser Val Lys
1 5 10 15

Gly

<210> SEQ ID NO 350
<211> LENGTH: 17
<212> TYPE: PRT
<213> ORGANISM: Homo sapiens

<400> SEQUENCE: 350

Phe Ile Arg Tyr Asp Gly Ser Asn Lys Tyr Tyr Ala Asp Ser Val Lys
1 5 10 15

Gly

<210> SEQ ID NO 351
<211> LENGTH: 17
<212> TYPE: PRT
<213> ORGANISM: Homo sapiens

<400> SEQUENCE: 351

Phe Ile Gln Tyr Asp Gly Ser Asn Lys Tyr Tyr Ala Asp Ser Val Lys
1 5 10 15

Gly

<210> SEQ ID NO 352
<211> LENGTH: 17
<212> TYPE: PRT
<213> ORGANISM: Homo sapiens

<400> SEQUENCE: 352

Phe Ile Thr Tyr Asp Gly Ser Asn Lys Tyr Tyr Ala Asp Ser Val Lys
1 5 10 15

Gly

<210> SEQ ID NO 353
<211> LENGTH: 17
<212> TYPE: PRT
<213> ORGANISM: Homo sapiens

<400> SEQUENCE: 353

Phe Ile Gly Tyr Asp Gly Ser Asn Lys Tyr Tyr Ala Asp Ser Val Lys
1 5 10 15

Gly

<210> SEQ ID NO 354
<211> LENGTH: 17
<212> TYPE: PRT
<213> ORGANISM: Homo sapiens

<400> SEQUENCE: 354

Phe Ile Ala Tyr Asp Gly Ser Asn Lys Tyr Tyr Ala Asp Ser Val Lys
1 5 10 15

Gly

<210> SEQ ID NO 355
<211> LENGTH: 17
<212> TYPE: PRT
<213> ORGANISM: Homo sapiens

<400> SEQUENCE: 355

Phe Ile Val Tyr Asp Gly Ser Asn Lys Tyr Tyr Ala Asp Ser Val Lys
1 5 10 15

Gly

<210> SEQ ID NO 356
<211> LENGTH: 17
<212> TYPE: PRT
<213> ORGANISM: Homo sapiens

<400> SEQUENCE: 356

Phe Ile Leu Tyr Asp Gly Ser Asn Lys Tyr Tyr Ala Asp Ser Val Lys
1 5 10 15

Gly

<210> SEQ ID NO 357
<211> LENGTH: 17
<212> TYPE: PRT
<213> ORGANISM: Homo sapiens

<400> SEQUENCE: 357

Phe Ile Trp Tyr Asp Gly Ser Asn Lys Tyr Tyr Ala Asp Ser Val Lys
1 5 10 15

Gly

<210> SEQ ID NO 358
<211> LENGTH: 17
<212> TYPE: PRT
<213> ORGANISM: Homo sapiens

<400> SEQUENCE: 358

Phe Ile Arg Tyr Asp Gly Ser Asn Lys Tyr Tyr Ala Asp Ser Val Lys
1 5 10 15

Gly

<210> SEQ ID NO 359
<211> LENGTH: 17
<212> TYPE: PRT
<213> ORGANISM: Homo sapiens

<400> SEQUENCE: 359

Phe Ile Arg Tyr Glu Gly Ser Asn Lys Tyr Tyr Ala Asp Ser Val Lys
1 5 10 15

Gly

<210> SEQ ID NO 360
<211> LENGTH: 17
<212> TYPE: PRT
<213> ORGANISM: Homo sapiens

<400> SEQUENCE: 360

Phe Ile Arg Tyr Ser Gly Ser Asn Lys Tyr Tyr Ala Asp Ser Val Lys
1 5 10 15

Gly

<210> SEQ ID NO 361
<211> LENGTH: 17
<212> TYPE: PRT
<213> ORGANISM: Homo sapiens

<400> SEQUENCE: 361

Phe Ile Arg Tyr Tyr Gly Ser Asn Lys Tyr Tyr Ala Asp Ser Val Lys
1 5 10 15

Gly

<210> SEQ ID NO 362
<211> LENGTH: 17
<212> TYPE: PRT
<213> ORGANISM: Homo sapiens

<400> SEQUENCE: 362

Phe Ile Arg Tyr Lys Gly Ser Asn Lys Tyr Tyr Ala Asp Ser Val Lys
1 5 10 15

Gly

<210> SEQ ID NO 363
<211> LENGTH: 17
<212> TYPE: PRT
<213> ORGANISM: Homo sapiens

<400> SEQUENCE: 363

Phe Ile Arg Tyr Arg Gly Ser Asn Lys Tyr Tyr Ala Asp Ser Val Lys
1 5 10 15

Gly

<210> SEQ ID NO 364
<211> LENGTH: 17
<212> TYPE: PRT
<213> ORGANISM: Homo sapiens

<400> SEQUENCE: 364

Phe Ile Arg Tyr Asn Gly Ser Asn Lys Tyr Tyr Ala Asp Ser Val Lys
1 5 10 15

Gly

<210> SEQ ID NO 365
<211> LENGTH: 17
<212> TYPE: PRT
<213> ORGANISM: Homo sapiens

<400> SEQUENCE: 365

Phe Ile Arg Tyr Gln Gly Ser Asn Lys Tyr Tyr Ala Asp Ser Val Lys
1 5 10 15

Gly

<210> SEQ ID NO 366
<211> LENGTH: 17
<212> TYPE: PRT
<213> ORGANISM: Homo sapiens

<400> SEQUENCE: 366

Phe Ile Arg Tyr Thr Gly Ser Asn Lys Tyr Tyr Ala Asp Ser Val Lys
1 5 10 15

Gly

<210> SEQ ID NO 367
<211> LENGTH: 17
<212> TYPE: PRT
<213> ORGANISM: Homo sapiens

<400> SEQUENCE: 367

Phe Ile Arg Tyr Ala Gly Ser Asn Lys Tyr Tyr Ala Asp Ser Val Lys
1 5 10 15

Gly

<210> SEQ ID NO 368
<211> LENGTH: 17
<212> TYPE: PRT
<213> ORGANISM: Homo sapiens

<400> SEQUENCE: 368

Phe Ile Arg Tyr Val Gly Ser Asn Lys Tyr Tyr Ala Asp Ser Val Lys
1 5 10 15

Gly

<210> SEQ ID NO 369
<211> LENGTH: 17
<212> TYPE: PRT
<213> ORGANISM: Homo sapiens

<400> SEQUENCE: 369

Phe Ile Arg Tyr Leu Gly Ser Asn Lys Tyr Tyr Ala Asp Ser Val Lys
1 5 10 15

Gly

<210> SEQ ID NO 370
<211> LENGTH: 17
<212> TYPE: PRT
<213> ORGANISM: Homo sapiens

<400> SEQUENCE: 370

Phe Ile Arg Tyr Ile Gly Ser Asn Lys Tyr Tyr Ala Asp Ser Val Lys
1 5 10 15

Gly

<210> SEQ ID NO 371
<211> LENGTH: 17
<212> TYPE: PRT
<213> ORGANISM: Homo sapiens

<400> SEQUENCE: 371

Phe Ile Arg Tyr Phe Gly Ser Asn Lys Tyr Tyr Ala Asp Ser Val Lys
1 5 10 15

Gly

<210> SEQ ID NO 372
<211> LENGTH: 17
<212> TYPE: PRT
<213> ORGANISM: Homo sapiens

<400> SEQUENCE: 372

Phe Ile Arg Tyr Asp Asp Ser Asn Lys Tyr Tyr Ala Asp Ser Val Lys
1 5 10 15

Gly

<210> SEQ ID NO 373
<211> LENGTH: 17
<212> TYPE: PRT
<213> ORGANISM: Homo sapiens

<400> SEQUENCE: 373

Phe Ile Arg Tyr Asp Glu Ser Asn Lys Tyr Tyr Ala Asp Ser Val Lys
1 5 10 15

Gly

<210> SEQ ID NO 374
<211> LENGTH: 17
<212> TYPE: PRT
<213> ORGANISM: Homo sapiens

<400> SEQUENCE: 374

Phe Ile Arg Tyr Asp Ser Ser Asn Lys Tyr Tyr Ala Asp Ser Val Lys
1               5                   10                  15

Gly

<210> SEQ ID NO 375
<211> LENGTH: 17
<212> TYPE: PRT
<213> ORGANISM: Homo sapiens

<400> SEQUENCE: 375

Phe Ile Arg Tyr Asp Tyr Ser Asn Lys Tyr Tyr Ala Asp Ser Val Lys
1               5                   10                  15

Gly

<210> SEQ ID NO 376
<211> LENGTH: 17
<212> TYPE: PRT
<213> ORGANISM: Homo sapiens

<400> SEQUENCE: 376

Phe Ile Arg Tyr Asp Lys Ser Asn Lys Tyr Tyr Ala Asp Ser Val Lys
1               5                   10                  15

Gly

<210> SEQ ID NO 377
<211> LENGTH: 17
<212> TYPE: PRT
<213> ORGANISM: Homo sapiens

<400> SEQUENCE: 377

Phe Ile Arg Tyr Asp Arg Ser Asn Lys Tyr Tyr Ala Asp Ser Val Lys
1               5                   10                  15

Gly

<210> SEQ ID NO 378
<211> LENGTH: 17
<212> TYPE: PRT
<213> ORGANISM: Homo sapiens

<400> SEQUENCE: 378

Phe Ile Arg Tyr Asp Asn Ser Asn Lys Tyr Tyr Ala Asp Ser Val Lys
1               5                   10                  15

Gly

<210> SEQ ID NO 379
<211> LENGTH: 17
<212> TYPE: PRT
<213> ORGANISM: Homo sapiens

<400> SEQUENCE: 379

Phe Ile Arg Tyr Asp Gln Ser Asn Lys Tyr Tyr Ala Asp Ser Val Lys
1               5                   10                  15

Gly

<210> SEQ ID NO 380
<211> LENGTH: 17
<212> TYPE: PRT
<213> ORGANISM: Homo sapiens

<400> SEQUENCE: 380

Phe Ile Arg Tyr Asp Thr Ser Asn Lys Tyr Tyr Ala Asp Ser Val Lys
1 5 10 15

Gly

<210> SEQ ID NO 381
<211> LENGTH: 17
<212> TYPE: PRT
<213> ORGANISM: Homo sapiens

<400> SEQUENCE: 381

Phe Ile Arg Tyr Asp Gly Ser Asn Lys Tyr Tyr Ala Asp Ser Val Lys
1 5 10 15

Gly

<210> SEQ ID NO 382
<211> LENGTH: 17
<212> TYPE: PRT
<213> ORGANISM: Homo sapiens

<400> SEQUENCE: 382

Phe Ile Arg Tyr Asp Val Ser Asn Lys Tyr Tyr Ala Asp Ser Val Lys
1 5 10 15

Gly

<210> SEQ ID NO 383
<211> LENGTH: 17
<212> TYPE: PRT
<213> ORGANISM: Homo sapiens

<400> SEQUENCE: 383

Phe Ile Arg Tyr Asp Phe Ser Asn Lys Tyr Tyr Ala Asp Ser Val Lys
1 5 10 15

Gly

<210> SEQ ID NO 384
<211> LENGTH: 17
<212> TYPE: PRT
<213> ORGANISM: Homo sapiens

<400> SEQUENCE: 384

Phe Ile Arg Tyr Asp Gly Ser Ser Lys Tyr Tyr Ala Asp Ser Val Lys
1 5 10 15

Gly

<210> SEQ ID NO 385
<211> LENGTH: 17
<212> TYPE: PRT
<213> ORGANISM: Homo sapiens

<400> SEQUENCE: 385

Phe Ile Arg Tyr Asp Gly Ser Tyr Lys Tyr Tyr Ala Asp Ser Val Lys
1 5 10 15

Gly

<210> SEQ ID NO 386
<211> LENGTH: 17

<212> TYPE: PRT
<213> ORGANISM: Homo sapiens

<400> SEQUENCE: 386

Phe Ile Arg Tyr Asp Gly Ser His Lys Tyr Tyr Ala Asp Ser Val Lys
1 5 10 15

Gly

<210> SEQ ID NO 387
<211> LENGTH: 17
<212> TYPE: PRT
<213> ORGANISM: Homo sapiens

<400> SEQUENCE: 387

Phe Ile Arg Tyr Asp Gly Ser Asn Lys Tyr Tyr Ala Asp Ser Val Lys
1 5 10 15

Gly

<210> SEQ ID NO 388
<211> LENGTH: 17
<212> TYPE: PRT
<213> ORGANISM: Homo sapiens

<400> SEQUENCE: 388

Phe Ile Arg Tyr Asp Gly Ser Thr Lys Tyr Tyr Ala Asp Ser Val Lys
1 5 10 15

Gly

<210> SEQ ID NO 389
<211> LENGTH: 17
<212> TYPE: PRT
<213> ORGANISM: Homo sapiens

<400> SEQUENCE: 389

Phe Ile Arg Tyr Asp Gly Ser Gly Lys Tyr Tyr Ala Asp Ser Val Lys
1 5 10 15

Gly

<210> SEQ ID NO 390
<211> LENGTH: 17
<212> TYPE: PRT
<213> ORGANISM: Homo sapiens

<400> SEQUENCE: 390

Phe Ile Arg Tyr Asp Gly Ser Met Lys Tyr Tyr Ala Asp Ser Val Lys
1 5 10 15

Gly

<210> SEQ ID NO 391
<211> LENGTH: 17
<212> TYPE: PRT
<213> ORGANISM: Homo sapiens

<400> SEQUENCE: 391

Phe Ile Arg Tyr Asp Gly Ser Leu Lys Tyr Tyr Ala Asp Ser Val Lys
1 5 10 15

Gly

<210> SEQ ID NO 392
<211> LENGTH: 17
<212> TYPE: PRT
<213> ORGANISM: Homo sapiens

<400> SEQUENCE: 392

Phe Ile Arg Tyr Asp Gly Ser Ile Lys Tyr Tyr Ala Asp Ser Val Lys
1 5 10 15

Gly

<210> SEQ ID NO 393
<211> LENGTH: 17
<212> TYPE: PRT
<213> ORGANISM: Homo sapiens

<400> SEQUENCE: 393

Phe Ile Arg Tyr Asp Gly Ser Pro Lys Tyr Tyr Ala Asp Ser Val Lys
1 5 10 15

Gly

<210> SEQ ID NO 394
<211> LENGTH: 17
<212> TYPE: PRT
<213> ORGANISM: Homo sapiens

<400> SEQUENCE: 394

Phe Ile Arg Tyr Asp Gly Ser Phe Lys Tyr Tyr Ala Asp Ser Val Lys
1 5 10 15

Gly

<210> SEQ ID NO 395
<211> LENGTH: 17
<212> TYPE: PRT
<213> ORGANISM: Homo sapiens

<400> SEQUENCE: 395

Phe Ile Arg Tyr Asp Gly Ser Asn Lys Glu Tyr Ala Asp Ser Val Lys
1 5 10 15

Gly

<210> SEQ ID NO 396
<211> LENGTH: 17
<212> TYPE: PRT
<213> ORGANISM: Homo sapiens

<400> SEQUENCE: 396

Phe Ile Arg Tyr Asp Gly Ser Asn Lys Ser Tyr Ala Asp Ser Val Lys
1 5 10 15

Gly

<210> SEQ ID NO 397
<211> LENGTH: 17
<212> TYPE: PRT
<213> ORGANISM: Homo sapiens

<400> SEQUENCE: 397

Phe Ile Arg Tyr Asp Gly Ser Asn Lys Tyr Tyr Ala Asp Ser Val Lys
1 5 10 15

Gly

<210> SEQ ID NO 398
<211> LENGTH: 17
<212> TYPE: PRT
<213> ORGANISM: Homo sapiens

<400> SEQUENCE: 398

Phe Ile Arg Tyr Asp Gly Ser Asn Lys Asn Tyr Ala Asp Ser Val Lys
1 5 10 15

Gly

<210> SEQ ID NO 399
<211> LENGTH: 17
<212> TYPE: PRT
<213> ORGANISM: Homo sapiens

<400> SEQUENCE: 399

Phe Ile Arg Tyr Asp Gly Ser Asn Lys Val Tyr Ala Asp Ser Val Lys
1 5 10 15

Gly

<210> SEQ ID NO 400
<211> LENGTH: 17
<212> TYPE: PRT
<213> ORGANISM: Homo sapiens

<400> SEQUENCE: 400

Phe Ile Arg Tyr Asp Gly Ser Asn Lys Leu Tyr Ala Asp Ser Val Lys
1 5 10 15

Gly

<210> SEQ ID NO 401
<211> LENGTH: 17
<212> TYPE: PRT
<213> ORGANISM: Homo sapiens

<400> SEQUENCE: 401

Phe Ile Arg Tyr Asp Gly Ser Asn Lys Ile Tyr Ala Asp Ser Val Lys
1 5 10 15

Gly

<210> SEQ ID NO 402
<211> LENGTH: 17
<212> TYPE: PRT
<213> ORGANISM: Homo sapiens

<400> SEQUENCE: 402

Phe Ile Arg Tyr Asp Gly Ser Asn Lys Pro Tyr Ala Asp Ser Val Lys
1 5 10 15

Gly

<210> SEQ ID NO 403
<211> LENGTH: 17
<212> TYPE: PRT
<213> ORGANISM: Homo sapiens

<400> SEQUENCE: 403

Phe Ile Arg Tyr Asp Gly Ser Asn Lys Phe Tyr Ala Asp Ser Val Lys
1 5 10 15

Gly

<210> SEQ ID NO 404
<211> LENGTH: 6
<212> TYPE: PRT
<213> ORGANISM: Homo sapiens

<400> SEQUENCE: 404

Glu Gly Ser His Asp Asn 1 5

<210> SEQ ID NO 405
<211> LENGTH: 6
<212> TYPE: PRT
<213> ORGANISM: Homo sapiens

<400> SEQUENCE: 405

Ser Gly Ser His Asp Asn
1 5

<210> SEQ ID NO 406
<211> LENGTH: 6
<212> TYPE: PRT
<213> ORGANISM: Homo sapiens

<400> SEQUENCE: 406

His Gly Ser His Asp Asn
1 5

<210> SEQ ID NO 407
<211> LENGTH: 6
<212> TYPE: PRT
<213> ORGANISM: Homo sapiens

<400> SEQUENCE: 407

Lys Gly Ser His Asp Asn
1 5

<210> SEQ ID NO 408
<211> LENGTH: 6
<212> TYPE: PRT
<213> ORGANISM: Homo sapiens

<400> SEQUENCE: 408

Gln Gly Ser His Asp Asn
1 5

<210> SEQ ID NO 409
<211> LENGTH: 6
<212> TYPE: PRT
<213> ORGANISM: Homo sapiens

<400> SEQUENCE: 409

Thr Gly Ser His Asp Asn
1 5

<210> SEQ ID NO 410
<211> LENGTH: 6
<212> TYPE: PRT
<213> ORGANISM: Homo sapiens

<400> SEQUENCE: 410

Ala Gly Ser His Asp Asn
1 5

<210> SEQ ID NO 411
<211> LENGTH: 6
<212> TYPE: PRT
<213> ORGANISM: Homo sapiens

<400> SEQUENCE: 411

Leu Gly Ser His Asp Asn
1 5

<210> SEQ ID NO 412
<211> LENGTH: 6
<212> TYPE: PRT
<213> ORGANISM: Homo sapiens

<400> SEQUENCE: 412

Pro Gly Ser His Asp Asn
1 5

<210> SEQ ID NO 413
<211> LENGTH: 6
<212> TYPE: PRT
<213> ORGANISM: Homo sapiens

<400> SEQUENCE: 413

Phe Gly Ser His Asp Asn
1 5

<210> SEQ ID NO 414
<211> LENGTH: 6
<212> TYPE: PRT
<213> ORGANISM: Homo sapiens

<400> SEQUENCE: 414

His Asp Ser His Asp Asn
1 5

<210> SEQ ID NO 415
<211> LENGTH: 6
<212> TYPE: PRT
<213> ORGANISM: Homo sapiens

<400> SEQUENCE: 415

His Cys Ser His Asp Asn
1 5

<210> SEQ ID NO 416
<211> LENGTH: 6
<212> TYPE: PRT
<213> ORGANISM: Homo sapiens

<400> SEQUENCE: 416

His His Ser His Asp Asn
1 5

<210> SEQ ID NO 417
<211> LENGTH: 6
<212> TYPE: PRT
<213> ORGANISM: Homo sapiens

<400> SEQUENCE: 417

His Arg Ser His Asp Asn
1 5

<210> SEQ ID NO 418
<211> LENGTH: 6
<212> TYPE: PRT
<213> ORGANISM: Homo sapiens

<400> SEQUENCE: 418

His Thr Ser His Asp Asn
1 5

<210> SEQ ID NO 419
<211> LENGTH: 6
<212> TYPE: PRT

<213> ORGANISM: Homo sapiens

<400> SEQUENCE: 419

His Gly Ser His Asp Asn
1 5

<210> SEQ ID NO 420
<211> LENGTH: 6
<212> TYPE: PRT
<213> ORGANISM: Homo sapiens

<400> SEQUENCE: 420

His Val Ser His Asp Asn
1 5

<210> SEQ ID NO 421
<211> LENGTH: 6
<212> TYPE: PRT
<213> ORGANISM: Homo sapiens

<400> SEQUENCE: 421

His Met Ser His Asp Asn
1 5

<210> SEQ ID NO 422
<211> LENGTH: 6
<212> TYPE: PRT
<213> ORGANISM: Homo sapiens

<400> SEQUENCE: 422

His Leu Ser His Asp Asn
1 5

<210> SEQ ID NO 423
<211> LENGTH: 6
<212> TYPE: PRT
<213> ORGANISM: Homo sapiens

<400> SEQUENCE: 423

His Ile Ser His Asp Asn
1 5

<210> SEQ ID NO 424
<211> LENGTH: 6
<212> TYPE: PRT
<213> ORGANISM: Homo sapiens

<400> SEQUENCE: 424

His Pro Ser His Asp Asn
1 5

<210> SEQ ID NO 425
<211> LENGTH: 6
<212> TYPE: PRT
<213> ORGANISM: Homo sapiens

<400> SEQUENCE: 425

His Trp Ser His Asp Asn
1 5

<210> SEQ ID NO 426
<211> LENGTH: 6
<212> TYPE: PRT
<213> ORGANISM: Homo sapiens

<400> SEQUENCE: 426

His Gly Asp His Asp Asn
1 5

<210> SEQ ID NO 427
<211> LENGTH: 6
<212> TYPE: PRT
<213> ORGANISM: Homo sapiens

<400> SEQUENCE: 427

His Gly Ser His Asp Asn
1 5

<210> SEQ ID NO 428
<211> LENGTH: 6
<212> TYPE: PRT
<213> ORGANISM: Homo sapiens

<400> SEQUENCE: 428

His Gly Tyr His Asp Asn
1 5

<210> SEQ ID NO 429
<211> LENGTH: 6
<212> TYPE: PRT
<213> ORGANISM: Homo sapiens

<400> SEQUENCE: 429

His Gly His His Asp Asn
1 5

<210> SEQ ID NO 430
<211> LENGTH: 6
<212> TYPE: PRT
<213> ORGANISM: Homo sapiens

<400> SEQUENCE: 430

His Gly Arg His Asp Asn
1 5

<210> SEQ ID NO 431
<211> LENGTH: 6
<212> TYPE: PRT
<213> ORGANISM: Homo sapiens

<400> SEQUENCE: 431

His Gly Asn His Asp Asn
1 5

<210> SEQ ID NO 432
<211> LENGTH: 6
<212> TYPE: PRT
<213> ORGANISM: Homo sapiens

<400> SEQUENCE: 432

His Gly Thr His Asp Asn
1 5

<210> SEQ ID NO 433
<211> LENGTH: 6
<212> TYPE: PRT
<213> ORGANISM: Homo sapiens

<400> SEQUENCE: 433

His Gly Gly His Asp Asn
1 5

<210> SEQ ID NO 434
<211> LENGTH: 6
<212> TYPE: PRT
<213> ORGANISM: Homo sapiens

<400> SEQUENCE: 434

His Gly Ala His Asp Asn
1               5

<210> SEQ ID NO 435
<211> LENGTH: 6
<212> TYPE: PRT
<213> ORGANISM: Homo sapiens

<400> SEQUENCE: 435

His Gly Ile His Asp Asn
1               5

<210> SEQ ID NO 436
<211> LENGTH: 6
<212> TYPE: PRT
<213> ORGANISM: Homo sapiens

<400> SEQUENCE: 436

His Gly Pro His Asp Asn
1               5

<210> SEQ ID NO 437
<211> LENGTH: 6
<212> TYPE: PRT
<213> ORGANISM: Homo sapiens

<400> SEQUENCE: 437

His Gly Trp His Asp Asn
1               5

<210> SEQ ID NO 438
<211> LENGTH: 6
<212> TYPE: PRT
<213> ORGANISM: Homo sapiens

<400> SEQUENCE: 438

His Gly Phe His Asp Asn
1               5

<210> SEQ ID NO 439
<211> LENGTH: 6
<212> TYPE: PRT
<213> ORGANISM: Homo sapiens

<400> SEQUENCE: 439

His Gly Ser His Asp Asn
1               5

<210> SEQ ID NO 440
<211> LENGTH: 6
<212> TYPE: PRT
<213> ORGANISM: Homo sapiens

<400> SEQUENCE: 440

His Gly Ser Arg Asp Asn
1               5

<210> SEQ ID NO 441

<211> LENGTH: 6
<212> TYPE: PRT
<213> ORGANISM: Homo sapiens

<400> SEQUENCE: 441

His Gly Ser Thr Asp Asn
1 5

<210> SEQ ID NO 442
<211> LENGTH: 6
<212> TYPE: PRT
<213> ORGANISM: Homo sapiens

<400> SEQUENCE: 442

His Gly Ser Ala Asp Asn
1 5

<210> SEQ ID NO 443
<211> LENGTH: 6
<212> TYPE: PRT
<213> ORGANISM: Homo sapiens

<400> SEQUENCE: 443

His Gly Ser Val Asp Asn
1 5

<210> SEQ ID NO 444
<211> LENGTH: 6
<212> TYPE: PRT
<213> ORGANISM: Homo sapiens

<400> SEQUENCE: 444

His Gly Ser Leu Asp Asn
1 5

<210> SEQ ID NO 445
<211> LENGTH: 6
<212> TYPE: PRT
<213> ORGANISM: Homo sapiens

<400> SEQUENCE: 445

His Gly Ser Ile Asp Asn
1 5

<210> SEQ ID NO 446
<211> LENGTH: 6
<212> TYPE: PRT
<213> ORGANISM: Homo sapiens

<400> SEQUENCE: 446

His Gly Ser Phe Asp Asn
1 5

<210> SEQ ID NO 447
<211> LENGTH: 6
<212> TYPE: PRT
<213> ORGANISM: Homo sapiens

<400> SEQUENCE: 447

His Gly Ser His Asp Asn
1 5

<210> SEQ ID NO 448
<211> LENGTH: 6
<212> TYPE: PRT
<213> ORGANISM: Homo sapiens

<400> SEQUENCE: 448

His Gly Ser His Ser Asn
1 5

<210> SEQ ID NO 449
<211> LENGTH: 6
<212> TYPE: PRT
<213> ORGANISM: Homo sapiens

<400> SEQUENCE: 449

His Gly Ser His Tyr Asn
1 5

<210> SEQ ID NO 450
<211> LENGTH: 6
<212> TYPE: PRT
<213> ORGANISM: Homo sapiens

<400> SEQUENCE: 450

His Gly Ser His His Asn
1 5

<210> SEQ ID NO 451
<211> LENGTH: 6
<212> TYPE: PRT
<213> ORGANISM: Homo sapiens

<400> SEQUENCE: 451

His Gly Ser His Arg Asn
1 5

<210> SEQ ID NO 452
<211> LENGTH: 6
<212> TYPE: PRT
<213> ORGANISM: Homo sapiens

<400> SEQUENCE: 452

His Gly Ser His Asn Asn
1 5

<210> SEQ ID NO 453
<211> LENGTH: 6
<212> TYPE: PRT
<213> ORGANISM: Homo sapiens

<400> SEQUENCE: 453

His Gly Ser His Gly Asn
1 5

<210> SEQ ID NO 454
<211> LENGTH: 6
<212> TYPE: PRT
<213> ORGANISM: Homo sapiens

<400> SEQUENCE: 454

His Gly Ser His Ala Asn
1 5

<210> SEQ ID NO 455
<211> LENGTH: 6
<212> TYPE: PRT
<213> ORGANISM: Homo sapiens

<400> SEQUENCE: 455

His Gly Ser His Val Asn
1 5

<210> SEQ ID NO 456
<211> LENGTH: 6
<212> TYPE: PRT
<213> ORGANISM: Homo sapiens

<400> SEQUENCE: 456

His Gly Ser His Ile Asn
1 5

<210> SEQ ID NO 457
<211> LENGTH: 6
<212> TYPE: PRT
<213> ORGANISM: Homo sapiens

<400> SEQUENCE: 457

His Gly Ser His Asp Ser
1 5

<210> SEQ ID NO 458
<211> LENGTH: 6
<212> TYPE: PRT
<213> ORGANISM: Homo sapiens

<400> SEQUENCE: 458

His Gly Ser His Asp His
1 5

<210> SEQ ID NO 459
<211> LENGTH: 6
<212> TYPE: PRT
<213> ORGANISM: Homo sapiens

<400> SEQUENCE: 459

His Gly Ser His Asp Lys
1 5

<210> SEQ ID NO 460
<211> LENGTH: 6
<212> TYPE: PRT
<213> ORGANISM: Homo sapiens

<400> SEQUENCE: 460

His Gly Ser His Asp Arg
1 5

<210> SEQ ID NO 461
<211> LENGTH: 6
<212> TYPE: PRT
<213> ORGANISM: Homo sapiens

<400> SEQUENCE: 461

His Gly Ser His Asp Asn
1 5

<210> SEQ ID NO 462
<211> LENGTH: 6
<212> TYPE: PRT
<213> ORGANISM: Homo sapiens

<400> SEQUENCE: 462

His Gly Ser His Asp Thr
1 5

<210> SEQ ID NO 463
<211> LENGTH: 6
<212> TYPE: PRT
<213> ORGANISM: Homo sapiens

<400> SEQUENCE: 463

His Gly Ser His Asp Gly
1               5

<210> SEQ ID NO 464
<211> LENGTH: 6
<212> TYPE: PRT
<213> ORGANISM: Homo sapiens

<400> SEQUENCE: 464

His Gly Ser His Asp Ala
1               5

<210> SEQ ID NO 465
<211> LENGTH: 6
<212> TYPE: PRT
<213> ORGANISM: Homo sapiens

<400> SEQUENCE: 465

His Gly Ser His Asp Leu
1               5

<210> SEQ ID NO 466
<211> LENGTH: 6
<212> TYPE: PRT
<213> ORGANISM: Homo sapiens

<400> SEQUENCE: 466

His Gly Ser His Asp Ile
1               5

<210> SEQ ID NO 467
<211> LENGTH: 6
<212> TYPE: PRT
<213> ORGANISM: Homo sapiens

<400> SEQUENCE: 467

His Gly Ser His Asp Pro
1               5

<210> SEQ ID NO 468
<211> LENGTH: 6
<212> TYPE: PRT
<213> ORGANISM: Homo sapiens

<400> SEQUENCE: 468

His Gly Ser His Asp Trp
1               5

<210> SEQ ID NO 469
<211> LENGTH: 6
<212> TYPE: PRT
<213> ORGANISM: Homo sapiens

<400> SEQUENCE: 469

His Gly Ser His Asp Phe
1               5

<210> SEQ ID NO 470
<211> LENGTH: 13

<212> TYPE: PRT
<213> ORGANISM: Homo sapiens

<400> SEQUENCE: 470

Ser Gly Gly Arg Ser Asn Ile Gly Asp Asn Thr Val Lys
1 5 10

<210> SEQ ID NO 471
<211> LENGTH: 13
<212> TYPE: PRT
<213> ORGANISM: Homo sapiens

<400> SEQUENCE: 471

Ser Gly Gly Arg Ser Asn Ile Gly Cys Asn Thr Val Lys
1 5 10

<210> SEQ ID NO 472
<211> LENGTH: 13
<212> TYPE: PRT
<213> ORGANISM: Homo sapiens

<400> SEQUENCE: 472

Ser Gly Gly Arg Ser Asn Ile Gly Ser Asn Thr Val Lys
1 5 10

<210> SEQ ID NO 473
<211> LENGTH: 13
<212> TYPE: PRT
<213> ORGANISM: Homo sapiens

<400> SEQUENCE: 473

Ser Gly Gly Arg Ser Asn Ile Gly Tyr Asn Thr Val Lys
1 5 10

<210> SEQ ID NO 474
<211> LENGTH: 13
<212> TYPE: PRT
<213> ORGANISM: Homo sapiens

<400> SEQUENCE: 474

Ser Gly Gly Arg Ser Asn Ile Gly Lys Asn Thr Val Lys
1 5 10

<210> SEQ ID NO 475
<211> LENGTH: 13
<212> TYPE: PRT
<213> ORGANISM: Homo sapiens

<400> SEQUENCE: 475

Ser Gly Gly Arg Ser Asn Ile Gly Arg Asn Thr Val Lys
1 5 10

<210> SEQ ID NO 476
<211> LENGTH: 13
<212> TYPE: PRT
<213> ORGANISM: Homo sapiens

<400> SEQUENCE: 476

Ser Gly Gly Arg Ser Asn Ile Gly Asn Asn Thr Val Lys
1 5 10

<210> SEQ ID NO 477
<211> LENGTH: 13
<212> TYPE: PRT
<213> ORGANISM: Homo sapiens

<400> SEQUENCE: 477

Ser Gly Gly Arg Ser Asn Ile Gly Thr Asn Thr Val Lys
1 5 10

<210> SEQ ID NO 478
<211> LENGTH: 13
<212> TYPE: PRT
<213> ORGANISM: Homo sapiens

<400> SEQUENCE: 478

Ser Gly Gly Arg Ser Asn Ile Gly Pro Asn Thr Val Lys
1 5 10

<210> SEQ ID NO 479
<211> LENGTH: 13
<212> TYPE: PRT
<213> ORGANISM: Homo sapiens

<400> SEQUENCE: 479

Ser Gly Gly Arg Ser Asn Ile Gly Ser Asp Thr Val Lys
1 5 10

<210> SEQ ID NO 480
<211> LENGTH: 13
<212> TYPE: PRT
<213> ORGANISM: Homo sapiens

<400> SEQUENCE: 480

Ser Gly Gly Arg Ser Asn Ile Gly Ser Glu Thr Val Lys
1 5 10

<210> SEQ ID NO 481
<211> LENGTH: 13
<212> TYPE: PRT
<213> ORGANISM: Homo sapiens

<400> SEQUENCE: 481

Ser Gly Gly Arg Ser Asn Ile Gly Ser Ser Thr Val Lys
1 5 10

<210> SEQ ID NO 482
<211> LENGTH: 13
<212> TYPE: PRT
<213> ORGANISM: Homo sapiens

<400> SEQUENCE: 482

Ser Gly Gly Arg Ser Asn Ile Gly Ser Tyr Thr Val Lys
1 5 10

<210> SEQ ID NO 483
<211> LENGTH: 13
<212> TYPE: PRT
<213> ORGANISM: Homo sapiens

<400> SEQUENCE: 483

Ser Gly Gly Arg Ser Asn Ile Gly Ser His Thr Val Lys
1 5 10

<210> SEQ ID NO 484
<211> LENGTH: 13
<212> TYPE: PRT
<213> ORGANISM: Homo sapiens

<400> SEQUENCE: 484

Ser Gly Gly Arg Ser Asn Ile Gly Ser Lys Thr Val Lys 1 5 10

<210> SEQ ID NO 485
<211> LENGTH: 13
<212> TYPE: PRT
<213> ORGANISM: Homo sapiens

<400> SEQUENCE: 485

Ser Gly Gly Arg Ser Asn Ile Gly Ser Asn Thr Val Lys
1 5 10

<210> SEQ ID NO 486
<211> LENGTH: 13
<212> TYPE: PRT
<213> ORGANISM: Homo sapiens

<400> SEQUENCE: 486

Ser Gly Gly Arg Ser Asn Ile Gly Ser Gln Thr Val Lys
1 5 10

<210> SEQ ID NO 487
<211> LENGTH: 13
<212> TYPE: PRT
<213> ORGANISM: Homo sapiens

<400> SEQUENCE: 487

Ser Gly Gly Arg Ser Asn Ile Gly Ser Thr Thr Val Lys
1 5 10

<210> SEQ ID NO 488
<211> LENGTH: 13
<212> TYPE: PRT
<213> ORGANISM: Homo sapiens

<400> SEQUENCE: 488

Ser Gly Gly Arg Ser Asn Ile Gly Ser Gly Thr Val Lys
1 5 10

<210> SEQ ID NO 489
<211> LENGTH: 13
<212> TYPE: PRT
<213> ORGANISM: Homo sapiens

<400> SEQUENCE: 489

Ser Gly Gly Arg Ser Asn Ile Gly Ser Met Thr Val Lys
1 5 10

<210> SEQ ID NO 490
<211> LENGTH: 13
<212> TYPE: PRT
<213> ORGANISM: Homo sapiens

<400> SEQUENCE: 490

Ser Gly Gly Arg Ser Asn Ile Gly Ser Ile Thr Val Lys
1 5 10

<210> SEQ ID NO 491
<211> LENGTH: 13
<212> TYPE: PRT
<213> ORGANISM: Homo sapiens

<400> SEQUENCE: 491

Ser Gly Gly Arg Ser Asn Ile Gly Ser Asn Asp Val Lys
1 5 10

<210> SEQ ID NO 492
<211> LENGTH: 13
<212> TYPE: PRT
<213> ORGANISM: Homo sapiens

<400> SEQUENCE: 492

Ser Gly Gly Arg Ser Asn Ile Gly Ser Asn Cys Val Lys
1 5 10

<210> SEQ ID NO 493
<211> LENGTH: 13
<212> TYPE: PRT
<213> ORGANISM: Homo sapiens

<400> SEQUENCE: 493

Ser Gly Gly Arg Ser Asn Ile Gly Ser Asn Ser Val Lys
1 5 10

<210> SEQ ID NO 494
<211> LENGTH: 13
<212> TYPE: PRT
<213> ORGANISM: Homo sapiens

<400> SEQUENCE: 494

Ser Gly Gly Arg Ser Asn Ile Gly Ser Asn Tyr Val Lys
1 5 10

<210> SEQ ID NO 495
<211> LENGTH: 13
<212> TYPE: PRT
<213> ORGANISM: Homo sapiens

<400> SEQUENCE: 495

Ser Gly Gly Arg Ser Asn Ile Gly Ser Asn His Val Lys
1 5 10

<210> SEQ ID NO 496
<211> LENGTH: 13
<212> TYPE: PRT
<213> ORGANISM: Homo sapiens

<400> SEQUENCE: 496

Ser Gly Gly Arg Ser Asn Ile Gly Ser Asn Lys Val Lys
1 5 10

<210> SEQ ID NO 497
<211> LENGTH: 13
<212> TYPE: PRT
<213> ORGANISM: Homo sapiens

<400> SEQUENCE: 497

Ser Gly Gly Arg Ser Asn Ile Gly Ser Asn Arg Val Lys
1 5 10

<210> SEQ ID NO 498
<211> LENGTH: 13
<212> TYPE: PRT
<213> ORGANISM: Homo sapiens

<400> SEQUENCE: 498

Ser Gly Gly Arg Ser Asn Ile Gly Ser Asn Asn Val Lys
1 5 10

<210> SEQ ID NO 499
<211> LENGTH: 13
<212> TYPE: PRT

<213> ORGANISM: Homo sapiens

<400> SEQUENCE: 499

Ser Gly Gly Arg Ser Asn Ile Gly Ser Asn Gln Val Lys
1 5 10

<210> SEQ ID NO 500
<211> LENGTH: 13
<212> TYPE: PRT
<213> ORGANISM: Homo sapiens

<400> SEQUENCE: 500

Ser Gly Gly Arg Ser Asn Ile Gly Ser Asn Thr Val Lys
1 5 10

<210> SEQ ID NO 501
<211> LENGTH: 13
<212> TYPE: PRT
<213> ORGANISM: Homo sapiens

<400> SEQUENCE: 501

Ser Gly Gly Arg Ser Asn Ile Gly Ser Asn Ala Val Lys
1 5 10

<210> SEQ ID NO 502
<211> LENGTH: 13
<212> TYPE: PRT
<213> ORGANISM: Homo sapiens

<400> SEQUENCE: 502

Ser Gly Gly Arg Ser Asn Ile Gly Ser Asn Val Val Lys
1 5 10

<210> SEQ ID NO 503
<211> LENGTH: 13
<212> TYPE: PRT
<213> ORGANISM: Homo sapiens

<400> SEQUENCE: 503

Ser Gly Gly Arg Ser Asn Ile Gly Ser Asn Leu Val Lys
1 5 10

<210> SEQ ID NO 504
<211> LENGTH: 13
<212> TYPE: PRT
<213> ORGANISM: Homo sapiens

<400> SEQUENCE: 504

Ser Gly Gly Arg Ser Asn Ile Gly Ser Asn Ile Val Lys
1 5 10

<210> SEQ ID NO 505
<211> LENGTH: 13
<212> TYPE: PRT
<213> ORGANISM: Homo sapiens

<400> SEQUENCE: 505

Ser Gly Gly Arg Ser Asn Ile Gly Ser Asn Pro Val Lys
1 5 10

<210> SEQ ID NO 506
<211> LENGTH: 7
<212> TYPE: PRT
<213> ORGANISM: Homo sapiens

<400> SEQUENCE: 506

Asp Asn Asp Gln Arg Pro Ser
1               5

<210> SEQ ID NO 507
<211> LENGTH: 7
<212> TYPE: PRT
<213> ORGANISM: Homo sapiens

<400> SEQUENCE: 507

Glu Asn Asp Gln Arg Pro Ser
1               5

<210> SEQ ID NO 508
<211> LENGTH: 7
<212> TYPE: PRT
<213> ORGANISM: Homo sapiens

<400> SEQUENCE: 508

Cys Asn Asp Gln Arg Pro Ser
1               5

<210> SEQ ID NO 509
<211> LENGTH: 7
<212> TYPE: PRT
<213> ORGANISM: Homo sapiens

<400> SEQUENCE: 509

Ser Asn Asp Gln Arg Pro Ser
1               5

<210> SEQ ID NO 510
<211> LENGTH: 7
<212> TYPE: PRT
<213> ORGANISM: Homo sapiens

<400> SEQUENCE: 510

Tyr Asn Asp Gln Arg Pro Ser
1               5

<210> SEQ ID NO 511
<211> LENGTH: 7
<212> TYPE: PRT
<213> ORGANISM: Homo sapiens

<400> SEQUENCE: 511

His Asn Asp Gln Arg Pro Ser
1               5

<210> SEQ ID NO 512
<211> LENGTH: 7
<212> TYPE: PRT
<213> ORGANISM: Homo sapiens

<400> SEQUENCE: 512

Lys Asn Asp Gln Arg Pro Ser
1               5

<210> SEQ ID NO 513
<211> LENGTH: 7
<212> TYPE: PRT
<213> ORGANISM: Homo sapiens

<400> SEQUENCE: 513

Arg Asn Asp Gln Arg Pro Ser
1               5

<210> SEQ ID NO 514
<211> LENGTH: 7
<212> TYPE: PRT
<213> ORGANISM: Homo sapiens

<400> SEQUENCE: 514

Asn Asn Asp Gln Arg Pro Ser
1 5

<210> SEQ ID NO 515
<211> LENGTH: 7
<212> TYPE: PRT
<213> ORGANISM: Homo sapiens

<400> SEQUENCE: 515

Gln Asn Asp Gln Arg Pro Ser
1 5

<210> SEQ ID NO 516
<211> LENGTH: 7
<212> TYPE: PRT
<213> ORGANISM: Homo sapiens

<400> SEQUENCE: 516

Thr Asn Asp Gln Arg Pro Ser
1 5

<210> SEQ ID NO 517
<211> LENGTH: 7
<212> TYPE: PRT
<213> ORGANISM: Homo sapiens

<400> SEQUENCE: 517

Gly Asn Asp Gln Arg Pro Ser
1 5

<210> SEQ ID NO 518
<211> LENGTH: 7
<212> TYPE: PRT
<213> ORGANISM: Homo sapiens

<400> SEQUENCE: 518

Ala Asn Asp Gln Arg Pro Ser
1 5

<210> SEQ ID NO 519
<211> LENGTH: 7
<212> TYPE: PRT
<213> ORGANISM: Homo sapiens

<400> SEQUENCE: 519

Val Asn Asp Gln Arg Pro Ser
1 5

<210> SEQ ID NO 520
<211> LENGTH: 7
<212> TYPE: PRT
<213> ORGANISM: Homo sapiens

<400> SEQUENCE: 520

Met Asn Asp Gln Arg Pro Ser
1 5

<210> SEQ ID NO 521

<211> LENGTH: 7
<212> TYPE: PRT
<213> ORGANISM: Homo sapiens

<400> SEQUENCE: 521

Leu Asn Asp Gln Arg Pro Ser
1 5

<210> SEQ ID NO 522
<211> LENGTH: 7
<212> TYPE: PRT
<213> ORGANISM: Homo sapiens

<400> SEQUENCE: 522

Ile Asn Asp Gln Arg Pro Ser
1 5

<210> SEQ ID NO 523
<211> LENGTH: 7
<212> TYPE: PRT
<213> ORGANISM: Homo sapiens

<400> SEQUENCE: 523

Pro Asn Asp Gln Arg Pro Ser
1 5

<210> SEQ ID NO 524
<211> LENGTH: 7
<212> TYPE: PRT
<213> ORGANISM: Homo sapiens

<400> SEQUENCE: 524

Trp Asn Asp Gln Arg Pro Ser
1 5

<210> SEQ ID NO 525
<211> LENGTH: 7
<212> TYPE: PRT
<213> ORGANISM: Homo sapiens

<400> SEQUENCE: 525

Phe Asn Asp Gln Arg Pro Ser
1 5

<210> SEQ ID NO 526
<211> LENGTH: 7
<212> TYPE: PRT
<213> ORGANISM: Homo sapiens

<400> SEQUENCE: 526

Gly Asn Asp Ser Arg Pro Ser
1 5

<210> SEQ ID NO 527
<211> LENGTH: 7
<212> TYPE: PRT
<213> ORGANISM: Homo sapiens

<400> SEQUENCE: 527

Gly Asn Asp Tyr Arg Pro Ser
1 5

<210> SEQ ID NO 528
<211> LENGTH: 7
<212> TYPE: PRT
<213> ORGANISM: Homo sapiens

<400> SEQUENCE: 528

Gly Asn Asp Arg Arg Pro Ser
1 5

<210> SEQ ID NO 529
<211> LENGTH: 7
<212> TYPE: PRT
<213> ORGANISM: Homo sapiens

<400> SEQUENCE: 529

Gly Asn Asp Gln Arg Pro Ser
1 5

<210> SEQ ID NO 530
<211> LENGTH: 7
<212> TYPE: PRT
<213> ORGANISM: Homo sapiens

<400> SEQUENCE: 530

Gly Asn Asp Thr Arg Pro Ser
1 5

<210> SEQ ID NO 531
<211> LENGTH: 7
<212> TYPE: PRT
<213> ORGANISM: Homo sapiens

<400> SEQUENCE: 531

Gly Asn Asp Ala Arg Pro Ser
1 5

<210> SEQ ID NO 532
<211> LENGTH: 7
<212> TYPE: PRT
<213> ORGANISM: Homo sapiens

<400> SEQUENCE: 532

Gly Asn Asp Ile Arg Pro Ser
1 5

<210> SEQ ID NO 533
<211> LENGTH: 7
<212> TYPE: PRT
<213> ORGANISM: Homo sapiens

<400> SEQUENCE: 533

Gly Asn Asp Pro Arg Pro Ser
1 5

<210> SEQ ID NO 534
<211> LENGTH: 12
<212> TYPE: PRT
<213> ORGANISM: Homo sapiens

<400> SEQUENCE: 534

Gln Ser Tyr Asp Arg Gly Thr His Pro Ala Leu Leu
1 5 10

<210> SEQ ID NO 535
<211> LENGTH: 12
<212> TYPE: PRT
<213> ORGANISM: Homo sapiens

<400> SEQUENCE: 535

Gln Ser Tyr Cys Arg Gly Thr His Pro Ala Leu Leu
1 5 10

<210> SEQ ID NO 536
<211> LENGTH: 12
<212> TYPE: PRT
<213> ORGANISM: Homo sapiens

<400> SEQUENCE: 536

Gln Ser Tyr Ser Arg Gly Thr His Pro Ala Leu Leu
1 5 10

<210> SEQ ID NO 537
<211> LENGTH: 12
<212> TYPE: PRT
<213> ORGANISM: Homo sapiens

<400> SEQUENCE: 537

Gln Ser Tyr Tyr Arg Gly Thr His Pro Ala Leu Leu
1 5 10

<210> SEQ ID NO 538
<211> LENGTH: 12
<212> TYPE: PRT
<213> ORGANISM: Homo sapiens

<400> SEQUENCE: 538

Gln Ser Tyr Asn Arg Gly Thr His Pro Ala Leu Leu
1 5 10

<210> SEQ ID NO 539
<211> LENGTH: 12
<212> TYPE: PRT
<213> ORGANISM: Homo sapiens

<400> SEQUENCE: 539

Gln Ser Tyr Gln Arg Gly Thr His Pro Ala Leu Leu
1 5 10

<210> SEQ ID NO 540
<211> LENGTH: 12
<212> TYPE: PRT
<213> ORGANISM: Homo sapiens

<400> SEQUENCE: 540

Gln Ser Tyr Thr Arg Gly Thr His Pro Ala Leu Leu
1 5 10

<210> SEQ ID NO 541
<211> LENGTH: 12
<212> TYPE: PRT
<213> ORGANISM: Homo sapiens

<400> SEQUENCE: 541

Gln Ser Tyr Gly Arg Gly Thr His Pro Ala Leu Leu
1 5 10

<210> SEQ ID NO 542
<211> LENGTH: 12
<212> TYPE: PRT
<213> ORGANISM: Homo sapiens

<400> SEQUENCE: 542

Gln Ser Tyr Ala Arg Gly Thr His Pro Ala Leu Leu
1 5 10

<210> SEQ ID NO 543
<211> LENGTH: 12
<212> TYPE: PRT
<213> ORGANISM: Homo sapiens

<400> SEQUENCE: 543

Gln Ser Tyr Leu Arg Gly Thr His Pro Ala Leu Leu
1 5 10

<210> SEQ ID NO 544
<211> LENGTH: 12
<212> TYPE: PRT
<213> ORGANISM: Homo sapiens

<400> SEQUENCE: 544

Gln Ser Tyr Ile Arg Gly Thr His Pro Ala Leu Leu
1 5 10

<210> SEQ ID NO 545
<211> LENGTH: 12
<212> TYPE: PRT
<213> ORGANISM: Homo sapiens

<400> SEQUENCE: 545

Gln Ser Tyr Trp Arg Gly Thr His Pro Ala Leu Leu
1 5 10

<210> SEQ ID NO 546
<211> LENGTH: 12
<212> TYPE: PRT
<213> ORGANISM: Homo sapiens

<400> SEQUENCE: 546

Gln Ser Tyr Phe Arg Gly Thr His Pro Ala Leu Leu
1 5 10

<210> SEQ ID NO 547
<211> LENGTH: 12
<212> TYPE: PRT
<213> ORGANISM: Homo sapiens

<400> SEQUENCE: 547

Gln Ser Tyr Asp Asp Gly Thr His Pro Ala Leu Leu
1 5 10

<210> SEQ ID NO 548
<211> LENGTH: 12
<212> TYPE: PRT
<213> ORGANISM: Homo sapiens

<400> SEQUENCE: 548

Gln Ser Tyr Asp Cys Gly Thr His Pro Ala Leu Leu
1 5 10

<210> SEQ ID NO 549
<211> LENGTH: 12
<212> TYPE: PRT
<213> ORGANISM: Homo sapiens

<400> SEQUENCE: 549

Gln Ser Tyr Asp Ser Gly Thr His Pro Ala Leu Leu
1 5 10

<210> SEQ ID NO 550
<211> LENGTH: 12

<212> TYPE: PRT
<213> ORGANISM: Homo sapiens

<400> SEQUENCE: 550

Gln Ser Tyr Asp Tyr Gly Thr His Pro Ala Leu Leu
1 5 10

<210> SEQ ID NO 551
<211> LENGTH: 12
<212> TYPE: PRT
<213> ORGANISM: Homo sapiens

<400> SEQUENCE: 551

Gln Ser Tyr Asp Arg Gly Thr His Pro Ala Leu Leu
1 5 10

<210> SEQ ID NO 552
<211> LENGTH: 12
<212> TYPE: PRT
<213> ORGANISM: Homo sapiens

<400> SEQUENCE: 552

Gln Ser Tyr Asp Asn Gly Thr His Pro Ala Leu Leu
1 5 10

<210> SEQ ID NO 553
<211> LENGTH: 12
<212> TYPE: PRT
<213> ORGANISM: Homo sapiens

<400> SEQUENCE: 553

Gln Ser Tyr Asp Gln Gly Thr His Pro Ala Leu Leu
1 5 10

<210> SEQ ID NO 554
<211> LENGTH: 12
<212> TYPE: PRT
<213> ORGANISM: Homo sapiens

<400> SEQUENCE: 554

Gln Ser Tyr Asp Thr Gly Thr His Pro Ala Leu Leu
1 5 10

<210> SEQ ID NO 555
<211> LENGTH: 12
<212> TYPE: PRT
<213> ORGANISM: Homo sapiens

<400> SEQUENCE: 555

Gln Ser Tyr Asp Gly Gly Thr His Pro Ala Leu Leu
1 5 10

<210> SEQ ID NO 556
<211> LENGTH: 12
<212> TYPE: PRT
<213> ORGANISM: Homo sapiens

<400> SEQUENCE: 556

Gln Ser Tyr Asp Ala Gly Thr His Pro Ala Leu Leu
1 5 10

<210> SEQ ID NO 557
<211> LENGTH: 12
<212> TYPE: PRT
<213> ORGANISM: Homo sapiens

<400> SEQUENCE: 557

Gln Ser Tyr Asp Val Gly Thr His Pro Ala Leu Leu
1 5 10

<210> SEQ ID NO 558
<211> LENGTH: 12
<212> TYPE: PRT
<213> ORGANISM: Homo sapiens

<400> SEQUENCE: 558

Gln Ser Tyr Asp Met Gly Thr His Pro Ala Leu Leu
1 5 10

<210> SEQ ID NO 559
<211> LENGTH: 12
<212> TYPE: PRT
<213> ORGANISM: Homo sapiens

<400> SEQUENCE: 559

Gln Ser Tyr Asp Leu Gly Thr His Pro Ala Leu Leu
1 5 10

<210> SEQ ID NO 560
<211> LENGTH: 12
<212> TYPE: PRT
<213> ORGANISM: Homo sapiens

<400> SEQUENCE: 560

Gln Ser Tyr Asp Ile Gly Thr His Pro Ala Leu Leu
1 5 10

<210> SEQ ID NO 561
<211> LENGTH: 12
<212> TYPE: PRT
<213> ORGANISM: Homo sapiens

<400> SEQUENCE: 561

Gln Ser Tyr Asp Pro Gly Thr His Pro Ala Leu Leu
1 5 10

<210> SEQ ID NO 562
<211> LENGTH: 12
<212> TYPE: PRT
<213> ORGANISM: Homo sapiens

<400> SEQUENCE: 562

Gln Ser Tyr Asp Trp Gly Thr His Pro Ala Leu Leu
1 5 10

<210> SEQ ID NO 563
<211> LENGTH: 12
<212> TYPE: PRT
<213> ORGANISM: Homo sapiens

<400> SEQUENCE: 563

Gln Ser Tyr Asp Arg Asp Thr His Pro Ala Leu Leu
1 5 10

<210> SEQ ID NO 564
<211> LENGTH: 12
<212> TYPE: PRT
<213> ORGANISM: Homo sapiens

<400> SEQUENCE: 564

Gln Ser Tyr Asp Arg Cys Thr His Pro Ala Leu Leu 1 5 10

<210> SEQ ID NO 565
<211> LENGTH: 12
<212> TYPE: PRT
<213> ORGANISM: Homo sapiens

<400> SEQUENCE: 565

Gln Ser Tyr Asp Arg Ser Thr His Pro Ala Leu Leu
1 5 10

<210> SEQ ID NO 566
<211> LENGTH: 12
<212> TYPE: PRT
<213> ORGANISM: Homo sapiens

<400> SEQUENCE: 566

Gln Ser Tyr Asp Arg Tyr Thr His Pro Ala Leu Leu
1 5 10

<210> SEQ ID NO 567
<211> LENGTH: 12
<212> TYPE: PRT
<213> ORGANISM: Homo sapiens

<400> SEQUENCE: 567

Gln Ser Tyr Asp Arg His Thr His Pro Ala Leu Leu
1 5 10

<210> SEQ ID NO 568
<211> LENGTH: 12
<212> TYPE: PRT
<213> ORGANISM: Homo sapiens

<400> SEQUENCE: 568

Gln Ser Tyr Asp Arg Arg Thr His Pro Ala Leu Leu
1 5 10

<210> SEQ ID NO 569
<211> LENGTH: 12
<212> TYPE: PRT
<213> ORGANISM: Homo sapiens

<400> SEQUENCE: 569

Gln Ser Tyr Asp Arg Asn Thr His Pro Ala Leu Leu
1 5 10

<210> SEQ ID NO 570
<211> LENGTH: 12
<212> TYPE: PRT
<213> ORGANISM: Homo sapiens

<400> SEQUENCE: 570

Gln Ser Tyr Asp Arg Gln Thr His Pro Ala Leu Leu
1 5 10

<210> SEQ ID NO 571
<211> LENGTH: 12
<212> TYPE: PRT
<213> ORGANISM: Homo sapiens

<400> SEQUENCE: 571

Gln Ser Tyr Asp Arg Thr Thr His Pro Ala Leu Leu
1 5 10

<210> SEQ ID NO 572
<211> LENGTH: 12
<212> TYPE: PRT
<213> ORGANISM: Homo sapiens

<400> SEQUENCE: 572

Gln Ser Tyr Asp Arg Gly Thr His Pro Ala Leu Leu
1 5 10

<210> SEQ ID NO 573
<211> LENGTH: 12
<212> TYPE: PRT
<213> ORGANISM: Homo sapiens

<400> SEQUENCE: 573

Gln Ser Tyr Asp Arg Ala Thr His Pro Ala Leu Leu
1 5 10

<210> SEQ ID NO 574
<211> LENGTH: 12
<212> TYPE: PRT
<213> ORGANISM: Homo sapiens

<400> SEQUENCE: 574

Gln Ser Tyr Asp Arg Val Thr His Pro Ala Leu Leu
1 5 10

<210> SEQ ID NO 575
<211> LENGTH: 12
<212> TYPE: PRT
<213> ORGANISM: Homo sapiens

<400> SEQUENCE: 575

Gln Ser Tyr Asp Arg Leu Thr His Pro Ala Leu Leu
1 5 10

<210> SEQ ID NO 576
<211> LENGTH: 12
<212> TYPE: PRT
<213> ORGANISM: Homo sapiens

<400> SEQUENCE: 576

Gln Ser Tyr Asp Arg Ile Thr His Pro Ala Leu Leu
1 5 10

<210> SEQ ID NO 577
<211> LENGTH: 12
<212> TYPE: PRT
<213> ORGANISM: Homo sapiens

<400> SEQUENCE: 577

Gln Ser Tyr Asp Arg Pro Thr His Pro Ala Leu Leu
1 5 10

<210> SEQ ID NO 578
<211> LENGTH: 12
<212> TYPE: PRT
<213> ORGANISM: Homo sapiens

<400> SEQUENCE: 578

Gln Ser Tyr Asp Arg Trp Thr His Pro Ala Leu Leu
1 5 10

<210> SEQ ID NO 579
<211> LENGTH: 12
<212> TYPE: PRT

<213> ORGANISM: Homo sapiens

<400> SEQUENCE: 579

Gln Ser Tyr Asp Arg Phe Thr His Pro Ala Leu Leu
1               5                   10

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594
<211> LENGTH: 100
<212> TYPE: PRT
<213> ORGANISM: Homo sapiens

<400> SEQUENCE: 594

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 595
<211> LENGTH: 100
<212> TYPE: PRT
<213> ORGANISM: Homo sapiens

<400> SEQUENCE: 595

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ser Trp Val Arg Gln Ala Gln Gly Lys Gly Leu Glu Leu Val
        35                  40                  45

Gly Leu Ile Arg Asn Lys Ala Asn Ser Tyr Thr Thr Glu Tyr Ala Ala
    50                  55                  60

Ser Val Lys Gly Arg Leu Thr Ile Ser Arg Glu Asp Ser Lys Asn Thr
65                  70                  75                  80

Leu Tyr Leu Gln Met Ser Ser Leu Lys Thr Glu Asp Leu Ala Val Tyr
                85                  90                  95

Tyr Cys Ala Arg
100

<210> SEQ ID NO 596
<211> LENGTH: 100
<212> TYPE: PRT
<213> ORGANISM: Homo sapiens

<400> SEQUENCE: 596

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Ser Trp Val Arg Gln Ala Gln Gly Lys Gly Leu Glu Leu Val
35 40 45

Gly Leu Ile Arg Asn Lys Ala Asn Ser Tyr Thr Thr Glu Tyr Ala Ala
50 55 60

Ser Val Lys Gly Arg Leu Thr Ile Ser Arg Glu Asp Ser Lys Asn Thr
65 70 75 80

Met Tyr Leu Gln Met Ser Asn Leu Lys Thr Glu Asp Leu Ala Val Tyr
85 90 95

Tyr Cys Ala Arg
100

<210> SEQ ID NO 597
<211> LENGTH: 100
<212> TYPE: PRT
<213> ORGANISM: Homo sapiens

<400> SEQUENCE: 597

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Ser Trp Val Arg Gln Ala Gln Gly Lys Gly Leu Glu Leu Val
35 40 45

Gly Leu Ile Arg Asn Lys Ala Asn Ser Tyr Thr Thr Glu Tyr Ala Ala
50 55 60

Ser Val Lys Gly Arg Leu Thr Ile Ser Arg Glu Asp Ser Lys Asn Thr
65 70 75 80

Leu Tyr Leu Gln Met Ser Ser Leu Lys Thr Glu Asp Leu Ala Val Tyr
85 90 95

Tyr Cys Ala Arg
100

<210> SEQ ID NO 598
<211> LENGTH: 98
<212> TYPE: PRT
<213> ORGANISM: Homo sapiens

<400> SEQUENCE: 598

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys

<210> SEQ ID NO 599
<211> LENGTH: 98
<212> TYPE: PRT
<213> ORGANISM: Homo sapiens

<400> SEQUENCE: 599

Glu Val Gln Leu Val Glu Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr His Cys
85 90 95

Ala Arg

<210> SEQ ID NO 600
<211> LENGTH: 98
<212> TYPE: PRT
<213> ORGANISM: Homo sapiens

<400> SEQUENCE: 600

Glu Val Gln Leu Val Glu Ser Gly Gly Val Val Val Gln Pro Gly Gly
1 5 10 15

Ser Leu Arg Leu Ser Cys Ala Ala Ser Gly Phe Thr Phe Asp Asp Tyr
20 25 30

Thr Met His Trp Val Arg Gln Ala Pro Gly Lys Gly Leu Glu Trp Val
35 40 45

Ser Leu Ile Ser Trp Asp Gly Gly Ser Thr Tyr Tyr Ala Asp Ser Val
50 55 60

Lys Gly Arg Phe Thr Ile Ser Arg Asp Asn Ser Lys Asn Ser Leu Tyr
65 70 75 80

Leu Gln Met Asn Ser Leu Arg Thr Glu Asp Thr Ala Leu Tyr Tyr Cys
85 90 95

Ala Lys

<210> SEQ ID NO 601
<211> LENGTH: 98
<212> TYPE: PRT
<213> ORGANISM: Homo sapiens

<400> SEQUENCE: 601

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val

```
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 602
<211> LENGTH: 98
<212> TYPE: PRT
<213> ORGANISM: Homo sapiens

<400> SEQUENCE: 602

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 603
<211> LENGTH: 100
<212> TYPE: PRT
<213> ORGANISM: Homo sapiens

<400> SEQUENCE: 603

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100


<210> SEQ ID NO 604
<211> LENGTH: 100
<212> TYPE: PRT
<213> ORGANISM: Homo sapiens

<400> SEQUENCE: 604

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100


<210> SEQ ID NO 605
<211> LENGTH: 100
<212> TYPE: PRT
<213> ORGANISM: Homo sapiens

<400> SEQUENCE: 605

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Glu Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100


<210> SEQ ID NO 606
<211> LENGTH: 100
<212> TYPE: PRT
<213> ORGANISM: Homo sapiens

<400> SEQUENCE: 606

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100


<210> SEQ ID NO 607
<211> LENGTH: 100
```

<212> TYPE: PRT
<213> ORGANISM: Homo sapiens

<400> SEQUENCE: 607

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asn Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Thr
100

<210> SEQ ID NO 608
<211> LENGTH: 100
<212> TYPE: PRT
<213> ORGANISM: Homo sapiens

<400> SEQUENCE: 608

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Asn Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Thr
100

<210> SEQ ID NO 609
<211> LENGTH: 100
<212> TYPE: PRT
<213> ORGANISM: Homo sapiens

<400> SEQUENCE: 609

Glu Val Gln Leu Val Glu Ser Gly Gly Ala Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Thr
100

<210> SEQ ID NO 610
<211> LENGTH: 98
<212> TYPE: PRT
<213> ORGANISM: Homo sapiens

<400> SEQUENCE: 610

Glu Val Gln Leu Val Glu Ser Gly Gly Gly Leu Val Gln Pro Gly Gly
1 5 10 15

Ser Leu Arg Leu Ser Cys Pro Ala Ser Gly Phe Thr Phe Ser Asn His
20 25 30

Tyr Met Ser Trp Val Arg Gln Ala Pro Gly Lys Gly Leu Glu Trp Val
35 40 45

Ser Tyr Ile Ser Gly Asp Ser Gly Tyr Thr Asn Tyr Ala Asp Ser Val
50 55 60

Lys Gly Arg Phe Thr Ile Ser Arg Asp Asn Ala Asn Asn Ser Pro Tyr
65 70 75 80

Leu Gln Met Asn Ser Leu Arg Ala Glu Asp Thr Ala Val Tyr Tyr Cys
85 90 95

Val Lys

<210> SEQ ID NO 611
<211> LENGTH: 98
<212> TYPE: PRT
<213> ORGANISM: Homo sapiens

<400> SEQUENCE: 611

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn His
20 25 30

Tyr Thr Ser Trp Val Arg Gln Ala Pro Gly Lys Gly Leu Glu Trp Val
35 40 45

Ser Tyr Ser Ser Gly Asn Ser Gly Tyr Thr Asn Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Val Lys

<210> SEQ ID NO 612
<211> LENGTH: 98
<212> TYPE: PRT
<213> ORGANISM: Homo sapiens

<400> SEQUENCE: 612

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Ser
20 25 30

Asp Met Asn Trp Val His Gln Ala Pro Gly Lys Gly Leu Glu Trp Val
35 40 45

Ser Gly Val Ser Trp Asn Gly Ser Arg Thr His Tyr Ala Asp Ser Val
50 55 60

Lys Gly Arg Phe Ile Ile Ser Arg Asp Asn Ser Arg Asn Thr Leu Tyr
65 70 75 80

Leu Gln Thr Asn Ser Leu Arg Ala Glu Asp Thr Ala Val Tyr Tyr Cys
85 90 95

Val Arg

<210> SEQ ID NO 613
<211> LENGTH: 98
<212> TYPE: PRT
<213> ORGANISM: Homo sapiens

<400> SEQUENCE: 613

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Ser
20 25 30

Asp Met Asn Trp Ala Arg Lys Ala Pro Gly Lys Gly Leu Glu Trp Val
35 40 45

Ser Gly Val Ser Trp Asn Gly Ser Arg Thr His Tyr Val Asp Ser Val
50 55 60

Lys Arg Arg Phe Ile Ile Ser Arg Asp Asn Ser Arg Asn Ser Leu Tyr
65 70 75 80

Leu Gln Lys Asn Arg Arg Arg Ala Glu Asp Met Ala Val Tyr Tyr Cys
85 90 95

Val Arg

<210> SEQ ID NO 614
<211> LENGTH: 98
<212> TYPE: PRT
<213> ORGANISM: Homo sapiens

<400> SEQUENCE: 614

Thr Val Gln Leu Val Glu Ser Gly Gly Gly Leu Val Glu Pro Gly Gly
1 5 10 15

Ser Leu Arg Leu Ser Cys Ala Ala Ser Gly Phe Thr Phe Ser Asn Ser
20 25 30

Asp Met Asn Trp Val Arg Gln Ala Pro Gly Lys Gly Leu Glu Trp Val
35 40 45

Ser Gly Val Ser Trp Asn Gly Ser Arg Thr His Tyr Ala Asp Ser Val
50 55 60

Lys Gly Arg Phe Ile Ile Ser Arg Asp Asn Ser Arg Asn Phe Leu Tyr
65 70 75 80

Gln Gln Met Asn Ser Leu Arg Pro Glu Asp Met Ala Val Tyr Tyr Cys
85 90 95

Val Arg

<210> SEQ ID NO 615
<211> LENGTH: 97
<212> TYPE: PRT
<213> ORGANISM: Homo sapiens

<400> SEQUENCE: 615

Glu Val His Leu Val Glu Ser Gly Gly Gly Leu Val Gln Pro Gly Gly
1 5 10 15

Ala Leu Arg Leu Ser Cys Ala Ala Ser Gly Phe Thr Phe Ser Asn Tyr
20 25 30

Asp Met His Trp Val Arg Gln Ala Thr Gly Lys Gly Leu Glu Trp Val
35 40 45

Ser Ala Asn Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 616
<211> LENGTH: 97
<212> TYPE: PRT
<213> ORGANISM: Homo sapiens

<400> SEQUENCE: 616

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 617
<211> LENGTH: 97
<212> TYPE: PRT
<213> ORGANISM: Homo sapiens

<400> SEQUENCE: 617

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 618
<211> LENGTH: 97
<212> TYPE: PRT
<213> ORGANISM: Homo sapiens

<400> SEQUENCE: 618

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr 20 25 30

Ala Met His Trp Val Arg Gln Ala Pro Gly Lys Gly Leu Glu Trp Val
35 40 45

Ser Ala Ile Gly Thr Gly Gly Gly Thr Tyr Tyr Ala Asp Ser Val Lys
50 55 60

Gly Arg Phe Thr Ile Ser Arg Asp Asn Ala Lys Asn Ser Leu Tyr Leu
65 70 75 80

Gln Met Asn Ser Leu Arg Ala Glu Asp Met Ala Val Tyr Tyr Cys Ala
85 90 95

Arg

<210> SEQ ID NO 619
<211> LENGTH: 98
<212> TYPE: PRT
<213> ORGANISM: Homo sapiens

<400> SEQUENCE: 619

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 620
<211> LENGTH: 98
<212> TYPE: PRT
<213> ORGANISM: Homo sapiens

<400> SEQUENCE: 620

Glu Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Val Gln Met Ser Ser Leu Arg Ala Glu Asp Thr Ala Val Tyr Tyr Cys
85 90 95

Val Lys

<210> SEQ ID NO 621
<211> LENGTH: 98
<212> TYPE: PRT
<213> ORGANISM: Homo sapiens

<400> SEQUENCE: 621

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Lys


<210> SEQ ID NO 622
<211> LENGTH: 98
<212> TYPE: PRT
<213> ORGANISM: Homo sapiens

<400> SEQUENCE: 622

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg


<210> SEQ ID NO 623
<211> LENGTH: 98
<212> TYPE: PRT
<213> ORGANISM: Homo sapiens

<400> SEQUENCE: 623

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys


<210> SEQ ID NO 624
<211> LENGTH: 98
<212> TYPE: PRT
```

<213> ORGANISM: Homo sapiens

<400> SEQUENCE: 624

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 625
<211> LENGTH: 98
<212> TYPE: PRT
<213> ORGANISM: Homo sapiens

<400> SEQUENCE: 625

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 626
<211> LENGTH: 98
<212> TYPE: PRT
<213> ORGANISM: Homo sapiens

<400> SEQUENCE: 626

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg

<210> SEQ ID NO 627
<211> LENGTH: 98
<212> TYPE: PRT
<213> ORGANISM: Homo sapiens

<400> SEQUENCE: 627

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 628
<211> LENGTH: 98
<212> TYPE: PRT
<213> ORGANISM: Homo sapiens

<400> SEQUENCE: 628

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 629
<211> LENGTH: 98
<212> TYPE: PRT
<213> ORGANISM: Homo sapiens

<400> SEQUENCE: 629

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95

Ala Arg


<210> SEQ ID NO 630
<211> LENGTH: 98
<212> TYPE: PRT
<213> ORGANISM: Homo sapiens

<400> SEQUENCE: 630

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 631
<211> LENGTH: 98
<212> TYPE: PRT
<213> ORGANISM: Homo sapiens

<400> SEQUENCE: 631

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 632
<211> LENGTH: 98
<212> TYPE: PRT
<213> ORGANISM: Homo sapiens

<400> SEQUENCE: 632

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

-continued

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 633
<211> LENGTH: 98
<212> TYPE: PRT
<213> ORGANISM: Homo sapiens

<400> SEQUENCE: 633

Gln Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Val Gln Met Ser Ser Leu Arg Ala Glu Asp Thr Ala Val Tyr Tyr Cys
85 90 95

Val Lys

<210> SEQ ID NO 634
<211> LENGTH: 98
<212> TYPE: PRT
<213> ORGANISM: Homo sapiens

<400> SEQUENCE: 634

Gln Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 635
<211> LENGTH: 98
<212> TYPE: PRT
<213> ORGANISM: Homo sapiens

<400> SEQUENCE: 635

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

```
Ala Val Ile Ser Tyr Asp Gly Ser Asn Lys Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 636
<211> LENGTH: 98
<212> TYPE: PRT
<213> ORGANISM: Homo sapiens

<400> SEQUENCE: 636

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 637
<211> LENGTH: 98
<212> TYPE: PRT
<213> ORGANISM: Homo sapiens

<400> SEQUENCE: 637

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys


<210> SEQ ID NO 638
<211> LENGTH: 97
<212> TYPE: PRT
<213> ORGANISM: Homo sapiens

<400> SEQUENCE: 638

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg


<210> SEQ ID NO 639
<211> LENGTH: 98
<212> TYPE: PRT
<213> ORGANISM: Homo sapiens

<400> SEQUENCE: 639

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 640
<211> LENGTH: 98
<212> TYPE: PRT
<213> ORGANISM: Homo sapiens

<400> SEQUENCE: 640

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Leu Arg Ala Arg Leu Cys Ile Thr Val
                85                  90                  95

Arg Glu


<210> SEQ ID NO 641
<211> LENGTH: 98
<212> TYPE: PRT
<213> ORGANISM: Homo sapiens

<400> SEQUENCE: 641
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 642
<211> LENGTH: 98
<212> TYPE: PRT
<213> ORGANISM: Homo sapiens

<400> SEQUENCE: 642

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 643
<211> LENGTH: 98
<212> TYPE: PRT
<213> ORGANISM: Homo sapiens

<400> SEQUENCE: 643

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg


<210> SEQ ID NO 644
<211> LENGTH: 98
<212> TYPE: PRT
```

<213> ORGANISM: Homo sapiens

<400> SEQUENCE: 644

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 645
<211> LENGTH: 98
<212> TYPE: PRT
<213> ORGANISM: Homo sapiens

<400> SEQUENCE: 645

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Arg Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 646
<211> LENGTH: 98
<212> TYPE: PRT
<213> ORGANISM: Homo sapiens

<400> SEQUENCE: 646

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 647
<211> LENGTH: 98
<212> TYPE: PRT
<213> ORGANISM: Homo sapiens

<400> SEQUENCE: 647

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 648
<211> LENGTH: 98
<212> TYPE: PRT
<213> ORGANISM: Homo sapiens

<400> SEQUENCE: 648

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Gly Thr Ala Val Tyr Tyr Cys
85 90 95

Ala Arg

<210> SEQ ID NO 649
<211> LENGTH: 98
<212> TYPE: PRT
<213> ORGANISM: Homo sapiens

<400> SEQUENCE: 649

Gln Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys 85 90 95

Ala Lys

<210> SEQ ID NO 650
<211> LENGTH: 98
<212> TYPE: PRT
<213> ORGANISM: Homo sapiens

<400> SEQUENCE: 650

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 651
<211> LENGTH: 98
<212> TYPE: PRT
<213> ORGANISM: Homo sapiens

<400> SEQUENCE: 651

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 652
<211> LENGTH: 98
<212> TYPE: PRT
<213> ORGANISM: Homo sapiens

<400> SEQUENCE: 652

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 653
<211> LENGTH: 95
<212> TYPE: PRT
<213> ORGANISM: Homo sapiens

<400> SEQUENCE: 653

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Arg Lys
85 90 95

<210> SEQ ID NO 654
<211> LENGTH: 98
<212> TYPE: PRT
<213> ORGANISM: Homo sapiens

<400> SEQUENCE: 654

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 655
<211> LENGTH: 98
<212> TYPE: PRT
<213> ORGANISM: Homo sapiens

<400> SEQUENCE: 655

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Ala 50 55 60

Lys Gly Arg Phe Thr Ile Ser Arg Asp Asn Ser Thr Asn Thr Leu Phe
65 70 75 80

Leu Gln Met Asn Ser Leu Arg Ala Glu Asp Thr Ala Val Tyr Tyr Cys
85 90 95

Ala Arg

<210> SEQ ID NO 656
<211> LENGTH: 98
<212> TYPE: PRT
<213> ORGANISM: Homo sapiens

<400> SEQUENCE: 656

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg

<210> SEQ ID NO 657
<211> LENGTH: 98
<212> TYPE: PRT
<213> ORGANISM: Homo sapiens

<400> SEQUENCE: 657

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 658
<211> LENGTH: 97
<212> TYPE: PRT
<213> ORGANISM: Homo sapiens

<400> SEQUENCE: 658

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Tyr Ile Tyr Tyr Ala Asp Ser Val Lys
50 55 60

Gly Arg Phe Thr Ile Ser Arg Asp Asn Ala Lys Asn Ser Leu Tyr Leu
65 70 75 80

Gln Met Asn Ser Leu Arg Ala Glu Asp Thr Ala Val Tyr Tyr Cys Ala
85 90 95

Arg

<210> SEQ ID NO 659
<211> LENGTH: 98
<212> TYPE: PRT
<213> ORGANISM: Homo sapiens

<400> SEQUENCE: 659

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 660
<211> LENGTH: 98
<212> TYPE: PRT
<213> ORGANISM: Homo sapiens

<400> SEQUENCE: 660

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 661
<211> LENGTH: 97
<212> TYPE: PRT
<213> ORGANISM: Homo sapiens

<400> SEQUENCE: 661

Glu Asp Gln Leu Val Glu Ser Gly Gly Gly Leu Val Gln Pro Gly Gly
1 5 10 15

Ser Leu Arg Pro Ser Cys Ala Ala Ser Gly Phe Ala Phe Ser Ser Tyr
20 25 30

Val Leu His Trp Val Arg Arg Ala Pro Gly Lys Gly Pro Glu Trp Val
35 40 45

Ser Ala Ile Gly Thr Gly Gly Asp Thr Tyr Tyr Ala Asp Ser Val Met
50 55 60

Gly Arg Phe Thr Ile Ser Arg Asp Asn Ala Lys Lys Ser Leu Tyr Leu
65 70 75 80

Gln Met Asn Ser Leu Ile Ala Glu Asp Met Ala Val Tyr Tyr Cys Ala
85 90 95

Arg

<210> SEQ ID NO 662
<211> LENGTH: 98
<212> TYPE: PRT
<213> ORGANISM: Homo sapiens

<400> SEQUENCE: 662

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met His Trp Val Arg Gln Ala Pro Gly Lys Gly Leu Val Trp Val
35 40 45

Ser Arg Ile Asn Ser Asp Gly Ser Ser Thr Ser Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 663
<211> LENGTH: 98
<212> TYPE: PRT
<213> ORGANISM: Homo sapiens

<400> SEQUENCE: 663

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met His Trp Val Arg Gln Ala Pro Gly Lys Gly Leu Val Trp Val
35 40 45

Ser Arg Ile Asn Ser Asp Gly Ser Ser Thr Ser Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 664
<211> LENGTH: 98
<212> TYPE: PRT
<213> ORGANISM: Homo sapiens

<400> SEQUENCE: 664

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 665
<211> LENGTH: 98
<212> TYPE: PRT
<213> ORGANISM: Homo sapiens

<400> SEQUENCE: 665

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met His Trp Val Arg Gln Ala Pro Gly Lys Gly Leu Val Trp Val
35 40 45

Ser Arg Ile Asn Ser Asp Gly Ser Ser Thr Ser Tyr Ala Asp Ser Met
50 55 60

Lys Gly Gln Phe Thr Ile Ser Arg Asp Asn Ala Lys Asn Thr Leu Tyr
65 70 75 80

Leu Gln Met Asn Ser Leu Arg Ala Glu Asp Met Ala Val Tyr Tyr Cys
85 90 95

Thr Arg

<210> SEQ ID NO 666
<211> LENGTH: 98
<212> TYPE: PRT
<213> ORGANISM: Homo sapiens

<400> SEQUENCE: 666

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 667

<211> LENGTH: 98
<212> TYPE: PRT
<213> ORGANISM: Homo sapiens

<400> SEQUENCE: 667

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Lys Ser Leu Arg Ala Glu Asp Thr Ala Val Tyr Tyr Cys
                85                  90                  95

Thr Thr
```

<210> SEQ ID NO 668
<211> LENGTH: 98
<212> TYPE: PRT
<213> ORGANISM: Homo sapiens

<400> SEQUENCE: 668

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala
```

<210> SEQ ID NO 669
<211> LENGTH: 98
<212> TYPE: PRT
<213> ORGANISM: Homo sapiens

<400> SEQUENCE: 669

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Met Gly Asn Tyr
            20                  25                  30

Ala Val Ser Trp Tyr Gln Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Trp
65                  70                  75                  80

Pro Glu Asp Glu Ala Asp Tyr Tyr Cys Leu Ala Trp Asp Thr Ser Pro
                85                  90                  95
```

Arg Ala

<210> SEQ ID NO 670
<211> LENGTH: 98
<212> TYPE: PRT
<213> ORGANISM: Homo sapiens

<400> SEQUENCE: 670

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly
```

<210> SEQ ID NO 671
<211> LENGTH: 98
<212> TYPE: PRT
<213> ORGANISM: Homo sapiens

<400> SEQUENCE: 671

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly
```

<210> SEQ ID NO 672
<211> LENGTH: 98
<212> TYPE: PRT
<213> ORGANISM: Homo sapiens

<400> SEQUENCE: 672

```
Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80
```

Ser Glu Asp Glu Ala Asp Tyr Tyr Cys Ala Ala Trp Asp Asp Ser Leu
85 90 95

Asn Gly

<210> SEQ ID NO 673
<211> LENGTH: 99
<212> TYPE: PRT
<213> ORGANISM: Homo sapiens

<400> SEQUENCE: 673

Gln Ser Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Val Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Gln Phe
50 55 60

Ser Gly Ser Lys Ser Gly Thr Ser Ala Ser Leu Ala Ile Thr Gly Leu
65 70 75 80

Gln Ser Glu Asp Glu Ala Asp Tyr Tyr Cys Lys Ala Trp Asp Asn Ser
85 90 95

Leu Asn Ala

<210> SEQ ID NO 674
<211> LENGTH: 99
<212> TYPE: PRT
<213> ORGANISM: Homo sapiens

<400> SEQUENCE: 674

Gln Ser Val Val Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Asp Val His Trp Tyr Gln Gln Leu Pro Gly Thr Ala Pro Lys Leu
35 40 45

Leu Ile Tyr Gly Asn Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Ser Ser
85 90 95

Leu Ser Gly

<210> SEQ ID NO 675
<211> LENGTH: 98
<212> TYPE: PRT
<213> ORGANISM: Homo sapiens

<400> SEQUENCE: 675

Ser Tyr Val Leu Thr Gln Pro Pro Ser Val Ser Gly Thr Pro Gly Gln
1 5 10 15

Arg Val Thr Ile Ser Cys Ser Gly Gly Arg Ser Asn Ile Gly Ser Asn
20 25 30

Thr Val Lys Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser

-continued

```
    50                  55                  60

Gly Ser Lys Ser Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Ser Ser Leu
                85                  90                  95

Arg Gly
```